(12) United States Patent
Hutchinson et al.

(10) Patent No.: US 7,919,621 B2
(45) Date of Patent: Apr. 5, 2011

(54) TRICYCLIC INHIBITORS OF 5-LIPOXYGENASE

(75) Inventors: John Howard Hutchinson, La Jolla, CA (US); Thomas Jonathan Seiders, San Diego, CA (US); Brian Andrew Stearns, San Diego, CA (US); Bowei Wang, San Diego, CA (US)

(73) Assignee: Amira Pharmaceuticals, Inc., San Diego, CA (US)

( * ) Notice: Subject to any disclaimer, the term of this patent is extended or adjusted under 35 U.S.C. 154(b) by 1108 days.

(21) Appl. No.: 11/626,222

(22) Filed: Jan. 23, 2007

(65) Prior Publication Data

US 2007/0173508 A1      Jul. 26, 2007

Related U.S. Application Data

(60) Provisional application No. 60/761,217, filed on Jan. 23, 2006.

(51) Int. Cl.
*C07D 487/06* (2006.01)
*A61K 31/4745* (2006.01)
*A61K 31/4738* (2006.01)

(52) U.S. Cl. .......................... 546/80; 514/290

(58) Field of Classification Search ................... 546/80; 514/290
See application file for complete search history.

(56) References Cited

U.S. PATENT DOCUMENTS

| | | | |
|---|---|---|---|
| 4,134,974 A | 1/1979 | Melloni et al. |
| 4,774,245 A | 9/1988 | Watjen et al. |
| 4,999,354 A | 3/1991 | Hansen et al. |
| 5,166,343 A | 11/1992 | Wade |
| 5,424,320 A | 6/1995 | Fortin et al. |
| 5,426,111 A | 6/1995 | Dellaria et al. |
| 5,552,437 A | 9/1996 | Delorme et al. |
| 5,610,158 A | 3/1997 | Bisaha et al. |
| 5,922,707 A | 7/1999 | Thomas et al. |

OTHER PUBLICATIONS

Dorwald F. A. Side Reactions in Organic Synthesis, 2005, Wiley: VCH, Weinheim p. IX of Preface.*
Bird, T.G. et al., "(Methoxyalkyl)thiazoles: A New Series of Potent, Selective, and Orally Active 5-Lipoxygenase Inhibitors Displaying High Enantioselectivity," J. Med. Chem. 34:2176-2186 (1991).
Elisa et al., "Fused pyrimidines. Synthesis of new derivatives of potential diureticactivity," Boll, Chim. Farm. 135:585 (1996).
Brink, C. et al., "International Union of Pharmacology XXXVII. Nomenclature for Leukotriene and Lipoxin Receptors," Pharmacol. Rev. 55:195-227 (2003).
Brooks, C.D. et al., "Design of inhibitors of leukotriene biosynthesis and their therapeutic potential," Pure & Applied Chem. 70(2):271-274 (1998).
Brooks, C.D. and Summers, J.B., "Modulators of Leukotriene Biosynthesis and Receptor Activation," J. Med. Chem. 39(14):2629-2654 (1996).
Busse, W.W., "The role of leukotrines in asthma and allergy rhinitis," Clin. Exp. Allergy 26:868-879 (1996).
Crawley, G.C. et al., "Methoxytetrahydropyrans. A New Series of Selective and Orally Potent 5-Lipoxygenase Inhibitors," J. Med. Chem. 35:2600-2609 (1992).
Folco, G. et al., "Leukotrienes in Cardiovascular Diseases," Am. J. Respir. Crit. Care Med. 161(2 Pt.2):S112-S116 (2000).
Ford-Hutchinson et al., A.W., "5-Lipoxygenase," Annu. Rev. Biochem. 63:383-417 (1994).
Homaidan, F.R. et al, "Protein Regulators of Eicosanoid Synthesis: Role in Inflammation," Current Protein and Peptide Science 3:467-484 (2002).
Jala et al., "Leukotrienes and atherosclerosis: new roles for old mediators," Trends in Immunol. 25:315-322 (2004).
Lambert-van der Brempt, C. et al., "Conformational Analysis of 5-Lipoxygenase Inhibitors: Role of the Substituents in Chiral Recognition and on the Active Conformations of the (Methoxyalkyl)thiazole and Methoxytetrahydropan Series," J. Med. Chem. 37:113-124 (1994).
Leff, A.R. et al., "Discovery of leukotrienes and development of antileukotriene agents,"Ann. Allergy Asthma Immunol. 86 (Suppl. 1):4-8 (2001).
Lotzer, K. et al., "The 5-lipoxygenase pathway in arterial wall biology and atherosclerosis," Biochim. Biophys. Acta 1736:30-37 (2005).
Mano et al., "Optimization of Imidazole-5-Lipoxygenase Inhibitors and Selection and Synthesis of a Development Candidate," Chem. Pharm. Bull. 53:965-973 (2005).
Marone, G. et al., "Cardiovascular and Metabolic Effects of Peptide Leukotrines in Man," *Biology of Leukotrienes*, eds. R. Levi and R.D. Krell, Ann. New York Acad. Sci. 524:321-333 (1988).
McQuaid, L.A. et al., "Synthesis and Excitatory Amino Acid Pharmacology of a Series of Heterocyclic-Fused Quinoxalinones and Quinazolinones," J. Med. Chem. 35(18):3319 -3324 (1992) >.
Musser, J.H. and Kreft, A.F., "5-Lipoxygenase: Properties, Pharmacology, and the Quinolinyl(bridged)aryl Class of Inhibitors," J. Med. Chem. 35:2501-2524 (1992).
O'Byrne, P.M., "Leukotrines in the Pathogenesis of Asthma," Chest 111 (Supp.2):27S-34S (1997).
Riccioni, G. et al, "Brief Review. Advances in Therapy with Antileukotriene Drugs," Ann. Clin. Lab Sci. 34(4):379-387 (2004).
Steinhilber, D., "5-Lipoxygenase: A Target for Antiinflammatory Drugs Revisited," Curr. Med. Chem. 6(1):71-85 (1999).
Werz, "Pharmacological intervention with 5-lipoxygenase: new insights and novel compounds," Exp. Op. Ther. Patents 15:505-519 (2005).
Young, R.N., "Inhibitors of 5-lipoxygenase: a therapeutic potential yet to be fully realized?" Eur. J. Med. Chem 34:671-685 (1999).
PCT/US07/01618 Search Report dated Nov. 26, 2007.

* cited by examiner

*Primary Examiner* — Rita J Desai
(74) *Attorney, Agent, or Firm* — Wilson Sonsini Goodrich & Rosati

(57) ABSTRACT

Described herein are compounds and pharmaceutical compositions containing such compounds, which inhibit the activity of 5-lipoxygenase (5-LO). Also described herein are methods of using such 5-LO inhibitors, alone and in combination with other compounds, for treating respiratory, cardiovascular, and other leukotriene-dependent or leukotriene mediated conditions, diseases, or disorders.

11 Claims, 8 Drawing Sheets

TRICYCLIC INHIBITORS OF 5-LIPOXYGENASE

RELATED APPLICATIONS

This application claims benefit of U.S. Provisional Application No. 60/761,217, entitled "TRICYCLIC INHIBITORS OF 5-LIPOXYGENASE" filed on Jan. 23, 2006, which is herein incorporated by reference.

FIELD OF THE INVENTION

Described herein are compounds, methods of making such compounds, pharmaceutical compositions and medicaments that include such compounds, and methods of using such compounds to treat or prevent diseases or conditions associated with 5-lipoxygenase activity.

BACKGROUND OF THE INVENTION

The protein 5-lipoxygenase (5-LO) is associated with the pathway of leukotriene synthesis. Upon presentation of inflammatory stimuli from the exterior of the cell, calcium is released and binds to phospholipase $A_2$ (PLA2) and 5-lipoxygenase. Cell activation results in the translocation of $PLA_2$ and 5-lipoxygenase from the cytoplasm to the endoplasmic reticulum and/or nuclear membranes, where in the presence of 5-lipoxygenase-activating protein (FLAP), 5-lipoxygenase can then catalyze the two-step oxygenation and dehydration of arachidonic acid, converting it into the intermediate compound 5-HPETE (5-hydroperoxyeicosatetraenoic acid), and in the presence of FLAP convert the 5-HPETE to Leukotriene $A_4$ ($LTA_4$).

Leukotrienes are biological compounds formed from arachidonic acid in the leukotriene synthesis pathway (Samuelsson et al., *Science*, 220, 568-575, 1983; Cooper, The Cell, A Molecular Approach, 2nd Ed. Sinauer Associates, Inc., Sunderland (MA), 2000). They are synthesized primarily by eosinophils, neutrophils, mast cells, basophils, dendritic cells, macrophages and monocytes. Leukotrienes have been implicated in biological actions including, by way of example only, smooth muscle contraction, leukocyte activation, cytokine secretion, mucous secretion, and vascular function.

SUMMARY OF THE INVENTION

Presented herein are methods, compounds, pharmaceutical compositions, and medicaments for (a) diagnosing, preventing, or treating allergic and non-allergic inflammation, (b) controlling signs and symptoms that are associated with inflammation, and/or (c) controlling proliferative or metabolic disorders. These disorders may arise from genetic, iatrogenic, immunological, infectious, metabolic, oncologic, toxic, and/or traumatic etiology. In one aspect, the methods, compounds, pharmaceutical compositions, and medicaments described herein include 5-lipoxygenase inhibitors described herein.

Compounds, pharmaceutically acceptable salts, pharmaceutically acceptable N-oxides, pharmaceutically active metabolites, pharmaceutically acceptable prodrugs, and/or pharmaceutically acceptable solvates thereof, which antagonize or inhibit 5-lipoxygenase and may be used to treat patients suffering from leukotriene-dependent conditions or diseases, including, but not limited to, asthma, chronic obstructive pulmonary disease, pulmonary hypertension, interstitial lung fibrosis, rhinitis, arthritis, allergy, psoriasis, inflammatory bowel disease, adult respiratory distress syndrome, myocardial infarction, aneurysm, stroke, cancer, endotoxic shock, proliferative disorders and inflammatory conditions, are provided.

Compounds described herein, or pharmaceutically acceptable salts, pharmaceutically acceptable N-oxides, pharmaceutically active metabolites, pharmaceutically acceptable prodrugs, and pharmaceutically acceptable solvates thereof may be used to treat leukotriene dependent or leukotriene-mediated diseases, disorders, or conditions in a patient, or 5-lipoxygenase dependent or 5-lipoxygenase-mediated diseases, disorders, or condition in a patient.

In one aspect, provided herein are compounds that have a structure represented by Formula (II):

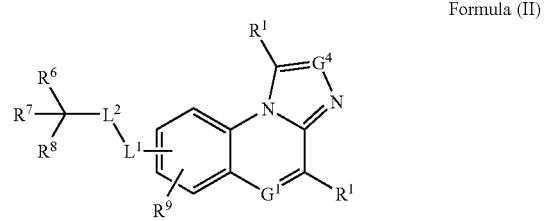

Formula (II)

wherein:
$G^1$ is N or $CR^1$;
$G^4$ is N or $CR^1$;
each $R^1$ is independently H, halide, —CN, —$NO_2$, —OH, —$OR^3$, —$SR^3$, —S(=O)$R^3$, —S(=O)$_2R^3$, —C(=O)$R^3$, —C(=O)$OR^3$, —CH($R^3$)$_2$, —N($R^3$)$_2$, —NH$CH_2$C(=O)$OR^3$, —C(=O)N($R^3$)$_2$, —NHC(=O)$R^3$, or —C(OH)($R^3$)$_2$, or an optionally substituted group selected from among $C_1$-$C_6$alkyl, $C_1$-$C_6$fluoroalkyl, $C_3$-$C_8$cycloalkyl, $C_2$-$C_6$alkenyl, $C_2$-$C_6$alkynyl, and $C_1$-$C_6$fluoroalkoxy; or
$R^1$ is $Q^1$-$Q^2$ where $Q^1$ is aryl, monocyclic heterocycloalkyl, monocyclic heteroaryl, bicyclic heteroaryl; and $Q^2$ is H, halide, —CN, —$NO_2$, $C_1$-$C_6$alkyl, $C_1$-$C_6$alkoxy, —$OR^3$, —$SR^3$, —S(=O)$R^3$, —S(=O)$_2R^3$, —C(=O)$R^3$, —C(=O)$OR^3$, —CH($R^3$)$_2$, —N($R^3$)$_2$, or —C(=O)N($R^3$)$_2$;
each $R^3$ is independently H, or an optionally substituted group selected from among $C_1$-$C_6$alkyl, $C_2$-$C_6$alkenyl, $C_2$-$C_6$alkynyl, $C_3$-$C_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl, and pyrimidinyl;
$L^1$ is —(CHR$^4$)$_n$X$^1$(CHR$^4$)$_n$— wherein,
each n is independently 0, 1, 2, or 3;
$X^1$ is a bond, O, S, S(=O), S(=O)$_2$, or NR$^5$;
each $R^4$ is independently H, or an optionally substituted group selected from among $C_1$-$C_6$alkyl, $C_3$-$C_8$cycloalkyl, $C_1$-$C_6$fluoroalkyl, $C_2$-$C_6$alkenyl, $C_2$-$C_6$alkynyl, phenyl, and benzyl; or $L^4$-$X^2$-$L^5$-$X^3$ wherein,
$L^4$ is a bond, or an optionally substituted group selected from among $C_1$-$C_6$ alkyl, $C_2$-$C_6$ alkenyl, $C_2$-$C_6$alkynyl, aryl, $C_2$-$C_{10}$heterocycloalkyl, and $C_3$-$C_8$cycloalkyl;
$X^2$ is a bond, O, S, S(=O), S(=O)$_2$, NH, C(=O)NH, or NHC(=O);
$L^5$ is a bond, $C_1$-$C_6$ alkyl, $C_3$-$C_8$cycloalkyl, phenyl, pyridyl, thiazolyl, or thienyl; and
$X^3$ is —OH, —CN, —$NO_2$, halide, —$CO_2$H, —$CO_2R^{10}$, —C(=O)$R^{10}$, —CON($R^{10}$)$_2$, —NHC(=O)$R^{10}$, —C(OH)($R^{10}$)$_2$, tetrazolyl, —C(=O)

NHSO$_2$R$^{10}$, —CH(OH)CF$_3$, —COCF$_3$, —SO$_2$NHC(=O)R$^{10}$, or —N(R$^{10}$)$_2$, where each R$^{10}$ is independently H, or an optionally substituted group selected from among C$_1$-C$_6$alkyl, C$_1$-C$_6$fluoroalkyl, C$_2$-C$_6$alkenyl, C$_2$-C$_6$alkynyl, C$_3$-C$_8$cycloalkyl, phenyl, and benzyl;

R$^5$ is H, or an optionally substituted group selected from among C$_1$-C$_6$alkyl, C$_3$-C$_8$cycloalkyl, C$_1$-C$_6$fluoroalkyl, C$_2$-C$_6$alkenyl, C$_2$-C$_6$alkynyl, phenyl, and benzyl; or R$^5$ is L$^6$-X$^5$-L$^7$-X$^6$ wherein, L$^6$ is an optionally substituted group selected from among C$_1$-C$_6$alkyl, C$_2$-C$_{10}$heterocycloalkyl, and C$_3$-C$_8$cycloalkyl;

X$^5$ is a bond, O, S, S(=O), S(=O)$_2$, NH, C(=O)NH, or NHC(=O);

L$^7$ is a bond, C$_1$-C$_6$ alkyl, C$_3$-C$_8$cycloalkyl, phenyl, pyridyl, thiazolyl, or thienyl; and X$^6$ is —OH, —CN, —NO$_2$, halide, —CO$_2$H, —CO$_2$R$^{10}$, —C(=O)R$^{10}$, —C(OH)(R$^{10}$)$_2$, tetrazolyl, —C(=O)NHSO$_2$R$^{10}$, —CH(OH)CF$_3$, —COCF$_3$, —SO$_2$NHC(=O)R$^{10}$, or —N(R$^{10}$)$_2$, where each R$^{10}$ is independently H, or an optionally substituted group selected from among C$_1$-C$_6$alkyl, C$_1$-C$_6$fluoroalkyl, C$_2$-C$_6$alkenyl, C$_2$-C$_6$alkynyl, C$_3$-C$_8$cycloalkyl, phenyl, and benzyl;

L$^2$ is an optionally substituted group selected from among C$_1$-C$_6$alkyl, aryl, monocyclic heteroaryl, and bicyclic heteroaryl;

R$^6$ and R$^7$ are independently H, or an optionally substituted group selected from among C$_1$-C$_6$haloalkyl, C$_1$-C$_6$alkyl, C$_3$-C$_8$cycloalkyl, C$_2$-C$_6$alkenyl, C$_2$-C$_6$alkynyl, phenyl, benzyl, thiazolyl, C$_1$-C$_6$alkoxy, C$_1$-C$_6$thioalkoxy, and C$_1$-C$_6$alkyl-X$^4$, wherein, X$^4$ is —CO$_2$H, —CO$_2$R$^{11}$, —C(=O)R$^{11}$, —C(OH)(R$^{11}$)$_2$, C$_1$-C$_6$alkoxy, tetrazolyl, —OH, halide, —CN, —NO$_2$, —SR$^{11}$, —S(=O)R$^{11}$, —S(=O)$_2$R$^{11}$, —N(R$^{11}$)$_2$, —CON(R$^{11}$)$_2$, —NHC(=O)R$^{11}$, —C(=O)NHSO$_2$R$^{11}$, —CH(OH)CF$_3$, —COCF$_3$, or —SO$_2$NHC(=O)R$^{11}$, where each R$^{11}$ is independently H, or an optionally substituted group selected from among C$_1$-C$_6$alkyl, C$_1$-C$_6$fluoroalkyl, C$_2$-C$_6$alkenyl, C$_2$-C$_6$alkynyl, C$_3$-C$_8$cycloalkyl, phenyl, and benzyl;

or R$^6$ and R$^7$ can together form an optionally substituted 5-, 6-, or 7-membered non-aromatic monocyclic ring containing 0, 1, or 2 heteroatoms selected from among S and O;

or R$^6$ and R$^7$ can together form an optionally substituted bicyclo[3,2,1]ring containing 1 or 2 heteroatoms selected from among S and O;

or R$^6$ and R$^7$ can together form a carbonyl (C=O); and

R$^8$ is H, —OH, —CONH$_2$, tetrazolyl, —CN, —N$_3$, C$_1$-C$_6$alkyl, C$_2$-C$_6$alkenyl, —CF$_3$, —CO$_2$H, —OR$^{12}$, —CON(R$^{12}$)$_2$, —CO$_2$—R$^{12}$, —SR$^{12}$, —S(=O)R$^{12}$, S(=O)$_2$R$^{12}$, —SO$_2$N(R$^{12}$)$_2$, C(=O)R$^{12}$, C(OH)(R$^{12}$)$_2$, —CH=N—OR$^{12}$, —N(R$^{12}$)$_2$, NHC(=O)R$^{12}$, —OC(=O)R$^{12}$, or an optionally substituted group selected from among C$_1$-C$_6$fluoroalkoxy, C$_3$-C$_8$cycloalkoxy, benzyl, and phenyl; where each R$^{12}$ is independently H, or an optionally substituted group selected from among C$_1$-C$_6$alkyl, C$_1$-C$_6$fluoroalkyl, C$_2$-C$_6$alkenyl, C$_2$-C$_6$alkynyl, C$_3$-C$_8$cycloalkyl, C$_4$-C$_8$cycloalkylalkyl, phenyl, and benzyl; or R$^6$ and R$^8$ can together form an optionally substituted C$_2$-C$_8$heterocycloalkyl having 1 or 2 O atoms in the ring;

R$^9$ is H, halide, —CN, —NO$_2$, —OH, or an optionally substituted group selected from among C$_1$-C$_6$alkyl, C$_3$-C$_8$cycloalkyl, C$_1$-C$_6$fluoroalkyl, C$_2$-C$_6$alkenyl, C$_2$-C$_6$alkynyl, C$_1$-C$_6$alkoxy, phenyl, and benzyl; or R$^9$ is L$^8$-X$^7$-L$^9$-X$^8$ where, L$^8$ is a bond, or an optionally substituted group selected from C$_1$-C$_6$ alkyl, C$_2$-C$_6$ alkenyl, C$_2$-C$_6$ alkynyl, aryl, C$_2$-C$_{10}$heterocycloalkyl or C$_3$-C$_8$cycloalkyl;

X$^7$ is a bond, O, S, S(=O), S(=O)$_2$, NH, C(=O)NH, or NHC(=O);

L$^9$ is a bond, C$_1$-C$_6$ alkyl, C$_3$-C$_8$ cycloalkyl, phenyl, pyridyl, thiazolyl, or thienyl; and X$^8$ is H, —OH, —CN, —NO$_2$, halide, —CO$_2$H, —CO$_2$R$^{16}$, —C(=O)R$^{16}$, —C(OH)(R$^{16}$)$_2$, —C(=O)N(R$^{16}$)$_2$, —NHC(=O)R$^{16}$, tetrazolyl, —C(O)NHSO$_2$R$^{16}$, —CH(OH)CF$_3$, —COCF$_3$, —SO$_2$NHC(=O)R$^{16}$, or —N(R$^{16}$)$_2$, where each R$^{16}$ is independently H, or an optionally substituted group selected from among C$_1$-C$_6$alkyl, C$_2$-C$_6$alkenyl, C$_2$-C$_6$alkynyl, C$_3$-C$_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl, and pyrimidinyl;

or a pharmaceutically acceptable salt, pharmaceutically acceptable N-oxide, pharmaceutically active metabolite, pharmaceutically acceptable prodrug, or pharmaceutically acceptable solvate thereof.

For any and all of the embodiments, substituents can be selected from among from a subset of the listed alternatives. For example, in some embodiments, R$^9$ is H, halide, —CN, —NO$_2$, —OH, or an optionally substituted group selected from among C$_1$-C$_6$alkyl, C$_1$-C$_6$fluoroalkyl, and C$_1$-C$_6$alkoxy. In other embodiments, R$^9$ is H, halide, —CN, —OH, or an optionally substituted group selected from among C$_1$-C$_6$alkyl, and C$_1$-C$_6$alkoxy. In yet other embodiments, R$^9$ is H, halide, or an optionally substituted group selected from among C$_1$-C$_6$alkyl, and C$_1$-C$_6$alkoxy.

In some embodiments, L$^1$ is selected from among —(CHR$^4$)$_n$—, —(CHR$^4$)$_n$O—, —(CHR$^4$)$_n$S—, —O(CHR$^4$)$_n$—, and —S(CHR$^4$)$_n$—; n is 0, 1, 2, or 3. In other embodiments, each R$^4$ is independently H, or an optionally substituted group selected from among C$_1$-C$_6$alkyl, C$_3$-C$_8$cycloalkyl, C$_1$-C$_6$fluoroalkyl; or L$^4$-X$^2$-L$^5$-X$^3$ where, L$^4$ is a bond, or an optionally substituted group selected from among C$_1$-C$_6$ alkyl, C$_2$-C$_{10}$ heterocycloalkyl, and C$_3$-C$_8$ cycloalkyl; X$^2$ is a bond, O, S, S(=O), or S(=O)$_2$; L$^5$ is a bond, C$_1$-C$_6$ alkyl, C$_3$-C$_8$cycloalkyl, phenyl, pyridyl, thiazolyl, or thienyl, and X$^3$ is OH, CN, NO$_2$, halide, CO$_2$H, CO$_2$R$^{10}$, C(=O)R$^{10}$, C(OH)(R$^{10}$)$_2$, tetrazolyl, C(=O) NHSO$_2$R$^{10}$, CH(OH)CF$_3$, COCF$_3$, SO$_2$NHC(=O)R$^{10}$, or N(R$^{10}$)$_2$, where each R$^{10}$ is independently H, or an optionally substituted group selected from among C$_1$-C$_6$alkyl, C$_3$-C$_8$cycloalkyl, phenyl, and benzyl. In some other embodiments, each R$^4$ is independently H, or an optionally substituted group selected from among C$_1$-C$_6$alkyl, and C$_1$-C$_6$fluoroalkyl; and n is 0, 1, or 2. In yet other embodiments, n is 0 or 1.

In some embodiments, each R$^1$ is independently H, halide, —CN, —NO$_2$, —OH, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, —NHCH$_2$C(=O)OR$^3$, —C(=O)N(R$^3$)$_2$, —NHC(=O)R$^3$, or —C(OH)(R$^3$)$_2$, or an optionally substituted group selected from among C$_1$-C$_6$alkyl, C$_1$-C$_6$fluoroalkyl, C$_3$-C$_8$cycloalkyl, C$_2$-C$_6$alkenyl, C$_2$-C$_6$alkynyl, and C$_1$-C$_6$fluoroalkoxy; or R$^1$ is Q$^1$-Q$^2$ where Q$^1$ is aryl, monocyclic heterocycloalkyl, monocyclic heteroaryl; and Q$^2$ is H, halide, —CN, —NO$_2$, C$_1$-C$_6$alkyl, $C_1$-$C_6$alkoxy, —$OR^3$, —$SR^3$, —$S(=O)R^3$, —$S(=O)_2R^3$, —$C(=O)R^3$, —$C(=O)OR^3$, —$CH(R^3)_2$, —$N(R^3)_2$, or —$C(=O)N(R^3)_2$.

In other embodiments, $R^6$ and $R^7$ are independently H, or an optionally substituted group selected from among $C_1$-$C_6$haloalkyl, $C_1$-$C_6$alkyl, $C_3$-$C_8$cycloalkyl, $C_2$-$C_6$alkenyl, $C_2$-$C_6$alkynyl, thiazolyl, $C_1$-$C_6$alkoxy, $C_1$-$C_6$thioalkoxy, and $C_1$-$C_6$alkyl-$X^4$, wherein, $X^4$ is —$CO_2H$, —$CO_2R^{11}$, $C_1$-$C_6$alkoxy, tetrazolyl, —OH, —$CON(R^{11})_2$, where each $R^{11}$ is independently H, or an optionally substituted group selected from among $C_1$-$C_6$alkyl, and $C_1$-$C_6$fluoroalkyl; or $R^6$ and $R^7$ can together form an optionally substituted 5-, 6-, or 7-membered monocyclic ring containing 0, 1, or 2 heteroatoms selected from among S and O; or $R^6$ and $R^7$ can together form a carbonyl (C=O).

In some embodiments, $R^6$ and $R^7$ are independently H, or an optionally substituted group selected from among $C_1$-$C_6$haloalkyl, $C_1$-$C_6$alkyl, $C_3$-$C_8$cycloalkyl, and $C_1$-$C_6$alkyl-$X^4$, wherein, $X^4$ is —$CO_2H$, —$CO_2R^{11}$, or —$CON(R^{11})_2$, where each $R^{11}$ is independently H, or an optionally substituted $C_1$-$C_6$alkyl; or $R^6$ and $R^7$ can together form an optionally substituted 5-, 6-, or 7-membered monocyclic ring containing 0, 1, or 2 heteroatoms selected from S and O; or $R^6$ and $R^7$ can together form a carbonyl (C=O).

In some embodiments, $R^6$ and $R^7$ are independently H, or an optionally substituted group selected from among $C_1$-$C_6$haloalkyl, $C_1$-$C_6$alkyl, $C_3$-$C_8$cycloalkyl, and $C_1$-$C_6$alkyl-$X^4$, wherein, $X^4$ is —$CO_2H$, —$CO_2R^{11}$, or —$CON(R^{11})_2$, where each $R^{11}$ is independently H, or an optionally substituted $C_1$-$C_6$alkyl; or $R^6$ and $R^7$ can together form an optionally substituted 6-membered monocyclic ring containing 1 O atom; or $R^6$ and $R^7$ can together form a carbonyl (C=O).

In some embodiments, $R^8$ is H, —OH, —$CONH_2$, tetrazolyl, —CN, $C_1$-$C_6$alkyl, $C_2$-$C_6$alkenyl, —$CF_3$, —$CO_2H$, —$OR^{12}$, —$CON(R^{12})_2$, —$CO_2$—$R^{12}$, —$SR^{12}$, —$S(=O)R^{12}$, $S(=O)_2R^{12}$, —$SO_2N(R^{12})_2$, $C(=O)R^{12}$, $C(OH)(R^{12})_2$, —CH=N—$OR^{12}$, —$OC(=O)R^{12}$, or an optionally substituted group selected from among $C_1$-$C_6$fluoroalkoxy, $C_3$-$C_8$cycloalkoxy, benzyl, and phenyl; where each $R^{12}$ is independently H, or an optionally substituted group selected from among $C_1$-$C_6$alkyl, $C_1$-$C_6$fluoroalkyl, $C_3$-$C_8$cycloalkyl, $C_4$-$C_8$cycloalkylalkyl, phenyl, and benzyl.

In some embodiments, provided herein are compounds that have a structure selected from among:

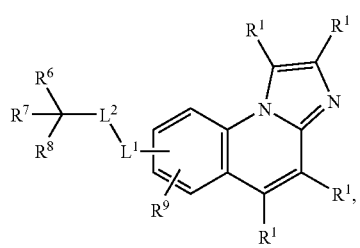

Formula (IIa)

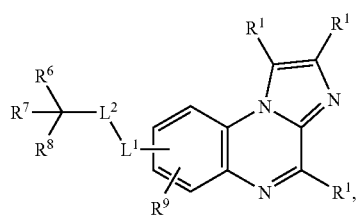

Formula (IIb)

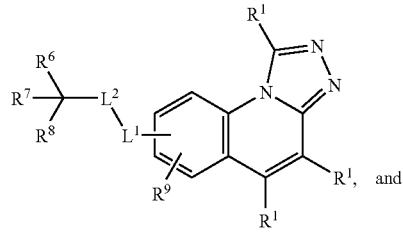

Formula (IIc)

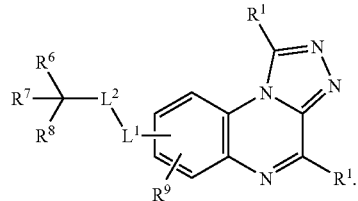

Formula (IId)

In some embodiments, compounds provided herein have a structure selected from among:

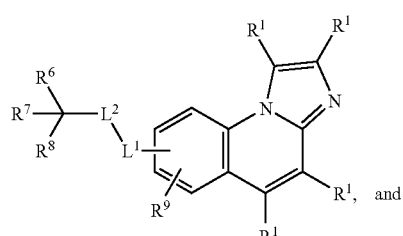

Formula (IIa)

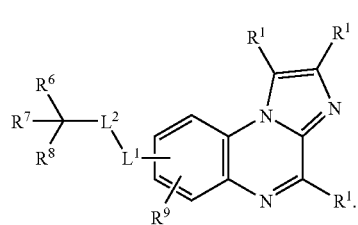

Formula (IIb)

In other embodiments, compounds provided herein have a structure of Formula (IIa):

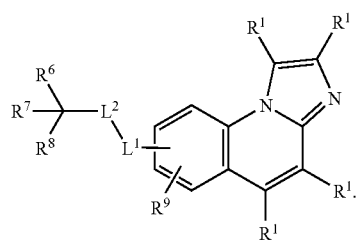

Formula (IIa)

In other embodiments, compounds provided herein have a structure of Formula (IIb):

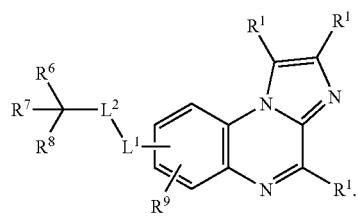

Formula (IIb)

In some embodiments, compounds provided herein have a structure selected from among:

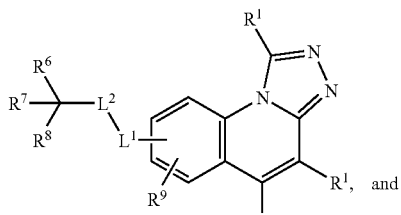

Formula (IIc)

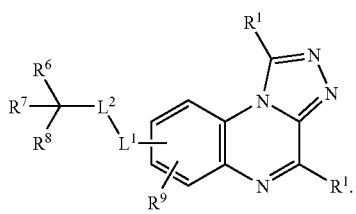

Formula (IId)

In other embodiments, compounds provided herein have a structure of Formula (IIc):

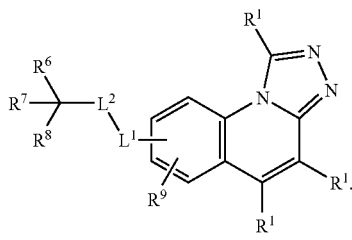

Formula (IIc)

In other embodiments, compounds provided herein have a structure of Formula (IId):

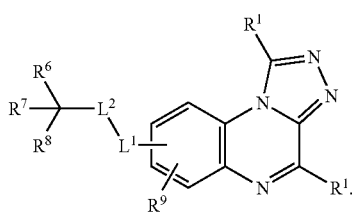

Formula (IId)

In some embodiments, L² is an optionally substituted group selected from among $C_1$-$C_6$alkyl, phenyl, and a 5- or 6-membered monocyclic heteroaryl. In some other embodiments, L² is an optionally substituted group selected from among $C_1$-$C_6$alkyl, phenyl, thienyl, thiazolyl, oxazolyl, furanyl, pyrrolyl, imidazolyl, and pyridyl.

In some embodiments, L² is selected from among $C_1$-$C_6$alkyl,

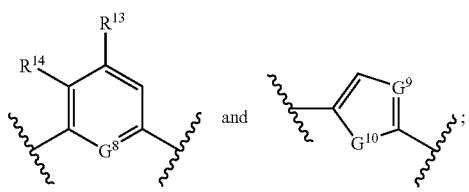

where, $G^8$ is N or CH; $G^9$ is N or CH; and $G^{10}$ is $NR^2$, O or S; $R^2$ is independently H, —C(=O)R³, C(=O)OR³, —CH $(R^3)_2$, —C(=O)N(R³)$_2$, or an optionally substituted group selected from $C_1$-$C_6$alkyl, $C_1$-$C_6$fluoroalkyl, $C_3$-$C_8$cycloalkyl, $C_2$-$C_6$alkenyl, $C_2$-$C_6$alkynyl, aryl, monocyclic heterocycloalkyl, monocyclic heteroaryl, and bicyclic heteroaryl; each R³ is independently H, or an optionally substituted group selected from among $C_1$-$C_6$alkyl, $C_2$-$C_6$alkenyl, $C_2$-$C_6$alkynyl, $C_3$-$C_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl, and pyrimidinyl; $R^{13}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$—S—, $R^{17}$—S(=O)—, $R^{17}$—S(=O)$_2$—, —CN, halide, $R^{17}$C(=O)—, $R^{17}$C(=O)O—, $R^{17}$NHC(=O)—, —$R^{17}$—C(=O)NH—, $R^{17}$S(=O)$_2$NH—, $R^{17}$—NHS(=O)$_2$—, $R^{17}$—OC(=O)NH—, $R^{17}$—NHC(=O)O—, —NO$_2$, $C_1$-$C_6$haloalkyl, and —N($R^{17}$)$_2$; $R^{17}$ is independently selected from among H, $C_1$-$C_6$alkyl, $C_3$-$C_8$cycloalkyl, aryl, heteroaryl, and $C_1$-$C_6$heteroalkyl; $R^{14}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$—S—, $R^{17}$—S(=O)—, $R^{17}$—S(=O)$_2$—, —CN, halide, $R^{17}$C(=O)—, $R^{17}$C(=O)O—, $R^{17}$NHC(=O)—, $R^{17}$—C(=O)NH—, $R^{17}$S(=O)$_2$NH—, $R^{17}$—NHS(=O)$_2$—, $R^{17}$—OC(=O)NH—, $R^{17}$—NHC(=O)O—, —NO$_2$, $C_1$-$C_6$haloalkyl, and —N($R^{17}$)$_2$; $R^{17}$ is independently selected from among H, $C_1$-$C_6$alkyl, $C_3$-$C_8$cycloalkyl, aryl, heteroaryl, and $C_1$-$C_6$heteroalkyl.

In some embodiments, L² is

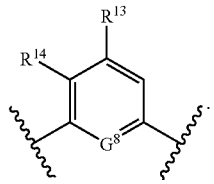

In some embodiments, $G^8$ is CH. In other embodiments, $G^8$ is N.

In some embodiments, L² is

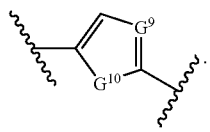

In some embodiments, $G^9$ is N; and $G^{10}$ is O or S. In other embodiments, $G^{10}$ is S.

In some embodiments, L² is an optionally substituted $C_1$-$C_6$alkyl.

In some embodiments, L² is selected from among $C_1$-$C_6$alkyl,

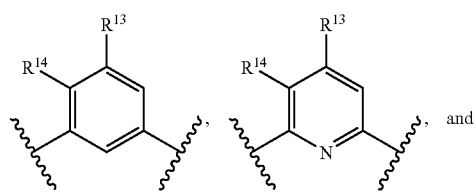

-continued

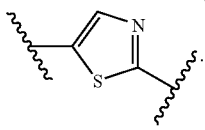

In some embodiments, $L^2$ is selected from among

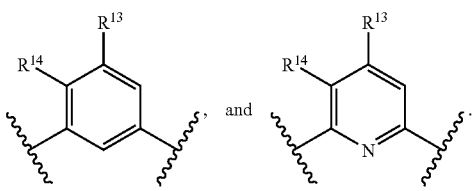

In some embodiments, $L^2$ is

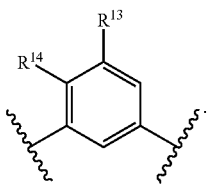

In some embodiments, compounds provided herein have a structure of Formula (III):

Formula (III)

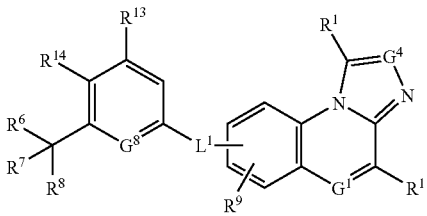

wherein:
$G^8$ is N or CH;
$R^{13}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$—S—, $R^{17}$S(=O)—, $R^{17}$—S(=O)$_2$—, —CN, halide, $R^{17}$C(=O)—, $R^{17}$C(=O)O—, $R^{17}$NHC(=O)—, $R^{17}$C(=O)NH—, $R^{17}$S(=O)$_2$NH—, $R^{17}$NHS(=O)$_2$—, $R^{17}$—OC(=O)NH—, $R^{17}$—NHC(=O)O—, —NO$_2$, $C_1$-$C_6$haloalkyl, and —N($R^{17}$)$_2$;
$R^{17}$ is independently selected from among H, $C_1$-$C_6$alkyl, $C_3$-$C_8$cycloalkyl, aryl, heteroaryl, and $C_1$-$C_6$heteroalkyl.
$R^{14}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$—S—, $R^{17}$—S(=O)—, $R^{17}$—S(=O)$_2$—, —CN, halide, $R^{17}$C(=O)—, $R^{17}$C(=O)O—, $R^{17}$NHC(=O)—, $R^{17}$—C(=O)NH—, $R^{17}$S(=O)$_2$NH—, $R^{17}$—NHS(=O)$_2$—, $R^{17}$—OC(=O)NH—, $R^{17}$—NHC(=O)O—, —NO$_2$, $C_1$-$C_6$haloalkyl, and —N($R^{17}$)$_2$;
$R^{17}$ is independently selected from among H, $C_1$-$C_6$alkyl, $C_3$-$C_8$cycloalkyl, aryl, heteroaryl, and $C_1$-$C_6$heteroalkyl; or $R^8$ and $R^{14}$ taken together can form a optionally substituted 5-, or 6-membered ring.

In some embodiments, compounds provided herein have a structure of Formula (IIIa):

Formula (IIIa)

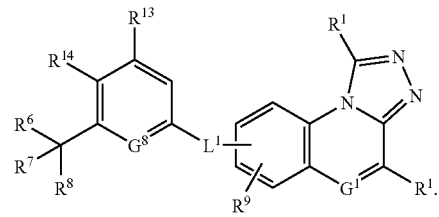

In some embodiments, compounds provided herein have a structure of Formula (IIIb):

Formula (IIIb)

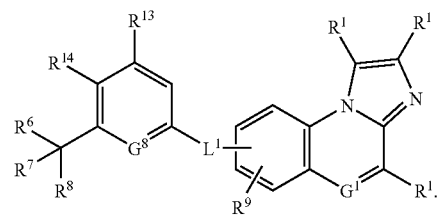

In some embodiments, described herein is a compound having a structure represented by Formula (IIIc):

Formula (IIIc)

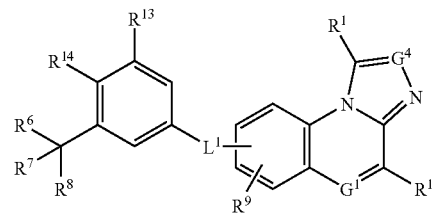

wherein:
$G^1$ is N or $CR^1$;
$G^4$ is N or $CR^1$;
each $R^1$ is independently H, halide, —CN, —NO$_2$, —OH, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, —NHCH$_2$C(=O)OR$^3$, —C(=O)N(R$^3$)$_2$, —NHC(=O)R$^3$, or —C(OH)(R$^3$)$_2$, or an optionally substituted group selected from among $C_1$-$C_6$alkyl, $C_1$-$C_6$fluoroalkyl, $C_3$-$C_8$cycloalkyl, $C_2$-$C_6$alkenyl, $C_2$-$C_6$alkynyl, and $C_1$-$C_6$fluoroalkoxy; or
$R^1$ is $Q^1$-$Q^2$ where $Q^1$ is aryl, monocyclic heterocycloalkyl, monocyclic heteroaryl, bicyclic heteroaryl; and $Q^2$ is H, halide, —CN, —NO$_2$, $C_1$-$C_6$alkyl, $C_1$-$C_6$alkoxy, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, or —C(=O)N(R$^3$)$_2$;
each $R^3$ is independently H, or an optionally substituted group selected from among $C_1$-$C_6$alkyl, $C_2$-$C_6$alkenyl, $C_2$-$C_6$alkynyl, $C_3$-$C_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl, and pyrimidinyl;

$L^1$ is —$(CHR^4)_nX^1(CHR^4)_n$— wherein, each n is independently 0, 1, 2, or 3;

$X^1$ is a bond, O, S, S(=O), S(=O)$_2$, or $NR^5$;

each $R^4$ is independently H, or an optionally substituted group selected from among $C_1$-$C_6$alkyl, $C_3$-$C_8$cycloalkyl, $C_1$-$C_6$fluoroalkyl, $C_2$-$C_6$alkenyl, $C_2$-$C_6$alkynyl, phenyl, and benzyl; or $L^4$-$X^2$-$L^5$-$X^3$ wherein, $L^4$ is a bond, or an optionally substituted group selected from among $C_1$-$C_6$ alkyl, $C_2$-$C_6$ alkenyl, $C_2$-$C_6$ alkynyl, aryl, $C_2$-$C_{10}$heterocycloalkyl, and $C_3$-$C_8$cycloalkyl;

$X^2$ is a bond, O, S, S(=O), S(=O)$_2$, NH, C(=O)NH, or NHC(=O);

$L^5$ is a bond, $C_1$-$C_6$ alkyl, $C_3$-$C_8$cycloalkyl, phenyl, pyridyl, thiazolyl, or thienyl; and $X^3$ is —OH, —CN, —NO$_2$, halide, —CO$_2$H, —CO$_2R^{10}$, —C(=O)$R^{10}$, —CON($R^{10}$)$_2$, —NHC(=O)$R^{10}$, —C(OH)($R^{10}$)$_2$, tetrazolyl, —C(=O)NHSO$_2R^{10}$, —CH(OH)CF$_3$, —COCF$_3$, —SO$_2$NHC(=O)$R^{10}$, or —N($R^{10}$)$_2$, where each $R^{10}$ is independently H, or an optionally substituted group selected from among $C_1$-$C_6$alkyl, $C_1$-$C_6$fluoroalkyl, $C_2$-$C_6$alkenyl, $C_2$-$C_6$alkynyl, $C_3$-$C_8$cycloalkyl, phenyl, and benzyl;

$R^5$ is H, or an optionally substituted group selected from among $C_1$-$C_6$alkyl, $C_3$-$C_8$cycloalkyl, $C_1$-$C_6$fluoroalkyl, $C_2$-$C_6$alkenyl, $C_2$-$C_6$alkynyl, phenyl, and benzyl;

$R^6$ and $R^7$ are independently H, or an optionally substituted group selected from among $C_1$-$C_6$haloalkyl, $C_1$-$C_6$alkyl, $C_3$-$C_8$cycloalkyl, $C_2$-$C_6$alkenyl, $C_2$-$C_6$alkynyl, phenyl, benzyl, thiazolyl, $C_1$-$C_6$alkoxy, $C_1$-$C_6$thioalkoxy, and $C_1$-$C_6$alkyl-$X^4$, wherein, $X^4$ is —CO$_2$H, —CO$_2R^{11}$, —C(=O)$R^{11}$, —C(OH)($R^{11}$)$_2$, $C_1$-$C_6$alkoxy, tetrazolyl, —OH, halide, —CN, —NO$_2$, —S$R^{11}$, —S(=O)$R^{11}$, —S(=O)$_2R^{11}$, —N($R^{11}$)$_2$, —CON($R^{11}$)$_2$, —NHC(=O)$R^{11}$—C(=O)NHSO$_2R^{11}$, —CH(OH)CF$_3$, —COCF$_3$, or —SO$_2$NHC(=O)$R^{11}$, where each $R^{11}$ is independently H, or an optionally substituted group selected from among $C_1$-$C_6$alkyl, $C_1$-$C_6$fluoroalkyl, $C_2$-$C_6$alkenyl, $C_2$-$C_6$alkynyl, $C_3$-$C_8$cycloalkyl, phenyl, and benzyl;

or $R^6$ and $R^7$ can together form an optionally substituted 5-, 6-, or 7-membered non-aromatic monocyclic ring containing 0, 1, or 2 heteroatoms selected from among S and O;

or $R^6$ and $R^7$ can together form an optionally substituted bicyclo[3,2,1]ring containing 1 or 2 heteroatoms selected from among S and O;

or $R^6$ and $R^7$ can together form a carbonyl (C=O); and $R^8$ is H, —OH, —CONH$_2$, tetrazolyl, —CN, —N$_3$, $C_1$-$C_6$alkyl, $C_2$-$C_6$alkenyl, —CF$_3$, —CO$_2$H, —O$R^{12}$, —CON($R^{12}$)$_2$, —CO$_2$—$R^{12}$, —S$R^{12}$, —S(=O)$R^{12}$, S(=O)$_2R^{12}$, —SO$_2$N($R^{12}$)$_2$, C(=O)$R^{12}$, C(OH)($R^{12}$)$_2$, —CH=N—O$R^{12}$, —N($R^{12}$)$_2$, NHC(=O)$R^{12}$, —OC(=O)$R^{12}$, or an optionally substituted group selected from among $C_1$-$C_6$fluoroalkoxy, $C_3$-$C_8$cycloalkoxy, benzyl, and phenyl; where each $R^{12}$ is independently H, or an optionally substituted group selected from among $C_1$-$C_6$alkyl, $C_1$-$C_6$fluoroalkyl, $C_2$-$C_6$alkenyl, $C_2$-$C_6$alkynyl, $C_3$-$C_8$cycloalkyl, $C_4$-$C_8$cycloalkylalkyl, phenyl, and benzyl;

$R^6$ and $R^8$ can together form an optionally substituted $C_2$-$C_8$heterocycloalkyl having 1 or 2 O atoms in the ring;

$R^9$ is H, halide, —CN, —NO$_2$, —OH, or an optionally substituted group selected from among $C_1$-$C_6$alkyl, $C_3$-$C_8$cycloalkyl, $C_1$-$C_6$fluoroalkyl, $C_2$-$C_6$alkenyl, $C_2$-$C_6$alkynyl, $C_1$-$C_6$alkoxy, phenyl, and benzyl;

$R^{13}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$S—, $R^{17}$S(=O)—, $R^{17}$S(=O)$_2$—, —CN, halide, $R^{17}$C(=O)—, $R^{17}$C(=O)O—, $R^{17}$NHC(=O)—, —$R^{17}$—C(=O)NH—, $R^{17}$S(=O)$_2$NH—, $R^{17}$—NHS(=O)$_2$—, $R^{17}$—OC(=O)NH—, $R^{17}$—NHC(=O)O—, —NO$_2$, $C_1$-$C_6$haloalkyl, and —N($R^{17}$)$_2$;

$R^{17}$ is independently selected from among H, $C_1$-$C_6$alkyl, $C_3$-$C_8$cycloalkyl, aryl, heteroaryl, and $C_1$-$C_6$heteroalkyl.

$R^{14}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$S—, $R^{17}$S(=O)—, $R^{17}$S(=O)$_2$—, —CN, halide, $R^{17}$C(=O)—, $R^{17}$C(=O)O—, $R^{17}$NHC(=O)—, —$R^{17}$—C(=O)NH—, $R^{17}$S(=O)$_2$NH—, $R^{17}$—NHS(=O)$_2$—, $R^{17}$—OC(=O)NH—, $R^{17}$—NHC(=O)O—, —NO$_2$, $C_1$-$C_6$haloalkyl, and —N($R^{17}$)$_2$;

$R^{17}$ is independently selected from among H, $C_1$-$C_6$alkyl, $C_3$-$C_8$cycloalkyl, aryl, heteroaryl, and $C_1$-$C_6$heteroalkyl; or $R^8$ and $R^{14}$ taken together can form an optionally substituted 5-, or 6-membered ring;

or a pharmaceutically acceptable salt, pharmaceutically acceptable N-oxide, pharmaceutically active metabolite, pharmaceutically acceptable prodrug, or pharmaceutically acceptable solvate thereof.

For any and all of the embodiments, substituents can be selected from among from a subset of the listed alternatives. For example, in some embodiments, $R^9$ is H, halide, —CN, —NO$_2$, —OH, or an optionally substituted group selected from among $C_1$-$C_6$alkyl, $C_1$-$C_6$fluoroalkyl, and $C_1$-$C_6$alkoxy. In other embodiments, $R^9$ is H.

In some embodiments, $L^1$ is selected from among —$(CHR^4)_n$—, —$(CHR^4)_n$O—, —$(CHR^4)_n$S—, —O$(CHR^4)_n$—, and —S$(CHR^4)_n$—; n is 0, 1, 2, or 3. In other embodiments, each $R^4$ is independently H, or an optionally substituted group selected from among $C_1$-$C_6$alkyl, $C_3$-$C_8$cycloalkyl, $C_1$-$C_6$fluoroalkyl; or $L^4$-$X^2$-$L^5$-$X^3$ where, $L^4$ is a bond, or an optionally substituted group selected from among $C_1$-$C_6$ alkyl, $C_2$-$C_{10}$ heterocycloalkyl, and $C_3$-$C_8$ cycloalkyl; $X^2$ is a bond, O, S, S(=O), or S(=O)$_2$; $L^5$ is a bond, $C_1$-$C_6$ alkyl, $C_3$-$C_8$ cycloalkyl, phenyl, pyridyl, thiazolyl, or thienyl; and $X^3$ is OH, CN, NO$_2$, halide, CO$_2$H, CO$_2R^{10}$, C(=O)$R^{10}$, C(OH)($R^{10}$)$_2$, tetrazolyl, C(=O)NHSO$_2R^{10}$, CH(OH)CF$_3$, COCF$_3$, SO$_2$NHC(=O)$R^{10}$, or N($R^{10}$)$_2$, where each $R^{10}$ is independently H, or an optionally substituted group selected from among $C_1$-$C_6$alkyl, $C_3$-$C_8$cycloalkyl, phenyl, and benzyl. In yet other embodiments, each $R^4$ is independently H, or an optionally substituted group selected from among $C_1$-$C_6$alkyl, and $C_1$-$C_6$fluoroalkyl; and n is 0, 1, or 2. In some other embodiments, n is 0 or 1. In some embodiments, $L^1$ is selected from among —$(CHR^4)_n$—, —$(CHR^4)_n$O—, —$(CHR^4)_n$S—, —O$(CHR^4)_n$—, and —S$(CHR^4)_n$—; each $R^4$ is independently H, or an optionally substituted group selected from among $C_1$-$C_6$alkyl, and $C_1$-$C_6$fluoroalkyl; n is 0, 1, or 2. In some other embodiments, each $R^4$ is H; n is 0 or 1.

In some embodiments, $R^{13}$ is H, $C_1$-$C_6$alkyl, —OH, $C_1$-$C_6$alkoxy, —CN, halide, $R^{17}$C(=O)O—, $R^{17}$—NHC(=O)O—, or $C_1$-$C_6$haloalkyl; $R^{17}$ is selected from among H, and $C_1$-$C_6$alkyl; $R^{14}$ is H, $C_1$-$C_6$alkyl, —OH, $C_1$-$C_6$alkoxy, —CN, halide, $R^{17}C(=O)O-$, $R^{17}-NHC(=O)O-$, or $C_1$-$C_6$haloalkyl; $R^{17}$ is selected from among H, and $C_1$-$C_6$alkyl. In some embodiments, $R^{13}$ is H, $C_1$-$C_6$alkyl, —OH, $C_1$-$C_6$alkoxy, —CN, halide, or $C_1$-$C_6$haloalkyl; $R^{14}$ is H, $C_1$-$C_6$alkyl, —OH, $C_1$-$C_6$alkoxy, —CN, halide, or $C_1$-$C_6$haloalkyl; or $R^8$ and $R^{14}$ taken together can form an optionally substituted 5-, or 6-membered ring.

In some embodiments, each $R^1$ is independently H, halide, —CN, —NO$_2$, —OH, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, —NHCH$_2$C(=O)OR$^3$, —C(=O)N(R$^3$)$_2$, —NHC(=O)R$^3$, or —C(OH)(R$^3$)$_2$, or an optionally substituted group selected from among $C_1$-$C_6$alkyl, $C_1$-$C_6$fluoroalkyl, $C_3$-$C_8$cycloalkyl, $C_2$-$C_6$alkenyl, $C_2$-$C_6$alkynyl, and $C_1$-$C_6$fluoroalkoxy; or $R^1$ is $Q^1$-$Q^2$ where $Q^1$ is aryl, monocyclic heterocycloalkyl, monocyclic heteroaryl; and $Q^2$ is H, halide, —CN, —NO$_2$, $C_1$-$C_6$alkyl, $C_1$-$C_6$alkoxy, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, or —C(=O)N(R$^3$)$_2$.

In some embodiments, $R^6$ and $R^7$ are independently H, or an optionally substituted group selected from among $C_1$-$C_6$haloalkyl, $C_1$-$C_6$alkyl, $C_3$-$C_8$cycloalkyl, $C_2$-$C_6$alkenyl, $C_2$-$C_6$alkynyl, thiazolyl, $C_1$-$C_6$alkoxy, $C_1$-$C_6$thioalkoxy, and $C_1$-$C_6$alkyl-$X^4$, wherein, $X^4$ is —CO$_2$H, —CO$_2$R$^{11}$, $C_1$-$C_6$alkoxy, tetrazolyl, —OH, —CON(R$^{11}$)$_2$, where each $R^{11}$ is independently H, or an optionally substituted group selected from among $C_1$-$C_6$alkyl, and $C_1$-$C_6$fluoroalkyl; or $R^6$ and $R^7$ can together form an optionally substituted 5-, 6-, or 7-membered monocyclic ring containing 0, 1, or 2 heteroatoms selected from among S and O; or $R^6$ and $R^7$ can together form a carbonyl (C=O).

In yet other embodiments, $R^6$ and $R^7$ are independently H, or an optionally substituted group selected from among $C_1$-$C_6$haloalkyl, $C_1$-$C_6$alkyl, $C_3$-$C_8$cycloalkyl, $C_2$-$C_6$alkenyl, and $C_1$-$C_6$alkyl-$X^4$, wherein, $X^4$ is —CO$_2$H, —CO$_2$R$^{11}$, or —CON(R$^{11}$)$_2$, where each $R^{11}$ is independently H, or an optionally substituted $C_1$-$C_6$alkyl; or $R^6$ and $R^7$ can together form an optionally substituted 6-membered monocyclic ring containing 0 or 1 O atoms; or $R^6$ and $R^7$ can together form a carbonyl (C=O).

In some embodiments, $R^8$ is H, —OH, —CONH$_2$, tetrazolyl, —CN, $C_1$-$C_6$alkyl, $C_2$-$C_6$alkenyl, —CF$_3$, —CO$_2$H, —OR$^{12}$, —CON(R$^{12}$)$_2$, —CO$_2$—R$^{12}$, —SR$^{12}$, —S(=O)R$^{12}$, S(=O)$_2$R$^{12}$, —SO$_2$N(R$^{12}$)$_2$, C(=O)R$^{12}$, C(OH)(R$^{12}$)$_2$, —CH=N—OR$^{12}$, or —OC(=O)R$^{12}$; where each $R^{12}$ is independently H, or an optionally substituted group selected from among $C_1$-$C_6$alkyl, $C_1$-$C_6$fluoroalkyl, $C_3$-$C_8$cycloalkyl, $C_4$-$C_8$cycloalkylalkyl, phenyl, and benzyl.

In some embodiments, $G^4$ is CR$^1$. In yet other embodiments, $G^4$ is N.

In some embodiments, $G^1$ is CR$^1$. In some other embodiments, $G^1$ is N.

In some embodiments, $G^8$ is CH. In other embodiments, $G^8$ is N.

In some embodiments, compounds provided herein have a structure of Formula (IV):

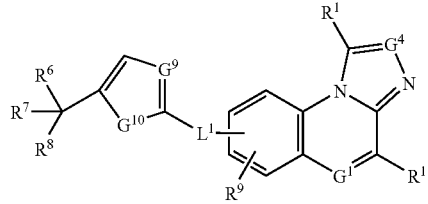

Formula (IV)

wherein:
$G^9$ is N or CH; and
$G^{10}$ is NR$^2$, O or S;
$R^2$ is independently H, —C(=O)R$^3$, C(=O)OR$^3$, —CH(R$^3$)$_2$, —C(=O)N(R$^3$)$_2$, or an optionally substituted group selected from $C_1$-$C_6$alkyl, $C_1$-$C_6$fluoroalkyl, $C_3$-$C_8$cycloalkyl, $C_2$-$C_6$alkenyl, $C_2$-$C_6$alkynyl, aryl, monocyclic heterocycloalkyl, monocyclic heteroaryl, and bicyclic heteroaryl;
$R^3$ is independently H, or an optionally substituted group selected from among $C_1$-$C_6$alkyl, $C_2$-$C_6$alkenyl, $C_2$-$C_6$alkynyl, $C_3$-$C_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl, and pyrimidinyl.

In some embodiments, $G^9$ is N; and $G^{10}$ is O or S. In other embodiments, $G^{10}$ is S.

In some embodiments, $R^9$ is H, halide, —CN, —NO$_2$, —OH, or an optionally substituted group selected from among $C_1$-$C_6$alkyl, $C_1$-$C_6$fluoroalkyl, and $C_1$-$C_6$alkoxy. In some other embodiments, $R^9$ is H.

In some embodiments, $L^1$ is selected from among —(CHR$^4$)$_n$—, —(CHR$^4$)$_n$O—, —(CHR$^4$)$_n$S—, —O(CHR$^4$)$_n$—, and —S(CHR$^4$)$_n$—; n is 0, 1, 2, or 3. In other embodiments, each $R^4$ is independently H, or an optionally substituted group selected from among $C_1$-$C_6$alkyl, $C_1$-$C_6$fluoroalkyl; and n is 0 or 1. In some other embodiments, $R^4$ is H; and n is 0 or 1.

In some embodiments, each $R^1$ is independently H, halide, —CN, —OH, or an optionally substituted group selected from among $C_1$-$C_6$alkyl, $C_1$-$C_6$fluoroalkyl; or $R^1$ is $Q^1$-$Q^2$ where $Q^1$ is aryl, monocyclic heterocycloalkyl, monocyclic heteroaryl; and $Q^2$ is H, halide, —CN, $C_1$-$C_6$alkyl, or $C_1$-$C_6$alkoxy.

In some embodiments, $R^6$ and $R^7$ are independently H, or an optionally substituted group selected from among $C_1$-$C_6$haloalkyl, $C_1$-$C_6$alkyl, $C_3$-$C_8$cycloalkyl, $C_2$-$C_6$alkenyl, $C_2$-$C_6$alkynyl, thiazolyl, $C_1$-$C_6$alkoxy, $C_1$-$C_6$thioalkoxy, and $C_1$-$C_6$alkyl-$X^4$, wherein, $X^4$ is —CO$_2$H, —CO$_2$R$^{11}$, $C_1$-$C_6$alkoxy, tetrazolyl, —OH, —CON(R$^{11}$)$_2$, where each $R^{11}$ is independently H, or an optionally substituted group selected from among $C_1$-$C_6$alkyl, and $C_1$-$C_6$fluoroalkyl; or $R^6$ and $R^7$ can together form an optionally substituted 5-, 6-, or 7-membered monocyclic ring containing 0, 1, or 2 heteroatoms selected from among S and O.

In some embodiments, $R^6$ and $R^7$ are independently H, or an optionally substituted group selected from among $C_1$-$C_6$haloalkyl, $C_1$-$C_6$alkyl, $C_3$-$C_8$cycloalkyl, and $C_1$-$C_6$alkyl-$X^4$, wherein, $X^4$ is —CO$_2$H, —CO$_2$R$^{11}$, or —CON(R$^{11}$)$_2$, where each $R^{11}$ is independently H, or an optionally substituted $C_1$-$C_6$alkyl; or $R^6$ and $R^7$ can together form an optionally substituted 6-membered monocyclic ring containing 1 O atom.

In some embodiments, $R^8$ is H, —OH, —CONH$_2$, tetrazolyl, —CN, $C_1$-$C_6$alkyl, $C_2$-$C_6$alkenyl, —CF$_3$, —CO$_2$H, —OR$^{12}$, —CON(R$^{12}$)$_2$, —CO$_2$—R$^{12}$, —SR$^{12}$, —S(=O)R$^{12}$, S(=O)$_2$R$^{12}$, —SO$_2$N(R$^{12}$)$_2$, C(=O)R$^{12}$, C(OH)(R$^{12}$)$_2$, —CH=N—OR$^{12}$, —OC(=O)R$^{12}$, or an optionally substituted group selected from among $C_1$-$C_6$fluoroalkoxy, $C_3$-$C_8$cycloalkoxy, benzyl, and phenyl; where each $R^{12}$ is independently H, or an optionally substituted group selected from among $C_1$-$C_6$alkyl, $C_1$-$C_6$fluoroalkyl, $C_3$-$C_8$cycloalkyl, $C_4$-$C_8$cycloalkylalkyl, phenyl, and benzyl.

In some other embodiments, $R^8$ is H, —OH, —CONH$_2$, —CN, $C_1$-$C_6$alkyl, $C_2$-$C_6$alkenyl, —CF$_3$, —CO$_2$H, —OR$^{12}$, —CON(R$^{12}$)$_2$, —CO$_2$—R$^{12}$, —OC(=O)R$^{12}$, or an optionally substituted group selected from among $C_3$-$C_8$cycloalkoxy; where each $R^{12}$ is independently H, or an optionally substituted $C_1$-$C_6$alkyl.

In some embodiments, compounds provided herein have a structure of Formula (V):

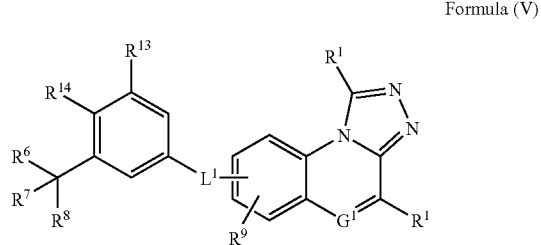

Formula (V)

wherein:
$G^1$ is N or $CR^1$;
each $R^1$ is independently H, halide, —CN, —NO$_2$, —OH, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, —NHCH$_2$C(=O)OR$^3$, —C(=O)N(R$^3$)$_2$, —NHC(=O)R$^3$, or —C(OH)(R$^3$)$_2$, or an optionally substituted group selected from among $C_1$-$C_6$alkyl, $C_1$-$C_6$fluoroalkyl, $C_3$-$C_8$cycloalkyl, $C_2$-$C_6$alkenyl, $C_2$-$C_6$alkynyl, and $C_1$-$C_6$fluoroalkoxy; or
$R^1$ is $Q^1$-$Q^2$ where $Q^1$ is aryl, monocyclic heterocycloalkyl, monocyclic heteroaryl, bicyclic heteroaryl; and $Q^2$ is H, halide, —CN, —NO$_2$, $C_1$-$C_6$alkyl, $C_1$-$C_6$alkoxy, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, or —C(=O)N(R$^3$)$_2$;
each $R^3$ is independently H, or an optionally substituted group selected from among $C_1$-$C_6$alkyl, $C_2$-$C_6$alkenyl, $C_2$-$C_6$alkynyl, $C_3$-$C_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl, and pyrimidinyl;
$L^1$ is —(CHR$^4$)$_n$X$^1$(CHR$^4$)$_n$— wherein,
each n is independently 0, 1, 2, or 3;
$X^1$ is a bond, O, S, S(=O), S(=O)$_2$, or NR$^5$;
each $R^4$ is independently H, or an optionally substituted group selected from among $C_1$-$C_6$alkyl, $C_3$-$C_8$cycloalkyl, $C_1$-$C_6$fluoroalkyl, $C_2$-$C_6$alkenyl, $C_2$-$C_6$alkynyl, phenyl, and benzyl; or $L^4$-$X^2$-$L^5$-$X^3$ wherein,
$L^4$ is a bond, or an optionally substituted group selected from among $C_1$-$C_6$ alkyl, $C_2$-$C_6$ alkenyl, $C_2$-$C_6$ alkynyl, aryl, $C_2$-$C_{10}$heterocycloalkyl, and $C_3$-$C_8$ cycloalkyl;
$X^2$ is a bond, O, S, S(=O), S(=O)$_2$, NH, C(=O)NH, or NHC(=O);
$L^5$ is a bond, $C_1$-$C_6$ alkyl, $C_3$-$C_8$ cycloalkyl, phenyl, pyridyl, thiazolyl, or thienyl; and
$X^3$ is —OH, —CN, —NO$_2$, halide, —CO$_2$H, —CO$_2$R$^{10}$, —C(=O)R$^{10}$, —CON(R$^{10}$)$_2$, —NHC(=O)R$^{10}$, —C(OH)(R$^{10}$)$_2$, tetrazolyl, —C(=O)NHSO$_2$R$^{10}$, —CH(OH)CF$_3$, —COCF$_3$, —SO$_2$NHC(=O)R$^{10}$, or —N(R$^{10}$)$_2$, where each $R^{10}$ is independently H, or an optionally substituted group selected from among $C_1$-$C_6$alkyl, $C_1$-$C_6$fluoroalkyl, $C_2$-$C_6$alkenyl, $C_2$-$C_6$alkynyl, $C_3$-$C_8$cycloalkyl, phenyl, and benzyl;
$R^5$ is H, or an optionally substituted group selected from among $C_1$-$C_6$alkyl, $C_3$-$C_8$cycloalkyl, $C_1$-$C_6$fluoroalkyl, $C_2$-$C_6$alkenyl, $C_2$-$C_6$alkynyl, phenyl, and benzyl;

$R^6$ and $R^7$ are independently H, or an optionally substituted group selected from among $C_1$-$C_6$haloalkyl, $C_1$-$C_6$alkyl, $C_3$-$C_8$cycloalkyl, $C_2$-$C_6$alkenyl, $C_2$-$C_6$alkynyl, phenyl, benzyl, thiazolyl, $C_1$-$C_6$alkoxy, $C_1$-$C_6$thioalkoxy, and $C_1$-$C_6$alkyl-$X^4$, wherein,
$X^4$ is —CO$_2$H, —CO$_2$R$^{11}$, —C(=O)R$^{11}$, —C(OH)(R$^{11}$)$_2$, $C_1$-$C_6$alkoxy, tetrazolyl, —OH, halide, —CN, —NO$_2$, —SR$^{11}$, —S(=O)R$^{11}$, —S(=O)$_2$R$^{11}$, —N(R$^{11}$)$_2$, —CON(R$^{11}$)$_2$, —NHC(=O)R$^{11}$—C(=O)NHSO$_2$R$^{11}$, —CH(OH)CF$_3$, —COCF$_3$, or —SO$_2$NHC(=O)R$^{11}$, where each $R^{11}$ is independently H, or an optionally substituted group selected from among $C_1$-$C_6$alkyl, $C_1$-$C_6$fluoroalkyl, $C_2$-$C_6$alkenyl, $C_2$-$C_6$alkynyl, $C_3$-$C_8$cycloalkyl, phenyl, and benzyl;
or $R^6$ and $R^7$ can together form an optionally substituted 5-, 6-, or 7-membered non-aromatic monocyclic ring containing 0, 1, or 2 heteroatoms selected from among S and O;
or $R^6$ and $R^7$ can together form an optionally substituted bicyclo[3,2,1]ring containing 1 or 2 heteroatoms selected from among S and O;
or $R^6$ and $R^7$ can together form a carbonyl (C=O); and
$R^8$ is H, —OH, —CONH$_2$, tetrazolyl, —CN, —N$_3$, $C_1$-$C_6$alkyl, $C_2$-$C_6$alkenyl, —CF$_3$, —CO$_2$H, —OR$^{12}$, —CON(R$^{12}$)$_2$, —CO$_2$—R$^{12}$, —SR$^{12}$, —S(=O)R$^{12}$, S(=O)$_2$R$^{12}$, —SO$_2$N(R$^{12}$)$_2$, C(=O)R$^{12}$, C(OH)(R$^{12}$)$_2$, —N(R$^{12}$)$_2$, NHC(=O)R$^{12}$, —OC(=O)R$^{12}$, or an optionally substituted group selected from among $C_1$-$C_6$fluoroalkoxy, $C_3$-$C_8$cycloalkoxy, benzyl, and phenyl; where each $R^{12}$ is independently H, Or an optionally substituted group selected from among $C_1$-$C_6$alkyl, $C_1$-$C_6$fluoroalkyl, $C_2$-$C_6$alkenyl, $C_2$-$C_6$alkynyl, $C_3$-$C_8$cycloalkyl, $C_4$-$C_8$cycloalkylalkyl, phenyl, and benzyl; or
$R^6$ and $R^8$ can together form an optionally substituted $C_2$-$C_8$heterocycloalkyl having 1 or 2 O atoms in the ring;
$R^9$ is H, halide, —CN, —NO$_2$, —OH, or an optionally substituted group selected from among $C_1$-$C_6$alkyl, $C_3$-$C_8$cycloalkyl, $C_1$-$C_6$fluoroalkyl, $C_2$-$C_6$alkenyl, $C_2$-$C_6$alkynyl, $C_1$-$C_6$alkoxy, phenyl, and benzyl;
$R^{13}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$—S—, $R^{17}$—S(=O)—, $R^{17}$—S(=O)$_2$—, —CN, halide, $R^{17}$C(=O)—, $R^{17}$C(=O)O—, $R^{17}$NHC(=O)—, —$R^{17}$—C(=O)NH—, $R^{17}$S(=O)$_2$NH—, $R^{17}$—NHS(=O)$_2$—, $R^{17}$—OC(=O)NH—, $R^{17}$—NHC(=O)O—, —NO$_2$, $C_1$-$C_6$haloalkyl, and —N(R$^{17}$)$_2$;
$R^{17}$ is independently selected from among H, $C_1$-$C_6$alkyl, $C_3$-$C_8$cycloalkyl, aryl, heteroaryl, and $C_1$-$C_6$heteroalkyl.
$R^{14}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$—S—, $R^{17}$—S(=O)—, $R^{17}$—S(=O)$_2$—, —CN, halide, $R^{17}$C(=O)—, $R^{17}$C(=O)O—, $R^{17}$NHC(=O)—, —$R^{17}$—C(=O)NH—, $R^{17}$S(=O)$_2$NH—, $R^{17}$—NHS(=O)$_2$—, $R^{17}$—OC(=O)NH—, $R^{17}$—NHC(=O)O—, —NO$_2$, $C_1$-$C_6$haloalkyl, and —N(R$^{17}$)$_2$;
$R^{17}$ is independently selected from among H, $C_1$-$C_6$alkyl, $C_3$-$C_8$cycloalkyl, aryl, heteroaryl, and $C_1$-$C_6$heteroalkyl; or
$R^8$ and $R^{14}$ taken together can form a optionally substituted 5-, or 6-membered ring;

or a pharmaceutically acceptable salt, pharmaceutically acceptable N-oxide, pharmaceutically active metabolite, pharmaceutically acceptable prodrug, or pharmaceutically acceptable solvate thereof.

In some embodiments, $G^1$ is $CR^1$. In other embodiments, $G^1$ is N.

In some embodiments, $R^9$ is H, halide, —CN, —NO$_2$, —OH, or an optionally substituted group selected from among $C_1$-$C_6$alkyl, $C_1$-$C_6$fluoroalkyl, and $C_1$-$C_6$alkoxy. In other embodiments, $R^9$ is H, or halide. In yet other embodiments, $R^9$ is H.

In some embodiments, $R^{13}$ is H, $C_1$-$C_6$alkyl, —OH, $C_1$-$C_6$alkoxy, —CN, halide; $R^{17}$ is independently selected from among H, and $C_1$-$C_6$alkyl; $R^{14}$ is H, $C_1$-$C_6$alkyl, —OH, $C_1$-$C_6$alkoxy, —CN, halide; or $R^8$ and $R^{14}$ taken together can form a optionally substituted 5-, or 6-membered ring.

In some embodiments, $L^1$ is selected from among —(CHR$^4$)$_n$—, —(CHR$^4$)$_n$O—, —(CHR$^4$)$_n$S—, —O(CHR$^4$)$_n$—, and —S(CHR$^4$)$_n$—; n is 0, 1, 2, or 3. In other embodiments, each $R^4$ is independently H, or an optionally substituted group selected from among $C_1$-$C_6$alkyl, $C_3$-$C_8$cycloalkyl, $C_1$-$C_6$fluoroalkyl. In other embodiments, $R^4$ is H; and n is 0, 1, or 2. In some embodiments, n is 0 or 1.

In some embodiments, each $R^1$ is independently H, halide, —CN, —NO$_2$, —OH, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, —NHCH$_2$C(=O)OR$^3$, —C(=O)N(R$^3$)$_2$, —NHC(=O)R$^3$, or —C(OH)(R$^3$)$_2$, or an optionally substituted group selected from among $C_1$-$C_6$alkyl, $C_1$-$C_6$fluoroalkyl, $C_3$-$C_8$cycloalkyl, $C_2$-$C_6$alkenyl, $C_2$-$C_6$alkynyl, and $C_1$-$C_6$fluoroalkoxy; or $R^1$ is $Q^1$-$Q^2$ where $Q^1$ is aryl, monocyclic heterocycloalkyl, monocyclic heteroaryl; and $Q^2$ is H, halide, —CN, —NO$_2$, $C_1$-$C_6$alkyl, $C_1$-$C_6$alkoxy, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, or —C(=O)N(R$^3$)$_2$.

In some embodiments, $R^6$ and $R^7$ are independently H, or an optionally substituted group selected from among $C_1$-$C_6$haloalkyl, $C_1$-$C_6$alkyl, $C_3$-$C_8$cycloalkyl, $C_2$-$C_6$alkenyl, $C_2$-$C_6$alkynyl, thiazolyl, $C_1$-$C_6$alkoxy, $C_1$-$C_6$thioalkoxy, and $C_1$-$C_6$alkyl-X$^4$, wherein, X$^4$ is —CO$_2$H, —CO$_2$R$^{11}$, $C_1$-$C_6$alkoxy, tetrazolyl, —OH, —CON(R$^{11}$)$_2$, where each $R^{11}$ is independently H, or an optionally substituted group selected from among $C_1$-$C_6$alkyl, and $C_1$-$C_6$fluoroalkyl; or $R^6$ and $R^7$ can together form an optionally substituted 5-, 6-, or 7-membered monocyclic ring containing 0, 1, or 2 heteroatoms selected from among S and O; or $R^6$ and $R^7$ can together form a carbonyl (C=O). In other embodiments, $R^6$ and $R^7$ are independently H, or an optionally substituted group selected from among $C_1$-$C_6$haloalkyl, $C_1$-$C_6$alkyl, $C_3$-$C_8$cycloalkyl, and $C_1$-$C_6$alkyl-X$^4$, wherein, X$^4$ is —CO$_2$H, —CO$_2$R$^{11}$, or —CON(R$^{11}$)$_2$, where each $R^{11}$ is independently H, or an optionally substituted $C_1$-$C_6$alkyl; or $R^6$ and $R^7$ can together form an optionally substituted 5-, 6-, or 7-membered monocyclic ring containing 0, 1, or 2 heteroatoms selected from S and O; or $R^6$ and $R^7$ can together form a carbonyl (C=O).

In some embodiments, $R^6$ and $R^7$ are independently H, or an optionally substituted group selected from among $C_1$-$C_6$haloalkyl, $C_1$-$C_6$alkyl, $C_3$-$C_8$cycloalkyl, and $C_1$-$C_6$alkyl-X$^4$, wherein, X$^4$ is —CO$_2$H, —CO$_2$R$^{11}$, or —CON(R$^{11}$)$_2$, where each $R^{11}$ is independently H, or an optionally substituted $C_1$-$C_6$alkyl; or $R^6$ and $R^7$ can together form an optionally substituted 6-membered monocyclic ring containing 0 or 1 O atoms; or $R^6$ and $R^7$ can together form a carbonyl (C=O).

In some embodiments, $R^8$ is H, —OH, —CONH$_2$, tetrazolyl, —CN, $C_1$-$C_6$alkyl, $C_2$-$C_6$alkenyl, —CF$_3$, —CO$_2$H, —OR$^{12}$, —CON(R$^{12}$)$_2$, —CO$_2$—R$^{12}$, —SR$^{12}$, —S(=O)R$^{12}$, S(=O)$_2$R$^{12}$, —SO$_2$N(R$^{12}$)$_2$, C(=O)R$^{12}$, C(OH)(R$^{12}$)$_2$, —CH=N—OR$^{12}$, —OC(=O)R$^{12}$, or an optionally substituted group selected from among $C_1$-$C_6$fluoroalkoxy, $C_3$-$C_8$cycloalkoxy, benzyl, and phenyl; where each $R^{12}$ is independently H, or an optionally substituted group selected from among $C_1$-$C_6$alkyl, $C_1$-$C_6$fluoroalkyl, $C_3$-$C_8$cycloalkyl, $C_4$-$C_8$cycloalkylalkyl, phenyl, and benzyl.

In some embodiments, compounds provided herein have a structure of Formula (VI):

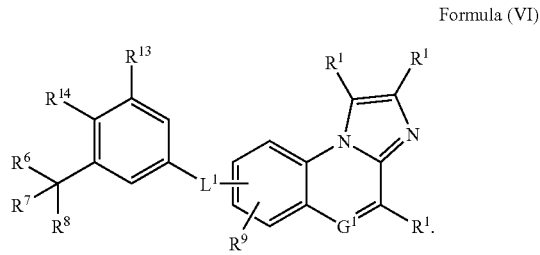

Formula (VI)

In some embodiments, $G^1$ is $CR^1$. In yet other embodiments, $G^1$ is N.

Any of the combinations of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In another aspect, provided are pharmaceutical compositions that include a compound, pharmaceutically acceptable salt, pharmaceutically acceptable N-oxide, pharmaceutically active metabolite, pharmaceutically acceptable prodrug, or pharmaceutically acceptable solvate of any compound described herein. In a further aspect, provided are compositions further including a pharmaceutically acceptable diluent, excipient or binder. In a further aspect, provided are compositions further including a second pharmaceutically active ingredient.

In certain embodiments, provided herein is a pharmaceutical composition containing: i) a physiologically acceptable carrier, diluent, and/or excipient; and ii) one or more compounds provided herein.

In another aspect, described herein is a pharmaceutical composition that includes a therapeutically effective amount of a compound described herein and a pharmaceutically acceptable excipient.

In another aspect, described herein is a method for treating inflammation in a mammal comprising administering a therapeutically effective amount of a compound described herein to the mammal in need.

In another aspect, described herein is a method for treating respiratory disease in a mammal comprising administering a therapeutically effective amount of a compound described herein to the mammal in need. In one aspect, the respiratory disease is asthma.

In another aspect, described herein is a method for treating cardiovascular disease in a mammal comprising administering a therapeutically effective amount of a compound described herein to the mammal in need.

In one aspect, provided herein are methods for treating a patient by administering a compound provided herein some embodiments, provided herein is a method of inhibiting the activity of 5-LO or of treating a disease, disorder, or condition, which would benefit from inhibition of 5-LO activity in a patient, which includes administering to the patient a therapeutically effective amount of at least one of any of the compounds herein, or pharmaceutically acceptable salt, pharmaceutically acceptable N-oxide, pharmaceutically active metabolite, pharmaceutically acceptable prodrug, or pharmaceutically acceptable solvate.

In another aspect, provided herein are methods of treating a leukotriene dependent or leukotriene-mediated disease or condition in a patient, that includes administering to the patient a therapeutically effective amount of the compound, pharmaceutically acceptable salt, pharmaceutically acceptable N-oxide, pharmaceutically active metabolite, pharmaceutically acceptable prodrug, or pharmaceutically acceptable solvate of any compound described herein, which inhibits the activity of 5-LO. In a further embodiment, the disease or condition is respiratory disease or cardiovascular disease. In an alternative embodiment, the disease or condition is asthma, chronic obstructive pulmonary disease, pulmonary hypertension, interstitial lung fibrosis, rhinitis, aortic aneurysm, myocardial infarction, or stroke. In an alternative embodiment, the disease or condition is asthma. In an alternative embodiment, the disease or condition is cancer or a non-cancerous disorder. In an alternative embodiment, the disease or condition is a non-cancerous disorder involving the skin or lymphatic tissues. In an alternative embodiment, the disease or disorder is a metabolic disorder. In an alternative embodiment, the disease or disorder relates to bone remodeling, loss or gain. In an alternative embodiment, the disease or condition is iatrogenic.

In some embodiments, the inflammatory conditions to be treated with the compounds described herein include, but are not limited to, asthma, chronic obstructive pulmonary disease, pulmonary hypertension, interstitial lung fibrosis, rhinitis, aortic aneurysm, myocardial infarction, and stroke. In other embodiments the proliferative disorders include, but are not limited to, cancer and non-cancerous disorders, including, but not limited to, those involving the skin or lymphatic tissues. In other embodiments the metabolic disorders include, but are not limited to, bone remodeling, loss or gain. In additional embodiments, such conditions are iatrogenic and increases in, or abnormal localization of, leukotrienes may be induced by other therapies or medical or surgical procedures.

In other embodiments, the methods, compounds, pharmaceutical compositions, and medicaments described herein may be used to prevent the cellular activation of 5-lipoxygenase, while in other embodiments the methods, compounds, pharmaceutical compositions, and medicaments described herein may be used to limit the formation of leukotrienes. In other embodiments, such methods, compounds, pharmaceutical compositions, and medicaments include compounds disclosed herein, which inhibit the activity of 5-lipoxygenase, for the treatment of asthma by: (a) lowering the concentrations of leukotrienes in certain tissue(s) of the body or in the entire body of a patient, (b) modulating the activity of enzymes or proteins in a patient wherein such enzymes or proteins are involved in the leukotriene pathway such as, by way of example, 5-lipoxygenase, or (c) combining the effects of (a) and (b). In yet other embodiments, the methods, compounds, pharmaceutical compositions, and medicaments described herein may be used in combination with other medical treatments or surgical modalities.

In some embodiments, provided herein are methods for reducing/inhibiting the leukotriene synthetic activity of 5-lipoxygenase in a mammal comprising administering to the mammal at least once an effective amount of a compound described herein.

In other embodiments, provided herein are methods for modulating, including reducing and/or inhibiting, the activity of 5-lipoxygenase, directly or indirectly, in a mammal comprising administering to the mammal at least once an effective amount of at least one compound described herein.

In further embodiments, provided herein are methods for treating leukotriene-dependent or leukotriene mediated conditions or diseases, comprising administering to the mammal at least once an effective amount of at least one compound described herein.

In yet further embodiments, provided herein are methods for treating inflammation comprising administering to the mammal at least once an effective amount of at least one compound described herein.

In other embodiments, provided herein are methods for treating respiratory diseases comprising administering to the mammal at least once an effective amount of at least one compound described herein. In a further embodiment of this aspect, the respiratory disease is asthma. In a further embodiment of this aspect, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma or seasonal asthma.

In yet other embodiments, provided herein are methods for preventing chronic obstructive pulmonary disease comprising administering to the mammal at least once an effective amount of at least one compound described herein. In a further embodiment of this aspect, chronic obstructive pulmonary disease includes, but is not limited to, chronic bronchitis or emphysema, pulmonary hypertension, interstitial lung fibrosis and/or airway inflammation and cystic fibrosis.

In some embodiments, provided herein are methods for preventing increased mucosal secretion and/or edema in a disease or condition comprising administering to the mammal at least once an effective amount of at least one compound described herein.

Yet in other embodiments, provided herein are methods for preventing or treating vasoconstriction, atherosclerosis and its sequelae myocardial ischemia, myocardial infarction, aortic aneurysm, vasculitis and stroke comprising administering to the mammal an effective amount of a compound described herein.

Additional embodiments provided herein include methods for reducing organ reperfusion injury following organ ischemia and/or endotoxic shock comprising administering to the mammal at least once an effective amount of at least one compound described herein.

Still further embodiments provided herein include methods for reducing the constriction of blood vessels in a mammal comprising administering to the mammal at least once an effective amount of at least one compound described herein.

Some other embodiments are methods for lowering or preventing an increase in blood pressure of a mammal comprising administering to the mammal at least once an effective amount of at least one compound described herein.

Other embodiments provided herein include methods for preventing eosinophil and/or basophil and/or dendritic cell and/or neutrophil and/or monocyte recruitment comprising administering to the mammal at least once an effective amount of at least one compound described herein.

Some further embodiments provided herein include methods for the prevention or treatment of abnormal bone remodeling, loss or gain, including diseases or conditions as, by way of example, osteopenia, osteoporosis, Paget's disease, cancer and other diseases comprising administering to the mammal at least once an effective amount of at least one compound described herein.

Additional embodiments provided herein include methods for preventing ocular inflammation and allergic conjunctivitis, vernal keratoconjunctivitis, and papillary conjunctivitis comprising administering to the mammal at least once an effective amount of at least one compound described herein.

Still further embodiments provided herein include methods for preventing CNS disorders comprising administering to the mammal at least once an effective amount of at least one compound described herein. CNS disorders include, but are not limited to, multiple sclerosis, Parkinson's disease, Alzheimer's disease, stroke, cerebral ischemia, retinal ischemia, post-surgical cognitive dysfunction, migraine, peripheral neuropathy/neuropathic pain, spinal cord injury, cerebral edema and head injury.

Some additional embodiments provided herein include methods for the treatment of cancer comprising administering to the mammal at least once an effective amount of at least one compound described herein. The type of cancer may include, but is not limited to, pancreatic cancer and other solid or hematological tumors.

In some embodiments, provided herein are methods for preventing endotoxic shock and septic shock comprising administering to the mammal at least once an effective amount of at least one compound described herein.

In further embodiments, provided herein are methods for preventing rheumatoid arthritis and osteoarthritis comprising administering to the mammal at least once an effective amount of at least one compound described herein.

In other embodiments, methods for preventing increased GI diseases comprising administering to the mammal at least once an effective amount of at least one compound described herein, are provided. Such diseases include, by way of example only, chronic gastritis, eosinophilic gastroenteritis, and gastric motor dysfunction.

In further embodiments, provided herein are methods for treating kidney diseases comprising administering to the mammal at least once an effective amount of at least one compound described herein. Such diseases include, by way of example only, glomerulonephritis, cyclosporine nephrotoxicity renal ischemia reperfusion.

In still further embodiments, provided herein are methods for preventing or treating acute or chronic renal insufficiency comprising administering to the mammal at least once an effective amount of at least one compound described herein.

In yet further embodiments, provided herein are methods for treating type II diabetes comprising administering to the mammal at least once an effective amount of at least one compound described herein In other embodiments, provided herein are methods to diminish the inflammatory aspects of acute infections within one or more solid organs or tissues such as the kidney with acute pyelonephritis comprising administering to the mammal at least once an effective amount of at least one compound described herein.

In further embodiments, provided herein are methods for preventing or treating acute or chronic disorders involving recruitment or activation of eosinophils comprising administering to the mammal at least once an effective amount of at least one compound described herein.

In another aspect, provided herein are methods for preventing or treating acute or chronic erosive disease or motor dysfunction of the gastrointestinal tract caused by non-steroidal anti-inflammatory drugs (including selective or non-selective cyclooxygenase-1 or -2 inhibitors) comprising administering to the mammal at least once an effective amount of at least one compound described herein.

Other embodiments provided herein include methods for the prevention or treatment of rejection or dysfunction in a transplanted organ or tissue comprising administering to the mammal at least once an effective amount of at least one compound described herein.

Further embodiments provided herein include methods for treating inflammatory responses of the skin comprising administering to the mammal at least once an effective amount of at least one compound described herein. Such inflammatory responses of the skin include, by way of example, dermatitis, contact dermatitis, eczema, urticaria, rosacea, and scarring. In another aspect are methods for reducing psoriatic lesions in the skin, joints, or other tissues or organs, comprising administering to the mammal an effective amount of a compound described herein.

In another aspect, provided herein are methods for the treatment of cystitis, including, by way of example only, interstitial cystitis, comprising administering to the mammal at least once an effective amount of at least one compound described herein.

Other further embodiments provided herein include methods for the treatment of metabolic syndromes such as Familial Mediterranean Fever comprising administering to the mammal at least once an effective amount of at least one compound described herein.

Additional further embodiments provided herein include methods to treat hepatorenal syndrome comprising administering to the mammal at least once an effective amount of at least one compound described herein.

In another embodiment, compounds described herein are used in the manufacture of a medicament for treating an inflammatory disease or condition in an animal in which the activity of at least one leukotriene protein contributes to the pathology and/or symptoms of the disease or condition. In one embodiment of this aspect, the leukotriene pathway protein is 5-lipoxygenase. In another or further embodiment of this aspect, the inflammatory disease or conditions are respiratory, cardiovascular, or proliferative diseases. In one embodiment, the respiratory disease is asthma.

In any of the aforementioned embodiments are further embodiments in which administration is enteral, parenteral, or both, and wherein (a) the effective amount of the compound is systemically administered to the mammal; (b) the effective amount of the compound is administered orally to the mammal; (c) the effective amount of the compound is intravenously administered to the mammal; (d) the effective amount of the compound administered by inhalation; (e) the effective amount of the compound is administered by nasal administration; or (f) the effective amount of the compound is administered by injection to the mammal; (g) the effective amount of the compound is administered topically (dermal) to the mammal; (h) the effective amount of the compound is administered by ophthalmic administration; or (i) the effective amount of the compound is administered rectally to the mammal.

In any of the aforementioned embodiments are further embodiments in which the mammal is a human, including embodiments wherein (a) the human has an asthmatic condition or trait selected from the group consisting of allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, or seasonal asthma, or chronic obstructive pulmonary disease, or pulmonary hypertension or interstitial lung fibrosis. In any of the aforementioned embodiments are further embodiments in which the mammal is an animal model for pulmonary inflammation, examples of which are provided herein.

In any of the aforementioned embodiments are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned embodiments are further embodiments comprising multiple administrations of the effective amount of the compound, including further embodiments in which (i) the compound is administered in a single dose; (ii) the time between multiple administrations is every 6 hours; (iii) the compound is administered to the mammal every 8 hours. In further or alternative embodiments, the method comprises a drug holiday, wherein the administration of the compound is temporarily suspended or the dose of the compound being administered is temporarily reduced; at the end of the drug holiday, dosing of the compound is resumed. The length of the drug holiday can vary from 2 days to 1 year.

In any of the aforementioned embodiments involving the treatment of leukotriene dependent diseases or conditions are further embodiments comprising administering at least one additional agent, including, by way of example, an anti-inflammatory agent, a different compound having the structure of Formula (I), a $CysLT_1$ receptor antagonist, or a $CysLT_1$/$CysLT_2$ dual receptor antagonist. In further or alternative embodiments, the $CysLT_1$ antagonist is selected from montelukast (Singulair®: [1-[[1-[3-[2-[(7-chloro-2-quinolyl)]vinyl]phenyl]-3-[2-(1-hydroxy-1-methyl-ethyl)phenyl]-propyl]sulfanylmethyl]cyclopropyl]acetic acid), zafirlukast (Accolate® 3-[[2-methoxy-4-(o-tolylsulfonylcarbamoyl)phenyl]methyl]-1-methyl-1H-indol-5-yl]aminoformic acid cyclopentyl ester) or pranlukast (Onon: 4-oxo-8-[p-(4-phenylbutyloxy)benzoylamino]-2-tetrazol-5-yl)-4H-1-benzopyran).

In further or alternative embodiments, the anti-inflammatory agent includes, but is not limited to, non-steroidal anti-inflammatory drugs such as a cyclooxygenase inhibitor (COX-1 and/or COX-2), lipoxygenase inhibitors and steroids such as prednisone or dexamethasone. In further or alternative embodiments, the anti-inflammatory agent is selected from the group consisting of Arthrotec® (diclofenac and misoprostol), Asacol® (5-aminosalicyclic acid), Auralgan® (antipyrine and benzocaine), Azulfidine® (sulfasalazine), Daypro® (oxaprozin), etodolac, Ponstan® (mefenamic acid), Salofalk® (5-aminosalicylic acid), Solu-Medrol® (methylprednisolone), aspirin, Indocin® (indomethacin), Vioxx® (rofecoxib), Celebrex® (celecoxib), Bextra® (valdecoxib), diclofenac, etodolac (Lodine®), ketoprofen, Mobic® (meloxicam), nabumetone, naproxen, Feldene® (piroxicam), Celestone® (betamethasone), Deltasone® (prednisone), or any generic equivalent thereof.

In any of the aforementioned embodiments involving the treatment of proliferative disorders, including cancer, are further embodiments comprising administering at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, paclitaxel (Taxol™), temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In any of the aforementioned embodiments involving the therapy of transplanted organs or tissues or cells are further embodiments that include administering at least one additional agent selected from the group consisting of azathioprine, a corticosteroid, cyclophosphamide, cyclosporin, dacluzimab, mycophenolate mofetil, OKT3, rapamycin, tacrolimus, or thymoglobulin.

In any of the aforementioned embodiments involving the therapy of interstitial cystitis are further embodiments that include administering at least one additional agent selected from dimethylsulfoxide, omalizumab, and pentosan polysulfate.

In any of the aforementioned embodiments involving the therapy of disorders of bone are further embodiments that include administering at least one additional agent selected from the group consisting of minerals, vitamins, bisphosphonates, anabolic steroids, parathyroid hormone or analogs, and cathepsin K inhibitors, dronabinol.

In any of the aforementioned embodiments involving the prevention or treatment of inflammation are further embodiments comprising: (a) monitoring inflammation in a mammal; (b) measuring bronchoconstriction in a mammal; (c) measuring eosinophil and/or basophil and/or dendritic cell and/or neutrophil and/or monocyte and/or lymphocyte recruitment in a mammal; (d) monitoring mucosal secretion in a mammal; (e) measuring mucosal edema in a mammal; (e) measuring levels of $LTB_4$ in the calcium ionophore-challenged blood of a mammal; (f) measuring levels of $LTE_4$ in the urinary excretion of a mammal; or (g) identifying a patient by measuring leukotriene-driven inflammatory biomarkers such as $LTB_4$, $LTC_4$, Il-6, CRP, SAA, MPO, EPO, MCP-1, MIP-α, sICAMs, Il-4, Il-13.

In any of the aforementioned embodiments the leukotriene-dependent or leukotriene mediated diseases or conditions include, but are not limited to, asthma, chronic obstructive pulmonary disease, pulmonary hypertension, interstitial lung fibrosis, rhinitis, arthritis, allergy, inflammatory bowel disease, adult respiratory distress syndrome, myocardial infarction, aneurysm, stroke, cancer, and endotoxic shock.

In some embodiments, compounds provided herein are administered to a human.

In some embodiments, compounds provided herein are orally administered.

In some embodiments, compounds provided herein are used for inhibiting the activity of 5-LO. In some embodiments, compounds provided herein are used for inhibiting the activity of 5-LO or for the treatment of a disease or condition that would benefit from inhibition of 5-LO activity.

In other embodiments, compounds provided herein are used for the formulation of a medicament for the inhibition of 5-LO activity.

Articles of manufacture containing packaging material, a compound described herein, or composition or pharmaceutically acceptable derivative thereof, which is effective for inhibiting the activity of 5-LO, within the packaging material, and a label that indicates that the compound or composition, or pharmaceutically acceptable salt, pharmaceutically active metabolite, pharmaceutically acceptable prodrug, or pharmaceutically acceptable solvate thereof, is used for inhibiting the activity of 5-LO, are provided.

Other objects, features and advantages of the methods, compounds, and compositions described herein will become apparent from the following detailed description. It should be understood, however, that the detailed description and the specific examples, while indicating specific embodiments, are given by way of illustration only, since various changes and modifications within the spirit and scope of the disclosure will become apparent to those skilled in the art from this detailed description. All references cited herein, including patents, patent applications, and publications, are hereby incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION

Figure 1:
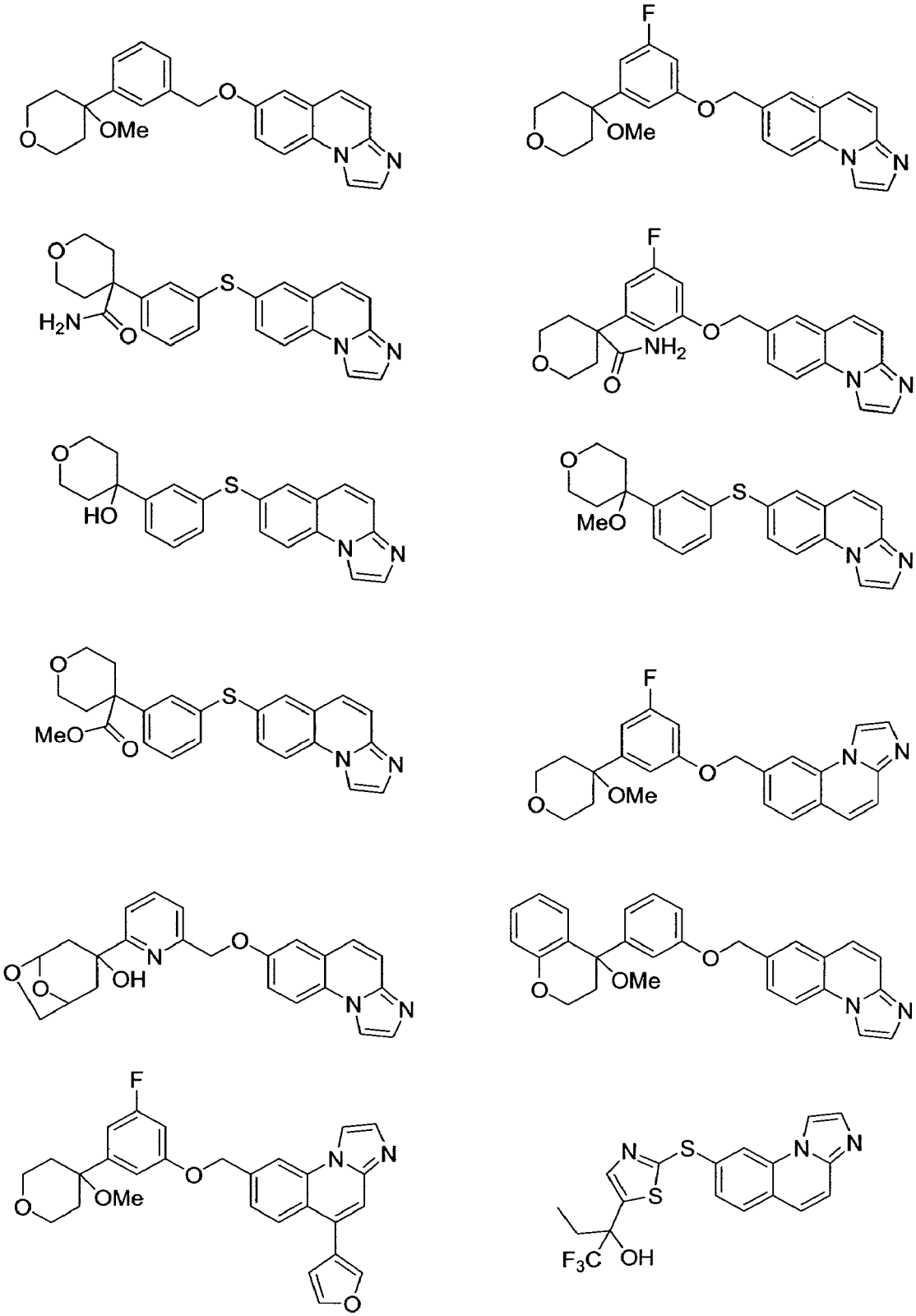
FIG. 1 presents non-limiting examples of compounds described herein.

Described herein are compounds, methods of making such compounds, pharmaceutical compositions and medicaments that include such compounds, and methods of using such compounds to treat or prevent diseases or conditions associated with 5-lipoxygenase activity. Described herein are compounds that inhibit the activity of 5-lipoxygenase (5-LO).

Leukotrienes (LTs) are potent contractile and inflammatory mediators produced by release of arachidonic acid from cell membranes and conversion to leukotrienes by the action of 5-lipoxygenase, 5-lipoxygenase-activating protein, $LTA_4$ hydrolase and $LTC_4$ synthase. The leukotriene synthesis pathway, or 5-lipoxygenase pathway, involves a series of enzymatic reactions in which arachidonic acid is converted to leukotriene $LTB_4$, or the cysteinyl leukotrienes, $LTC_4$, $LTD_4$, and $LTE_4$. The pathway occurs mainly at the nuclear envelope and has been described. See, e.g., Wood, J W et al., *J. Exp. Med.*, 178: 1935-1946, 1993; Peters-Golden, *Am. J. Respir. Crit. Care Med.* 157:S227-S232, 1998; Drazen, et al., ed. Five-Lipoxygenase Products in Asthma, Lung Biology in Health and Disease Series, Vol. 120, Chs. 1, 2, and 7, Marcel Dekker, Inc. NY, 1998. Protein components dedicated to the leukotriene synthesis pathway include 5-lipoxygenase (5-LO), 5-lipoxygenase-activating protein (FLAP), $LTA_4$ hydrolase, and $LTC_4$ synthase. The synthesis of leukotrienes has been described in the literature, e.g., by Samuelsson et al., *Science,* 220, 568-575, 1983; Peters-Golden, "Cell Biology of the 5-Lipoxygenase Pathway" *Am J Respir Crit Care Med* 157:S227-S232 (1998). Leukotrienes are synthesized directly from arachidonic acid by different cells including eosinophils, neutrophils, basophils, lymphocytes, macrophages, monocytes and mast cells. Excess $LTA_4$, for example from an activated neutrophil, may enter a cell by a transcellular pathway. Most cells in the body have $LTA_4$ hydrolase so can produce $LTB_4$. Platelets and endothelial cells have $LTC_4$ synthase, so can make $LTC_4$ when presented with $LTA_4$ by a transcellular pathway.

Arachidonic acid is a polyunsaturated fatty acid and is present mainly in the membranes of the body's cells. Upon presentation of inflammatory stimuli from the exterior of the cell, calcium is released and binds to phospholipase $A_2$ (PLA2) and 5-LO. Cell activation results in the translocation of $PLA_2$ and 5-LO from the cytoplasm to the endoplasmic reticulum and/or nuclear membranes, where in the presence of FLAP, the released arachidonic acid is converted via a 5-HPETE intermediate to the epoxide $LTA_4$. Depending on the cell type, the $LTA_4$ may be immediately converted to $LTC_4$ by the nuclear-bound $LTC_4$ synthase or to $LTB_4$ by the action of cytosolic $LTA_4$ hydrolase. $LTB_4$ is exported from cells by an as yet uncharacterized transporter and may activate other cells, or the cell it was made in, via high affinity binding to one of two G protein-coupled receptors (GPCRs), namely $BLT_1R$ or $BLT_2R$. $LTC_4$ is exported to the blood via the MRP-1 anion pump and rapidly converted to $LTD_4$ by the action of γ-glutamyl transpeptidase and $LTD_4$ and is then converted to $LTE_4$ by the action of dipeptidases. $LTC_4$, $LTD_4$ and $LTE_4$, which are collectively referred to as the cysteinyl leukotrienes (or previously as slow reacting substance of anaphylaxis, SRS-A). The cysteinyl leukotrienes activate other cells, or the cells they are made in, via high affinity binding to one of two GPCRs, namely $CysLT_1R$ or $CysLT_2R$. $CysLT_1$ receptors are found in the human airway eosinophils, neutrophils, macrophages, mast cells, B-lymphocytes and smooth muscle and induce bronchoconstriction. Zhu et al., *Am. J. Respir. Cell Mol Biol.* Epub. Aug. 25, 2005. $CysLT_2$ receptors are located in human airway eosinophils, macrophages, mast cells the human pulmonary vasculature (Figueroa et al., *Clin. Exp Allergy* 33:1380-1388; 2003).

5-Lipoxygenase-activating protein has been shown to form two distinct multimeric complexes that regulate the formation of leukotrienes in RBL-2H3 cells; Mandal et al, *PNAS,* 101, 6587-6592 (2004). The first complex is the formation of homodimers or homotrimers of 5-lipoxygenase-activating protein, the second is the formation of heterodimers or heterotrimers involving 5-lipoxygenase-activating protein and $LTC_4$ synthase. The tight association of $LTC_4$ synthase with 5-lipoxygenase-activating protein and the low expression level of $LTC_4$ synthase implies that all the $LTC_4$ synthase is tied up in the heteromultimers with 5-lipoxygenase-activating protein. The formation of $LTC_4$ is likely regulated through the heterodimer or heterotrimer while the homodimer or homotrimer of 5-lipoxygenase-activating protein regulates the generation of $LTA_4$ that is then available for the conversion to $LTB_4$. Inhibition of 5-lipoxygenase results in the complete downstream inhibition of the formation of leukotrienes. In contrast, the existence of different multimeric complexes of 5-lipoxygenase-activating protein offers the possibility of differentially regulating the inhibition of the production of $LTB_4$ or the cysteinyl leukotrienes $LTC_4$, $LTD_4$ and $LTE_4$ through the preparation of 5-lipoxygenase-activating protein inhibitors selective for each multimeric complex.

Involvement of Leukotrienes in Diseases or Conditions

The involvement of leukotrienes in disease is described in detail in the literature. See e.g., Busse, *Clin. Exp. Allergy* 26:868-79, 1996; O'Byrne, *Chest* 111(Supp. 2): 27S-34S, 1977; Sheftell, F. D., et al., *Headache*, 40:158-163, 2000; Klickstein et al., *J. Clin. Invest.*, 66:1166-1170, 1950; Davidson et al., *Ann. Rheum. Dis.*, 42:677-679, 1983. Leukotrienes produce marked inflammatory responses in human skin. Evidence for the involvement of leukotrienes in a human disease is found in psoriasis, in which leukotrienes have been detected in psoriatic lesions (Kragballe et al., *Arch. Dermatol.*, 119:548-552, 1983).

For example, inflammatory responses have been suggested to reflect three types of changes in the local blood vessels. The primary change is an increase in vascular diameter, which results in an increase in local blood flow and leads to an increased temperature, redness and a reduction in the velocity of blood flow, especially along the surfaces of small blood vessels. The second change is the activation of endothelial cells lining the blood vessel to express adhesion molecules that promote the binding of circulating leukocytes. The combination of slowed blood flow and induced adhesion molecules allows leukocytes to attach to the endothelium and migrate into the tissues, a process known as extravasation. These changes are initiated by cytokines and leukotrienes produced by activated macrophages. Once inflammation has begun, the first cells attracted to the site of infection are generally neutrophils. They are followed by monocytes, which differentiate into more tissue macrophages. In the latter stages of inflammation, other leukocytes, such as eosinophils and lymphocytes also enter the infected site. The third major change in the local blood vessels is an increase in vascular permeability. Instead of being tightly joined together, the endothelial cells lining the blood vessel walls become separated, leading to exit of fluid and proteins from the blood and their local accumulation in the tissue. (See Janeway, et al., Immunobiology: the immune system in health and disease, 5th ed., Garland Publishing, New York, 2001).

$LTB_4$ produces relatively weak contractions of isolated trachea and lung parenchyma, and these contractions are blocked in part by inhibitors of cyclooxygenase, suggesting that the contraction are secondary to the release of prostaglandins. However, $LTB_4$ has been shown to be a potent chemotactic agent for eosinophils and progenitors of mast cells; and the $LTB_4$ receptor BLT1-/- knockout mouse is protected from eosinophilic inflammation and T-cell mediated allergic airway hyperreactivity. (Miyahara et al., *J. Immunol.* 174:4979-4784; Weller et al *J Exp Med* 201:1961-1971 (2005)).

Leukotrienes $C_4$ and $D_4$ are potent smooth muscle contractile agents, promoting bronchoconstriction in a variety of species, including humans (Dahlen et al., *Nature*, 288:484-486, 1980). These compounds have profound hemodynamic effects, constricting coronary blood vessels, and resulting in a reduction of cardiac output efficiency (Marone et al., in *Biology of Leukotrienes*, ed. By R. Levi and R. D. Krell, Ann. New York Acad. Sci. 524:321-333, 1988). Leukotrienes also act as vasoconstrictors, however, marked differences exist for different vascular beds. There are reports suggesting that leukotrienes contribute to cardiac reperfusion injury following myocardial ischemia (Barst and Mullane, *Eur. J. Pharmacol.*, 114: 383-387, 1985; Sasaki et al., *Cardiovasc. Res.*, 22: 142-148, 1988). $LTC_4$ and $LTD_4$ directly increase vascular permeability probably by promoting retraction of capillary endothelial cells via activation of the $CysLT_2$ receptor and possibly other as yet undefined CysLT receptors [Lotzer et al *Arterioscler Thromb Vasc Biol* 23: e32-36. (2003)]. $LTB_4$ enhances atherosclerotic progression in two atherosclerotic mouse models, namely low density receptor lipoprotein receptor deficient (LDLr-/-) and apolipoprotein E-deficient (ApoE-/-) mice (Aiello et al., *Arterioscler Thromb Vase Biol* 22:443-449 (2002); Subbarao et al., *Arterioscler Thromb Vasc Biol* 24:369-375 (2004); Heller et al Circulation 112: 578-586 (2005). $LTB_4$ has also been shown to increase human monocyte chemoattractant protein (MCP-1) a known enhancer of atherosclerotic progression (Huang et al *Arterioscler Thromb Vasc Biol* 24:1783-1788, 2004).

The role of 5-lipoxygenase in the leukotriene synthesis pathway is significant because 5-lipoxygenase in concert with 5-lipoxygenase-activating protein performs the first step in the pathway for the synthesis of leukotrienes. Therefore, the leukotriene synthesis pathway provides a number of targets for compounds useful in the treatment of leukotriene-dependent or leukotriene mediated diseases or conditions, including, by way of example, vascular and inflammatory disorders, proliferative diseases, and non-cancerous disorders.

Leukotriene-dependent or leukotriene mediated conditions treated using the methods, compounds, pharmaceutical compositions and medicaments described herein, include, but are not limited to, bone diseases and disorder, cardiovascular diseases and disorders, inflammatory diseases and disorders, dermatological diseases and disorders, ocular diseases and disorders, cancer and other proliferative diseases and disorders, respiratory diseases and disorders, such as, for example, asthma, and non-cancerous disorders.

Treatment Options

Leukotrienes are known to contribute to the inflammation of the airways of patients with asthma. $CysLT_1$ receptor antagonists such as montelukast (Singulair®) have been shown to be efficacious in asthma and allergic rhinitis [Reiss et al. *Arch Intern Med* 158:1213-1220 (1998); Phillip et al. *Clin. Exp Allergy* 32:1020-1028 (2002)]. $CysLT_1R$ antagonists pranlukast (Onon) and zafirlukast (Accolate®) have also been shown to be efficacious in asthma.

Several inhibitors of 5-lipoxygenase have been described: Zyflo® (zileuton; approved by the FDA for the prevention and treatment of asthma, Israel et al. *Ann Intern Med* 119: 1059-1066); ZD2138 (6-[(3-fluoro-5-[4-methoxy-3,4,5,6-tetrahydro-2H-pyran-4-yl])phenoxy-methyl]-1-methyl-2-quinolone), which has shown efficacy in inhibiting the fall of FEV1 resulting from aspirin-induced asthma (Nasser et al, *Thorax*, 49, 749-756, 1994); CJ-13,610 (Mano et al, *Chem. Pharm. Bull.*, 53, 965-973, 2005); ABT-761 (atreleuton; Stewart et al, *J. Med. Chem.*, 1997, 40, 1955-1968); AZD-4407 [5-((4-((2S,4R)-tetrahydro-4-hydroxy-2-methyl-2H-pyran-4-yl)thiophen-2-yl)sulfanyl)-1-methylindolin-2-one] (European Patent EP 623614); L-739,010 ([1S,5R]-3-cyano-1-(3-furyl)-6-{6-[3-(3-hydroxy-6,8-dioxabicyclo[3.2.1]octanyl)]pyridin-2-yl-methoxyl}naphthalene) (Hamel et al, *J. Med. Chem.*, 40, 2866-2875, 1997); Wy-50,295 ((S)-2-(2-((quinolin-2-yl)methoxy)naphthalen-7-yl)propanoate tromethamine) (Musser and Kreft, *Drugs of the Future*, 15, 73-80, 1990) and TMK688 (Tohda et al, *Clin. Exp. Allergy*, 27, 110-118, 1997). See also Young, *Eur. J. Med. Chem.*, 34, 671-685, 1999 and Werz *Expert Opin. Ther. Patents*, 15, 505-519, 2005. Several inhibitors of 5-lipoxygenase-activating protein have also been described: MK886 (2-((1-(4-chlorobenzyl)-3-(tert-butylthio)-5-isopropyl-1H-indol-2-yl)methyl)-2-methylpropanoic acid) (Gillard et al, *Can. J. Physiol.*

*Pharmacol.*, 67, 456-464, 1989); MK591 (2-((5-((quinolin-2-yl)methoxy)-1-(4-chlorobenzyl)-3-(tert-butylthio)-1H-indol-2-yl)methyl)-2-methylpropanoic acid) (Brideau et al, *Can. J. Physiol. Pharmacol.*); BAY X1005 ((R)-2-(4-((quinolin-2-yl)methoxy)phenyl)-2-cyclopentylacetic acid) (Fruchtmann et al, *Agents Action*, 38, 188-195, 1993); VML-530 (Abt-080; Kolasa et al, *J. Med. Chem.*, 43, 3322-3334, 2000); and ETH615 (Kirstein et al, *Pharm. Toxicol.*, 68, 125-130, 1991). See also: Musser et al, *J. Med. Chem.*, 35, 2501-2524, 1992; Brooks et al. *J. Med. Chem.*, 1996, Vol. 39, No. 14, 2629-2654; Steinhilber, *Curr. Med. Chem.* 6(1):71-85, 1999; Riendeau, *Bioorg Med Chem Lett.*, 15(14):3352-5, 2005; Flamand, et al., *Mol. Pharmacol.* 62(2):250-6, 2002; Folco, et al., *Am. J. Respir. Crit. Care Med.* 161(2 Pt 2):S112-6, 2000; Hakonarson, *JAMA*, 293(18):2245-56, 2005).

5-Lipoxygenase inhibition will decrease $LTB_4$ from monocytes, neutrophils and other cells involved in vascular inflammation and thereby decrease atherosclerotic progression. The FLAP inhibitor MK-886 has been shown to decrease the post-angioplasty vasoconstrictive response in a porcine carotid injury model. Provost et al., *Brit. J. Pharmacol.* 123: 251-258 (1998). MK-886 has also been shown to suppress femoral artery intimal hyperplasia in a rat photochemical model of endothelial injury. Kondo et al. *Thromb. Haemost.* 79:635-639 (1998). The 5-lipoxygenase inhibitor zileuton has been shown to reduce renal ischemia in a mouse model. Nimesh et al., *Mol. Pharm.* 66:220-227 (2004).

Leukotriene pathway modulators have been used for the treatment of a variety of diseases or conditions, including, by way of example only, (i) inflammation (see e.g. Leff A R et al., *Ann. Allergy Asthma Immunol.*, 2001, 86 (Suppl. 1) 4-8; Riccioni G, et al., *Ann. Clin. Lab Sci.* 2004, 34(4): 379-870); (ii) respiratory diseases including asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma (see e.g. Riccioni et al., *Ann. Clin. Lab. Sci.*, v34, 379-387 (2004)), (iii) chronic obstructive pulmonary disease, including chronic bronchitis or emphysema, pulmonary hypertension, interstitial lung fibrosis and/or airway inflammation and cystic fibrosis (see e.g. Kostikas K et al., *Chest* 2004; 127:1553-9); (iv) increased mucosal secretion and/or edema in a disease or condition (see e.g. Shahab, R., et al., *J. Laryngol. Otol.*, 2004; 118; 500-7); (v) vasoconstriction, atherosclerosis and its sequelae, myocardial ischemia, myocardial infarction, aortic aneurysm, vasculitis and stroke (see e.g. Jala et al., *Trends in Immunol.*, v25, 315-322 (2004) and Mehrabian et al., *Curr. Opin. Lipidol.*, v14, 447-457 (2003)); (vi) reducing organ reperfusion injury following organ ischemia and/or endotoxic shock (see e.g. Matsui N et al., *Planta Med.* 2005 August; 71(8):717-20); (vii) reducing the constriction of blood vessels (see e.g. Stanke-Labesque F et al., *Br J Pharmacol.* 2003 September; 140(1): 186-94); (viii) lowering or preventing an increase in blood pressure (see e.g. Stanke-Labesque F et al, *Br J Pharmacol.* 2003 September; 140(1):186-94, and Walch L, et al. *Br J Pharmacol.* 2002 December; 137(8):1339-45); (ix) preventing eosinophil and/or basophil and/or dendritic cell and/or neutrophil and/or monocyte recruitment (see e.g. Miyahara N, et al. *Immunol.* 2005 Apr. 15; 174(8):4979-84); (x) abnormal bone remodeling, loss or gain, including osteopenia, osteoporosis, Paget's disease, cancer and other diseases (see e.g. Anderson G I, et al., *Biomed Mater Res.* 2001; 58(4):406-140; (xi) ocular inflammation and allergic conjunctivitis, vernal keratoconjunctivitis, and papillary conjunctivitis (see e.g. Lambiase et al., *Arch. Opthalmol.*, v121, 615-620 (2003)); (xii) CNS disorders, including, but are not limited to, multiple sclerosis, Parkinson's disease, Alzheimer's disease, stroke, cerebral ischemia, retinal ischemia, post-surgical cognitive dysfunction, migraine (see e.g. de Souza Carvalho D, et al. *Headache*, 2002, November-December; 42(10): 1044-7; Sheftell F, et al., *Headache*, 2000, February; 40(2): 158-63); (xiii) peripheral neuropathy/neuropathic pain, spinal cord injury (see e.g. Akpek E A, et al., *Spine*, 1999, Jan. 15, 24(2): 128-32), cerebral edema and head injury; (xiv) cancer, including, but is not limited to, pancreatic cancer and other solid or hematological tumors, (see e.g. Poff and Balazy, *Curr. Drug Targets Inflamm. Allergy*, v3, 19-33 (2004) and Steele et al., *Cancer Epidemiology & Prevention*, v8, 467-483 (1999); (xv) endotoxic shock and septic shock (see e.g. Leite M S, et al., *Shock.* 2005 February; 23(2): 173-8); (xvi) rheumatoid arthritis and osteoarthritis (see e.g. Alten R, et al., *Ann. Rheum. Dis.* 2004 February; 63(2): 170-6); (xvii) preventing increased GI diseases, including, by way of example only, chronic gastritis, eosinophilic gastroenteritis, and gastric motor dysfunction, (see e.g. Gyomber et al., *J Gastroenterol Hepatol.*, v11,922-927 (1996); Quack I et al., *BMC Gastroenterol* v18,24 (2005); Cuzzocrea S, et al., *Lab Invest.* 2005 June; 85(6):808-22); (xviii) kidney diseases, including, by way of example only, glomerulonephritis, cyclosporine nephrotoxicity renal ischemia reperfusion. (see e.g. Guasch et al *Kidney Int.*, v56, 261-267; Butterly et al., v 57, 2586-2593 (2000); Guasch A et al., *Kidney Int.* 1999; 56:261-7; Butterly D W et al., *Kidney Int.* 2000; 57:2586-93); (xix) preventing or treating acute or chronic renal insufficiency (see e.g. Maccarrone M, et al., *J Am Soc Nephrol.* 1999; 10:1991-6); (xx) type II diabetes (see e.g. Valdivielso J M, et al., *J. Nephrol.* 2003, 16(1):85-94; Parlapiano C, et al., *Diabetes Res. Clin. Pract.*, 1999, October, 46(1): 43-5); (xxi) diminish the inflammatory aspects of acute infections within one or more solid organs or tissues such as the kidney with acute pyelonephritis (see e.g. Tardif M, et al., *Antimicrob. Agents Chemother.*, 1994, July, 38(7): 1555-60); (xxii) preventing or treating acute or chronic disorders involving recruitment or activation of eosinophils (see e.g. Quack I, et al., *BMC Gastroenterol.*, 2005; 5:24); (xxiii) preventing or treating acute or chronic erosive disease or motor dysfunction of the gastrointestinal tract caused by non-steroidal anti-inflammatory drugs (including selective or non-selective cyclooxygenase-1 or -2 inhibitors) (see e.g. Marusova I B, et al., *Eksp. Klin. Farmakol.*, 2002, 65:16-8 and Gyomber E, et al., *J. Gastroenterol. Hepatol.*, 1996, 11, 922-7; Martin St et al., *Eur. J. Gastroenterol. Hepatol.*, 2005, 17: 983-6); (xxiv) treatment of metabolic syndromes, including, by way of example only, Familial Mediterranean Fever (see e.g. Bentancur A G, et al., *Clin. Exp. Rheumatol.*, 2004, July-August, 22(4 Suppl. 34): S56-8; and (xxv) treat hepatorenal syndrome [see e.g. Capella G L., Prostaglandins *Leukot. Essent. Fatty Acids.* 2003 April; 68(4): 263-5].

Identification of Leukotriene Synthesis Pathway Inhibitors

The development and testing of novel 5-lipoxygenase inhibitors, which are effective either alone or in combination with other drugs, and which result in minimal negative side effects would be beneficial for treating leukotriene-dependent or leukotriene mediated diseases, disorders, or conditions. Inhibitors of the leukotriene synthesis pathway described herein may target any step of the pathway to prevent or reduce the formation of leukotrienes. Such leukotriene synthesis inhibitors can, by way of example, inhibit at the level of 5-lipoxygenase, or 5-lipoxygenase-activating protein, thus minimizing the formation of various products in the leukotriene pathway, thereby decreasing the amounts of such compounds available in the cell. Leukotriene synthesis inhibitors can be identified based on their ability to bind to proteins in the leukotriene synthesis pathway. For example, 5-lipoxygenase inhibitors can be identified based on the inhibition of formation of the intermediate product 5-HPETE/5-HETE in cytosol fractions or purified 5-lipoxygenase, with product measured by HPLC or spectrophotometry, or by the inhibition of $LTB_4$ production from stimulated human leukocytes or by the inhibition of $LTB_4$ production from stimulated human blood (with product $LTB_4$ measured in both cases by $LTB_4$ specific ELISA.

Compounds

Described herein are compounds that inhibit the activity of 5-lipoxygenase. Also described herein are pharmaceutically acceptable salts, pharmaceutically acceptable N-oxides, pharmaceutically active metabolites and pharmaceutically acceptable prodrugs of such compounds. Pharmaceutical compositions that include at least one such compound or a pharmaceutically acceptable salt, pharmaceutically acceptable N-oxide, pharmaceutically active metabolite or pharmaceutically acceptable prodrug of such compound are provided.

In one aspect, provided herein are compounds of Formula (I). Formula (I) is as follows:

$$A\text{-}L^1\text{-}Z \qquad \text{Formula (I)}$$

wherein A is:

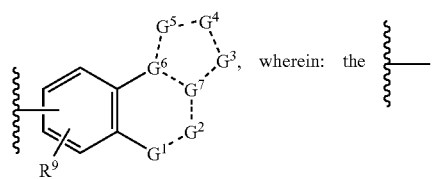

(A)

wherein: the represents a variable point of attachment to the benzo ring;
each ------ is independently a single bond, a double bond or an aromatic bond;
$G^1$ is N or $CR^1$ when the bond ------ joining $G^1$ to $G^2$ represents a double bond or an aromatic bond, or $G^1$ is O, S, $NR^2$ or $C(R^1)_2$ when the bond ------ joining $G^1$ to $G^2$ represents a single bond;
$G^2$ is N or $CR^1$ when the bond ------ joining $G^1$ to $G^2$ represents a double bond or an aromatic bond, or $G^2$ is O, S, $NR^2$ or $C(R^1)_2$ when the bond ------ joining $G^1$ to $G^2$ represents a single bond;
$G^3$ is N or $CR^1$ when either of the bonds ------ connecting $G^3$ to its adjacent ring atoms represents a double bond or an aromatic bond, or $G^3$ is O, S, $NR^2$ or $C(R^1)_2$ when each of the bonds ------ connecting $G^3$ to its adjacent ring atoms represents a single bond;
$G^4$ is N or $CR^1$ when either of the bonds ------ connecting $G^4$ to its adjacent ring atoms represents a double bond or an aromatic bond, or $G^4$ is O, S, $NR^2$ or $C(R^1)_2$ when each of the bonds ------ connecting $G^4$ to its adjacent ring atoms represents a single bond;
$G^5$ is N or $CR^1$ when either of the bonds ------ connecting $G^5$ to its adjacent ring atoms represents a double bond or an aromatic bond, or $G^5$ is O, S, $NR^2$ or $C(R^1)_2$ when each of the bonds ------ connecting $G^5$ to its adjacent ring atoms represents a single bond;
$G^6$ is C when any of the bonds ------ connecting $G^6$ to its three adjacent ring atoms represents a double bond or an aromatic bond, or $G^6$ is N when each of the bonds ------ connecting $G^6$ to its three adjacent ring atoms represents a single bond;
$G^7$ is C when any of the bonds ------ connecting $G^7$ to its three adjacent ring atoms represents a double bond or an aromatic bond, or $G^7$ is N when each of the bonds ------ connecting $G^7$ to its three adjacent ring atoms represents a single bond;
wherein A can contain from 1 to 5 heteroatoms selected from N, O, or S, provided that at least one heteroatom is N;
each $R^1$ is independently H, halide, —CN, —$NO_2$, —OH, or an optionally substituted group selected from $C_1$-$C_6$alkyl, $C_1$-$C_6$fluoroalkyl, $C_3$-$C_8$cycloalkyl, $C_2$-$C_6$alkenyl, $C_2$-$C_6$alkynyl, $C_1$-$C_6$fluoroalkoxy; or —$OR^3$, —$SR^3$, —S(=O)$R^3$, —S(=O)$_2R^3$, —C(=O)$R^3$, —C(=O)O$R^3$, —CH($R^3$)$_2$, —N($R^3$)$_2$, —C(=O)N($R^3$)$_2$, —NHC(=O)$R^3$, or —C(OH)($R^3$)$_2$, where each $R^3$ is independently H, or an optionally substituted group selected from $C_1$-$C_6$alkyl, $C_2$-$C_6$alkenyl, $C_2$-$C_6$alkynyl, $C_3$-$C_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl or pyrimidinyl; or
$R^1$ is $Q^1$-$Q^2$ where $Q^1$ is aryl, monocyclic heterocycloalkyl, monocyclic heteroaryl, bicyclic heteroaryl; and $Q^2$ is H, halide, —CN, —$NO_2$, $C_1$-$C_6$alkyl, $C_1$-$C_6$alkoxy, —$OR^3$, —$SR^3$, —S(=O)$R^3$, —S(=O)$_2R^3$, —C(=O)$R^3$, —C(=O)O$R^3$, —CH($R^3$)$_2$, —N($R^3$)$_2$, or —C(=O)N($R^3$)$_2$, where each $R^3$ is independently H, or an optionally substituted group selected from $C_1$-$C_6$alkyl, $C_2$-$C_6$alkenyl, $C_2$-$C_6$alkynyl, $C_3$-$C_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl or pyrimidinyl; or
two $R^1$ groups attached to the same carbon atom taken together can form a carbonyl (C=O); or
two $R^1$ groups can together form an optionally substituted 4-, 5-, 6-, or 7-membered monocyclic ring containing 0, 1 or 2 heteroatoms selected from among S and O;
each $R^2$ is independently H, or an optionally substituted group selected from $C_1$-$C_6$alkyl, $C_1$-$C_6$fluoroalkyl, $C_3$-$C_8$cycloalkyl, $C_2$-$C_6$alkenyl, $C_2$-$C_6$alkynyl, aryl, monocyclic heterocycloalkyl, monocyclic heteroaryl, bicyclic heteroaryl; or —C(=O)$R^3$, C(=O)O$R^3$, —CH($R^3$)$_2$ or —C(=O)N($R^3$)$_2$, where each $R^3$ is independently H, or an optionally substituted group selected from $C_1$-$C_6$alkyl, $C_2$-$C_6$alkenyl, $C_2$-$C_6$alkynyl, $C_3$-$C_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl or pyrimidinyl;
$L^1$ is $(CHR^4)_nX^1(CHR^4)_n$ wherein
each n is independently 0, 1, 2, or 3;
$X^1$ is a bond, O, S, S(=O), S(=O)$_2$, or $NR^5$;
each $R^4$ is independently H, or an optionally substituted group selected from $C_1$-$C_6$alkyl, $C_3$-$C_8$cycloalkyl, $C_1$-$C_6$fluoroalkyl, $C_2$-$C_6$alkenyl, $C_2$-$C_6$alkynyl, phenyl, benzyl; or $L^4$-$X^2$-$L^5$-$X^3$ where $L^4$ is a bond, or an optionally substituted group selected from $C_1$-$C_6$ alkyl, $C_2$-$C_6$ alkenyl, $C_2$-$C_6$ alkynyl, aryl, $C_2$-$C_{10}$ heterocycloalkyl or $C_3$-$C_8$ cycloalkyl; $X^2$ is a bond, O, S, S(=O), S(=O)$_2$, NH, C(=O)NH, or NHC(=O); $L^5$ is a bond, $C_1$-$C_6$ alkyl, $C_3$-$C_8$cycloalkyl, phenyl, pyridyl, thiazolyl, or thienyl; and $X^3$ is —OH, —CN, —$NO_2$, halide, —$CO_2$H, —$CO_2R^{10}$, —C(=O)$R^{10}$, —CON($R^{10}$)$_2$, —NHC(=O)$R^{10}$, —C(OH)($R^{10}$)$_2$, tetrazolyl, —C(=O)NHSO$_2R^{10}$, —CH(OH)CF$_3$, —COCF$_3$, —SO$_2$NHC(=O)R$^{10}$, or —N(R$^{10}$)$_2$, where each R$^{10}$ is independently H, or an optionally substituted group selected from C$_1$-C$_6$alkyl, C$_1$-C$_6$fluoroalkyl, C$_2$-C$_6$alkenyl, C$_2$-C$_6$alkynyl, C$_3$-C$_8$cycloalkyl, phenyl, or benzyl;

R$^5$ is H, or an optionally substituted group selected from C$_1$-C$_6$alkyl, C$_3$-C$_8$cycloalkyl, C$_1$-C$_6$fluoroalkyl, C$_2$-C$_6$alkenyl, C$_2$-C$_6$alkynyl, phenyl, benzyl; or R$^5$ is L$^6$-X$^5$-L$^7$-X$^6$ where
  L$^6$ is an optionally substituted group selected from C$_1$-C$_6$ alkyl, C$_2$-C$_{10}$ heterocycloalkyl or C$_3$-C$_8$cycloalkyl;
  X$^5$ is a bond, O, S, S(=O), S(=O)$_2$, NH, C(=O)NH, or NHC(=O);
  L$^7$ is a bond, C$_1$-C$_6$ alkyl, C$_3$-C$_8$cycloalkyl, phenyl, pyridyl, thiazolyl, or thienyl; and
  X$^6$ is —OH, —CN, —NO$_2$, halide, —CO$_2$H, —CO$_2$R$^{10}$, —C(=O)R$^{10}$, —C(OH)(R$^{10}$)$_2$, tetrazolyl, —C(=O)NHSO$_2$R$^{10}$, —CH(OH)CF$_3$, —COCF$_3$, —SO$_2$NHC(=O)R$^{10}$, or —N(R$^{10}$)$_2$, where each R$^{10}$ is independently H, or an optionally substituted group selected from C$_1$-C$_6$alkyl, C$_1$-C$_6$fluoroalkyl, C$_2$-C$_6$alkenyl, C$_2$-C$_6$alkynyl, C$_3$-C$_8$cycloalkyl, phenyl, or benzyl;

Z is L$^2$-L3-CR$^6$,R$^7$,R$^8$ wherein
  L$^2$ is an optionally substituted group selected from aryl, monocyclic heteroaryl and bicyclic heteroaryl;
  L$^3$ is a bond, C(=O), —CH(OH)—, —CH(lower alkoxy)-, =N-lower alkyl, or =N—O-lower alkyl;
  R$^6$ and R$^7$ are independently selected from H, or an optionally substituted group selected from C$_1$-C$_6$haloalkyl, C$_1$-C$_6$alkyl, C$_3$-C$_8$cycloalkyl, C$_2$-C$_6$alkenyl, C$_2$-C$_6$alkynyl, phenyl, benzyl, thiazolyl, C$_1$-C$_6$alkoxy, or C$_1$-C$_6$thioalkoxy; or C$_1$-C$_6$alkyl-X$^4$, wherein X$^4$ is —CO$_2$H, —CO$_2$R$^{11}$, —C(=O)R$^{11}$, —C(OH)(R$^{11}$)$_2$, C$_1$-C$_6$alkoxy, tetrazolyl, —OH, halide, —CN, —NO$_2$, —SR$^{11}$, —S(=O)R$^{11}$, —S(=O)$_2$R$^{11}$, —N(R$^{11}$)$_2$, —CON(R$^{11}$)$_2$, —NHC(=O)R$^{11}$, —C(=O)NHSO$_2$R$^{11}$, —CH(OH)CF$_3$, —COCF$_3$, or —SO$_2$NHC(=O)R$^{11}$, where each R$^{11}$ is independently H, or an optionally substituted group selected from C$_1$-C$_6$alkyl, C$_1$-C$_6$fluoroalkyl, C$_2$-C$_6$alkenyl, C$_2$-C$_6$alkynyl, C$_3$-C$_8$cycloalkyl, phenyl, or benzyl;
  or R$^6$ and R$^7$ can together form an optionally substituted 5-, 6-, or 7-membered monocyclic ring containing 1 or 2 heteroatoms selected from S and O;
  or R$^6$ and R$^7$ can together form an optionally substituted bicyclo[3,2,1]ring containing 1 or 2 heteroatoms selected from S and O;
  or R$^6$ and R$^7$ can together form an optionally substituted bicyclic heteroaryl ring containing 1 or 2 heteroatoms selected from S, N and O; or
  R$^6$ and R$^7$ can together form a carbonyl (C=O);
  R$^8$ is H, —OH, —CONH$_2$, tetrazolyl, —CN, —N$_3$, C$_1$-C$_6$alkyl, C$_2$-C$_6$alkenyl, —CF$_3$, or —CO$_2$H; or an optionally substituted group selected from C$_1$-C$_6$fluoroalkoxy, C$_3$-C$_8$cycloalkoxy, —OR$^{12}$, —CON(R$^{12}$)$_2$, —CO$_2$R$^{12}$, —SR$^{12}$, —S(=O)R$^{12}$, S(=O)$_2$R$^{12}$, C(=O)R$^{12}$, C(OH)(R$^{12}$)$_2$, —N(R$^{12}$)$_2$, NHC(=O)R$^{12}$, —OC(=O)R$^{12}$, benzyl, and phenyl; where each R$^{12}$ is independently H, or an optionally substituted group selected from C$_1$-C$_6$alkyl, C$_1$-C$_6$fluoroalkyl, C$_2$-C$_6$alkenyl, C$_2$-C$_6$alkynyl, C$_3$-C$_8$cycloalkyl, phenyl, or benzyl; or R$^6$ and R$^8$ can together form an optionally substituted C$_2$-C$_8$heterocycloalkyl having 1 or 2 O atoms in the ring;

R$^9$ is H, halide, —CN, —NO$_2$, —OH, or an optionally substituted group selected from C$_1$-C$_6$alkyl, C$_3$-C$_8$cycloalkyl, C$_1$-C$_6$fluoroalkyl, C$_2$-C$_6$alkenyl, C$_2$-C$_6$alkynyl, C$_1$-C$_6$alkoxy, phenyl, benzyl; or R$^9$ is L$^8$-X$^7$-L$^9$-X$^8$ where
  L$^8$ is a bond, or an optionally substituted group selected from C$_1$-C$_6$ alkyl, C$_2$-C$_6$ alkenyl, C$_2$-C$_6$ alkynyl, aryl, C$_2$-C$_{10}$ heterocycloalkyl or C$_3$-C$_8$ cycloalkyl;
  X$^7$ is a bond, O, S, S(=O), S(=O)$_2$, NH, C(=O)NH, or NHC(=O);
  L$^9$ is a bond, C$_1$-C$_6$ alkyl, C$_3$-C$_8$ cycloalkyl, phenyl, pyridyl, thiazolyl, or thienyl; and
  X$^8$ is H, —OH, —CN, —NO$_2$, halide, —CO$_2$H, —CO$_2$R$^{16}$, —C(=O)R$^{16}$, —C(OH)(R$^{16}$)$_2$, —C(=O)N(R$^{16}$)$_2$, —NHC(=O)R$^{16}$, tetrazolyl, —C(O)NHSO$_2$R$^{16}$, —CH(OH)CF$_3$, —COCF$_3$, —SO$_2$NHC(=O)R$^{16}$, or —N(R$^{16}$)$_2$, where each R$^{16}$ is independently H, or an optionally substituted group selected from C$_1$-C$_6$alkyl, C$_2$-C$_6$alkenyl, C$_2$-C$_6$alkynyl, C$_3$-C$_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl or pyrimidinyl;

or a pharmaceutically acceptable salt, pharmaceutically acceptable N-oxide, pharmaceutically active metabolite, pharmaceutically acceptable prodrug, or pharmaceutically acceptable solvate thereof.

For any and all of the embodiments, substituents are selected from among a list of alternatives. For example, in one embodiment, G$^2$ is C=O and G$^1$ is NR$^2$. In other embodiments, G$^2$ is CR$^1$ and G$^1$ is N. In some other embodiments, G$^1$ is CR$^1$ and G$^2$ is N. In yet other embodiments, each of G$^2$ and G$^1$ is independently CR$^1$.

In further or alternative embodiments, G$^6$ is N and G$^7$ is C. In other embodiments, G$^7$ is N and G$^6$ is C. In further or alternative embodiments, G$^3$ is N. In further or alternative embodiments, G$^4$ is N. In further or alternative embodiments, G$^5$ is CR$^1$. In some other embodiments, G$^5$ is C=O. In yet other embodiments, G$^5$ is O. In other embodiments, G$^5$ is S. In some embodiments, G$^5$ is C(R$^1$)$_2$.

In some embodiments, G$^1$ is N or CR$^1$ when the bond ------ joining G$^1$ to G$^2$ represents a double bond or an aromatic bond, or G$^1$ is NR$^2$ or C(R$^1$)$_2$ when the bond ------ joining G$^1$ to G$^2$ represents a single bond; G$^2$ is N or CR$^1$ when the bond ------ joining G$^1$ to G$^2$ represents a double bond or an aromatic bond, or G$^2$ is NR$^2$ or C(R$^1$)$_2$ when the bond ------ joining G$^1$ to G$^2$ represents a single bond; G$^3$ is N or CR$^1$ when either of the bonds ------ connecting G$^3$ to its adjacent ring atoms represents a double bond or an aromatic bond, or G$^3$ is NR$^2$ or C(R$^1$)$_2$ when each of the bonds ------ connecting G$^3$ to its adjacent ring atoms represents a single bond; G$^4$ is N or CR$^1$ when either of the bonds ------ connecting G$^4$ to its adjacent ring atoms represents a double bond or an aromatic bond, or G$^4$ is NR$^2$ or C(R$^1$)$_2$ when each of the bonds ------ connecting G$^4$ to its adjacent ring atoms represents a single bond; G$^5$ is N or CR$^1$ when either of the bonds ------ connecting G$^5$ to its adjacent ring atoms represents a double bond or an aromatic bond, or G$^5$ is NR$^2$ or C(R$^1$)$_2$ when each of the bonds ------ connecting G$^5$ to its adjacent ring atoms represents a single bond; G$^6$ is C when any of the bonds ------ connecting G$^6$ to its three adjacent ring atoms represents a double bond or an aromatic bond, or G$^6$ is N when each of the bonds ------ connecting G$^6$ to its three adjacent ring atoms represents a single bond; G$^7$ is C when any of the bonds ------ connecting $G^7$ to its three adjacent ring atoms represents a double bond or an aromatic bond, or $G^7$ is N when each of the bonds ------ connecting $G^7$ to its three adjacent ring atoms represents a single bond.

In other embodiments, $G^1$ is N or $CR^1$ when the bond ------ joining $G^1$ to $G^2$ represents a double bond or an aromatic bond, or $G^1$ is $NR^2$ or $C(R^1)_2$ when the bond ------ joining $G^1$ to $G^2$ represents a single bond; $G^2$ is N or $CR^1$ when the bond ------ joining $G^1$ to $G^2$ represents a double bond or an aromatic bond, or $G^2$ is $NR^2$ or $C(R^1)_2$ when the bond ------ joining $G^1$ to $G^2$ represents a single bond; $G^3$ is N or $CR^1$ and the bond ------ connecting $G^3$ to $G^7$ represents a double bond or an aromatic bond, and the bond ------ connecting $G^3$ to $G^4$ represents a single bond; $G^4$ is N or $CR^1$ when the bond ------ connecting $G^4$ to $G^5$ represents a double bond or an aromatic bond, or $G^4$ is $NR^2$ or $C(R^1)_2$ when the bond ------ connecting $G^4$ to $G^5$ represents a single bond; $G^5$ is N or $CR^1$ when the bond ------ connecting $G^5$ to $G^4$ represents a double bond or an aromatic bond, or $G^5$ is $NR^2$ or $C(R^1)_2$ when the bond ------ connecting $G^5$ to $G^4$ represents a single bond; $G^6$ is N and each of the bonds ------ connecting $G^6$ to its three adjacent ring atoms represents a single bond; and $G^7$ is C and the bond ------ connecting $G^7$ to $G^3$ represents a double bond or an aromatic bond.

In some other embodiments, $G^1$ is N or $CR^1$ and the bond ------ joining $G^1$ to $G^2$ represents a double bond or an aromatic bond; $G^2$ is $CR^1$ and the bond ------ joining $G^1$ to $G^2$ represents a double bond or an aromatic bond; $G^3$ is N or $CR^1$ and the bond ------ connecting $G^3$ to $G^7$ represents a double bond or an aromatic bond, and the bond ------ connecting $G^3$ to $G^4$ represents a single bond; $G^4$ is N or $CR^1$ when the bond ------ connecting $G^4$ to $G^5$ represents a double bond or an aromatic bond, or $G^4$ is $NR^2$ or $C(R^1)_2$ when the bond ------ connecting $G^4$ to $G^5$ represents a single bond; $G^5$ is N or $CR^1$ when the bond ------ connecting $G^5$ to $G^4$ represents a double bond or an aromatic bond, or $G^5$ is $NR^2$ or $C(R^1)_2$ when the bond ------ connecting $G^5$ to $G^4$ represents a single bond; $G^6$ is N and each of the bonds ------ connecting $G^6$ to its three adjacent ring atoms represents a single bond; and $G^7$ is C and the bond ------ connecting $G^7$ to $G^3$ represents a double bond or an aromatic bond.

In yet other embodiments, $G^1$ is N or $CR^1$ and the bond ------ joining $G^1$ to $G^2$ represents a double bond or an aromatic bond; $G^2$ is $CR^1$ and the bond ------ joining $G^1$ to $G^2$ represents a double bond or an aromatic bond; $G^3$ is N and the bond ------ connecting $G^3$ to $G^7$ represents a double bond or an aromatic bond, and the bond ------ connecting $G^3$ to $G^4$ represents a single bond; $G^4$ is N or $CR^1$ when the bond ------ connecting $G^4$ to $G^5$ represents a double bond or an aromatic bond, or $G^4$ is $NR^2$ or $C(R^1)_2$ when the bond ------ connecting $G^4$ to $G^5$ represents a single bond; $G^5$ is N or $CR^1$ when the bond ------ connecting $G^5$ to $G^4$ represents a double bond or an aromatic bond, or $G^5$ is $NR^2$ or $C(R^1)_2$ when the bond ------ connecting $G^5$ to $G^4$ represents a single bond; $G^6$ is N and each of the bonds ------ connecting $G^6$ to its three adjacent ring atoms represents a single bond; and $G^7$ is C and the bond ------ connecting $G^7$ to $G^3$ represents a double bond or an aromatic bond.

In some embodiments, $G^1$ is N or $CR^1$ and the bond ------ joining $G^1$ to $G^2$ represents a double bond or an aromatic bond; $G^2$ is $CR^1$ and the bond ------ joining $G^1$ to $G^2$ represents a double bond or an aromatic bond; $G^3$ is $CR^1$ and the bond ------ connecting $G^3$ to $G^7$ represents a double bond or an aromatic bond, and the bond ------ connecting $G^3$ to $G^4$ represents a single bond; $G^4$ is N or $CR^1$ when the bond ------ connecting $G^4$ to $G^5$ represents a double bond or an aromatic bond, or $G^4$ is $NR^2$ or $C(R^1)_2$ when the bond ------ connecting $G^4$ to $G^5$ represents a single bond; $G^5$ is N or $CR^1$ when the bond ------ connecting $G^5$ to $G^4$ represents a double bond or an aromatic bond, or $G^5$ is $NR^2$ or $C(R^1)_2$ when the bond ------ connecting $G^5$ to $G^4$ represents a single bond; $G^6$ is N and each of the bonds ------ connecting $G^6$ to its three adjacent ring atoms represents a single bond; and $G^7$ is C and the bond ------ connecting $G^7$ to $G^3$ represents a double bond or an aromatic bond.

In other embodiments, $G^1$ is N or $CR^1$ and the bond ------ joining $G^1$ to $G^2$ represents a double bond; $G^2$ is $CR^1$ and the bond ------ joining $G^1$ to $G^2$ represents a double bond; $G^3$ is N or $CR^1$ and the bond ------ connecting $G^3$ to $G^7$ represents a double bond, and the bond ------ connecting $G^3$ to $G^4$ represents a single bond; $G^4$ is $NR^2$ or $C(R^1)_2$ and the bond ------ connecting $G^4$ to $G^5$ represents a single bond; $G^5$ is $NR^2$ or $C(R^1)_2$ and the bond ------ connecting $G^5$ to $G^4$ represents a single bond; $G^6$ is N and each of the bonds ------ connecting $G^6$ to its three adjacent ring atoms represents a single bond; and $G^7$ is C and the bond ------ connecting $G^7$ to $G^3$ represents a double bond.

In further embodiments, $G^1$ is N or $CR^1$ and the bond ------ joining $G^1$ to $G^2$ represents a double bond; $G^2$ is $CR^1$ and the bond ------ joining $G^1$ to $G^2$ represents a double bond; $G^3$ is N or $CR^1$ and the bond ------ connecting $G^3$ to $G^7$ represents a double bond, and the bond ------ connecting $G^3$ to $G^4$ represents a single bond; $G^4$ is $NR^2$ or $C(R^1)_2$ and the bond ------ connecting $G^4$ to $G^5$ represents a single bond; $G^5$ is $C(R^1)_2$ and the bond ------ connecting $G^5$ to $G^4$ represents a single bond; $G^6$ is N and each of the bonds ------ connecting $G^6$ to its three adjacent ring atoms represents a single bond; $G^7$ is C and the bond ------ connecting $G^7$ to $G^3$ represents a double bond.

In some embodiments, $G^1$ is N or $CR^1$ and the bond ------ joining $G^1$ to $G^2$ represents a double bond; $G^2$ is $CR^1$ and the bond ------ joining $G^1$ to $G^2$ represents a double bond; $G^3$ is N and the bond ------ connecting $G^3$ to $G^7$ represents a double bond, and the bond ------ connecting $G^3$ to $G^4$ represents a single bond; $G^4$ is $C(R^1)_2$ and the bond ------ connecting $G^4$ to $G^5$ represents a single bond; $G^5$ is $C(R^1)_2$ and the bond ------ connecting $G^5$ to $G^4$ represents a single bond; $G^6$ is N and each of the bonds ------ connecting $G^6$ to its three adjacent ring atoms represents a single bond; and $G^7$ is C and the bond ------ connecting $G^7$ to $G^3$ represents a double bond.

In further embodiments, $G^1$ is N or $CR^1$ when the bond ------ joining $G^1$ to $G^2$ represents a double bond or an aromatic bond; $G^2$ is $CR^1$ when the bond ------ joining $G^1$ to $G^2$ represents a double bond or an aromatic bond; $G^3$ is N or $CR^1$ and the bond ------ connecting $G^3$ to $G^7$ represents a double bond or an aromatic bond, and the bond ------ connecting $G^3$ to $G^4$ represents a single bond; $G^4$ is N or $CR^1$ when the bond ------ connecting $G^4$ to $G^5$ represents a double bond or an aromatic bond; $G^5$ is N or $CR^1$ when the bond ------ connecting $G^5$ to $G^4$ represents a double bond or an aromatic bond; $G^6$ is N and each of the bonds ------ connecting $G^6$ to its three adjacent ring atoms represents a single bond; $G^7$ is C and the bond ------ connecting $G^7$ to $G^3$ represents a double bond or an aromatic bond.

In other embodiments, $G^1$ is N or $CR^1$ when the bond ------ joining $G^1$ to $G^2$ represents a double bond or an aromatic bond; $G^2$ is $CR^1$ when the bond ------ joining $G^1$ to $G^2$ represents a double bond or an aromatic bond; $G^1$ is N or $CR^1$ and the bond ------ connecting $G^3$ to $G^7$ represents a double bond or an aromatic bond, and the bond ------ connecting $G^3$ to $G^4$ represents a single bond; $G^4$ is N and the bond ------ connecting $G^4$ to $G^5$ represents a double bond or an aromatic bond; $G^5$ is N or $CR^1$ when the bond ------ connecting $G^5$ to $G^4$ represents a double bond or an aromatic bond; $G^6$ is N and each of the bonds ------ connecting $G^6$ to its three adjacent ring atoms represents a single bond; $G^7$ is C and the bond ------ connecting $G^7$ to $G^3$ represents a double bond or an aromatic bond.

In one embodiment, $G^1$ is N or $CR^1$ when the bond ------ joining $G^1$ to $G^2$ represents a double bond or an aromatic bond; $G^2$ is $CR^1$ when the bond ------ joining $G^1$ to $G^2$ represents a double bond or an aromatic bond; $G^3$ is N or $CR^1$ and the bond ------ connecting $G^3$ to $G^7$ represents a double bond or an aromatic bond, and the bond ------ connecting $G^3$ to $G^4$ represents a single bond; $G^4$ is N or $CR^1$ and the bond ------ connecting $G^4$ to $G^5$ represents a double bond or an aromatic bond; $G^5$ is N and the bond ------ connecting $G^5$ to $G^4$ represents a double bond or an aromatic bond; $G^6$ is N and each of the bonds ------ connecting $G^6$ to its three adjacent ring atoms represents a single bond; $G^7$ is C and the bond ------ connecting $G^7$ to $G^3$ represents a double bond or an aromatic bond.

In another embodiment, $G^1$ is N or $CR^1$ and the bond ------ joining $G^1$ to $G^2$ represents a double bond; $G^2$ is $CR^1$ and the bond ------ joining $G^1$ to $G^2$ represents a double bond; $G^3$ is $CR^1$ and the bond ------ connecting $G^3$ to $G^7$ represents a double bond or an aromatic bond, and the bond ------ connecting $G^3$ to $G^4$ represents a single bond; $G^4$ is N and the bond ------ connecting $G^4$ to $G^5$ represents a double bond; $G^5$ is $CR^1$ and the bond ------ connecting $G^5$ to $G^4$ represents a double bond; $G^6$ is N and each of the bonds ------ connecting $G^6$ to its three adjacent ring atoms represents a single bond; $G^7$ is C and the bond ------ connecting $G^7$ to $G^3$ represents a double bond or an aromatic bond.

In some embodiments, $G^1$ is N or $CR^1$ when the bond ------ joining $G^1$ to $G^2$ represents a double bond or an aromatic bond; $G^2$ is $CR^1$ when the bond ------ joining $G^1$ to $G^2$ represents a double bond or an aromatic bond; $G^3$ is N and the bond ------ connecting $G^3$ to $G^7$ represents a double bond or an aromatic bond, and the bond ------ connecting $G^3$ to $G^4$ represents a single bond; $G^4$ is N and the bond ------ connecting $G^4$ to $G^5$ represents a double bond or an aromatic bond; $G^5$ is N or $CR^1$ and the bond ------ connecting $G^5$ to $G^4$ represents a double bond or an aromatic bond; $G^6$ is N and each of the bonds ------ connecting $G^6$ to its three adjacent ring atoms represents a single bond; $G^7$ is C and the bond ------ connecting $G^7$ to $G^3$ represents a double bond or an aromatic bond.

In other embodiments, $G^1$ is N or $CR^1$ when the bond ------ joining $G^1$ to $G^2$ represents a double bond or an aromatic bond; $G^2$ is $CR^1$ when the bond ------ joining $G^1$ to $G^2$ represents a double bond or an aromatic bond; $G^3$ is N and the bond ------ connecting $G^3$ to $G^7$ represents a double bond or an aromatic bond, and the bond ------ connecting $G^3$ to $G^4$ represents a single bond; $G^4$ is N and the bond ------ connecting $G^4$ to $G^5$ represents a double bond or an aromatic bond; $G^5$ is N and the bond ------ connecting $G^5$ to $G^4$ represents a double bond or an aromatic bond; $G^6$ is N and each of the bonds ------ connecting $G^6$ to its three adjacent ring atoms represents a single bond; $G^7$ is C and the bond ------ connecting $G^7$ to $G^3$ represents a double bond or an aromatic bond.

In further or alternative embodiments, $L^1$ is selected from among —$(CHR^4)_n$—, —$(CHR^4)_nO$—, —$(CHR^4)_nS$—, —$O(CHR^4)_n$—, —$S(CHR^4)_n$—, wherein n is 0, 1, 2, or 3. In a further embodiment, $R^4$ is independently H, or an optionally substituted group selected from among lower alkyl, lower cycloalkyl, and lower fluoroalkyl; or $L^4$-$X^2$-$L^5$-$X^3$ where $L^4$ is a bond, or an optionally substituted group selected from among $C_1$-$C_6$ alkyl, $C_2$-$C_{10}$heterocycloalkyl or $C_3$-$C_8$cycloalkyl; $X^2$ is a bond, O, S, S(O), or S(O)$_2$; $L^5$ is a bond, $C_1$-$C_6$ alkyl, $C_3$-$C_8$cycloalkyl, phenyl, pyridyl, thiazolyl, or thienyl; and $X^3$ is OH, CN, NO$_2$, halide, CO$_2$H, CO$_2R^{10}$, C(=O)$R^{10}$, C(OH)($R^{10}$)$_2$, tetrazolyl, C(=O)NHSO$_2R^{10}$, CH(OH)CF$_3$, COCF$_3$, SO$_2$NHC(=O)$R^{10}$, or N($R^{10}$)$_2$, where each $R^{10}$ is independently H, or an optionally substituted group selected from among lower alkyl, lower cycloalkyl, phenyl, and benzyl.

In some embodiments, $L^2$ is an optionally substituted group selected from among phenyl, thienyl, thiazolyl, oxazolyl, and pyridyl.

In some embodiments, $L^3$ is a bond.

In some embodiments, $R^8$ is H, OH, or CONH$_2$, or an optionally substituted group selected from among lower alkoxy, lower thioalkoxy, lower fluoroalkoxy, and lower cycloalkoxy.

In some embodiments, $R^6$ and $R^7$ can together form an optionally substituted 5 or 6 membered monocyclic ring containing 1 or 2 heteroatoms that are O; or $R^6$ and $R^7$ can together form an optionally substituted bicyclic heteroaryl ring containing 1 or 2 heteroatoms that are O.

In a further aspect, compounds of Formula I have the structure of Formula (Ia):

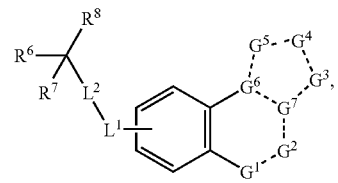

wherein $L^1$ is selected from —$(CHR^4)_n$—, —$(CHR^4)_nO$—, —$(CHR^4)_nS$—, —$O(CHR^4)_n$— and —$S(CHR^4)_n$—, wherein n is 0, 1, 2, or 3; $L^2$ is an optionally substituted group selected from among phenyl, thienyl, thiazolyl, oxazolyl, and pyridyl; and $R^8$ is OH, CO$_2R^3$, CONH$_2$ or an optionally substituted lower alkoxyl, lower thioalkoxy, lower cycloalkoxyl, or lower fluoroalkoxyl; or $R^6$ and $R^8$ can together form a substituted or unsubstituted lower heterocycloalkyl having 1 or 2 oxygen atoms in the ring; $R^9$ is H, halide, OH, lower alkoxy, CN, or NO$_2$.

In some embodiments, $G^2$ is C=O and $G^1$ is $NR^2$. In other embodiments, $G^2$ is $CR^1$ and $G^1$ is N. In yet other embodiments, $G^1$ is $CR^1$ and $G^2$ is N. In some embodiments, each of $G^2$ and $G^1$ is independently $CR^1$.

In some embodiments, $G^6$ is N and $G^7$ is C. In other embodiments, $G^7$ is N and $G^6$ is C.

In some embodiments, $G^3$ is N.

In some embodiments, $G^4$ is N.

In another aspect, $G^5$ is $CR^1$. In a further aspect, $G^5$ is N. In yet another aspect, $G^5$ is C=O. In a further aspect, $G^5$ is O. In another aspect, $G^5$ is S. In another aspect, $G^5$ is C($R^1$)$_2$.

In one embodiment, $R^6$ and $R^7$ can together form an optionally substituted 5 or 6 membered monocyclic ring containing 1 or 2 heteroatoms that are O.

In one embodiment, compounds provided herein have the structure of Formula (Ib):

Formula (Ib)

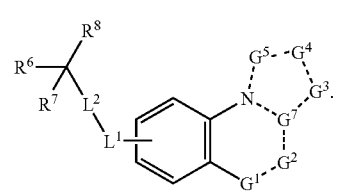

In other embodiments, compounds provided herein have the structure of Formula (Ic):

Formula (Ic)

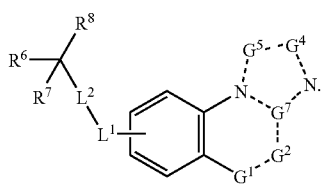

In another aspect, compounds provided herein have the structure of Formula (Id):

Formula (Id)

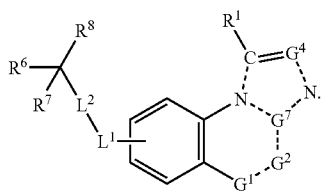

In another aspect, compounds provided herein have the structure of Formula (Ie):

Formula (Ie)

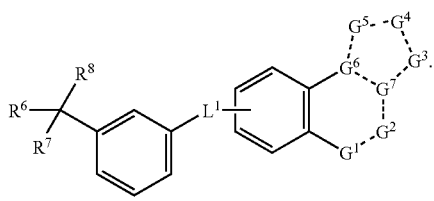

In a further aspect, compounds provided herein have the structure of Formula (If):

Formula (If)

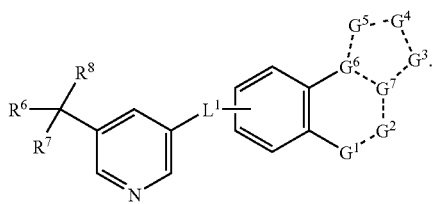

In a further aspect, compounds provided herein have the structure of Formula (Ig):

Formula (Ig)

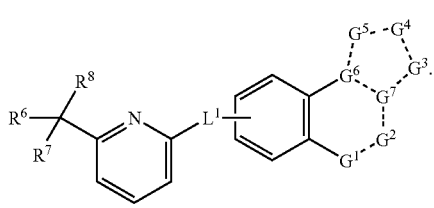

In a further aspect, compounds provided herein have the structure of Formula (Ih) or Formula (Ii):

Formula (Ih)

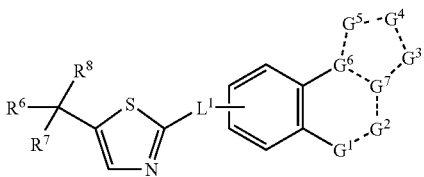

or

Formula (Ii)

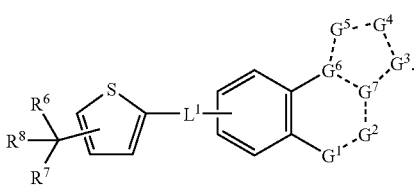

In another aspect, compounds provided herein have the structure of Formula (Ij):

Formula (Ij)

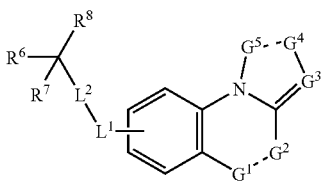

where,
$G^1$ is N or $CR^1$ when the bond ------ joining $G^1$ to $G^2$ represents a double bond or an aromatic bond, or $G^1$ is $NR^2$ or $C(R^1)_2$ when the bond ------ joining $G^1$ to $G^2$ represents a single bond;
$G^2$ is N or $CR^1$ when the bond ------ joining $G^1$ to $G^2$ represents a double bond or an aromatic bond, or $G^2$ is $NR^2$ or $C(R^1)_2$ when the bond ------ joining $G^1$ to $G^2$ represents a single bond;
$G^3$ is N or $CR^1$;
$G^4$ is N or $CR^1$ when the bond ------ connecting $G^4$ to $G^5$ represents a double bond or an aromatic bond, or $G^4$ is $NR^2$ or $C(R^1)_2$ when the bond ------ connecting $G^4$ to $G^5$ represents a single bond;
$G^5$ is N or $CR^1$ when the bond ------ connecting $G^5$ to $G^4$ represents a double bond or an aromatic bond, or $G^5$ is $NR^2$ or $C(R^1)_2$ when the bond ------ connecting $G^5$ to $G^4$ represents a single bond.

In another aspect, compounds provided herein have the structure of Formula (Ik):

Formula (Ik)

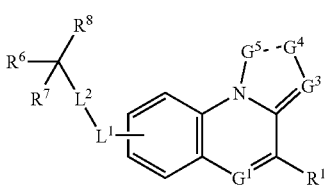

where,
$G^1$ is N or $CR^1$;
$G^3$ is N or $CR^1$;
$G^4$ is N or $CR^1$ when the bond ------ connecting $G^4$ to $G^5$ represents a double bond or an aromatic bond, or $G^4$ is $NR^2$ or $C(R^1)_2$ when the bond ------ connecting $G^4$ to $G^5$ represents a single bond;

$G^5$ is N or $CR^1$ when the bond ----- connecting $G^5$ to $G^4$ represents a double bond or an aromatic bond, or $G^5$ is $NR^2$ or $C(R^1)_2$ when the bond ----- connecting $G^5$ to $G^4$ represents a single bond.

In a further aspect, compounds provided herein have the structure of Formula (Il):

Formula (Il)

where,
$G^1$ is N or $CR^1$;
$G^5$ is N or $CR^1$.

In one aspect, $G^5$ is $CR^1$.

In another aspect, compounds provided herein have the structure Formula (Im):

Formula (Im)

where,
$G^1$ is N or $CR^1$;
$G^4$ is $NR^2$ or $C(R^1)_2$;
$G^5$ is $C(R^1)_2$.

In one aspect, $R^8$ is selected from among OH, $CO_2R^3$, $CONH_2$, optionally substituted $C_1$-$C_6$alkoxy, optionally substituted $C_1$-$C_6$thioalkoxy, optionally substituted $C_3$-$C_8$cycloalkoxy, and optionally substituted $C_1$-$C_6$fluoroalkoxy.

In one aspect, A is selected from among:

(a)

(b)

(c)

(d)

(e)

(f)

(g)

(h)

(i)

-continued
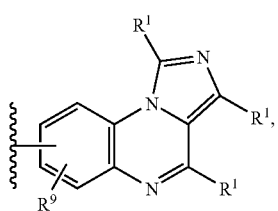
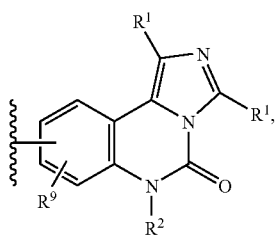
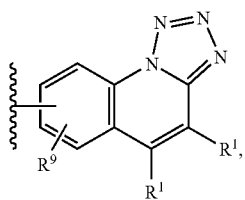
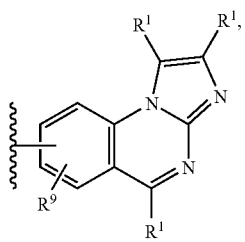
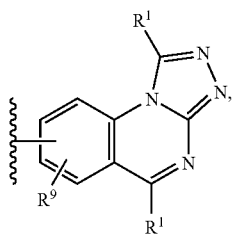
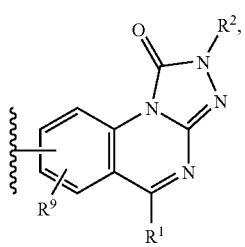
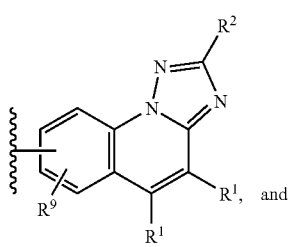, and
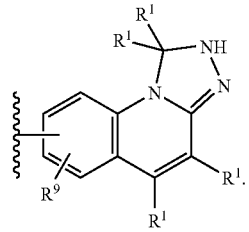
In one aspect, A has a structure represented by the formula:
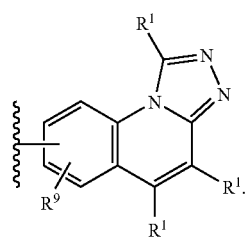
In another aspect, A has a structure represented by the formula:
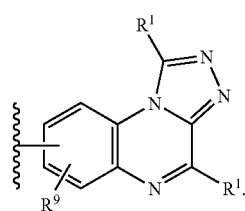
In some embodiments, A has a structure represented by the formula:
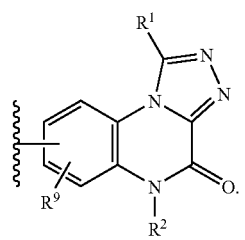
In yet other embodiments, A has a structure represented by the formula:
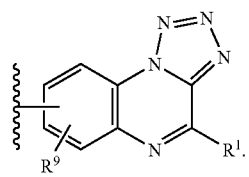
In some embodiments, A has a structure represented by the formula:

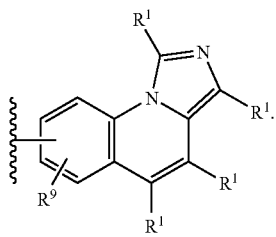

In yet other embodiments, A has a structure represented by the formula:

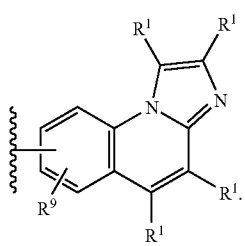

In some embodiments, A has a structure represented by the formula:

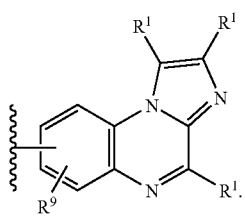

In other embodiments, A has a structure represented by the formula:

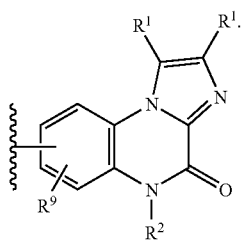

In one aspect, A has a structure represented by the formula:

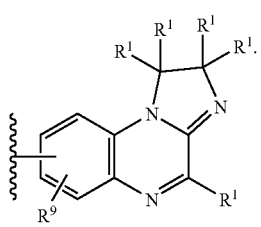

In another aspect, A has a structure represented by the formula:

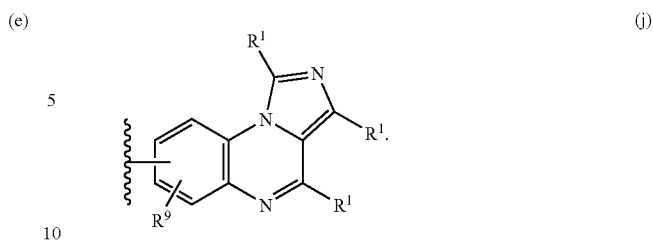

In a further aspect, A has a structure represented by the formula:

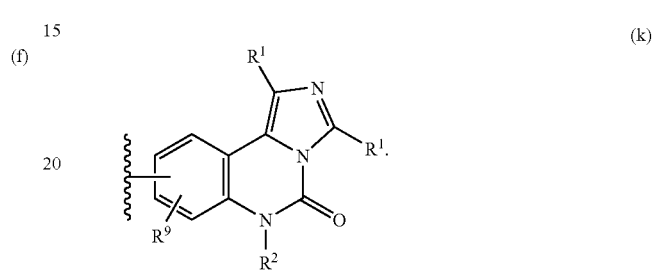

In one embodiment, A has a structure represented by the formula:

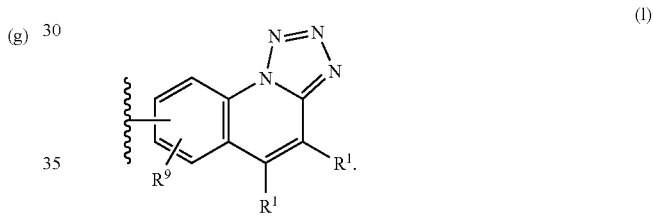

In another embodiment, A has a structure represented by the formula:

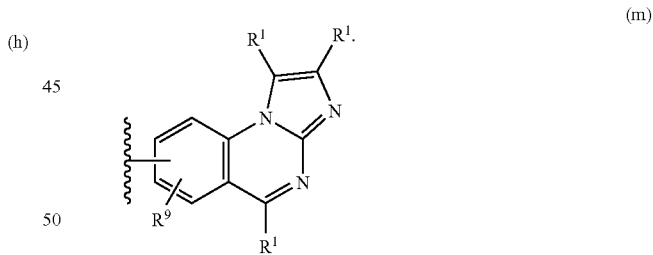

In some embodiments, A has a structure represented by the formula:

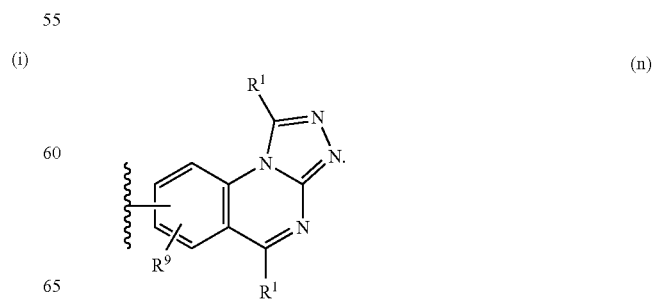

In yet other embodiments, A has a structure represented by the formula:

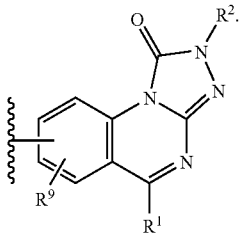
(o)

In yet other embodiments, A has a structure represented by the formula:

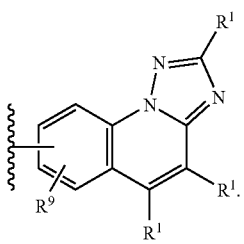
(p)

In yet other embodiments, A has a structure represented by the formula:

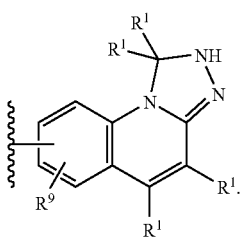
(q)

Any of the combinations of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In one aspect, provided herein are compounds that have a structure represented by Formula (II):

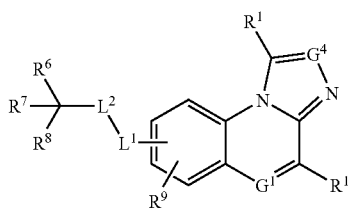
Formula (II)

wherein:
$G^1$ is N or $CR^1$;
$G^4$ is N or $CR^1$;
each $R^1$ is independently H, halide, —CN, —NO$_2$, —OH, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, —NHCH$_2$C(=O)OR$^3$, —C(=O)N(R$^3$)$_2$, —NHC(=O)R$^3$, or —C(OH)(R$^3$)$_2$, or an optionally substituted group selected from among C$_1$-C$_6$alkyl, C$_1$-C$_6$fluoroalkyl, C$_3$-C$_8$cycloalkyl, C$_2$-C$_6$alkenyl, C$_2$-C$_6$alkynyl, and C$_1$-C$_6$fluoroalkoxy; or $R^1$ is $Q^1$-$Q^2$ where $Q^1$ is aryl, monocyclic heterocycloalkyl, monocyclic heteroaryl, bicyclic heteroaryl; and $Q^2$ is H, halide, —CN, —NO$_2$, C$_1$-C$_6$alkyl, C$_1$-C$_6$alkoxy, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, or —C(=O)N(R$^3$)$_2$;

each $R^3$ is independently H, or an optionally substituted group selected from among C$_1$-C$_6$alkyl, C$_2$-C$_6$alkenyl, C$_2$-C$_6$alkynyl, C$_3$-C$_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl, and pyrimidinyl;

$L^1$ is —(CHR$^4$)$_n$X$^1$(CHR$^4$)$_n$— wherein,
each n is independently 0, 1, 2, or 3;
$X^1$ is a bond, O, S, S(=O), S(=O)$_2$, or NR$^5$;
each $R^4$ is independently H, or an optionally substituted group selected from among C$_1$-C$_6$alkyl, C$_3$-C$_8$cycloalkyl, C$_1$-C$_6$fluoroalkyl, C$_2$-C$_6$alkenyl, C$_2$-C$_6$alkynyl, phenyl, and benzyl; or $L^4$-X$^2$-L$^5$-X$^3$ wherein,
$L^4$ is a bond, or an optionally substituted group selected from among C$_1$-C$_6$ alkyl, C$_2$-C$_6$ alkenyl, C$_2$-C$_6$alkynyl, aryl, C$_2$-C$_{10}$heterocycloalkyl, and C$_3$-C$_8$cycloalkyl;
$X^2$ is a bond, O, S, S(=O), S(=O)$_2$, NH, C(=O)NH, or NHC(=O);
$L^5$ is a bond, C$_1$-C$_6$ alkyl, C$_3$-C$_8$cycloalkyl, phenyl, pyridyl, thiazolyl, or thienyl; and
$X^3$ is —OH, —CN, —NO$_2$, halide, —CO$_2$H, —CO$_2$R$^{10}$, —C(=O)R$^{10}$, —CON(R$^{10}$)$_2$, —NHC(=O)R$^{10}$, —C(OH)(R$^{10}$)$_2$, tetrazolyl, —C(=O)NHSO$_2$R$^{10}$, —CH(OH)CF$_3$, —COCF$_3$, —SO$_2$NHC(=O)R$^{10}$, or —N(R$^{10}$)$_2$, where each $R^{10}$ is independently H, or an optionally substituted group selected from among C$_1$-C$_6$alkyl, C$_1$-C$_6$fluoroalkyl, C$_2$-C$_6$alkenyl, C$_2$-C$_6$alkynyl, C$_3$-C$_8$cycloalkyl, phenyl, and benzyl;

$R^5$ is H, or an optionally substituted group selected from among C$_1$-C$_6$alkyl, C$_3$-C$_8$cycloalkyl, C$_1$-C$_6$fluoroalkyl, C$_2$-C$_6$alkenyl, C$_2$-C$_6$alkynyl, phenyl, and benzyl; or
$R^5$ is $L^6$-X$^5$-L$^7$-X$^6$ wherein,
$L^6$ is an optionally substituted group selected from among C$_1$-C$_6$alkyl, C$_2$-C$_{10}$heterocycloalkyl, and C$_3$-C$_8$cycloalkyl;
$X^5$ is a bond, O, S, S(=O), S(=O)$_2$, NH, C(=O)NH, or NHC(=O);
$L^7$ is a bond, C$_1$-C$_6$ alkyl, C$_3$-C$_8$cycloalkyl, phenyl, pyridyl, thiazolyl, or thienyl; and
$X^6$ is —OH, —CN, —NO$_2$, halide, —CO$_2$H, —CO$_2$R$^{10}$, —C(=O)R$^{10}$, —C(OH)(R$^{10}$)$_2$, tetrazolyl, —C(=O)NHSO$_2$R$^{10}$, —CH(OH)CF$_3$, —COCF$_3$, —SO$_2$NHC(=O)R$^{10}$, or —N(R$^{10}$)$_2$, where each $R^{10}$ is independently H, or an optionally substituted group selected from among C$_1$-C$_6$alkyl, C$_1$-C$_6$fluoroalkyl, C$_2$-C$_6$alkenyl, C$_2$-C$_6$alkynyl, C$_3$-C$_8$cycloalkyl, phenyl, and benzyl;

$L^2$ is an optionally substituted group selected from among C$_1$-C$_6$alkyl, aryl, monocyclic heteroaryl, and bicyclic heteroaryl;

$R^6$ and $R^7$ are independently H, or an optionally substituted group selected from among C$_1$-C$_6$haloalkyl, $C_1$-$C_6$alkyl, $C_3$-$C_8$cycloalkyl, $C_2$-$C_6$alkenyl, $C_2$-$C_6$alkynyl, phenyl, benzyl, thiazolyl, $C_1$-$C_6$alkoxy, $C_1$-$C_6$thioalkoxy, and $C_1$-$C_6$alkyl-$X^4$, wherein, $X^4$ is —$CO_2H$, —$CO_2R^{11}$, —C(=O)$R^{11}$, —C(OH)($R^{11}$)$_2$, $C_1$-$C_6$alkoxy, tetrazolyl, —OH, halide, —CN, —$NO_2$, —$SR^{11}$, —S(=O)$R^{11}$, —S(=O)$_2R^{11}$, —N($R^{11}$)$_2$, —CON($R^{11}$)$_2$, —NHC(=O)$R^{11}$—C(=O)NHSO$_2R^{11}$, —CH(OH)CF$_3$, —COCF$_3$, or —SO$_2$NHC(=O)$R^{11}$, where each $R^{11}$ is independently H, or an optionally substituted group selected from among $C_1$-$C_6$alkyl, $C_1$-$C_6$fluoroalkyl, $C_2$-$C_6$alkenyl, $C_2$-$C_6$alkynyl, $C_3$-$C_8$cycloalkyl, phenyl, and benzyl;

or $R^6$ and $R^7$ can together form an optionally substituted 5-, 6-, or 7-membered non-aromatic monocyclic ring containing 0, 1, or 2 heteroatoms selected from among S and O;

or $R^6$ and $R^7$ can together form an optionally substituted bicyclo[3,2,1]ring containing 1 or 2 heteroatoms selected from among S and O;

or $R^6$ and $R^7$ can together form a carbonyl (C=O); and $R^8$ is H, —OH, —CONH$_2$, tetrazolyl, —CN, —N$_3$, $C_1$-$C_6$alkyl, $C_2$-$C_6$alkenyl, —CF$_3$, —CO$_2$H, —OR$^{12}$, —CON(R$^{12}$)$_2$, —CO$_2$—R$^{12}$, —SR$^{12}$, —S(=O)R$^{12}$, S(=O)$_2$R$^{12}$, —SO$_2$N(R$^{12}$)$_2$, C(=O)R$^{12}$, C(OH)(R$^{12}$)$_2$, —CH=N—OR$^{12}$, —N(R$^{12}$)$_2$, NHC(=O)R$^{12}$, —OC(=O)R$^{12}$, or an optionally substituted group selected from among $C_1$-$C_6$fluoroalkoxy, $C_3$-$C_8$cycloalkoxy, benzyl, and phenyl; where each $R^{12}$ is independently H, or an optionally substituted group selected from among $C_1$-$C_6$alkyl, $C_1$-$C_6$fluoroalkyl, $C_2$-$C_6$alkenyl, $C_2$-$C_6$alkynyl, $C_3$-$C_8$cycloalkyl, $C_4$-$C_8$cycloalkylalkyl, phenyl, and benzyl; or $R^6$ and $R^8$ can together form an optionally substituted $C_2$-$C_8$heterocycloalkyl having 1 or 2 O atoms in the ring;

$R^9$ is H, halide, —CN, —NO$_2$, —OH, or an optionally substituted group selected from among $C_1$-$C_6$alkyl, $C_3$-$C_8$cycloalkyl, $C_1$-$C_6$fluoroalkyl, $C_2$-$C_6$alkenyl, $C_2$-$C_6$alkynyl, $C_1$-$C_6$alkoxy, phenyl, and benzyl; or $R^9$ is $L^8$-$X^7$-$L^9$-$X^8$ where, $L^8$ is a bond, or an optionally substituted group selected from $C_1$-$C_6$ alkyl, $C_2$-$C_6$ alkenyl, $C_2$-$C_6$ alkynyl, aryl, $C_2$-$C_{10}$heterocycloalkyl or $C_3$-$C_8$cycloalkyl;

$X^7$ is a bond, O, S, S(=O), S(=O)$_2$, NH, C(=O)NH, or NHC(=O);

$L^9$ is a bond, $C_1$-$C_6$ alkyl, $C_3$-$C_8$ cycloalkyl, phenyl, pyridyl, thiazolyl, or thienyl; and $X^8$ is H, —OH, —CN, —NO$_2$, halide, —CO$_2$H, —CO$_2$R$^{16}$, —C(=O)R$^{16}$, —C(OH)(R$^{16}$)$_2$, —C(=O)N(R$^{16}$)$_2$, —NHC(=O)R$^{16}$, tetrazolyl, —C(O)NHSO$_2$R$^{16}$, —CH(OH)CF$_3$, —COCF$_3$, —SO$_2$NHC(=O)R$^{16}$, or —N(R$^{16}$)$_2$, where each R$^{16}$ is independently H, or an optionally substituted group selected from among $C_1$-$C_6$alkyl, $C_2$-$C_6$alkenyl, $C_2$-$C_6$alkynyl, $C_3$-$C_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl, and pyrimidinyl;

or a pharmaceutically acceptable salt, pharmaceutically acceptable N-oxide, pharmaceutically active metabolite, pharmaceutically acceptable prodrug, or pharmaceutically acceptable solvate thereof For any and all of the embodiments, substituents can be selected from among from a subset of the listed alternatives. For example, in some embodiments, $R^9$ is H, halide, —CN, —NO$_2$, —OH, or an optionally substituted group selected from among $C_1$-$C_6$alkyl, $C_1$-$C_6$fluoroalkyl, and $C_1$-$C_6$alkoxy.

In other embodiments, $R^9$ is H, halide, —CN, —OH, or an optionally substituted group selected from among $C_1$-$C_6$alkyl, and $C_1$-$C_6$alkoxy. In yet other embodiments, $R^9$ is H, halide, or an optionally substituted group selected from among $C_1$-$C_6$alkyl, and $C_1$-$C_6$alkoxy. In some other embodiments, $R^9$ is H.

In some embodiments, $L^1$ is selected from among —(CHR$^4$)$_n$—, —(CHR$^4$)$_n$O—, —(CHR$^4$)$_n$S—, —O(CHR$^4$)$_n$—, and —S(CHR$^4$)$_n$—; n is 0, 1, 2, or 3. In other embodiments, each $R^4$ is independently H, or an optionally substituted group selected from among $C_1$-$C_6$alkyl, $C_3$-$C_8$cycloalkyl, $C_1$-$C_6$fluoroalkyl; or $L^4$-$X^2$-$L^5$-$X^3$ where, $L^4$ is a bond, or an optionally substituted group selected from among $C_1$-$C_6$ alkyl, $C_2$-$C_{10}$ heterocycloalkyl, and $C_3$-$C_8$ cycloalkyl; $X^2$ is a bond, O, S, S(=O), or S(=O)$_2$; $L^5$ is a bond, $C_1$-$C_6$ alkyl, $C_3$-$C_8$cycloalkyl, phenyl, pyridyl, thiazolyl, or thienyl; and $X^3$ is OH, CN, NO$_2$, halide, CO$_2$H, CO$_2$R$^{10}$, C(=O)R$^{10}$, C(OH)(R$^{10}$)$_2$, tetrazolyl, C(=O)NHSO$_2$R$^{10}$, CH(OH)CF$_3$, COCF$_3$, SO$_2$NHC(=O)R$^{10}$, or N(R$^{10}$)$_2$, where each R$^{10}$ is independently H, or an optionally substituted group selected from among $C_1$-$C_6$alkyl, $C_3$-$C_8$cycloalkyl, phenyl, and benzyl. In some other embodiments, each $R^4$ is independently H, or an optionally substituted group selected from among $C_1$-$C_6$alkyl, and $C_1$-$C_6$fluoroalkyl; and n is 0, 1, or 2. In yet other embodiments, n is 0 or 1. In some other embodiments, each $R^4$ is independently H, or a $C_1$-$C_6$alkyl. In some other embodiments, $R^4$ is H.

In some embodiments, each $R^1$ is independently H, halide, —CN, —NO$_2$, —OH, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, —NHCH$_2$C(=O)OR$^3$, —C(=O)N(R$^3$)$_2$, —NHC(=O)R$^3$, or —C(OH)(R$^3$)$_2$, or an optionally substituted group selected from among $C_1$-$C_6$alkyl, $C_1$-$C_6$fluoroalkyl, $C_3$-$C_8$cycloalkyl, $C_2$-$C_6$alkenyl, $C_2$-$C_6$alkynyl, and $C_1$-$C_6$fluoroalkoxy; or $R^1$ is $Q^1$-$Q^2$ where $Q^1$ is aryl, monocyclic heterocycloalkyl, monocyclic heteroaryl; and $Q^2$ is H, halide, —CN, —NO$_2$, $C_1$-$C_6$alkyl, $C_1$-$C_6$alkoxy, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, or —C(=O)N(R$^3$)$_2$.

In other embodiments, $R^6$ and $R^7$ are independently H, or an optionally substituted group selected from among $C_1$-$C_6$haloalkyl, $C_1$-$C_6$alkyl, $C_3$-$C_8$cycloalkyl, $C_2$-$C_6$alkenyl, $C_2$-$C_6$alkynyl, thiazolyl, $C_1$-$C_6$alkoxy, $C_1$-$C_6$thioalkoxy, and $C_1$-$C_6$alkyl-$X^4$, wherein, $X^4$ is —CO$_2$H, —CO$_2$R$^{11}$, $C_1$-$C_6$alkoxy, tetrazolyl, —OH, —CON(R$^{11}$)$_2$, where each R$^{11}$ is independently H, or an optionally substituted group selected from among $C_1$-$C_6$alkyl, and $C_1$-$C_6$fluoroalkyl; or $R^6$ and $R^7$ can together form an optionally substituted 5-, 6-, or 7-membered monocyclic ring containing 0, 1, or 2 heteroatoms selected from among S and O; or $R^6$ and $R^7$ can together form a carbonyl (C=O).

In some embodiments, $R^6$ and $R^7$ are independently H, or an optionally substituted group selected from among $C_1$-$C_6$haloalkyl, $C_1$-$C_6$alkyl, $C_3$-$C_8$cycloalkyl, and $C_1$-$C_6$alkyl-$X^4$, wherein, $X^4$ is —CO$_2$H, —CO$_2$R$^{11}$, or —CON(R$^{11}$)$_2$, where each R$^{11}$ is independently H, or an optionally substituted $C_1$-$C_6$alkyl; or $R^6$ and $R^7$ can together form an optionally substituted 5-, 6-, or 7-membered monocyclic ring containing 0, 1, or 2 heteroatoms selected from S and O; or $R^6$ and $R^7$ can together form a carbonyl (C=O).

In some embodiments, $R^6$ and $R^7$ are independently H, or an optionally substituted group selected from among $C_1$-$C_6$haloalkyl, $C_1$-$C_6$alkyl, $C_3$-$C_8$cycloalkyl, and $C_1$-$C_6$alkyl-$X^4$, wherein, $X^4$ is —CO$_2$H, —CO$_2$R$^{11}$, or —CON(R$^{11}$)$_2$, where each R$^{11}$ is independently H, or an optionally substituted $C_1$-$C_6$alkyl; or $R^6$ and $R^7$ can together form an optionally substituted 6-membered monocyclic ring containing 1 O atom; or $R^6$ and $R^7$ can together form a carbonyl (C=O).

In some embodiments, $R^8$ is H, —OH, —$CONH_2$, tetrazolyl, —CN, $C_1$-$C_6$alkyl, $C_2$-$C_6$alkenyl, —$CF_3$, —$CO_2H$, —$OR^{12}$, —$CON(R^{12})_2$, —$CO_2$—$R^{12}$, —$SR^{12}$, —S(=O) $R^{12}$, S(=O)$_2R^{12}$, —$SO_2N(R^{12})_2$, C(=O)$R^{12}$, C(OH)($R^{12}$)$_2$, —CH=N—$OR^{12}$, —OC(=O)$R^{12}$, or an optionally substituted group selected from among $C_1$-$C_6$fluoroalkoxy, $C_3$-$C_8$cycloalkoxy, benzyl, and phenyl; where each $R^{12}$ is independently H, or an optionally substituted group selected from among $C_1$-$C_6$alkyl, $C_1$-$C_6$fluoroalkyl, $C_3$-$C_8$cycloalkyl, $C_4$-$C_8$cycloalkylalkyl, phenyl, and benzyl.

In some embodiments, provided herein are compounds that have a structure selected from among:

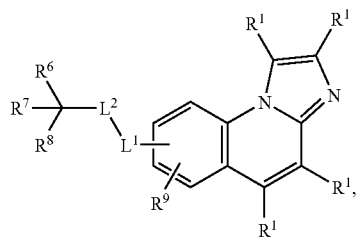
Formula (IIa)

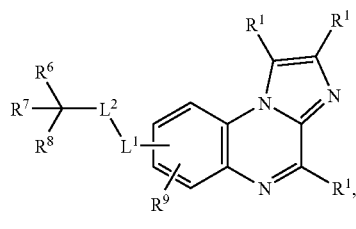
Formula (IIb)

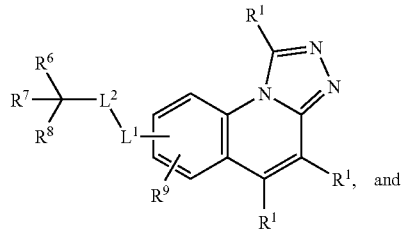
Formula (IIc)

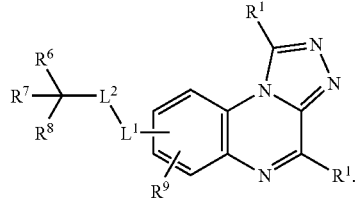
Formula (IId)

In some embodiments, compounds provided herein have a structure selected from among:

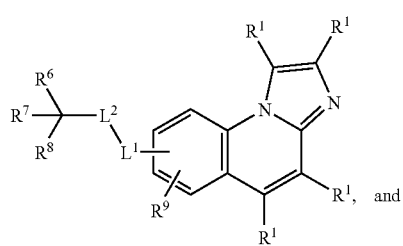
Formula (IIa)

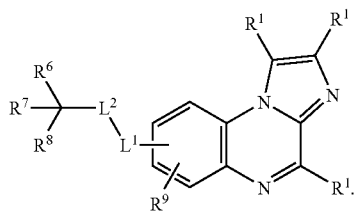
Formula (IIb)

In some embodiments, compounds provided herein have a structure of Formula (IIa):

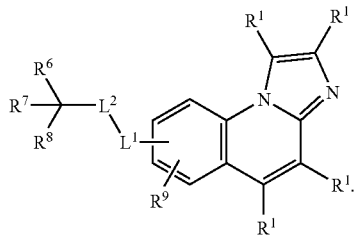
Formula (IIa)

In some embodiments, compounds provided herein have a structure of Formula (IIb):

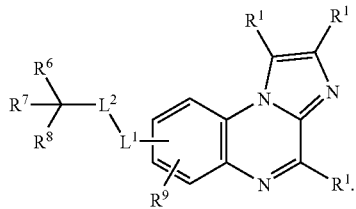
Formula (IIb)

In some embodiments, compounds provided herein have a structure selected from among:

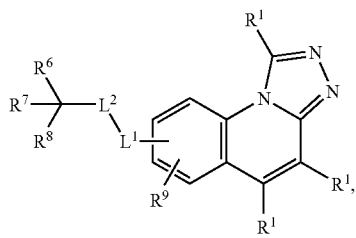
Formula (IIc)

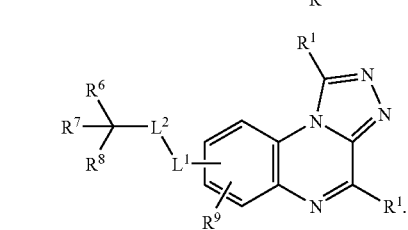
Formula (IId)

In some embodiments, compounds provided herein have a structure of Formula (IIc):

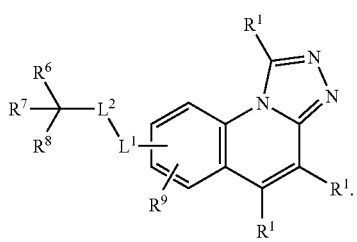

Formula (IIc)

In some embodiments, compounds provided herein have a structure of Formula (IId):

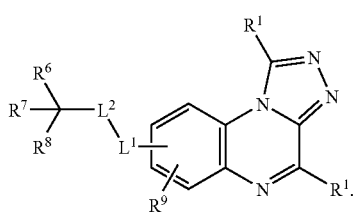

Formula (IId)

In some embodiments, L² is an optionally substituted group selected from among $C_1$-$C_6$alkyl, phenyl, and a 5- or 6-membered monocyclic heteroaryl. In some other embodiments, L² is an optionally substituted group selected from among $C_1$-$C_6$alkyl, phenyl, thienyl, thiazolyl, oxazolyl, furanyl, pyrrolyl, imidazolyl, and pyridyl.

In some embodiments, L² is selected from among $C_1$-$C_6$alkyl,

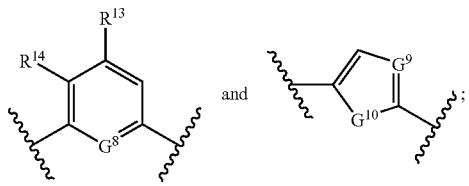

where, $G^8$ is N or CH; $G^9$ is N or CH; and $G^{10}$ is NR², O or S; R² is independently H, —C(=O)R³, C(=O)OR³, —CH(R³)₂, —C(=O)N(R³)₂, or an optionally substituted group selected from $C_1$-$C_6$alkyl, $C_1$-$C_6$fluoroalkyl, $C_3$-$C_8$cycloalkyl, $C_2$-$C_6$alkenyl, $C_2$-$C_6$alkynyl, aryl, monocyclic heterocycloalkyl, monocyclic heteroaryl, and bicyclic heteroaryl; each R³ is independently H, or an optionally substituted group selected from among $C_1$-$C_6$alkyl, $C_2$-$C_6$alkenyl, $C_2$-$C_6$alkynyl, $C_3$-$C_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl, and pyrimidinyl; $R^{13}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$—S—, $R^{17}$—S(=O)—, $R^{17}$—S(=O)₂—, —CN, halide, $R^{17}$C(=O)—, $R^{17}$C(=O)O—, $R^{17}$NHC(=O)—, —$R^{17}$—C(=O)NH—, $R^{17}$S(=O)₂NH—, $R^{17}$—NHS(=O)₂—, $R^{17}$—OC(=O)NH—, $R^{17}$—NHC(=O)O—, —NO₂, $C_1$-$C_6$haloalkyl, and —N($R^{17}$)₂; $R^{17}$ is independently selected from among H, $C_1$-$C_6$alkyl, $C_3$-$C_8$cycloalkyl, aryl, heteroaryl, and $C_1$-$C_6$heteroalkyl; $R^{14}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$—S—, $R^{17}$—S(=O)—, $R^{17}$—S(=O)₂—, —CN, halide, $R^{17}$C(=O)—, $R^{17}$C(=O)O—, $R^{17}$NHC(=O)—, $R^{17}$—C(=O)NH—, $R^{17}$S(=O)₂NH—, $R^{17}$—NHS(=O)₂—, $R^{17}$—OC(=O)NH—, $R^{17}$—NHC(=O)O—, —NO₂, $C_1$-$C_6$haloalkyl, and —N($R^{17}$)₂; $R^{17}$ is independently selected from among H, $C_1$-$C_6$alkyl, $C_3$-$C_8$cycloalkyl, aryl, heteroaryl, and $C_1$-$C_6$heteroalkyl.

In some embodiments, L² is

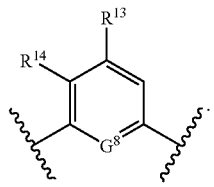

In some embodiments, $G^8$ is CH. In other embodiments, $G^8$ is N.

In some embodiments, L² is

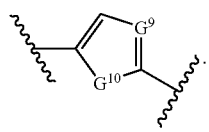

In some embodiments, $G^9$ is N; and $G^{10}$ is O or S. In other embodiments, $G^{10}$ is S.

In some embodiments, L² is an optionally substituted $C_1$-$C_6$alkyl.

In some embodiments, L² is selected from among $C_1$-$C_6$alkyl,

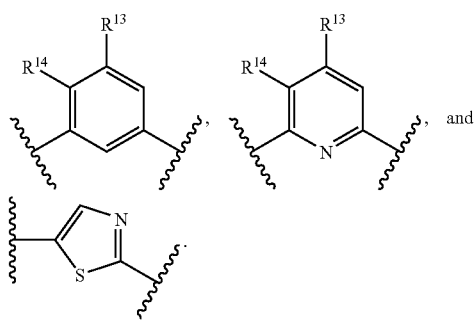

In other embodiments, L² is selected from among

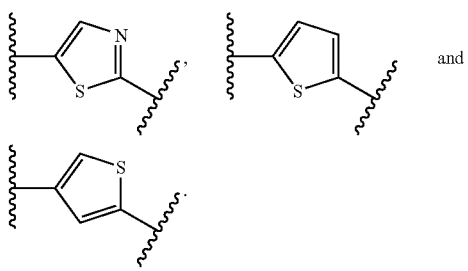

In some other embodiments, L² is

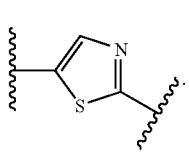

In some embodiments, $L^2$ is selected from among

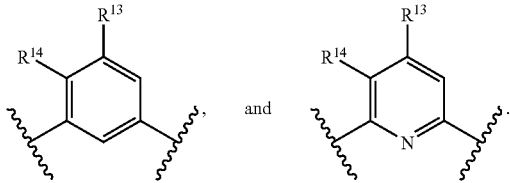

and

In some embodiments, $L^2$ is

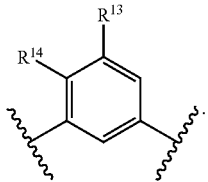

In other embodiments, $L^2$ is

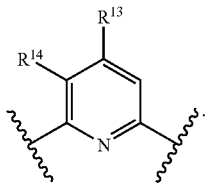

In some embodiments, $R^{13}$ is H, $C_1$-$C_6$alkyl, —OH, $C_1$-$C_6$alkoxy, —CN, or halide; $R^{14}$ is H, $C_1$-$C_6$alkyl, —OH, $C_1$-$C_6$alkoxy, —CN, or halide. In some other embodiments, $R^{13}$ is H, $C_1$-$C_6$alkyl, $C_1$-$C_6$alkoxy, or halide; $R^{14}$ is H, $C_1$-$C_6$alkyl, —OH, $C_1$-$C_6$alkoxy, or halide. In yet other embodiments, $R^{13}$ is H, or halide; $R^{14}$ is H, —OH, $C_1$-$C_6$alkoxy, or halide.

In some embodiments, compounds provided herein have a structure of Formula (III):

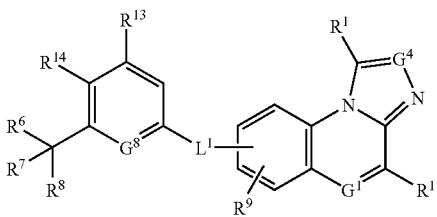

Formula (III)

wherein:
$G^8$ is N or CH;
$R^{13}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$—S—,
$R^{17}$—S(=O)—, $R^{17}$—S(=O)$_2$—, —CN, halide, $R^{17}$C(=O)—, $R^{17}$C(=O)O—, $R^{17}$NHC(=O)—, $R^{17}$—C(=O)NH—, $R^{17}$S(=O)$_2$NH—,
$R^{17}$—NHS(=O)$_2$—, $R^{17}$—OC(=O)NH—, $R^7$—NHC(=O)O—, —NO$_2$, $C_1$-$C_6$haloalkyl, and —N($R^{17}$)$_2$;
$R^{17}$ is independently selected from among H, $C_1$-$C_6$alkyl, $C_3$-$C_8$cycloalkyl, aryl, heteroaryl, and $C_1$-$C_6$heteroalkyl.
$R^{14}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$—S—,
$R^{17}$—S(=O)—, $R^{17}$—S(=O)$_2$—, —CN, halide, $R^{17}$C(=O)—, $R^{17}$C(=O)O—, $R^{17}$NHC(=O)—, $R^{17}$—C(=O)NH—, $R^{17}$S(=O)$_2$NH—,
$R^{17}$—NHS(=O)$_2$—, $R^{17}$—OC(=O)NH—, $R^{17}$—NHC(=O)O—, —NO$_2$, $C_1$-$C_6$haloalkyl, and —N($R^{17}$)$_2$;
$R^{17}$ is independently selected from among H, $C_1$-$C_6$alkyl, $C_3$-$C_8$cycloalkyl, aryl, heteroaryl, and $C_1$-$C_6$heteroalkyl; or
$R^8$ and $R^{14}$ taken together can form a optionally substituted 5-, or 6-membered ring.

In some embodiments, compounds provided herein have a structure of Formula (IIIa):

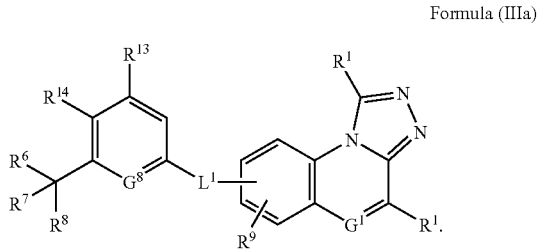

Formula (IIIa)

In some embodiments, compounds provided herein have a structure of Formula (IIIb):

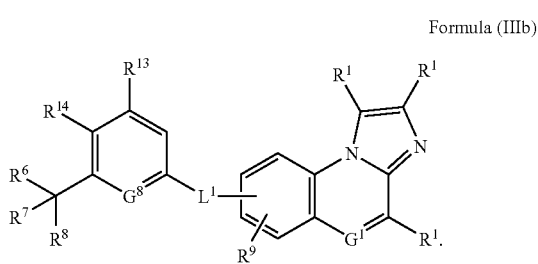

Formula (IIIb)

In some embodiments, $G^8$ is CH. In other embodiments, $G^8$ is N.

In some embodiments, $G^1$ is $CR^1$. In yet other embodiments, $G^1$ is N.

In some embodiments, described herein is a compound having a structure represented by Formula (IIIc):

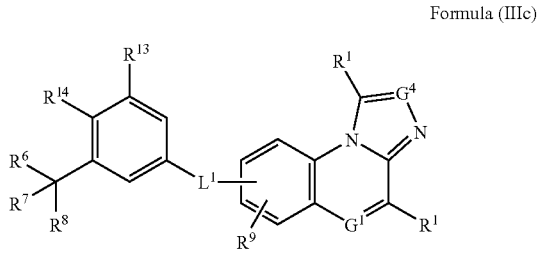

Formula (IIIc)

wherein:
$G^1$ is N or $CR^1$;
$G^4$ is N or $CR^1$;
each $R^1$ is independently H, halide, —CN, —NO$_2$, —OH, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, —NHCH$_2$C(=O)OR$^3$, —C(=O)N(R$^3$)$_2$, —NHC(=O)R$^3$, or —C(OH)(R$^3$)$_2$, or an optionally substituted group selected from among $C_1$-$C_6$alkyl, $C_1$-$C_6$fluoroalkyl, $C_3$-$C_8$cycloalkyl, $C_2$-$C_6$alkenyl, $C_2$-$C_6$alkynyl, and $C_1$-$C_6$fluoroalkoxy; or $R^1$ is $Q^1$-$Q^2$ where $Q^1$ is aryl, monocyclic heterocycloalkyl, monocyclic heteroaryl, bicyclic heteroaryl; and $Q^2$ is H, halide, —CN, —NO$_2$, $C_1$-$C_6$alkyl, $C_1$-$C_6$alkoxy, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, or —C(=O)N(R$^3$)$_2$;

each $R^3$ is independently H, or an optionally substituted group selected from among $C_1$-$C_6$alkyl, $C_2$-$C_6$alkenyl, $C_2$-$C_6$alkynyl, $C_3$-$C_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl, and pyrimidinyl;

$L^1$ is —(CHR$^4$)$_n$X$^1$(CHR$^4$)$_n$— wherein,
each n is independently 0, 1, 2, or 3;
$X^1$ is a bond, O, S, S(=O), S(=O)$_2$, or NR$^5$;
each $R^4$ is independently H, or an optionally substituted group selected from among $C_1$-$C_6$alkyl, $C_3$-$C_8$cycloalkyl, $C_1$-$C_6$fluoroalkyl, $C_2$-$C_6$alkenyl, $C_2$-$C_6$alkynyl, phenyl, and benzyl; or $L^4$-$X^2$-$L^5$-$X^3$ wherein,
 $L^4$ is a bond, or an optionally substituted group selected from among $C_1$-$C_6$ alkyl, $C_2$-$C_6$ alkenyl, $C_2$-$C_6$ alkynyl, aryl, $C_2$-$C_{10}$heterocycloalkyl, and $C_3$-$C_8$cycloalkyl;
 $X^2$ is a bond, O, S, S(=O), S(=O)$_2$, NH, C(=O)NH, or NHC(=O);
 $L^5$ is a bond, $C_1$-$C_6$ alkyl, $C_3$-$C_8$cycloalkyl, phenyl, pyridyl, thiazolyl, or thienyl; and
 $X^3$ is —OH, —CN, —NO$_2$, halide, —CO$_2$H, —CO$_2$R$^{10}$, —C(=O)R$^{10}$, —CON(R$^{10}$)$_2$, —NHC(=O)R$^{10}$, —C(OH)(R$^{10}$)$_2$, tetrazolyl, —C(=O)NHSO$_2$R$^{10}$, —CH(OH)CF$_3$, —COCF$_3$, —SO$_2$NHC(=O)R$^{10}$, or —N(R$^{10}$)$_2$, where each $R^{10}$ is independently H, or an optionally substituted group selected from among $C_1$-$C_6$alkyl, $C_1$-$C_6$fluoroalkyl, $C_2$-$C_6$alkenyl, $C_2$-$C_6$alkynyl, $C_3$-$C_8$cycloalkyl, phenyl, and benzyl;

$R^5$ is H, or an optionally substituted group selected from among $C_1$-$C_6$alkyl, $C_3$-$C_8$cycloalkyl, $C_1$-$C_6$fluoroalkyl, $C_2$-$C_6$alkenyl, $C_2$-$C_6$alkynyl, phenyl, and benzyl;

$R^6$ and $R^7$ are independently H, or an optionally substituted group selected from among $C_1$-$C_6$haloalkyl, $C_1$-$C_6$alkyl, $C_3$-$C_8$cycloalkyl, $C_2$-$C_6$alkenyl, $C_2$-$C_6$alkynyl, phenyl, benzyl, thiazolyl, $C_1$-$C_6$alkoxy, $C_1$-$C_6$thioalkoxy, and $C_1$-$C_6$alkyl-X$^4$, wherein,
 $X^4$ is —CO$_2$H, —CO$_2$R$^{11}$, —C(=O)R$^{11}$, —C(OH)(R$^{11}$)$_2$, $C_1$-$C_6$alkoxy, tetrazolyl, —OH, halide, —CN, —NO$_2$, —SR$^{11}$, —S(=O)R$^{11}$, —S(=O)$_2$R$^{11}$, —N(R$^{11}$)$_2$, —CON(R$^{11}$)$_2$, —NHC(=O)R$^{11}$—C(=O)NHSO$_2$R$^{11}$, —CH(OH)CF$_3$, —COCF$_3$, or —SO$_2$NHC(=O)R$^{11}$, where each $R^{11}$ is independently H, or an optionally substituted group selected from among $C_1$-$C_6$alkyl, $C_1$-$C_6$fluoroalkyl, $C_2$-$C_6$alkenyl, $C_2$-$C_6$alkynyl, $C_3$-$C_8$cycloalkyl, phenyl, and benzyl;

or $R^6$ and $R^7$ can together form an optionally substituted 5-, 6-, or 7-membered non-aromatic monocyclic ring containing 0, 1, or 2 heteroatoms selected from among S and O;

or $R^6$ and $R^7$ can together form an optionally substituted bicyclo[3,2,1]ring containing 1 or 2 heteroatoms selected from among S and O;

or $R^6$ and $R^7$ can together form a carbonyl (C=O); and $R^8$ is H, —OH, —CONH$_2$, tetrazolyl, —CN, —N$_3$, $C_1$-$C_6$alkyl, $C_2$-$C_6$alkenyl, —CF$_3$, —CO$_2$H, —OR$^2$, —CON(R$^{12}$)$_2$, —CO$_2$—R$^{12}$, —SR$^{12}$, —S(=O)R$^{12}$, S(=O)$_2$R$^{12}$, —SO$_2$N(R$^{12}$)$_2$, C(=O)R$^{12}$, C(OH)(R$^{12}$)$_2$, —CH=N—OR$^{12}$, —N(R$^{12}$)$_2$, NHC(=O)R$^{12}$, —OC(=O)R$^{12}$, or an optionally substituted group selected from among $C_1$-$C_6$fluoroalkoxy, $C_3$-$C_8$cycloalkoxy, benzyl, and phenyl; where each $R^{12}$ is independently H, or an optionally substituted group selected from among $C_1$-$C_6$alkyl, $C_1$-$C_6$fluoroalkyl, $C_2$-$C_6$alkenyl, $C_2$-$C_6$alkynyl, $C_3$-$C_8$cycloalkyl, $C_4$-$C_8$cycloalkylalkyl, phenyl, and benzyl;

$R^6$ and $R^8$ can together form an optionally substituted $C_2$-$C_8$heterocycloalkyl having 1 or 2 O atoms in the ring;

$R^9$ is H, halide, —CN, —NO$_2$, —OH, or an optionally substituted group selected from among $C_1$-$C_6$alkyl, $C_3$-$C_8$cycloalkyl, $C_1$-$C_6$fluoroalkyl, $C_2$-$C_6$alkenyl, $C_2$-$C_6$alkynyl, $C_1$-$C_6$alkoxy, phenyl, and benzyl;

$R^{13}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$S—,
$R^{17}$S(=O)—, $R^{17}$S(=O)$_2$—, —CN, halide, $R^{17}$C(=O)—, $R^{17}$C(=O)O—, $R^{17}$NHC(=O)—, —R$^{17}$—C(=O)NH—, $R^{17}$S(=O)$_2$NH—,
$R^{17}$—NHS(=O)$_2$—, $R^{17}$—OC(=O)NH—, $R^{17}$—NHC(=O)O—, —NO$_2$, $C_1$-$C_6$haloalkyl, and —N(R$^{17}$)$_2$;

$R^{17}$ is independently selected from among H, $C_1$-$C_6$alkyl, $C_3$-$C_8$cycloalkyl, aryl, heteroaryl, and $C_1$-$C_6$heteroalkyl.

$R^{14}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$S—,
$R^{17}$S(=O)—, $R^{17}$S(=O)$_2$—, —CN, halide, $R^{17}$C(=O)—, $R^{17}$C(=O)O—, $R^{17}$NHC(=O)—, —R$^{17}$—C(=O)NH—, $R^{17}$S(=O)$_2$NH—,
$R^{17}$—NHS(=O)$_2$—, $R^{17}$—OC(=O)NH—, $R^{17}$—NHC(=O)O—, —NO$_2$, $C_1$-$C_6$haloalkyl, and —N(R$^{17}$)$_2$;

$R^{17}$ is independently selected from among H, $C_1$-$C_6$alkyl, $C_3$-$C_8$cycloalkyl, aryl, heteroaryl, and $C_1$-$C_6$heteroalkyl; or $R^8$ and $R^{14}$ taken together can form an optionally substituted 5-, or 6-membered ring;

or a pharmaceutically acceptable salt, pharmaceutically acceptable N-oxide, pharmaceutically active metabolite, pharmaceutically acceptable prodrug, or pharmaceutically acceptable solvate thereof.

For any and all of the embodiments, substituents can be selected from among from a subset of the listed alternatives. For example, in some embodiments, $R^9$ is H, halide, —CN, —NO$_2$, —OH, or an optionally substituted group selected from among $C_1$-$C_6$alkyl, $C_1$-$C_6$fluoroalkyl, and $C_1$-$C_6$alkoxy. In other embodiments, $R^9$ is H.

In some embodiments, $L^1$ is selected from among —(CHR$^4$)$_n$—, —(CHR$^4$)$_n$O—, —(CHR$^4$)$_n$S—, —O(CHR$^4$)$_n$—, and —S(CHR$^4$)$_n$—; each $R^4$ is independently H, or an optionally substituted group selected from among $C_1$-$C_6$alkyl, and $C_1$-$C_6$fluoroalkyl; n is 0, 1, or 2. In some other embodiments, each $R^4$ is H; n is 0 or 1.

In some embodiments, $R^{13}$ is H, $C_1$-$C_6$alkyl, —OH, $C_1$-$C_6$alkoxy, —CN, halide, or $C_1$-$C_6$haloalkyl; $R^{14}$ is H, $C_1$-$C_6$alkyl, —OH, $C_1$-$C_6$alkoxy, —CN, halide, or $C_1$-$C_6$haloalkyl; or $R^8$ and $R^{14}$ taken together can form an optionally substituted 5-, or 6-membered ring.

In some embodiments, each $R^1$ is independently H, halide, —CN, —NO$_2$, —OH, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, —NHCH$_2$C(=O)OR$^3$, —C(=O)N(R$^3$)$_2$, —NHC(=O)R$^3$, or —C(OH)(R$^3$)$_2$, or an optionally substituted group selected from among $C_1$-$C_6$alkyl, $C_1$-$C_6$fluoroalkyl, $C_3$-$C_8$cycloalkyl, $C_2$-$C_6$alkenyl, $C_2$-$C_6$alkynyl, and $C_1$-$C_6$fluoroalkoxy; or $R^1$ is $Q^1$-$Q^2$ where $Q^1$ is aryl, monocyclic heterocycloalkyl, monocyclic heteroaryl; and $Q^2$ is H, halide, —CN, —NO$_2$, $C_1$-$C_6$alkyl, $C_1$-$C_6$alkoxy, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, or —C(=O)N(R$^3$)$_2$.

In some embodiments, $R^6$ and $R^7$ are independently H, or an optionally substituted group selected from among $C_1$-$C_6$haloalkyl, $C_1$-$C_6$alkyl, $C_3$-$C_8$cycloalkyl, $C_2$-$C_6$alkenyl, $C_2$-$C_6$alkynyl, thiazolyl, $C_1$-$C_6$alkoxy, $C_1$-$C_6$thioalkoxy, and $C_1$-$C_6$alkyl-X$^4$, wherein, X$^4$ is —CO$_2$H, —CO$_2$R$^{11}$, $C_1$-$C_6$alkoxy, tetrazolyl, —OH, —CON(R$^{11}$)$_2$, where each $R^{11}$ is independently H, or an optionally substituted group selected from among $C_1$-$C_6$alkyl, and $C_1$-$C_6$fluoroalkyl; or $R^6$ and $R^7$ can together form an optionally substituted 5-, 6-, or 7-membered monocyclic ring containing 0, 1, or 2 heteroatoms selected from among S and O; or $R^6$ and $R^7$ can together form a carbonyl (C=O).

In yet other embodiments, $R^6$ and $R^7$ are independently H, or an optionally substituted group selected from among $C_1$-$C_6$haloalkyl, $C_1$-$C_6$alkyl, $C_3$-$C_8$cycloalkyl, $C_2$-$C_6$alkenyl, and $C_1$-$C_6$alkyl-X$^4$, wherein, X$^4$ is —CO$_2$H, —CO$_2$R$^{11}$, or —CON(R$^{11}$)$_2$, where each $R^{11}$ is independently H, or an optionally substituted $C_1$-$C_6$alkyl; or $R^6$ and $R^7$ can together form an optionally substituted 6-membered monocyclic ring containing 0 or 1 O atoms; or $R^6$ and $R^7$ can together form a carbonyl (C=O).

In some embodiments, $R^8$ is H, —OH, —CONH$_2$, tetrazolyl, —CN, $C_1$-$C_6$alkyl, $C_2$-$C_6$alkenyl, —CF$_3$, —CO$_2$H, —OR$^2$, —CON(R$^2$)$_2$, —CO$_2$—R$^2$, —SR$^2$, —S(=O)R$^2$, S(=O)$_2$R$^2$, —SO$_2$N(R$^2$)$_2$, C(=O)R$^2$, C(OH)(R$^2$)$_2$, —CH=N—OR$^{12}$, or —OC(=O)R$^{12}$; where each $R^{12}$ is independently H, or an optionally substituted group selected from among $C_1$-$C_6$alkyl, $C_1$-$C_6$fluoroalkyl, $C_3$-$C_8$cycloalkyl, $C_4$-$C_8$cycloalkylalkyl, phenyl, and benzyl.

In some embodiments, $G^4$ is CR$^1$. In yet other embodiments, $G^4$ is N.

In some embodiments, $G^1$ is CR$^1$. In some other embodiments, $G^1$ is N.

In some embodiments, compounds provided herein have a structure of Formula (IV):

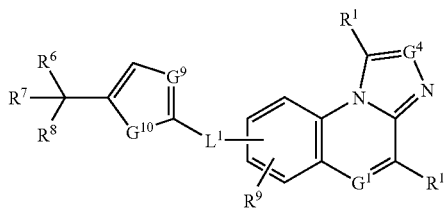

Formula (IV)

wherein:
$G^9$ is N or CH; and
$G^{10}$ is NR$^2$, O or S;
$R^2$ is independently H, —C(=O)R$^3$, C(=O)OR$^3$, —CH(R$^3$)$_2$, —C(=O)N(R$^3$)$_2$, or an optionally substituted group selected from $C_1$-$C_6$alkyl, $C_1$-$C_6$fluoroalkyl, $C_3$-$C_8$cycloalkyl, $C_2$-$C_6$alkenyl, $C_2$-$C_6$alkynyl, aryl, monocyclic heterocycloalkyl, monocyclic heteroaryl, and bicyclic heteroaryl;
$R^3$ is independently H, or an optionally substituted group selected from among $C_1$-$C_6$alkyl, $C_2$-$C_6$alkenyl, $C_2$-$C_6$alkynyl, $C_3$-$C_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl, and pyrimidinyl.

In some embodiments, $G^9$ is N; and $G^{10}$ is O or S. In other embodiments, $G^{10}$ is S.

In some embodiments, compounds provided herein have a structure of Formula (V):

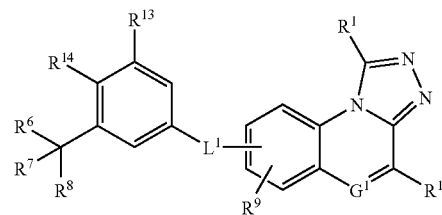

Formula (V)

wherein:
$G^1$ is N or CR$^1$;
each $R^1$ is independently H, halide, —CN, —NO$_2$, —OH, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, —NHCH$_2$C(=O)OR$^3$, —C(=O)N(R$^3$)$_2$, —NHC(=O)R$^3$, or —C(OH)(R$^3$)$_2$, or an optionally substituted group selected from among $C_1$-$C_6$alkyl, $C_1$-$C_6$fluoroalkyl, $C_3$-$C_8$cycloalkyl, $C_2$-$C_6$alkenyl, $C_2$-$C_6$alkynyl, and $C_1$-$C_6$fluoroalkoxy; or
$R^1$ is $Q^1$-$Q^2$ where $Q^1$ is aryl, monocyclic heterocycloalkyl, monocyclic heteroaryl, bicyclic heteroaryl; and $Q^2$ is H, halide, —CN, —NO$_2$, $C_1$-$C_6$alkyl, $C_1$-$C_6$alkoxy, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, or —C(=O)N(R$^3$)$_2$;
each $R^3$ is independently H, or an optionally substituted group selected from among $C_1$-$C_6$alkyl, $C_2$-$C_6$alkenyl, $C_2$-$C_6$alkynyl, $C_3$-$C_8$cycloalkyl, phenyl, benzyl, thienyl, furanyl, thiazolyl, pyridyl, oxazolyl, oxadiazolyl, thiadiazolyl, imidazolyl, triazolyl, tetrazolyl, pyridonyl, and pyrimidinyl;
$L^1$ is —(CHR$^4$)$_n$X$^1$(CHR$^4$)$_n$— wherein,
each n is independently 0, 1, 2, or 3;
$X^1$ is a bond, O, S, S(=O), S(=O)$_2$, or NR$^5$;
each $R^4$ is independently H, or an optionally substituted group selected from among $C_1$-$C_6$alkyl, $C_3$-$C_8$cycloalkyl, $C_1$-$C_6$fluoroalkyl, $C_2$-$C_6$alkenyl, $C_2$-$C_6$alkynyl, phenyl, and benzyl; or $L^4$-$X^2$-$L^5$-$X^3$ wherein,
$L^4$ is a bond, or an optionally substituted group selected from among $C_1$-$C_6$ alkyl, $C_2$-$C_6$ alkenyl, $C_2$-$C_6$ alkynyl, aryl, $C_2$-$C_{10}$heterocycloalkyl, and $C_3$-$C_8$cycloalkyl;
$X^2$ is a bond, O, S, S(=O), S(=O)$_2$, NH, C(=O)NH, or NHC(=O);
$L^5$ is a bond, $C_1$-$C_6$ alkyl, $C_3$-$C_8$ cycloalkyl, phenyl, pyridyl, thiazolyl, or thienyl; and
$X^3$ is —OH, —CN, —NO$_2$, halide, —CO$_2$H, —CO$_2$R$^{10}$, —C(=O)R$^{10}$, —CON(R$^{10}$)$_2$, —NHC(=O)R$^{10}$, —C(OH)(R$^{10}$)$_2$, tetrazolyl, —C(=O)NHSO$_2$R$^{10}$, —CH(OH)CF$_3$, —COCF$_3$, —SO$_2$NHC(=O)R$^{10}$, or —N(R$^{10}$)$_2$, where each $R^{10}$ is independently H, or an optionally substituted group selected from among $C_1$-$C_6$alkyl, $C_1$-$C_6$fluoroalkyl, $C_2$-$C_6$alkenyl, $C_2$-$C_6$alkynyl, $C_3$-$C_8$cycloalkyl, phenyl, and benzyl;

$R^5$ is H, or an optionally substituted group selected from among $C_1$-$C_6$alkyl, $C_3$-$C_8$cycloalkyl, $C_1$-$C_6$fluoroalkyl, $C_2$-$C_6$alkenyl, $C_2$-$C_6$alkynyl, phenyl, and benzyl;

$R^6$ and $R^7$ are independently H, or an optionally substituted group selected from among $C_1$-$C_6$haloalkyl, $C_1$-$C_6$alkyl, $C_3$-$C_8$cycloalkyl, $C_2$-$C_6$alkenyl, $C_2$-$C_6$alkynyl, phenyl, benzyl, thiazolyl, $C_1$-$C_6$alkoxy, $C_1$-$C_6$thioalkoxy, and $C_1$-$C_6$alkyl-$X^4$, wherein, $X^4$ is —$CO_2$H, —$CO_2R^{11}$, —C(=O)$R^{11}$, —C(OH)($R^{11}$)$_2$, $C_1$-$C_6$alkoxy, tetrazolyl, —OH, halide, —CN, —$NO_2$, —$SR^{11}$, —S(=O)$R^{11}$, —S(=O)$_2R^{11}$, —N($R^{11}$)$_2$, —CON($R^{11}$)$_2$, —NHC(=O)$R^{11}$—C(=O)NHSO$_2R^{11}$, —CH(OH)CF$_3$, —COCF$_3$, or —SO$_2$NHC(=O)$R^{11}$, where each $R^{11}$ is independently H, or an optionally substituted group selected from among $C_1$-$C_6$alkyl, $C_1$-$C_6$fluoroalkyl, $C_2$-$C_6$alkenyl, $C_2$-$C_6$alkynyl, $C_3$-$C_8$cycloalkyl, phenyl, and benzyl;

or $R^6$ and $R^7$ can together form an optionally substituted 5-, 6-, or 7-membered non-aromatic monocyclic ring containing 0, 1, or 2 heteroatoms selected from among S and O;

or $R^6$ and $R^7$ can together form an optionally substituted bicyclo[3,2,1]ring containing 1 or 2 heteroatoms selected from among S and O;

or $R^6$ and $R^7$ can together form a carbonyl (C=O); and $R^8$ is H, —OH, —CONH$_2$, tetrazolyl, —CN, —N$_3$, $C_1$-$C_6$alkyl, $C_2$-$C_6$alkenyl, —CF$_3$, —CO$_2$H, —OR$^{12}$, —CON(R$^{12}$)$_2$, —CO$_2$—R$^{12}$, —SR$^{12}$, —S(=O)R$^{12}$, S(=O)$_2$R$^{12}$, —SO$_2$N(R$^{12}$)$_2$, C(=O)R$^{12}$, C(OH)(R$^{12}$)$_2$, —N(R$^{12}$)$_2$, NHC(=O)R$^{12}$, —OC(=O)R$^{12}$, or an optionally substituted group selected from among $C_1$-$C_6$fluoroalkoxy, $C_3$-$C_8$cycloalkoxy, benzyl, and phenyl; where each $R^{12}$ is independently H, or an optionally substituted group selected from among $C_1$-$C_6$alkyl, $C_1$-$C_6$fluoroalkyl, $C_2$-$C_6$alkenyl, $C_2$-$C_6$alkynyl, $C_3$-$C_8$cycloalkyl, $C_4$-$C_8$cycloalkylalkyl, phenyl, and benzyl; or $R^6$ and $R^8$ can together form an optionally substituted $C_2$-$C_8$heterocycloalkyl having 1 or 2 O atoms in the ring;

$R^9$ is H, halide, —CN, —NO$_2$, —OH, or an optionally substituted group selected from among $C_1$-$C_6$alkyl, $C_3$-$C_8$cycloalkyl, $C_1$-$C_6$fluoroalkyl, $C_2$-$C_6$alkenyl, $C_2$-$C_6$alkynyl, $C_1$-$C_6$alkoxy, phenyl, and benzyl;

$R^{13}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$—S—, $R^{17}$—S(=O)—, $R^{17}$—S(=O)$_2$—, —CN, halide, $R^{17}$C(=O)—, $R^{17}$C(=O)O—, $R^{17}$NHC(=O)—, —$R^{17}$—C(=O)NH—, $R^{17}$S(=O)$_2$NH—, $R^{17}$—NHS(=O)$_2$—, $R^{17}$—OC(=O)NH—, $R^{17}$—NHC(=O)O—, —NO$_2$, $C_1$-$C_6$haloalkyl, and —N($R^{17}$)$_2$;

$R^{17}$ is independently selected from among H, $C_1$-$C_6$alkyl, $C_3$-$C_8$cycloalkyl, aryl, heteroaryl, and $C_1$-$C_6$heteroalkyl.

$R^{14}$ is H, $C_1$-$C_6$alkyl, $C_3$-$C_8$cycloalkyl, aryl, heteroaryl, $C_2$-$C_{10}$heterocycloalkyl, —OH, $C_1$-$C_6$alkoxy, aryloxy, $R^{17}$—S—, $R^{17}$—S(=O)—, $R^{17}$—S(=O)$_2$—, —CN, halide, $R^{17}$C(=O)—, $R^{17}$C(=O)O—, $R^{17}$NHC(=O)—, —$R^{17}$—C(=O)NH—, $R^{17}$S(=O)$_2$NH—, $R^{17}$—NHS(=O)$_2$—, $R^{17}$—OC(=O)NH—, $R^{17}$—NHC(=O)O—, —NO$_2$, $C_1$-$C_6$haloalkyl, and —N($R^{17}$)$_2$;

$R^{17}$ is independently selected from among H, $C_1$-$C_6$alkyl, $C_3$-$C_8$cycloalkyl, aryl, heteroaryl, and $C_1$-$C_6$heteroalkyl; or $R^8$ and $R^{14}$ taken together can form a optionally substituted 5-, or 6-membered ring;

or a pharmaceutically acceptable salt, pharmaceutically acceptable N-oxide, pharmaceutically active metabolite, pharmaceutically acceptable prodrug, or pharmaceutically acceptable solvate thereof.

For any and all of the embodiments, substituents can be selected from among from a subset of the listed alternatives. For example, in some embodiments, $G^1$ is $CR^1$. In other embodiments, $G^1$ is N.

In some embodiments, $R^9$ is H, halide, —CN, —NO$_2$, —OH, or an optionally substituted group selected from among $C_1$-$C_6$alkyl, $C_1$-$C_6$fluoroalkyl, and $C_1$-$C_6$alkoxy. In some other embodiments, $R^9$ is H, halide, —CN, —OH, or a $C_1$-$C_6$alkyl. In some other embodiments, $R^9$ is H.

In some embodiments, $R^{13}$ is H, $C_1$-$C_6$alkyl, —OH, $C_1$-$C_6$alkoxy, —CN, halide, $R^{17}$C(=O)O—, $R^{17}$—NHC(=O)O—, or $C_1$-$C_6$haloalkyl; $R^{17}$ is independently selected from among H, and $C_1$-$C_6$alkyl; $R^{14}$ is H, $C_1$-$C_6$alkyl, —OH, $C_1$-$C_6$alkoxy, —CN, halide, $R^{17}$C(=O)O—, $R^{17}$—NHC(=O)O—, or $C_1$-$C_6$haloalkyl; $R^{17}$ is independently selected from among H, and $C_1$-$C_6$alkyl; or $R^8$ and $R^{14}$ taken together can form a optionally substituted 5-, Or 6-membered ring.

In other embodiments, $R^{13}$ is H, $C_1$-$C_6$alkyl, —OH, or halide; $R^{14}$ is H, $C_1$-$C_6$alkyl, —OH, or halide.

In some other embodiments, $R^{13}$ is H, or halide; $R^{14}$ is H, —OH, or halide; or $R^8$ and $R^{14}$ taken together can form a optionally substituted 5-, or 6-membered ring.

In some embodiments, $L^1$ is selected from among —(CHR$^4$)$_n$—, —(CHR$^4$)$_n$O—, —(CHR$^4$)$_n$S—, —O(CHR$^4$)$_n$—, and —S(CHR$^4$)$_n$—; n is 0, 1, 2, or 3. In other embodiments, each $R^4$ is independently H, or an optionally substituted group selected from among $C_1$-$C_6$alkyl, $C_3$-$C_8$cycloalkyl, $C_1$-$C_6$fluoroalkyl; or L$^4$-X$^2$-L$^5$-X$^3$ where, L$^4$ is a bond, or an optionally substituted group selected from among $C_1$-$C_6$ alkyl, $C_2$-$C_{10}$ heterocycloalkyl, and $C_3$-$C_8$cycloalkyl; X$^2$ is a bond, O, S, S(=O), or S(=O)$_2$; Ls is a bond, $C_1$-$C_6$ alkyl, $C_3$-$C_8$ cycloalkyl, phenyl, pyridyl, thiazolyl, or thienyl; and X$^3$ is OH, CN, NO$_2$, halide, CO$_2$H, CO$_2$R$^{10}$, C(=O)R$^{10}$, C(OH)(R$^{10}$)$_2$, tetrazolyl, C(=O)NHSO$_2$R$^{10}$, CH(OH)CF$_3$, COCF$_3$, SO$_2$NHC(=O)R$^{10}$, or N(R$^{10}$)$_2$, where each R$^{10}$ is independently H, or an optionally substituted group selected from among $C_1$-$C_6$alkyl, $C_3$-$C_8$cycloalkyl, phenyl, and benzyl. In other embodiments, each $R^4$ is independently H, or an optionally substituted group selected from among $C_1$-$C_6$alkyl, and $C_1$-$C_6$fluoroalkyl; and n is 0; 1, or 2. In some embodiments, n is 0 or 1. In some other embodiments, $R^4$ is H; and n is 0 or 1.

In some embodiments, each $R^1$ is independently H, halide, —CN, —NO$_2$, —OH, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, —NHCH$_2$C(=O)OR$^3$, —C(=O)N(R$^3$)$_2$, —NHC(=O)R$^3$, or —C(OH)(R$^3$)$_2$, or an optionally substituted group selected from among $C_1$-$C_6$alkyl, $C_1$-$C_6$fluoroalkyl, $C_3$-$C_8$cycloalkyl, $C_2$-$C_6$alkenyl, $C_2$-$C_6$alkynyl, and $C_1$-$C_6$fluoroalkoxy; or R$^1$ is Q$^1$-Q$^2$ where Q$^1$ is aryl, monocyclic heterocycloalkyl, monocyclic heteroaryl; and Q$^2$ is H, halide, —CN, —NO$_2$, $C_1$-$C_6$alkyl, $C_1$-$C_6$alkoxy, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, or —C(=O)N(R$^3$)$_2$.

In some embodiments, $R^6$ and $R^7$ are independently H, or an optionally substituted group selected from among $C_1$-$C_6$haloalkyl, $C_1$-$C_6$alkyl, $C_3$-$C_8$cycloalkyl, $C_2$-$C_6$alkenyl, $C_2$-$C_6$alkynyl, thiazolyl, $C_1$-$C_6$alkoxy, $C_1$-$C_6$thioalkoxy, and $C_1$-$C_6$alkyl-$X^4$, wherein, $X^4$ is —$CO_2H$, —$CO_2R^{11}$, $C_1$-$C_6$alkoxy, tetrazolyl, —OH, —$CON(R^{11})_2$, where each $R^{11}$ is independently H, or an optionally substituted group selected from among $C_1$-$C_6$alkyl, and $C_1$-$C_6$fluoroalkyl; or $R^6$ and $R^7$ can together form an optionally substituted 5-, 6-, or 7-membered monocyclic ring containing 0, 1, or 2 heteroatoms selected from among S and O; or $R^6$ and $R^7$ can together form a carbonyl (C=O). In other embodiments, $R^6$ and $R^7$ are independently H, or an optionally substituted group selected from among $C_1$-$C_6$haloalkyl, $C_1$-$C_6$alkyl, $C_3$-$C_8$cycloalkyl, and $C_1$-$C_6$alkyl-$X^4$, wherein, $X^4$ is —$CO_2H$, —$CO_2R^{11}$, or —$CON(R^{11})_2$, where each $R^{11}$ is independently H, or an optionally substituted $C_1$-$C_6$alkyl; or $R^6$ and $R^7$ can together form an optionally substituted 5-, 6-, or 7-membered monocyclic ring containing 0, 1, or 2 heteroatoms selected from S and O; or $R^6$ and $R^7$ can together form a carbonyl (C=O).

In some embodiments, $R^6$ and $R^7$ are independently H, or an optionally substituted group selected from among $C_1$-$C_6$haloalkyl, $C_1$-$C_6$alkyl, $C_3$-$C_8$cycloalkyl, and $C_1$-$C_6$alkyl-$X^4$, wherein, $X^4$ is —$CO_2H$, —$CO_2R^{11}$, or —$CON(R^{11})_2$, where each $R^{11}$ is independently H, or an optionally substituted $C_1$-$C_6$alkyl; or $R^6$ and $R^7$ can together form an optionally substituted 6-membered monocyclic ring containing 0 or 1 O atoms; or $R^6$ and $R^7$ can together form a carbonyl (C=O).

In some embodiments, $R^8$ is H, —OH, —$CONH_2$, tetrazolyl, —CN, $C_1$-$C_5$alkyl, $C_2$-$C_6$alkenyl, —$CF_3$, —$CO_2H$, —$OR^{12}$, —$CON(R^{12})_2$, —$CO_2$—$R^{12}$, —$SR^{12}$, —S(=O)$R^{12}$, S(=O)$_2R^{12}$, —$SO_2N(R^{12})_2$, C(=O)$R^{12}$, C(OH)($R^{12}$)$_2$, —CH=N—$OR^{12}$, —OC(=O)$R^{12}$, or an optionally substituted group selected from among $C_1$-$C_6$fluoroalkoxy, $C_3$-$C_8$cycloalkoxy, benzyl, and phenyl; where each $R^{12}$ is independently H, or an optionally substituted group selected from among $C_1$-$C_6$alkyl, $C_1$-$C_6$fluoroalkyl, $C_3$-$C_8$cycloalkyl, $C_4$-$C_8$cycloalkylalkyl, phenyl, and benzyl.

In some embodiments, compounds provided herein have a structure of Formula (VI):

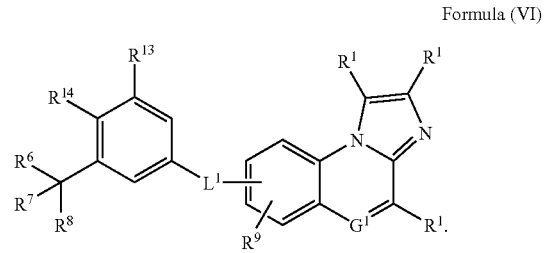

Formula (VI)

In some embodiments, $G^1$ is $CR^1$. In yet other embodiments, $G^1$ is N.

Any of the combinations of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Any of the combinations of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Figure 2:
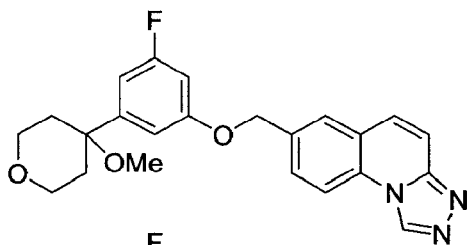
FIG. 2 presents non-limiting examples of compounds described herein.
Figure 2:
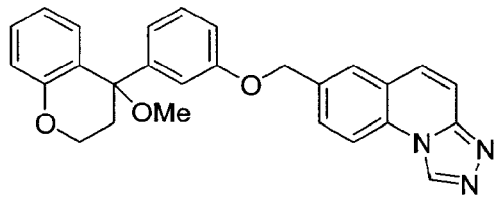
Figure 2:
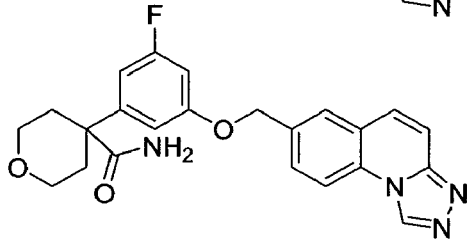
Figure 2:
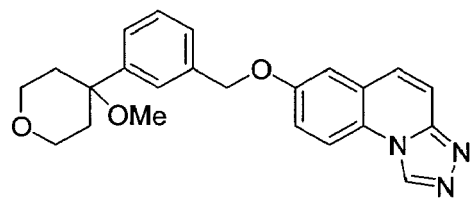
Figure 2:
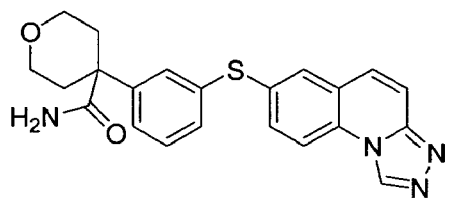
Figure 2:
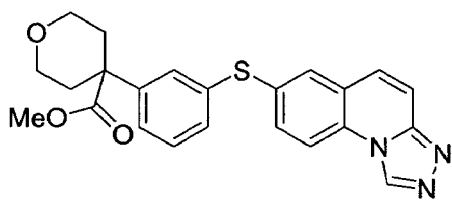
Figure 2:
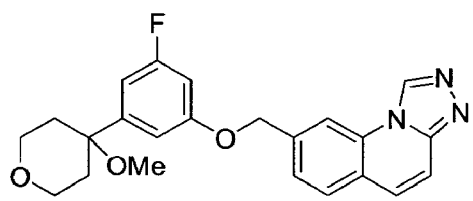
Figure 2:
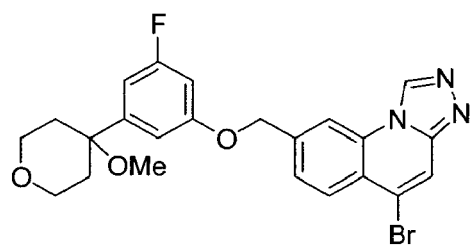
Figure 2:
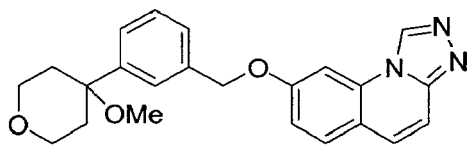
Figure 2:
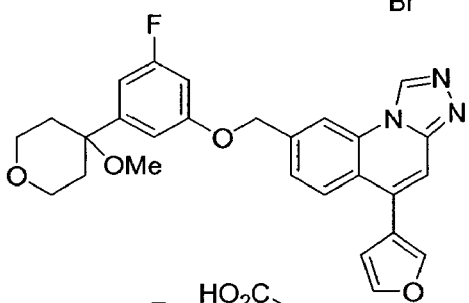
Figure 2:
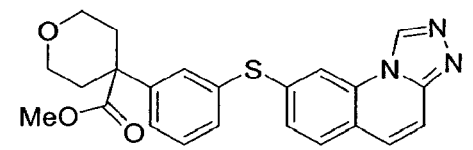
Figure 2:
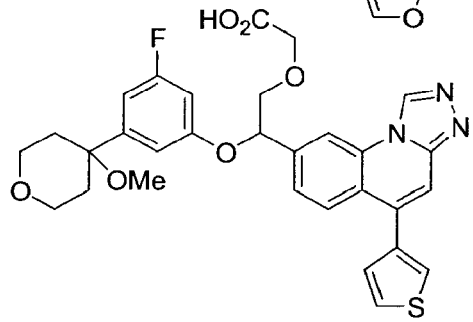
Figure 3:
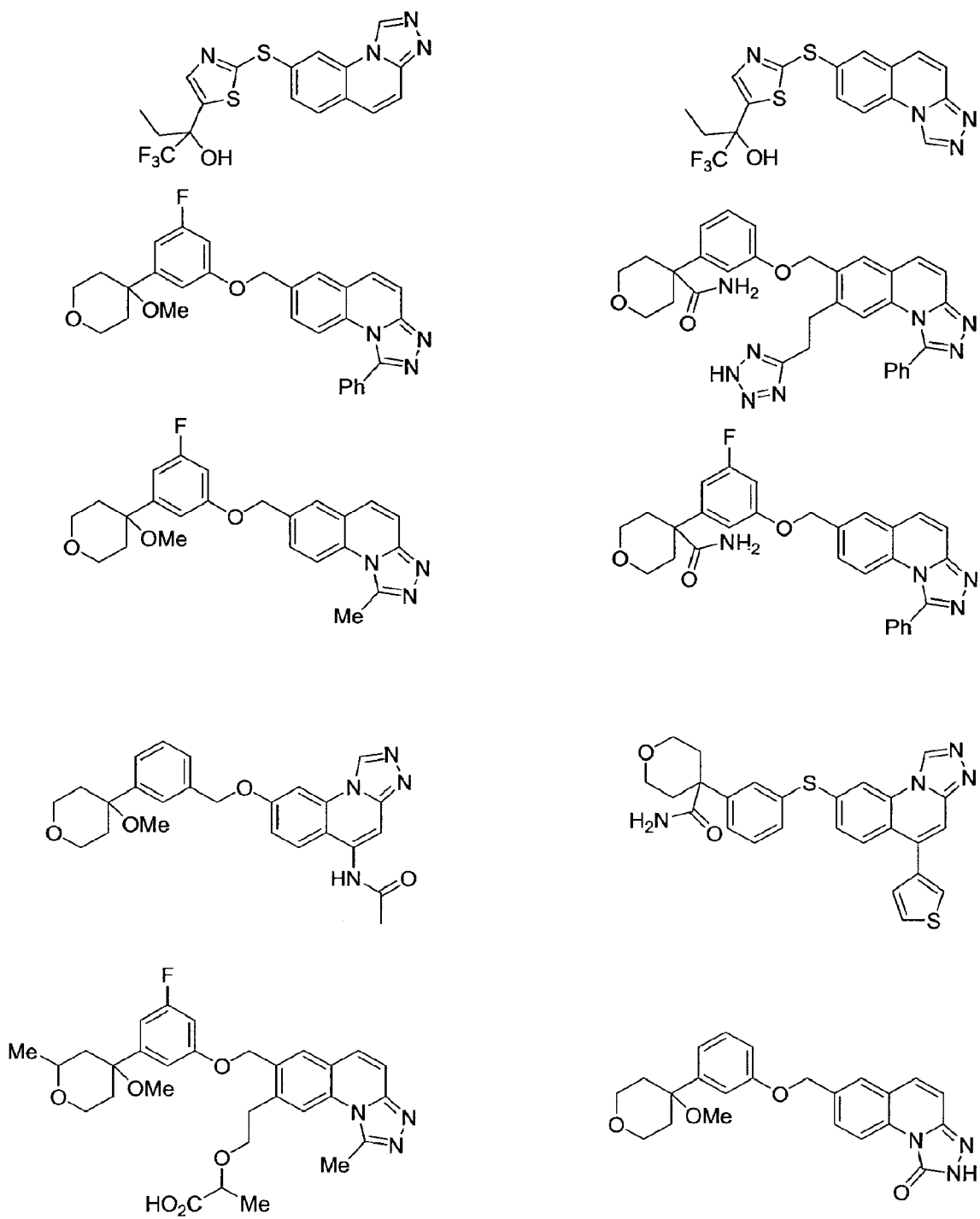
FIG. 3 presents non-limiting examples of compounds described herein.
Figure 4:
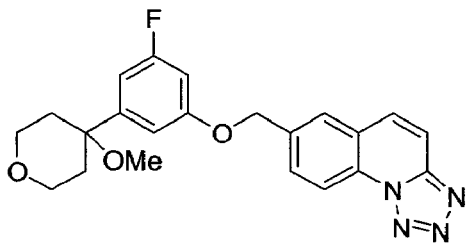
FIG. 4 presents non-limiting examples of compounds described herein.
Figure 4:
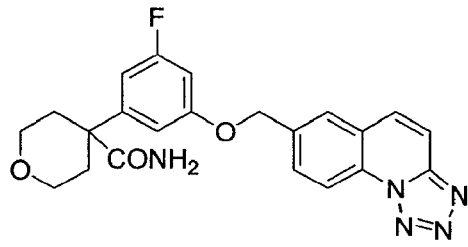
Figure 4:
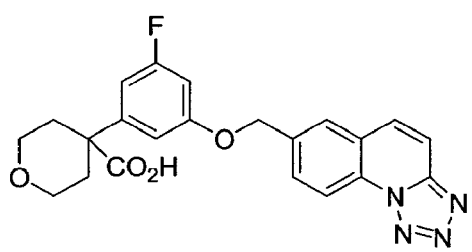
Figure 4:
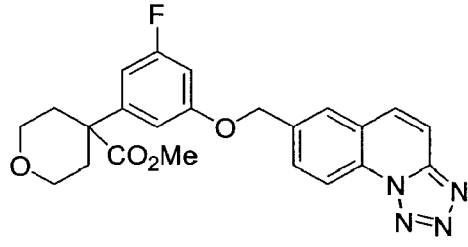
Figure 4:
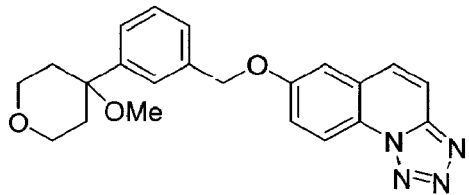
Figure 4:
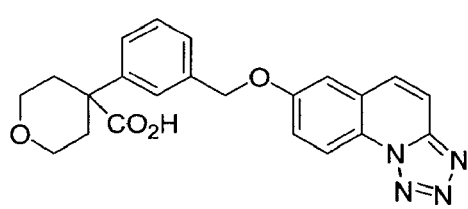
Figure 4:
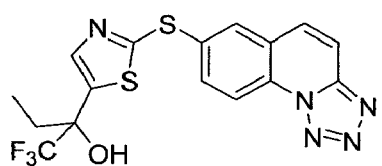
Figure 4:
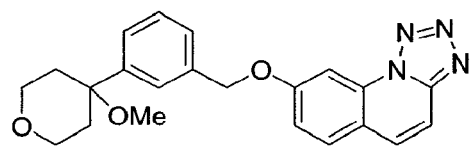
Figure 4:
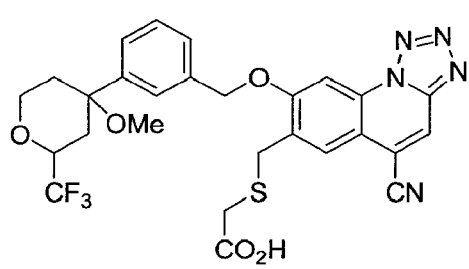
Figure 4:
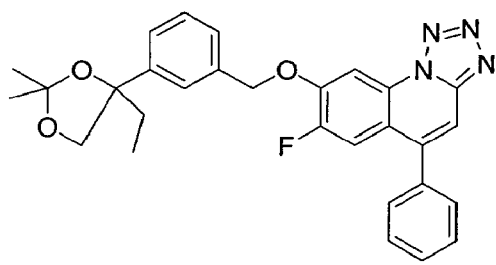
Figure 5:
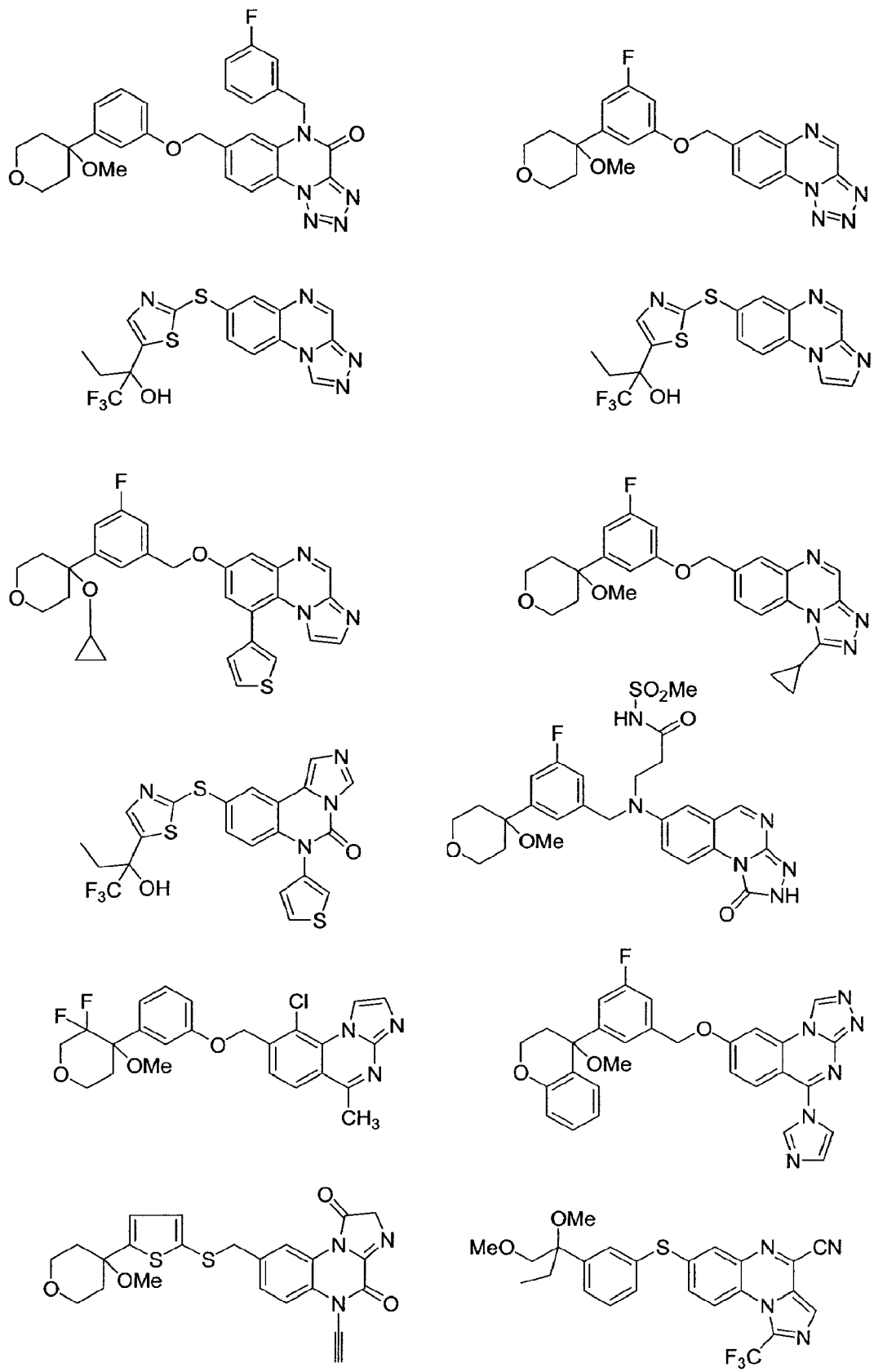
FIG. 5 presents non-limiting examples of compounds described herein.

Further embodiments of compounds described herein, include, but are not limited to, compounds shown in FIGS. 1-5 and in Tables 1-11.

TABLE 1

Imidazo[1,2-a]quinoline

| Compound # | $R^8$ | $R^{13}$ | $R^1$ | $G^8$ | $L^1$ | $G^1$ | M + H |
|---|---|---|---|---|---|---|---|
| 1-1 | OMe | H | H | C | 7-$CH_2O$ | C | 389 |
| 1-2 | OMe | F | H | C | 7-$OCH_2$ | C | 407 |
| 1-3 | $CO_2Me$ | F | H | C | 7-$OCH_2$ | C | 435 |
| 1-4 | $CO_2H$ | F | H | C | 7-$OCH_2$ | C | 421 |
| 1-5 | $CONH_2$ | F | H | C | 7-$OCH_2$ | C | 420 |
| 1-6 | OH | F | H | C | 7-$OCH_2$ | C | 393 |
| 1-7 | $CO_2Me$ | F | 1-Bromo | C | 7-$OCH_2$ | C | 513 |
| 1-8 | $CO_2Me$ | F | 1-Phenyl | C | 7-$OCH_2$ | C | 511 |
| 1-9 | OH | H | H | C | 7-S | C | 377 |
| 1-10 | OMe | H | H | C | 7-S | C | 391 |
| 1-11 | $CONH_2$ | H | H | C | 7-S | C | 404 |
| 1-12 | CN | H | 2-Methyl | C | 7-S | C | 400 |
| 1-13 | CN | H | H | C | 7-S | C | 386 |
| 1-14 | CN | H | 1-Methyl | C | 7-S | C | 400 |
| 1-15 | CN | H | 1-(1-Methyl-1H-Pyrazol-4-yl) | C | 7-S | C | 466 |
| 1-16 | CN | F | H | C | 7-S | C | 404 |
| 1-17 | CN | F | 1-Bromo | C | 7-S | C | 482 |
| 1-18 | CN | F | 1-Phenyl | C | 7-S | C | 480 |
| 1-19 | CN | F | 2-Phenyl | C | 7-S | C | 480 |
| 1-20 | CN | F | 2-Carboxylic Acid Ethyl Ester | C | 7-S | C | 478 |

TABLE 1-continued

Imidazo[1,2-a]quinoline

| Compound # | R8 | R13 | R1 | G8 | L1 | G1 | M + H |
|---|---|---|---|---|---|---|---|
| 1-21 | CN | F | 2-Carboxylic Acid | C | 7-S | C | 448 |
| 1-22 | CN | H | H | N | 7-S | C | 387 |
| 1-23 | CONH2 | H | H | N | 7-S | C | 405 |
| 1-24 | OMe | F | H | C | 7-S | N | 410 |
| 1-25 | OMe | F | H | C | 8-OCH2 | C | 407 |
| 1-26 | CO2Me | F | 5-Chloro | C | 8-OCH2 | C | 469 |
| 1-27 | CONH2 | F | 5-Chloro | C | 8-OCH2 | C | 454 |
| 1-28 | CO2H | F | 5-Methylsulfanyl | C | 8-OCH2 | C | 467 |
| 1-29 | CONH2 | F | 5-Methylsulfanyl | C | 8-OCH2 | C | 466 |
| 1-30 | CO2Me | F | 5-Phenyl | C | 8-OCH2 | C | 511 |
| 1-31 | CO2H | F | 5-Cyclopentylsulfanyl | C | 8-OCH2 | C | 521 |
| 1-32 | CONH2 | F | 5-Cyclopentylsulfanyl | C | 8-OCH2 | C | 520 |
| 1-33 | CO2Me | F | 5-Bromo | C | 8-OCH2 | C | 514 |
| 1-34 | CO2H | F | 5-Bromo | C | 8-OCH2 | C | 499 |
| 1-35 | CONH2 | F | 5-Bromo | C | 8-OCH2 | C | 499 |
| 1-36 | CONH2 | F | 5-Phenyl | C | 8-OCH2 | C | 496 |
| 1-37 | CONH2 | F | 5-Pyridin-3-yl | C | 8-OCH2 | C | 497 |
| 1-38 | CONH2 | F | 5-(3-Methoxyphenyl) | C | 8-OCH2 | C | 526 |
| 1-39 | CONH2 | F | 5-(1H-Pyrazol-4-yl) | C | 8-OCH2 | C | 486 |
| 1-40 | CONH2 | F | 5-(1-Methyl-1H-Pyrazol-4-yl) | C | 8-OCH2 | C | 500 |
| 1-41 | CONH2 | F | 5-Pyridin-4-yl | C | 8-OCH2 | C | 497 |
| 1-42 | CONH2 | F | 5-(3-Methylphenyl) | C | 8-OCH2 | C | 510 |
| 1-43 | CONH2 | F | 5-(4-Aminophenyl) | C | 8-OCH2 | C | 511 |
| 1-44 | CONH2 | F | 5-(4-Fluorophenyl) | C | 8-OCH2 | C | 514 |
| 1-45 | CONH2 | F | 5-(2-Methoxyphenyl) | C | 8-OCH2 | C | 526 |
| 1-46 | CONH2 | F | 5-(4-Methoxyphenyl) | C | 8-OCH2 | C | 526 |
| 1-47 | CONH2 | F | 5-Pyrimidin-5-yl | C | 8-OCH2 | C | 498 |
| 1-48 | CONH2 | F | 5-(4-Methoxypyridin-3-yl) | C | 8-OCH2 | C | 527 |
| 1-49 | CONH2 | F | 5-(6-Methoxypyridin-3-yl) | C | 8-OCH2 | C | 527 |
| 1-50 | CN | H | 5-Phenyl | C | 8-S | C | 462 |
| 1-51 | CONH2 | H | 5-Phenyl | C | 8-S | C | 480 |
| 1-52 | CN | H | 2-Carboxylic Acid Ethyl Ester, 5-Chloro | C | 8-S | C | 492 |
| 1-53 | CN | H | 2-Carboxylic Acid, 5-Chloro | C | 8-S | C | 464 |
| 1-54 | CN | H | 2-Carboxamide, 5-Chloro | C | 8-S | C | 463 |
| 1-55 | CN | H | 2-Chloro, 5-Phenyl | C | 8-S | C | 496 |
| 1-56 | OH | H | 5-Phenyl | C | 8-S | C | 453 |
| 1-57 | CN | H | 5-Methyl | C | 8-S | C | 400 |
| 1-58 | OH | H | 2-Chloro, 5-Phenyl | C | 8-S | C | 487 |
| 1-59 | CN | H | 5-Isopropyl | C | 8-S | C | 428 |
| 1-60 | OH | H | 5-Isopropyl | C | 8-S | C | 419 |
| 1-61 | CN | H | 2-Carboxylic Acid Ethyl Ester, 5-Phenyl | C | 8-S | C | 534 |
| 1-62 | CN | H | 2-Carboxylic Acid, 5-Phenyl | C | 8-S | C | 506 |
| 1-63 | CO2Me | H | 5-Phenyl | C | 8-S | C | 495 |
| 1-64 | CO2H | H | 5-Phenyl | C | 8-S | C | 481 |
| 1-65 | OH | H | 2-Chloro, 5-Isopropyl | C | 8-S | C | 453 |
| 1-66 | OH | H | 2-Carboxylic Acid, 5-Isopropyl | C | 8-S | C | 463 |
| 1-67 | OH | H | 2-Carboxylic Acid, 5-Phenyl | C | 8-S | C | 497 |
| 1-68 | CONH2 | H | 5-Methyl | C | 8-S | C | 418 |
| 1-69 | CONH2 | H | 5-Isopropyl | C | 8-S | C | 446 |
| 1-70 | CN | H | 2-Cyano, 5-Chloro | C | 8-S | C | 445 |
| 1-71 | CN | H | 2-Chloro, 5-Isopropyl | C | 8-S | C | 462 |
| 1-72 | OH | H | 2-Cyano, 5-Isopropyl | C | 8-S | C | 444 |
| 1-73 | OH | H | 2-Cyano, 5-Phenyl | C | 8-S | C | 478 |
| 1-74 | CONH2 | H | 2-Chloro, 5-Isopropyl | C | 8-S | C | 480 |
| 1-75 | OH | H | 2-Hydroxymethyl, 5-Phenyl | C | 8-S | C | 483 |
| 1-76 | OH | H | 2-(2-Hydroxyprop-2-yl), 5-Phenyl | C | 8-S | C | 511 |
| 1-77 | OH | H | 2-Hydroxymethyl, 5-Methyl | C | 8-S | C | 421 |
| 1-78 | OH | H | 2-(2-Hydroxyprop-2-yl), 5-Methyl | C | 8-S | C | 449 |
| 1-79 | OH | H | 2-Carboxylic Acid, 5-Methyl | C | 8-S | C | 435 |
| 1-80 | OH | H | 2-Fluoromethyl, 5-Phenyl | C | 8-S | C | 485 |
| 1-81 | OH | H | 2-(CH2OC(O)CH2CH2CO2H), 5-Phenyl | C | 8-S | C | 583 |
| 1-82 | OH | H | 2-Carboxylic Acid Ethyl Ester, 5-Phenyl | C | 8-S | C | 525 |
| 1-83 | OH | H | 2-Ethanone, 5-Phenyl | C | 8-S | C | 495 |
| 1-84 | OH | H | 2-Carbaldehyde, 5-Phenyl | C | 8-S | C | 481 |
| 1-85 | CN | F | 5-Chloro | C | 8-S | C | 438 |

TABLE 1-continued

Imidazo[1,2-a]quinoline

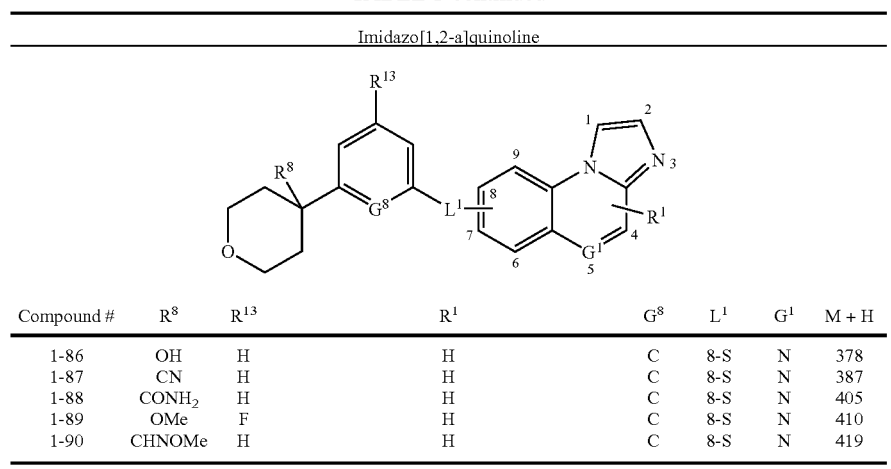

| Compound # | R⁸ | R¹³ | R¹ | G⁸ | L¹ | G¹ | M + H |
|---|---|---|---|---|---|---|---|
| 1-86 | OH | H | H | C | 8-S | N | 378 |
| 1-87 | CN | H | H | C | 8-S | N | 387 |
| 1-88 | CONH₂ | H | H | C | 8-S | N | 405 |
| 1-89 | OMe | F | H | C | 8-S | N | 410 |
| 1-90 | CHNOMe | H | H | C | 8-S | N | 419 |

Compounds in Table 1 are named:
7-[3-(4-Methoxy-tetrahydro-pyran-4-yl)-benzyloxy]-imidazo[1,2-a]quinoline (Compound 1-1); 7-[3-Fluoro-5-(4-methoxy-tetrahydro-pyran-4-yl)-phenoxymethyl]-imidazo[1,2-a]quinoline (Compound 1-2); 4-[3-Fluoro-5-(imidazo[1,2-a]quinolin-7-ylmethoxy)-phenyl]-tetrahydro-pyran-4-carboxylic acid methyl ester (Compound 1-3); 4-[3-Fluoro-5-(imidazo[1,2-a]quinolin-7-ylmethoxy)-phenyl]-tetrahydro-pyran-4-carboxylic acid (Compound 1-4); 4-[3-Fluoro-5-(imidazo[1,2-a]quinolin-7-ylmethoxy)-phenyl]-tetrahydro-pyran-4-carboxylic acid amide (Compound 1-5); 4-[3-Fluoro-5-(imidazo[1,2-a]quinolin-7-ylmethoxy)-phenyl]-tetrahydro-pyran-4-ol (Compound 1-6); 4-[3-(1-Bromo-imidazo[1,2-a]quinolin-7-ylmethoxy)-5-fluoro-phenyl]-tetrahydro-pyran-4-carboxylic acid methyl ester (Compound 1-7); 4-[3-Fluoro-5-(1-phenyl-imidazo[1,2-a]quinolin-7-ylmethoxy)-phenyl]-tetrahydro-pyran-4-carboxylic acid methyl ester (Compound 1-8); 4-[3-(Imidazo[1,2-a]quinolin-7-ylsulfanyl)-phenyl]-tetrahydro-pyran-4-ol (Compound 1-9); 7-[3-(4-Methoxy-tetrahydro-pyran-4-yl)-phenylsulfanyl]-imidazo[1,2-a]quinoline (Compound 1-10); 4-[3-(Imidazo[1,2-a]quinolin-7-ylsulfanyl)-phenyl]-tetrahydro-pyran-4-carboxylic acid amide (Compound 1-11); 4-[3-(2-Methyl-imidazo[1,2-a]quinolin-7-ylsulfanyl)-phenyl]-tetrahydro-pyran-4-carbonitrile (Compound 1-12); 4-[3-(Imidazo[1,2-a]quinolin-7-ylsulfanyl)-phenyl]-tetrahydro-pyran-4-carbonitrile (Compound 1-13); 4-[3-(1-Methyl-imidazo[1,2-a]quinolin-7-ylsulfanyl)-phenyl]-tetrahydro-pyran-4-carbonitrile (Compound 1-14); 4-{3-[1-(1-Methyl-1H-pyrazol-4-yl)-imidazo[1,2-a]quinolin-7-ylsulfanyl]-phenyl}-tetrahydro-pyran-4-carbonitrile (Compound 1-15); 4-[3-Fluoro-5-(imidazo[1,2-a]quinolin-7-ylsulfanyl)-phenyl]-tetrahydro-pyran-4-carbonitrile (Compound 1-16); 4-[3-(1-Bromo-imidazo[1,2-a]quinolin-7-ylsulfanyl)-5-fluoro-phenyl]-tetrahydro-pyran-4-carbonitrile (Compound 1-17); 4-[3-Fluoro-5-(1-phenyl-imidazo[1,2-a]quinolin-7-ylsulfanyl)-phenyl]-tetrahydro-pyran-4-carbonitrile (Compound 1-18); 4-[3-Fluoro-5-(2-phenyl-imidazo[1,2-a]quinolin-7-ylsulfanyl)-phenyl]-tetrahydro-pyran-4-carbonitrile (Compound 1-19); 7-[3-(4-Cyano-tetrahydro-pyran-4-yl)-5-fluoro-phenylsulfanyl]-imidazo[1,2-a]quinoline-2-carboxylic acid ethyl ester (Compound 1-20); 7-[3-(4-Cyano-tetrahydro-pyran-4-yl)-5-fluoro-phenylsulfanyl]-imidazo[1,2-a]quinoline-2-carboxylic acid (Compound 1-21); 4-[6-(Imidazo[1,2-a]quinolin-7-ylsulfanyl)-pyridin-2-yl]-tetrahydro-pyran-4-carbonitrile (Compound 1-22); 4-[6-(Imidazo[1,2-a]quinolin-7-ylsulfanyl)-pyridin-2-yl]-tetrahydro-pyran-4-carboxylic acid amide (Compound 1-23); 7-[3-Fluoro-5-(4-methoxy-tetrahydro-pyran-4-yl)-phenylsulfanyl]-imidazo[1,2-a]quinoxaline (Compound 1-24); 8-[3-Fluoro-5-(4-methoxy-tetrahydro-pyran-4-yl)-phenoxymethyl]-imidazo[1,2-a]quinoline (Compound 1-25); 4-[3-(5-Chloro-imidazo[1,2-a]quinolin-8-ylmethoxy)-5-fluoro-phenyl]-tetrahydro-pyran-4-carboxylic acid methyl ester (Compound 1-26); 4-[3-(5-Chloro-imidazo[1,2-a]quinolin-8-ylmethoxy)-5-fluoro-phenyl]-tetrahydro-pyran-4-carboxylic acid amide (Compound 1-27); 4-[3-Fluoro-5-(5-methylsulfanyl-imidazo[1,2-a]quinolin-8-ylmethoxy)-phenyl]-tetrahydro-pyran-4-carboxylic acid (Compound 1-28); 4-[3-Fluoro-5-(5-methylsulfanyl-imidazo[1,2-a]quinolin-8-ylmethoxy)-phenyl]-tetrahydro-pyran-4-carboxylic acid amide (Compound 1-29); 4-[3-Fluoro-5-(5-phenyl-imidazo[1,2-a]quinolin-8-ylmethoxy)-phenyl]-tetrahydro-pyran-4-carboxylic acid methyl ester (Compound 1-30); 4-[3-(5-Cyclopentylsulfanyl-imidazo[1,2-a]quinolin-8-ylmethoxy)-5-fluoro-phenyl]-tetrahydro-pyran-4-carboxylic acid (Compound 1-31); 4-[3-(5-Cyclopentylsulfanyl-imidazo[1,2-a]quinolin-8-ylmethoxy)-5-fluoro-phenyl]-tetrahydro-pyran-4-carboxylic acid amide (Compound 1-32); 4-[3-(5-Bromo-imidazo[1,2-a]quinolin-8-ylmethoxy)-5-fluoro-phenyl]-tetrahydro-pyran-4-carboxylic acid methyl ester (Compound 1-33); 4-[3-(5-Bromo-imidazo[1,2-a]quinolin-8-ylmethoxy)-5-fluoro-phenyl]-tetrahydro-pyran-4-carboxylic acid (Compound 1-34); 4-[3-(5-Bromo-imidazo[1,2-a]quinolin-8-ylmethoxy)-5-fluoro-phenyl]-tetrahydro-pyran-4-carboxylic acid amide (Compound 1-35); 4-[3-Fluoro-5-(5-phenyl-imidazo[1,2-a]quinolin-8-ylmethoxy)-phenyl]-tetrahydro-pyran-4-carboxylic acid amide (Compound 1-36); 4-[3-Fluoro-5-(5-pyridin-3-yl-imidazo[1,2-a]quinolin-8-ylmethoxy)-phenyl]-tetrahydro-pyran-4-carboxylic acid amide (Compound 1-37); 4-{3-Fluoro-5-[5-(3-methoxy-phenyl)-imidazo[1,2-a]quinolin-8-ylmethoxy]-phenyl}-tetrahydro-pyran-4-carboxylic acid amide (Compound 1-38); 4-{3-Fluoro-5-[5-(1H-pyrazol-4-yl)-imidazo[1,2-a]quinolin-8-ylmethoxy]-phenyl}-tetrahydro-pyran-4-carboxylic acid amide (Compound 1-39); 4-{3-Fluoro-5-[5-(1-methyl-1H-pyrazol-4-yl)-imidazo[1,2-a]quinolin-8-ylmethoxy]-phenyl}-tetrahydro-pyran-4-carboxylic acid amide (Compound 1-40); 4-[3-Fluoro-5-(5-pyridin-4-yl-imidazo[1,2-a]quinolin-8-ylmethoxy)-phenyl]-tetrahydro-pyran-4-carboxylic acid amide (Compound 1-41); 4-[3-Fluoro-5-(5-m-tolyl-imidazo[1,2-a]quinolin-8-ylmethoxy)-phenyl]-tetrahydro-pyran-4-carboxylic acid amide (Compound 1-42); 4-{3-[5-(4-Amino-phenyl)-imidazo[1,2-a]quinolin-8-ylmethoxy]-5-fluoro-phenyl}-tetrahydro-pyran-4-carboxylic acid amide (Compound 1-43); 4-{3-Fluoro-5-[5-(4-fluoro-phenyl)-imidazo[1,2-a]quinolin-8-ylmethoxy]-phenyl}-tetrahydro-pyran-4-carboxylic acid amide (Compound 1-44); 4-{3-Fluoro-5-[5-(2-methoxy-phenyl)-imidazo[1,2-a]quinolin-8-ylmethoxy]-phenyl}-tetrahydro-pyran-4-carboxylic acid amide (Compound 1-45); 4-{3-Fluoro-5-[5-(4-methoxy-phenyl)-imidazo[1,2-a]quinolin-8-ylmethoxy]-phenyl}-tetrahydro-pyran-4-carboxylic acid amide (Compound 1-46); 4-[3-Fluoro-5-(5-pyrimidin-5-yl-imidazo[1,2-a]quinolin-8-ylmethoxy)-phenyl]-tetrahydro-pyran-4-carboxylic acid amide (Compound 1-47); 4-{3-Fluoro-5-[5-(4-methoxy-pyridin-3-yl)-imidazo[1,2-a]quinolin-8-ylmethoxy]-phenyl}-tetrahydro-pyran-4-carboxylic acid amide (Compound 1-48); 4-{3-Fluoro-5-[5-(6-methoxy-pyridin-3-yl)-imidazo[1,2-a]quinolin-8-ylmethoxy]-phenyl}-tetrahydro-pyran-4-carboxylic acid amide (Compound 1-49); 4-[3-(5-Phenyl-imidazo[1,2-a]quinolin-8-ylsulfanyl)-phenyl]-tetrahydro-pyran-4-carbonitrile (Compound 1-50); 4-[3-(5-Phenyl-imidazo[1,2-a]quinolin-8-ylsulfanyl)-phenyl]-tetrahydro-pyran-4-carboxylic acid amide (Compound 1-51); 5-Chloro-8-[3-(4-cyano-tetrahydro-pyran-4-yl)-phenylsulfanyl]-imidazo[1,2-a]quinoline-2-carboxylic acid ethyl ester (Compound 1-52); 5-Chloro-8-[3-(4-cyano-tetrahydro-pyran-4-yl)-phenylsulfanyl]-imidazo[1,2-a]quinoline-2-carboxylic acid (Compound 1-53); 5-Chloro-8-[3-(4-cyano-tetrahydro-pyran-4-yl)-phenylsulfanyl]-imidazo[1,2-a]quinoline-2-carboxylic acid amide (Compound 1-54); 4-[3-(2-Chloro-5-phenyl-imidazo[1,2-a]quinolin-8-ylsulfanyl)-phenyl]-tetrahydro-pyran-4-carbonitrile (Compound 1-55); 4-[3-(5-Phenyl-imidazo[1,2-a]quinolin-8-ylsulfanyl)-phenyl]-tetrahydro-pyran-4-ol (Compound 1-56); 4-[3-(5-Methyl-imidazo[1,2-a]quinolin-8-ylsulfanyl)-phenyl]-tetrahydro-pyran-4-carbonitrile (Compound 1-57); 4-[3-(2-Chloro-5-phenyl-imidazo[1,2-a]quinolin-8-ylsulfanyl)-phenyl]-tetrahydro-pyran-4-ol (Compound 1-58); 4-[3-(5-Isopropyl-imidazo[1,2-a]quinolin-8-ylsulfanyl)-phenyl]-tetrahydro-pyran-4-carbonitrile (Compound 1-59); 4-[3-(5-Isopropyl-imidazo[1,2-a]quinolin-8-ylsulfanyl)-phenyl]-tetrahydro-pyran-4-ol (Compound 1-60); 8-[3-(4-Cyano-tetrahydro-pyran-4-yl)-phenylsulfanyl]-5-phenyl-imidazo[1,2-a]quinoline-2-carboxylic acid ethyl ester (Compound 1-61); 8-[3-(4-Cyano-tetrahydro-pyran-4-yl)-phenylsulfanyl]-5-phenyl-imidazo[1,2-a]quinoline-2-carboxylic acid (Compound 1-62); 4-[3-(5-Phenyl-imidazo[1,2-a]quinolin-8-ylsulfanyl)-phenyl]-tetrahydro-pyran-4-carboxylic acid methyl ester (Compound 1-63); 4-[3-(5-Phenyl-imidazo[1,2-a]quinolin-8-ylsulfanyl)-phenyl]-tetrahydro-pyran-4-carboxylic acid (Compound 1-64); 4-[3-(2-Chloro-5-isopropyl-imidazo[1,2-a]quinolin-8-ylsulfanyl)-phenyl]-tetrahydro-pyran-4-ol (Compound 1-65); 8-[3-(4-Hydroxy-tetrahydro-pyran-4-yl)-phenylsulfanyl]-5-isopropyl-imidazo[1,2-a]quinoline-2-carboxylic acid (Compound 1-66); 8-[3-(4-Hydroxy-tetrahydro-pyran-4-yl)-phenylsulfanyl]-5-phenyl-imidazo[1,2-a]quinoline-2-carboxylic acid (Compound 1-67); 4-[3-(5-Methyl-imidazo[1,2-a]quinolin-8-ylsulfanyl)-phenyl]-tetrahydro-pyran-4-carboxylic acid amide (Compound 1-68); 4-[3-(5-Isopropyl-imidazo[1,2-a]quinolin-8-ylsulfanyl)-phenyl]-tetrahydro-pyran-4-carboxylic acid amide (Compound 1-69); 5-Chloro-8-[3-(4-cyano-tetrahydro-pyran-4-yl)-phenylsulfanyl]-imidazo[1,2-a]quinoline-2-carbonitrile (Compound 1-70); 4-[3-(2-Chloro-5-isopropyl-imidazo[1,2-a]quinolin-8-ylsulfanyl)-phenyl]-tetrahydro-pyran-4-carbonitrile (Compound 1-71); 8-[3-(4-Hydroxy-tetrahydro-pyran-4-yl)-phenylsulfanyl]-5-isopropyl-imidazo[1,2-a]quinoline-2-carbonitrile (Compound 1-72); 8-[3-(4-Hydroxy-tetrahydro-pyran-4-yl)-phenylsulfanyl]-5-phenyl-imidazo[1,2-a]quinoline-2-carbonitrile (Compound 1-73); 4-[3-(2-Chloro-5-isopropyl-imidazo[1,2-a]quinolin-8-ylsulfanyl)-phenyl]-tetrahydro-pyran-4-carboxylic acid amide (Compound 1-74); 4-[3-(2-Hydroxymethyl-5-phenyl-imidazo[1,2-a]quinolin-8-ylsulfanyl)-phenyl]-tetrahydro-pyran-4-ol (Compound 1-75); 4-{3-[2-(1-Hydroxy-1-methyl-ethyl)-5-phenyl-imidazo[1,2-a]quinolin-8-ylsulfanyl]-phenyl}-tetrahydro-pyran-4-ol (Compound 1-76); 4-[3-(2-Hydroxymethyl-5-methyl-imidazo[1,2-a]quinolin-8-ylsulfanyl)-phenyl]-tetrahydro-pyran-4-ol (Compound 1-77); 4-{3-[2-(1-Hydroxy-1-methyl-ethyl)-5-methyl-imidazo[1,2-a]quinolin-8-ylsulfanyl]-phenyl}-tetrahydro-pyran-4-ol (Compound 1-78); 8-[3-(4-Hydroxy-tetrahydro-pyran-4-yl)-phenylsulfanyl]-5-methyl-imidazo[1,2-a]quinoline-2-carboxylic acid (Compound 1-79); 4-[3-(2-Fluoromethyl-5-phenyl-imidazo[1,2-a]quinolin-8-ylsulfanyl)-phenyl]-tetrahydro-pyran-4-ol (Compound 1-80); Succinic acid mono-{8-[3-(4-hydroxy-tetrahydro-pyran-4-yl)-phenylsulfanyl]-5-phenyl-imidazo[1,2-a]quinolin-2-ylmethyl}ester (Compound 1-81); 8-[3-(4-Hydroxy-tetrahydro-pyran-4-yl)-phenylsulfanyl]-5-phenyl-imidazo[1,2-a]quinoline-2-carboxylic acid ethyl ester (Compound 1-82); 1-{8-[3-(4-Hydroxy-tetrahydro-pyran-4-yl)-phenylsulfanyl]-5-phenyl-imidazo[1,2-a]quinolin-2-yl}-ethanone (Compound 1-83); 8-[3-(4-Hydroxy-tetrahydro-pyran-4-yl)-phenylsulfanyl]-5-phenyl-imidazo[1,2-a]quinoline-2-carbaldehyde (Compound 1-84); 4-[3-(5-Chloro-imidazo[1,2-a]quinolin-8-ylsulfanyl)-5-fluoro-phenyl]-tetrahydro-pyran-4-carbonitrile (Compound 1-85); 4-[3-(Imidazo[1,2-a]quinoxalin-8-ylsulfanyl)-phenyl]-tetrahydro-pyran-4-ol (Compound 1-86); 4-[3-(Imidazo[1,2-a]quinoxalin-8-ylsulfanyl)-phenyl]-tetrahydro-pyran-4-carbonitrile (Compound 1-87); 4-[3-(Imidazo[1,2-a]quinoxalin-8-ylsulfanyl)-phenyl]-tetrahydro-pyran-4-carboxylic acid amide (Compound 1-88); 8-[3-Fluoro-5-(4-methoxy-tetrahydro-pyran-4-yl)-phenylsulfanyl]-imidazo[1,2-a]quinoxaline (Compound 1-89); 4-[3-(Imidazo[1,2-a]quinoxalin-8-ylsulfanyl)-phenyl]-tetrahydro-pyran-4-carbaldehyde O-methyl-oxime (Compound 1-90).

TABLE 2

1,2-Dihydro-imidazo[1,2-a]quinoline

| Compound # | R$^8$ | M + H |
|---|---|---|
| 2-1 | OH | 379 |
| 2-2 | OMe | 398 |

Compounds in Table 2 are named:

4-[3-(1,2-Dihydro-imidazo[1,2-a]quinolin-7-ylsulfanyl)-phenyl]-tetrahydro-pyran-4-ol (Compound 2-1); 7-[3-(4-Methoxy-tetrahydro-pyran-4-yl)-phenylsulfanyl]-1,2-dihydro-imidazo[1,2-a]quinoline (Compound 2-2).

TABLE 3

Imidazo[1,2-a]quinolin-2-one

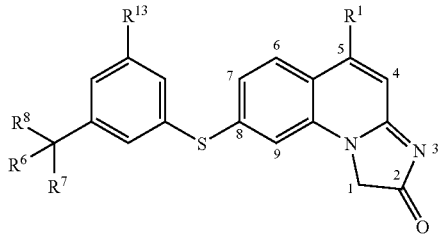

| Compound # | R8 | R6 | R7 | R13 | R1 | M + H |
|---|---|---|---|---|---|---|
| 3-1 | CN | THP | | H | Phenyl | 478 |
| 3-2 | CN | THP | | H | 4-Fluorophenyl | 496 |
| 3-3 | CN | THP | | H | 3-Methylphenyl | 492 |
| 3-4 | CN | THP | | H | 4-Methoxypyridin-3-yl | 509 |
| 3-5 | CN | THP | | F | 4-Fluorophenyl | 514 |
| 3-6 | OH | CF3 | Et | H | 4-Fluorophenyl | 513 |

Compounds in Table 3 are named:
4-[3-(2-Oxo-5-phenyl-1,2-dihydro-imidazo[1,2-a]quinolin-8-ylsulfanyl)-phenyl]-tetrahydro-pyran-4-carbonitrile (Compound 3-1); 4-{3-[5-(4-Fluoro-phenyl)-2-oxo-1,2-dihydro-imidazo[1,2-a]quinolin-8-ylsulfanyl]-phenyl}-tetrahydro-pyran-4-carbonitrile (Compound 3-2); 4-[3-(2-Oxo-5-m-tolyl-1,2-dihydro-imidazo[1,2-a]quinolin-8-ylsulfanyl)-phenyl]-tetrahydro-pyran-4-carbonitrile (Compound 3-3); 4-{3-[5-(4-Methoxy-pyridin-3-yl)-2-oxo-1,2-dihydro-imidazo[1,2-a]quinolin-8-ylsulfanyl]-phenyl}-tetrahydro-pyran-4-carbonitrile (Compound 3-4); 4-{3-Fluoro-5-[5-(4-fluoro-phenyl)-2-oxo-1,2-dihydro-imidazo[1,2-a]quinolin-8-ylsulfanyl]-phenyl}-tetrahydro-pyran-4-carbonitrile (Compound 3-5); 5-(4-Fluoro-phenyl)-8-[3-(1-hydroxy-1-trifluoromethyl-propyl)-phenylsulfanyl]-imidazo[1,2-a]quinolin-2-one (Compound 3-6).

TABLE 4

Imidazo[1,5-a]quinoline

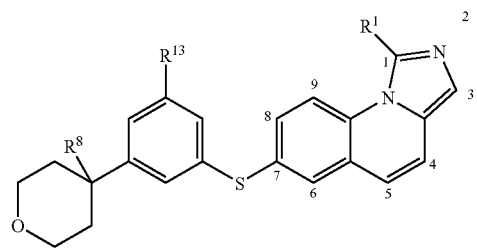

| Compound No. | R8 | R13 | R1 | M + H |
|---|---|---|---|---|
| 4-1 | CN | F | Me | 418 |
| 4-2 | OH | H | Me | 391 |
| 4-3 | OMe | H | Me | 405 |
| 4-4 | CN | F | Ph | 480 |
| 4-5 | CONH2 | F | Ph | 498 |

Compounds in Table 4 are named:
4-[3-Fluoro-5-(1-methyl-imidazo[1,5-a]quinolin-7-ylsulfanyl)-phenyl]-tetrahydro-pyran-4-carbonitrile (Compound 4-1); 4-[3-(1-Methyl-imidazo[1,5-a]quinolin-7-ylsulfanyl)-phenyl]-tetrahydro-pyran-4-ol (Compound 4-2); 7-[3-(4-Methoxy-tetrahydro-pyran-4-yl)-phenylsulfanyl]-1-methyl-imidazo[1,5-a]quinoline (Compound 4-3); 4-[3-Fluoro-5-(1-phenyl-imidazo[1,5-a]quinolin-7-ylsulfanyl)-phenyl]-tetrahydro-pyran-4-carbonitrile (Compound 4-4); 4-[3-Fluoro-5-(1-phenyl-imidazo[1,5-a]quinolin-7-ylsulfanyl)-phenyl]-tetrahydro-pyran-4-carboxylic acid amide (Compound 4-5).

TABLE 5

[1,2,4]Triazolo[4,3-a]quinoline

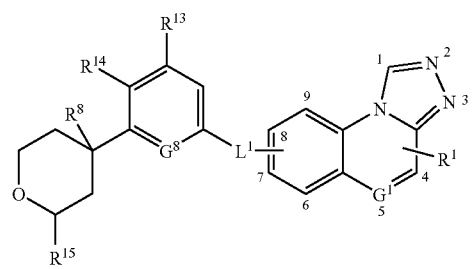

| Compound # | R8 | R14 | R13 | R1 | R15 | G8 | L1 | G1 | M + H |
|---|---|---|---|---|---|---|---|---|---|
| 5-1 | OMe | H | F | H | H | C | 6-OCH2 | C | 408 |
| 5-2 | OMe | H | F | 5-Chloro | H | C | 6-OCH2 | C | 432 |
| 5-3 | OMe | H | H | H | H | C | 7-OCH2 | C | 408 |
| 5-4 | CONH2 | H | H | 1-Pyridin-2-yl | H | C | 7-OCH2 | C | 480 |
| 5-5 | CN | H | H | 1-Pyridin-2-yl | H | C | 7-OCH2 | C | 482 |
| 5-6 | CO2Et | H | F | H | H | C | 7-OCH2 | C | 450 |
| 5-7 | OMe | H | F | 1-Thiazol-2-yl | H | C | 7-OCH2 | C | 491 |
| 5-8 | OMe | H | F | 5-Furan-3-yl | H | C | 7-OCH2 | C | 474 |
| 5-9 | OMe | H | F | 5-Bromo | H | C | 7-OCH2 | C | 488 |
| 5-10 | OMe | H | F | 1-Phenyl | H | C | 7-OCH2 | C | 484 |
| 5-11 | OMe | H | F | 1-Methyl | H | C | 7-OCH2 | C | 444 [M + Na] |
| 5-12 | OH | H | F | H | H | C | 7-OCH2 | C | 394 |
| 5-13 | OMe | H | F | 1-Quinolin-2-yl | H | C | 7-OCH2 | C | 535 |
| 5-14 | OMe | H | F | 1-Pyridin-2-yl | H | C | 7-OCH2 | C | 485 |

TABLE 5-continued

[1,2,4]Triazolo[4,3-a]quinoline

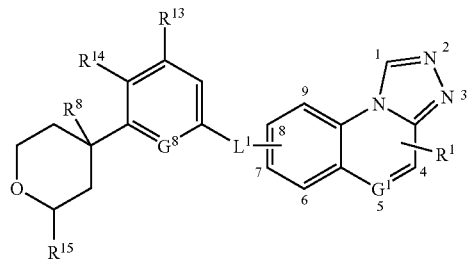

| Compound # | $R^8$ | $R^{14}$ | $R^{13}$ | $R^1$ | $R^{15}$ | $G^8$ | $L^1$ | $G^1$ | M + H |
|---|---|---|---|---|---|---|---|---|---|
| 5-15 | $CO_2H$ | H | F | H | H | C | 7-$OCH_2$ | C | 422 |
| 5-16 | $CONH_2$ | H | F | H | H | C | 7-$OCH_2$ | C | 421 |
| 5-17 | OMe | H | F | 1-Trifluoromethyl | H | C | 7-$OCH_2$ | C | 476 |
| 5-18 | OMe | H | F | 1-Carboxylic Acid Ethyl Ester | H | C | 7-$OCH_2$ | C | 480 |
| 5-19 | OMe | H | F | 1-Amino | H | C | 7-$OCH_2$ | C | 423 |
| 5-20 | OMe | H | F | H | H | C | 7-$OCH_2$ | N | 409 |
| 5-21 | CN | H | H | H | H | C | 7-S | C | 387 |
| 5-22 | $CONH_2$ | H | H | H | H | C | 7-S | C | 405 |
| 5-23 | CN | H | H | 1-Thiazol-2-yl | H | C | 7-S | C | 470 |
| 5-24 | CN | H | H | 1-Phenyl | H | C | 7-S | C | 463 |
| 5-25 | $CONH_2$ | H | H | 1-Phenyl | H | C | 7-S | C | 481 |
| 5-26 | $CONH_2$ | H | H | 1-Thiazol-2-yl | H | C | 7-S | C | 488 |
| 5-27 | CN | H | H | 1-Methyl | H | C | 7-S | C | 401 |
| 5-28 | CN | H | H | 1-Pyridin-2-yl | H | C | 7-S | C | 464 |
| 5-29 | CN | H | H | 1-Pyridin-3-yl | H | C | 7-S | C | 464 |
| 5-30 | CN | H | H | 1-Pyridin-4-yl | H | C | 7-S | C | 464 |
| 5-31 | CN | H | H | 1-(1H-Imidazol-2-yl) | H | C | 7-S | C | 453 |
| 5-32 | CN | H | H | 1-(4-Fluorophenyl) | H | C | 7-S | C | 503 [M + Na] |
| 5-33 | CN | H | H | 1-(3-Benzoic Acid) | H | C | 7-S | C | 507 |
| 5-34 | CN | H | H | 1-(4-Benzoic Acid) | H | C | 7-S | C | 507 |
| 5-35 | CN | H | H | 1-(4-Methoxyphenyl) | H | C | 7-S | C | 515 [M + Na] |
| 5-36 | CN | H | H | 1-Trifluoromethyl | H | C | 7-S | C | 455 |
| 5-37 | CN | H | H | 1-(2-Fluorophenyl) | H | C | 7-S | C | 503 [M + Na] |
| 5-38 | CN | H | H | 1-(3-Fluorophenyl) | H | C | 7-S | C | 503 [M + Na] |
| 5-39 | CN | H | H | 1-Cyclohexyl | H | C | 7-S | C | 469 |
| 5-40 | CN | H | H | 1-Ethyl | H | C | 7-S | C | 415 |
| 5-41 | CN | H | H | 1-Isopropyl | H | C | 7-S | C | 451 [M + Na] |
| 5-42 | CN | H | H | 1-Isobutyl | H | C | 7-S | C | 443 |
| 5-43 | CN | H | H | 1-Phenyl | Me | C | 7-S | C | 477 |
| 5-44 | OH | H | H | 1-Phenyl | H | C | 7-S | C | 454 |
| 5-45 | OMe | H | H | 1-Phenyl | H | C | 7-S | C | 468 |
| 5-46 | Cyclopropyl-methoxy | H | H | 1-Phenyl | H | C | 7-S | C | 508 |
| 5-47 | CN | H | H | 1-Cyclopentyl | H | C | 7-S | C | 455 |
| 5-48 | CN | H | H | 1-Cyclopropyl | H | C | 7-S | C | 427 |
| 5-49 | CN | H | H | 1-(1-Methyl-1H-imidazol-2-yl) | H | C | 7-S | C | 467 |
| 5-50 | $CONH_2$ | H | H | 1-Pyridin-3-yl | H | C | 7-S | C | 482 |
| 5-51 | $CONH_2$ | H | H | 1-Pyridin-2-yl | H | C | 7-S | C | 482 |
| 5-52 | OH | H | H | 1-Pyridin-2-yl | H | C | 7-S | C | 455 |
| 5-53 | OH | H | H | 1-Pyridin-2-yl | Me | C | 7-S | C | 469 |
| 5-54 | OH | H | H | 1-Pyridin-3-yl | H | C | 7-S | C | 455 |
| 5-55 | CN | H | H | 1-(4-Benzamide) | H | C | 7-S | C | 506 |
| 5-56 | CN | H | H | 1-(N-BOC-Aminomethyl) | H | C | 7-S | C | 516 |
| 5-57 | CN | H | H | 1-(N-CBZ-Aminomethyl) | H | C | 7-S | C | 564 |
| 5-58 | CN | H | H | 1-((S)-N-BOC-Pyrrolidin-2-yl) | H | C | 7-S | C | 556 |
| 5-59 | CN | H | H | 1-((R)-N-BOC-Pyrrolidin-2-yl) | H | C | 7-S | C | 556 |
| 5-60 | CN | H | H | 1-Propionic Acid | H | C | 7-S | C | 459 |
| 5-61 | CN | H | H | 1-Aminomethyl | H | C | 7-S | C | 416 |
| 5-62 | CN | H | H | 1-((S)-Pyrrolidin-2-yl) | H | C | 7-S | C | 456 |
| 5-63 | CN | H | H | 1-((R)-Pyrrolidin-2-yl) | H | C | 7-S | C | 456 |

TABLE 5-continued

[1,2,4]Triazolo[4,3-a]quinoline

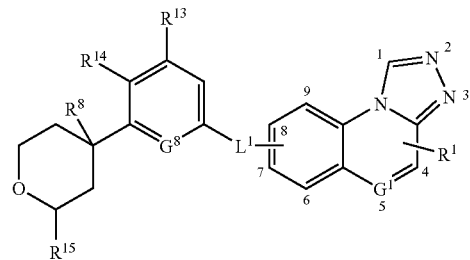

| Compound # | $R^8$ | $R^{14}$ | $R^{13}$ | $R^1$ | $R^{15}$ | $G^8$ | $L^1$ | $G^1$ | M + H |
|---|---|---|---|---|---|---|---|---|---|
| 5-64 | CN | H | H | 1-(6-Methoxypyridin-2-yl) | H | C | 7-S | C | 516 [M + Na] |
| 5-65 | CN | H | H | 1-(N-Acetylaminomethyl) | H | C | 7-S | C | 480 [M + Na] |
| 5-66 | CN | H | H | 1-(N,N-Dimethylaminomethyl) | H | C | 7-S | C | 444 |
| 5-67 | CN | H | H | 1-((S)-N-Methylpyrrolidin-2-yl) | H | C | 7-S | C | 470 |
| 5-68 | CN | H | H | 1-((R)-N-Methylpyrrolidin-2-yl) | H | C | 7-S | C | 470 |
| 5-69 | CN | H | H | 1-((S)-N-Acetylpyrrolidin-2-yl) | H | C | 7-S | C | 498 |
| 5-70 | CN | H | H | 1-((R)-N-Acetylpyrrolidin-2-yl) | H | C | 7-S | C | 498 |
| 5-71 | CN | H | H | 1-Pentanoic Acid Methyl Ester | H | C | 7-S | C | 501 |
| 5-72 | CN | H | H | 1-(6-Methoxypyridin-3-yl) | H | C | 7-S | C | 494 |
| 5-73 | CN | H | H | 1-(3-Methoxypyridin-4-yl) | H | C | 7-S | C | 494 |
| 5-74 | CN | H | H | 1-(5-Methoxypyridin-3-yl) | H | C | 7-S | C | 494 |
| 5-75 | CN | H | H | 1-Pentanoic Acid | H | C | 7-S | C | 487 |
| 5-76 | CN | H | H | 1-Pyridin-2-yl | Me | C | 7-S | C | 478 |
| 5-77 | CN | H | H | 1-Pyridin-2-yl, 4-Carboxylic Acid Methyl Ester | H | C | 7-S | C | 522 |
| 5-78 | $C(O)NH_2$ | H | H | 1-Pyridin-2-yl | Me | C | 7-S | C | 496 |
| 5-79 | CHNOMe | H | H | 1-Pyridin-2-yl | H | C | 7-S | C | 496 |
| 5-80 | $CO_2Me$ | H | H | 1-Pyridin-2-yl | H | C | 7-S | C | 519 [M + Na] |
| 5-81 | $CH_2OH$ | H | H | 1-Pyridin-2-yl | H | C | 7-S | C | 469 |
| 5-82 | CH(OH)Me | H | H | 1-Pyridin-2-yl | H | C | 7-S | C | 505 [M + Na] |
| 5-83 | $SO_2Me$ | H | H | 1-Pyridin-2-yl | H | C | 7-S | C | 517 |
| 5-84 | $SO_2NMe_2$ | H | H | 1-Pyridin-2-yl | H | C | 7-S | C | 546 |
| 5-85 | $CO_2H$ | H | H | 1-Pyridin-2-yl | H | C | 7-S | C | 505 [M + Na] |
| 5-86 | C(O)NHMe | H | H | 1-Pyridin-2-yl | H | C | 7-S | C | 518 [M + Na] |
| 5-87 | C(O)NH—($CH_2CH_2OH$) | H | H | 1-Pyridin-2-yl | H | C | 7-S | C | 526 |
| 5-88 | $C(O)NMe_2$ | H | H | 1-Pyridin-2-yl | H | C | 7-S | C | 532 [M + Na] |
| 5-89 | C(O)Me | H | H | 1-Pyridin-2-yl | H | C | 7-S | C | 503 [M + Na] |
| 5-90 | $C(OH)Me_2$ | H | H | 1-Pyridin-2-yl | H | C | 7-S | C | 497 |
| 5-91 | $CH_2$=CH | H | H | 1-Pyridin-2-yl | H | C | 7-S | C | 465 |
| 5-92 | Et | H | H | 1-Pyridin-2-yl | H | C | 7-S | C | 467 |
| 5-93 | CN | H | F | 1-Phenyl | H | C | 7-S | C | 481 |
| 5-94 | CN | H | F | 1-(2-Hydroxyprop-2-yl) | H | C | 7-S | C | 485 [M + N] |
| 5-95 | CN | H | F | 1-Pyridin-2-yl | H | C | 7-S | C | 482 |
| 5-96 | $C(O)NH_2$ | H | F | 1-Pyridin-2-yl | H | C | 7-S | C | 500 |
| 5-97 | CN | H | F | H | H | C | 7-S | C | 405 |
| 5-98 | OMe | H | F | 1-Pyridin-2-yl | H | C | 7-S | C | 509 [M + Na] |
| 5-99 | CN | H | H | 1-Pyridin-2-yl | H | N | 7-S | C | 465 |
| 5-100 | $C(O)NH_2$ | H | H | 1-Pyridin-2-yl | H | N | 7-S | C | 483 |
| 5-101 | CN | H | H | H | H | N | 7-S | C | 388 |
| 5-102 | $C(O)NH_2$ | H | H | H | H | N | 7-S | C | 406 |
| 5-103 | CN | H | H | 1-Phenyl | H | C | 7-S | N | 464 |
| 5-104 | CN | H | H | 1-Pyridin-2-yl | H | C | 7-S | N | 465 |
| 5-105 | OH | H | H | 1-Pyridin-2-yl | H | C | 7-S | N | 456 |

TABLE 5-continued

[1,2,4]Triazolo[4,3-a]quinoline

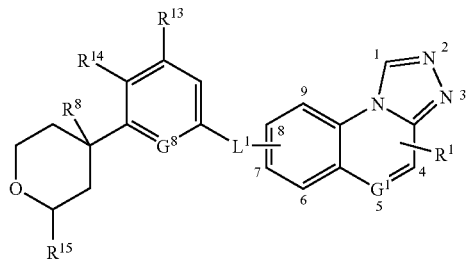

| Compound # | R8 | R14 | R13 | R1 | R15 | G8 | L1 | G1 | M + H |
|---|---|---|---|---|---|---|---|---|---|
| 5-106 | OH | H | H | 1-Pyridin-2-yl | Me | C | 7-S | N | 470 |
| 5-107 | CN | H | H | 1-Pyridin-3-yl | H | C | 7-S | N | 465 |
| 5-108 | OH | H | H | 1-Pyridin-3-yl | H | C | 7-S | N | 456 |
| 5-109 | CN | H | H | 1-Phenyl, 4-(Aminoacetic Acid Methyl Ester) | H | C | 7-S | N | 551 |
| 5-110 | CN | H | H | 1-Phenyl, 4-(Aminoacetic Acid) | H | C | 7-S | N | 537 |
| 5-111 | C(O)NH$_2$ | H | H | 1-Pyridin-2-yl | H | C | 7-S | N | 483 |
| 5-112 | CHNOMe | H | H | 1-Pyridin-2-yl | H | C | 7-S | N | 497 |
| 5-113 | C(O)Me | H | H | 1-Pyridin-2-yl | H | C | 7-S | N | 482 |
| 5-114 | OMe | H | H | 1-Pyridin-2-yl, 4,6-Dimethyl | H | C | 7-S | N | 520 [M + Na] |
| 5-115 | CHNOH | H | H | 1-Pyridin-2-yl | H | C | 7-S | N | 483 |
| 5-116 | OH | H | F | 1-Pyridin-2-yl | H | C | 7-S | N | 474 |
| 5-117 | OMe | H | F | 1-Pyridin-2-yl | H | C | 7-S | N | 488 |
| 5-118 | CN | H | H | 1-Phenyl | H | C | 7-SO | C | 479 |
| 5-119 | C(O)NH$_2$ | H | H | 1-Pyridin-2-yl | H | C | 7-SO | C | 498 |
| 5-120 | CN | H | H | 1-Phenyl | H | C | 7-SO$_2$ | C | 495 |
| 5-121 | C(O)NH$_2$ | H | H | 1-Pyridin-2-yl | H | C | 7-SO$_2$ | C | 514 |
| 5-122 | OMe | H | F | H | H | C | 8-OCH$_2$ | C | 408 |
| 5-123 | OMe | H | F | 5-Bromo | H | C | 8-OCH$_2$ | C | 486 |
| 5-124 | OMe | H | F | 5-Furan-3-yl | H | C | 8-OCH$_2$ | C | 474 |
| 5-125 | OMe | H | F | 5-Chloro | H | C | 8-OCH$_2$ | C | 432 |
| 5-126 | OMe | H | F | 5-Phenyl | H | C | 8-OCH$_2$ | C | 484 |
| 5-127 | OMe | H | F | 5-(3-Benzoic Acid) | H | C | 8-OCH$_2$ | C | 528 |
| 5-128 | CO$_2$Me | H | F | 5-Chloro | H | C | 8-OCH$_2$ | C | 470 |
| 5-129 | CO$_2$Me | H | F | 5-Methylsulfanyl | H | C | 8-OCH$_2$ | C | 482 |
| 5-130 | CO$_2$Me | H | F | 5-Methoxy | H | C | 8-OCH$_2$ | C | 467 |
| 5-131 | CO$_2$Me | H | F | H | H | C | 8-OCH$_2$ | C | 436 |
| 5-132 | CO$_2$Me | H | F | 5-Pyridin-3-yl | H | C | 8-OCH$_2$ | C | 513 |
| 5-133 | CO$_2$Me | H | F | 5-Pyridin-4-yl | H | C | 8-OCH$_2$ | C | 513 |
| 5-134 | CO$_2$Me | H | F | 5-Thiophen-3-yl | H | C | 8-OCH$_2$ | C | 518 |
| 5-135 | CO$_2$Me | H | F | 5-(3-Cyanophenyl) | H | C | 8-OCH$_2$ | C | 537 |
| 5-136 | CO$_2$Me | H | F | 5-(3-Methoxyphenyl) | H | C | 8-OCH$_2$ | C | 542 |
| 5-137 | CO$_2$Me | H | F | 5-(3-Methylphenyl) | H | C | 8-OCH$_2$ | C | 526 |
| 5-138 | CO$_2$Me | H | F | 5-Phenyl | H | C | 8-OCH$_2$ | C | 512 |
| 5-139 | C(O)NH$_2$ | H | F | 5-Chloro | H | C | 8-OCH$_2$ | C | 455 |
| 5-140 | C(O)NH$_2$ | H | F | 5-(1-Methyl-1H-pyrazol-4-yl) | H | C | 8-OCH$_2$ | C | 501 |
| 5-141 | C(O)NH$_2$ | H | F | 5-(3-Methylphenyl) | H | C | 8-OCH$_2$ | C | 511 |
| 5-142 | C(O)NH$_2$ | H | F | 5-(4-Fluorophenyl) | H | C | 8-OCH$_2$ | C | 515 |
| 5-143 | CN | H | H | 1-Thiazol-2-yl | H | C | 8-S | C | 492 [M + Na] |
| 5-144 | CN | H | H | H | H | C | 8-S | C | 387 |
| 5-145 | CN | H | H | 5-Chloro | H | C | 8-S | C | 421 |
| 5-146 | CN | H | H | 5-(3-Methylphenyl) | H | C | 8-S | C | 477 |
| 5-147 | CN | H | H | 5-(1-Methyl-1H-pyrazol-4-yl) | H | C | 8-S | C | 467 |
| 5-148 | CN | H | H | 5-(4-Fluorophenyl) | H | C | 8-S | C | 481 |
| 5-149 | OH | H | H | 5-Phenyl | H | C | 8-S | C | 454 |
| 5-150 | CN | H | H | 5-Phenyl | H | C | 8-S | C | 463 |
| 5-151 | CN | H | H | 5-Methyl | H | C | 8-S | C | 401 |
| 5-152 | OH | H | H | 5-Phenyl | H | N | 8-S | C | 455 |
| 5-153 | CN | H | H | 1-Methyl, 5-Phenyl | H | C | 8-S | C | 477 |
| 5-154 | OH | H | H | 1-Methyl, 5-Phenyl | H | C | 8-S | C | 468 |
| 5-155 | OH | H | H | 1-Amino, 5-Phenyl | H | C | 8-S | C | 469 |
| 5-156 | C(O)NH$_2$ | H | H | 5-Phenyl | H | C | 8-S | C | 481 |
| 5-157 | CN | H | H | 1-Trifluoromethyl, 5-Phenyl | H | C | 8-S | C | 531 |
| 5-158 | CO$_2$H | H | H | 5-Phenyl | H | C | 8-S | C | 482 |
| 5-159 | CN | H | F | 5-Chloro | H | C | 8-S | C | 439 |
| 5-160 | OMe | H | F | H | H | C | 8-S | N | 411 |

TABLE 5-continued

[1,2,4]Triazolo[4,3-a]quinoline

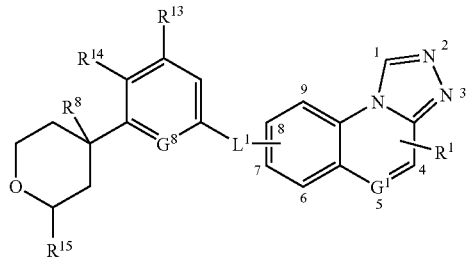

| Compound # | R8 | R14 | R13 | R1 | R15 | G8 | L1 | G1 | M + H |
|---|---|---|---|---|---|---|---|---|---|
| 5-161 | CO2Me | OMe | H | 1-Pyridin-2-yl | H | C | 7-S | C | 527 |
| 5-162 | —C(=O)O— | | H | 1-Pyridin-2-yl | H | C | 7-S | C | 481 |

Compounds in Table 5 are named:
6-[3-Fluoro-5-(4-methoxy-tetrahydro-pyran-4-yl)-phenoxymethyl]-[1,2,4]triazolo[4,3-a]quinoline (Compound 5-1); 5-Chloro-6-[3-fluoro-5-(4-methoxy-tetrahydro-pyran-4-yl)-phenyoxymethyl]-[1,2,4]triazolo[4,3-a]quinoline (Compound 5-2); 7-[3-(4-Methoxy-tetrahydro-pyran-4-yl)-phenoxymethyl]-[1,2,4]triazolo[4,3-a]quinoline (Compound 5-3); 4-[3-(1-Pyridin-2-yl-[1,2,4]triazolo[4,3-a]quinolin-7-ylmethoxy)-phenyl]-tetrahydro-pyran-4-carboxylic acid amide (Compound 5-4); 4-[3-(1-Pyridin-2-yl-[1,2,4]triazolo[4,3-a]quinolin-7-ylmethoxy)-phenyl]-tetrahydro-pyran-4-carbonitrile (Compound 5-5); 4-[3-Fluoro-5-([1,2,4]triazolo[4,3-a]quinolin-7-ylmethoxy)-phenyl]-tetrahydro-pyran-4-carboxylic acid ethyl ester (Compound 5-6); 7-[3-Fluoro-5-(4-methoxy-tetrahydro-pyran-4-yl)-phenoxymethyl]-1-thiazol-2-yl-[1,2,4]triazolo[4,3-a]quinoline (Compound 5-7); 7-[3-Fluoro-5-(4-methoxy-tetrahydro-pyran-4-yl)-phenoxymethyl]-5-furan-3-yl-[1,2,4]triazolo[4,3-a]quinoline (Compound 5-8); 5-Bromo-7-[3-fluoro-5-(4-methoxy-tetrahydro-pyran-4-yl)-phenoxymethyl]-[1,2,4]triazolo[4,3-a]quinoline (Compound 5-9); 7-[3-Fluoro-5-(4-methoxy-tetrahydro-pyran-4-yl)-phenoxymethyl]-1-phenyl-[1,2,4]triazolo[4,3-a]quinoline (Compound 5-10); 7-[3-Fluoro-5-(4-methoxy-tetrahydro-pyran-4-yl)-phenoxymethyl]-1-methyl-[1,2,4]triazolo[4,3-a]quinoline (Compound 5-11); 4-[3-Fluoro-5-([1,2,4]triazolo[4,3-a]quinolin-7-ylmethoxy)-phenyl]-tetrahydro-pyran-4-ol (Compound 5-12); 7-[3-Fluoro-5-(4-methoxy-tetrahydro-pyran-4-yl)-phenoxymethyl]-1-quinolin-2-yl-[1,2,4]triazolo[4,3-a]quinoline (Compound 5-13); 7-[3-Fluoro-5-(4-methoxy-tetrahydro-pyran-4-yl)-phenoxymethyl]-1-pyridin-2-yl-[1,2,4]triazolo[4,3-a]quinoline (Compound 5-14); 4-[3-Fluoro-5-([1,2,4]triazolo[4,3-a]quinolin-7-ylmethoxy)-phenyl]-tetrahydro-pyran-4-carboxylic acid (Compound 5-15); 4-[3-Fluoro-5-([1,2,4]triazolo[4,3-a]quinolin-7-ylmethoxy)-phenyl]-tetrahydro-pyran-4-carboxylic acid amide (Compound 5-16); 7-[3-Fluoro-5-(4-methoxy-tetrahydro-pyran-4-yl)-phenoxymethyl]-1-trifluoromethyl-[1,2,4]triazolo[4,3-a]quinoline (Compound 5-17); 7-[3-Fluoro-5-(4-methoxy-tetrahydro-pyran-4-yl)-phenoxymethyl]-[1,2,4]triazolo[4,3-a]quinoline-1-carboxylic acid ethyl ester (Compound 5-18); 7-[3-Fluoro-5-(4-methoxy-tetrahydro-pyran-4-yl)-phenoxymethyl]-[1,2,4]triazolo[4,3-a]quinolin-1-ylamine (Compound 5-19); 7-[3-Fluoro-5-(4-methoxy-tetrahydro-pyran-4-yl)-phenoxymethyl]-[1,2,4]triazolo[4,3-a]quinoxaline (Compound 5-20); 4-[3-([1,2,4]Triazolo[4,3-a]quinolin-7-ylsulfanyl)-phenyl]-tetrahydro-pyran-4-carbonitrile (Compound 5-21); 4-[3-([1,2,4]Triazolo[4,3-a]quinolin-7-ylsulfanyl)-phenyl]-tetrahydro-pyran-4-carboxylic acid amide (Compound 5-22); 4-[3-(1-Thiazol-2-yl-[1,2,4]triazolo[4,3-a]quinolin-7-ylsulfanyl)-phenyl]-tetrahydro-pyran-4-carbonitrile (Compound 5-23); 4-[3-(1-Phenyl-[1,2,4]triazolo[4,3-a]quinolin-7-ylsulfanyl)-phenyl]-tetrahydro-pyran-4-carbonitrile (Compound 5-24); 4-[3-(1-Phenyl-[1,2,4]triazolo[4,3-a]quinolin-7-ylsulfanyl)-phenyl]-tetrahydro-pyran-4-carboxylic acid amide (Compound 5-25); 4-[3-(1-Thiazol-2-yl-[1,2,4]triazolo[4,3-a]quinolin-7-ylsulfanyl)-phenyl]-tetrahydro-pyran-4-carboxylic acid amide (Compound 5-26); 4-[3-(1-Methyl-[1,2,4]triazolo[4,3-a]quinolin-7-ylsulfanyl)-phenyl]-tetrahydro-pyran-4-carbonitrile (Compound 5-27); 4-[3-(1-Pyridin-2-yl-[1,2,4]triazolo[4,3-a]quinolin-7-ylsulfanyl)-phenyl]-tetrahydro-pyran-4-carbonitrile (Compound 5-28); 4-[3-(1-Pyridin-3-yl-[1,2,4]triazolo[4,3-a]quinolin-7-ylsulfanyl)-phenyl]-tetrahydro-pyran-4-carbonitrile (Compound 5-29); 4-[3-(1-Pyridin-4-yl-[1,2,4]triazolo[4,3-a]quinolin-7-ylsulfanyl)-phenyl]-tetrahydro-pyran-4-carbonitrile (Compound 5-30); 4-{3-[1-(1H-Imidazol-2-yl)-[1,2,4]triazolo[4,3-a]quinolin-7-ylsulfanyl]-phenyl}-tetrahydro-pyran-4-carbonitrile (Compound 5-31); 4-{3-[1-(4-Fluoro-phenyl)-[1,2,4]triazolo[4,3-a]quinolin-7-ylsulfanyl]-phenyl}-tetrahydro-pyran-4-carbonitrile (Compound 5-32); 3-{7-[3-(4-Cyano-tetrahydro-pyran-4-yl)-phenylsulfanyl]-[1,2,4]triazolo[4,3-a]quinolin-1-yl}-benzoic acid (Compound 5-33); 4-{7-[3-(4-Cyano-tetrahydro-pyran-4-yl)-phenylsulfanyl]-[1,2,4]triazolo[4,3-a]quinolin-1-yl}-benzoic acid (Compound 5-34); 4-{3-[1-(4-Methoxy-phenyl)-[1,2,4]triazolo[4,3-a]quinolin-7-ylsulfanyl]-phenyl}-tetrahydro-pyran-4-carbonitrile (Compound 5-35); 4-[3-(1-Trifluoromethyl-[1,2,4]triazolo[4,3-a]quinolin-7-ylsulfanyl)-phenyl]-tetrahydro-pyran-4-carbonitrile (Compound 5-36); 4-{3-[1-(2-Fluoro-phenyl)-[1,2,4]triazolo[4,3-a]quinolin-7-ylsulfanyl]-phenyl}-tetrahydro-pyran-4-carbonitrile (Compound 5-37); 4-{3-[1-(3-Fluoro-phenyl)-[1,2,4]triazolo[4,3-a]quinolin-7-ylsulfanyl]-phenyl}-tetrahydro-pyran-4-carbonitrile (Compound 5-38); 4-[3-(1-Cyclohexyl-[1,2,4]triazolo[4,3-a]quinolin-7-ylsulfanyl)-phenyl]-tetrahydro-pyran-4-carbonitrile (Compound 5-39); 4-[3-(1-Ethyl-[1,2,4]triazolo[4,3-a]quinolin-7-ylsulfanyl)- phenyl]-tetrahydro-pyran-4-carbonitrile (Compound 5-40); 4-[3-(1-Isopropyl-[1,2,4]triazolo[4,3-a]quinolin-7-ylsulfanyl)-phenyl]-tetrahydro-pyran-4-carbonitrile (Compound 5-41); 4-[3-(1-Isobutyl-[1,2,4]triazolo[4,3-a]quinolin-7-ylsulfanyl)-phenyl]-tetrahydro-pyran-4-carbonitrile (Compound 5-42); 2-Methyl-4-[3-(1-phenyl-[1,2,4]triazolo[4,3-a]quinolin-7-ylsulfanyl)-phenyl]-tetrahydro-pyran-4-carbonitrile (Compound 5-43); 4-[3-(1-Phenyl-[1,2,4]triazolo[4,3-a]quinolin-7-ylsulfanyl)-phenyl]-tetrahydro-pyran-4-ol (Compound 5-44); 7-[3-(4-Methoxy-tetrahydro-pyran-4-yl)-phenylsulfanyl]-1-phenyl-[1,2,4]triazolo[4,3-a]quinoline (Compound 5-45); 7-[3-(4-Cyclopropylmethoxy-tetrahydro-pyran-4-yl)-phenylsulfanyl]-1-phenyl-[1,2,4]triazolo[4,3-a]quinoline (Compound 5-46); 4-[3-(1-Cyclopentyl-[1,2,4]triazolo[4,3-a]quinolin-7-ylsulfanyl)-phenyl]-tetrahydro-pyran-4-carbonitrile (Compound 5-47); 4-[3-(1-Cyclopropyl-[1,2,4]triazolo[4,3-a]quinolin-7-ylsulfanyl)-phenyl]-tetrahydro-pyran-4-carbonitrile (Compound 5-48); 4-{3-[1-(1-Methyl-1H-imidazol-2-yl)-[1,2,4]triazolo[4,3-a]quinolin-7-ylsulfanyl]-phenyl}-tetrahydro-pyran-4-carbonitrile (Compound 5-49); 4-[3-(1-Pyridin-3-yl-[1,2,4]triazolo[4,3-a]quinolin-7-ylsulfanyl)-phenyl]-tetrahydro-pyran-4-carboxylic acid amide (Compound 5-50); 4-[3-(1-Pyridin-2-yl-[1,2,4]triazolo[4,3-a]quinolin-7-ylsulfanyl)-phenyl]-tetrahydro-pyran-4-carboxylic acid amide (Compound 5-51); 4-[3-(1-Pyridin-2-yl-[1,2,4]triazolo[4,3-a]quinolin-7-ylsulfanyl)-phenyl]-tetrahydro-pyran-4-ol (Compound 5-52); (2S,4R)-2-Methyl-4-[3-(1-pyridin-2-yl-[1,2,4]triazolo[4,3-a]quinolin-7-ylsulfanyl)-phenyl]-tetrahydro-pyran-4-ol (Compound 5-53); 4-[3-(1-Pyridin-3-yl-[1,2,4]triazolo[4,3-a]quinolin-7-ylsulfanyl)-phenyl]-tetrahydro-pyran-4-ol (Compound 5-54); 4-{7-[3-(4-Cyano-tetrahydro-pyran-4-yl)-phenylsulfanyl]-[1,2,4]triazolo[4,3-a]quinolin-1-yl}-benzamide (Compound 5-55); {7-[3-(4-Cyano-tetrahydro-pyran-4-yl)-phenylsulfanyl]-[1,2,4]triazolo[4,3-a]quinolin-1-ylmethyl}-carbamic acid tert-butyl ester (Compound 5-56); (2-{7-[3-(4-Cyano-tetrahydro-pyran-4-yl)-phenylsulfanyl]-[1,2,4]triazolo[4,3-a]quinolin-1-yl}-ethyl)-carbamic acid benzyl ester (Compound 5-57); (S)-2-{7-[3-(4-Cyano-tetrahydro-pyran-4-yl)-phenylsulfanyl]-[1,2,4]triazolo[4,3-a]quinolin-1-yl}-pyrrolidine-1-carboxylic acid tert-butyl ester (Compound 5-58); (R)-2-{7-[3-(4-Cyano-tetrahydro-pyran-4-yl)-phenylsulfanyl]-[1,2,4]triazolo[4,3-a]quinolin-1-yl}-pyrrolidine-1-carboxylic acid tert-butyl ester (Compound 5-59); 3-{7-[3-(4-Cyano-tetrahydro-pyran-4-yl)-phenylsulfanyl]-[1,2,4]triazolo[4,3-a]quinolin-1-yl}-propionic acid (Compound 5-60); 4-[3-(1-Aminomethyl-[1,2,4]triazolo[4,3-a]quinolin-7-ylsulfanyl)-phenyl]-tetrahydro-pyran-4-carbonitrile (Compound 5-61); 4-[3-((S)-1-Pyrrolidin-2-yl-[1,2,4]triazolo[4,3-a]quinolin-7-ylsulfanyl)-phenyl]-tetrahydro-pyran-4-carbonitrile (Compound 5-62); 4-[3-((R)-1-Pyrrolidin-2-yl-[1,2,4]triazolo[4,3-a]quinolin-7-ylsulfanyl)-phenyl]-tetrahydro-pyran-4-carbonitrile (Compound 5-63); 4-{3-[1-(6-Methoxy-pyridin-2-yl)-[1,2,4]triazolo[4,3-a]quinolin-7-ylsulfanyl]-phenyl}-tetrahydro-pyran-4-carbonitrile (Compound 5-64); N-{7-[3-(4-Cyano-tetrahydro-pyran-4-yl)-phenylsulfanyl]-[1,2,4]triazolo[4,3-a]quinolin-1-ylmethyl}-acetamide (Compound 5-65); 4-[3-(1-Dimethylaminomethyl-[1,2,4]triazolo[4,3-a]quinolin-7-ylsulfanyl)-phenyl]-tetrahydro-pyran-4-carbonitrile (Compound 5-66); 4-{3-[1-((S)-1-Methyl-pyrrolidin-2-yl)-[1,2,4]triazolo[4,3-a]quinolin-7-ylsulfanyl]-phenyl}-tetrahydro-pyran-4-carbonitrile (Compound 5-67); 4-{3-[1-((R)-1-Methyl-pyrrolidin-2-yl)-[1,2,4]triazolo[4,3-a]quinolin-7-ylsulfanyl]-phenyl}-tetrahydro-pyran-4-carbonitrile (Compound 5-68); 4-{3-[1-((S)-1-Acetyl-pyrrolidin-2-yl)-[1,2,4]triazolo[4,3-a]quinolin-7-ylsulfanyl]-phenyl}-tetrahydro-pyran-4-carbonitrile (Compound 5-69); 4-{3-[1-((R)-1-Acetyl-pyrrolidin-2-yl)-[1,2,4]triazolo[4,3-a]quinolin-7-ylsulfanyl]-phenyl}-tetrahydro-pyran-4-carbonitrile (Compound 5-70); 5-{7-[3-(4-Cyano-tetrahydro-pyran-4-yl)-phenylsulfanyl]-[1,2,4]triazolo[4,3-a]quinolin-1-yl}-pentanoic acid methyl ester (Compound 5-71); 4-{3-[1-(6-Methoxy-pyridin-3-yl)-[1,2,4]triazolo[4,3-a]quinolin-7-ylsulfanyl]-phenyl}-tetrahydro-pyran-4-carbonitrile (Compound 5-72); 4-{3-[1-(3-Methoxy-pyridin-4-yl)-[1,2,4]triazolo[4,3-a]quinolin-7-ylsulfanyl]-phenyl}-tetrahydro-pyran-4-carbonitrile (Compound 5-73); 4-{3-[1-(5-Methoxy-pyridin-3-yl)-[1,2,4]triazolo[4,3-a]quinolin-7-ylsulfanyl]-phenyl}-tetrahydro-pyran-4-carbonitrile (Compound 5-74); 5-{7-[3-(4-Cyano-tetrahydro-pyran-4-yl)-phenylsulfanyl]-[1,2,4]triazolo[4,3-a]quinolin-1-yl}-pentanoic acid (Compound 5-75); 2-Methyl-4-[3-(1-pyridin-2-yl-[1,2,4]triazolo[4,3-a]quinolin-7-ylsulfanyl)-phenyl]-tetrahydro-pyran-4-carbonitrile (Compound 5-76); 7-[3-(4-Cyano-tetrahydro-pyran-4-yl)-phenylsulfanyl]-1-pyridin-2-yl-[1,2,4]triazolo[4,3-a]quinoline-4-carboxylic acid methyl ester (Compound 5-77); 2-Methyl-4-[3-(1-pyridin-2-yl-[1,2,4]triazolo[4,3-a]quinolin-7-ylsulfanyl)-phenyl]-tetrahydro-pyran-4-carboxylic acid amide (Compound 5-78); 4-[3-(1-Pyridin-2-yl-[1,2,4]triazolo[4,3-a]quinolin-7-ylsulfanyl)-phenyl]-tetrahydro-pyran-4-carbaldehyde O-methyl-oxime (Compound 5-79); 4-[3-(1-Pyridin-2-yl-[1,2,4]triazolo[4,3-a]quinolin-7-ylsulfanyl)-phenyl]-tetrahydro-pyran-4-carboxylic acid methyl ester (Compound 5-80); {4-[3-(1-Pyridin-2-yl-[1,2,4]triazolo[4,3-a]quinolin-7-ylsulfanyl)-phenyl]-tetrahydro-pyran-4-yl}-methanol (Compound 5-81); 1-{4-[3-(1-Pyridin-2-yl-[1,2,4]triazolo[4,3-a]quinolin-7-ylsulfanyl)-phenyl]-tetrahydro-pyran-4-yl}-ethanol (Compound 5-82); 7-[3-(4-Methanesulfonyl-tetrahydro-pyran-4-yl)-phenylsulfanyl]-1-pyridin-2-yl-[1,2,4]triazolo[4,3-a]quinoline (Compound 5-83); 4-[3-(1-Pyridin-2-yl-[1,2,4]triazolo[4,3-a]quinolin-7-ylsulfanyl)-phenyl]-tetrahydro-pyran-4-sulfonic acid dimethylamide (Compound 5-84); 4-[3-(1-Pyridin-2-yl-[1,2,4]triazolo[4,3-a]quinolin-7-ylsulfanyl)-phenyl]-tetrahydro-pyran-4-carboxylic acid (Compound 5-85); 4-[3-(1-Pyridin-2-yl-[1,2,4]triazolo[4,3-a]quinolin-7-ylsulfanyl)-phenyl]-tetrahydro-pyran-4-carboxylic acid methylamide (Compound 5-86); 4-[3-(1-Pyridin-2-yl-[1,2,4]triazolo[4,3-a]quinolin-7-ylsulfanyl)-phenyl]-tetrahydro-pyran-4-carboxylic acid (2-hydroxy-ethyl)-amide (Compound 5-87); 4-[3-(1-Pyridin-2-yl-[1,2,4]triazolo[4,3-a]quinolin-7-ylsulfanyl)-phenyl]-tetrahydro-pyran-4-carboxylic acid dimethylamide (Compound 5-88); 1-{4-[3-(1-Pyridin-2-yl-[1,2,4]triazolo[4,3-a]quinolin-7-ylsulfanyl)-phenyl]-tetrahydro-pyran-4-yl}-ethanone (Compound 5-89); 2-{4-[3-(1-Pyridin-2-yl-[1,2,4]triazolo[4,3-a]quinolin-7-ylsulfanyl)-phenyl]-tetrahydro-pyran-4-yl}-propan-2-ol (Compound 5-90); 1-Pyridin-2-yl-7-[3-(4-vinyl-tetrahydro-pyran-4-yl)-phenylsulfanyl]-[1,2,4]triazolo[4,3-a]quinoline (Compound 5-91); 7-[3-(4-Ethyl-tetrahydro-pyran-4-yl)-phenylsulfanyl]-1-pyridin-2-yl-[1,2,4]triazolo[4,3-a]quinoline (Compound 5-92); 4-[3-Fluoro-5-(1-phenyl-[1,2,4]triazolo[4,3-a]quinolin-7-ylsulfanyl)-phenyl]-tetrahydro-pyran-4-carbonitrile (Compound 5-93); 4-{3-Fluoro-5-[1-(1-hydroxy-1-methyl-ethyl)-[1,2,4]triazolo[4,3-a]quinolin-7-ylsulfanyl]-phenyl}-tetrahydro-pyran-4-carbonitrile (Compound 5-94); 4-[3-Fluoro-5-(1-pyridin-2-yl-[1,2,4]

triazolo[4,3-a]quinolin-7-ylsulfanyl)-phenyl]-tetrahydro-pyran-4-carbonitrile (Compound 5-95); 4-[3-Fluoro-5-(1-pyridin-2-yl-[1,2,4]triazolo[4,3-a]quinolin-7-ylsulfanyl)-phenyl]-tetrahydro-pyran-4-carboxylic acid amide (Compound 5-96); 4-[3-Fluoro-5-([1,2,4]triazolo[4,3-a]quinolin-7-ylsulfanyl)-phenyl]-tetrahydro-pyran-4-carbonitrile (Compound 5-97); 7-[3-Fluoro-5-(4-methoxy-tetrahydro-pyran-4-yl)-phenylsulfanyl]-1-pyridin-2-yl-[1,2,4]triazolo[4,3-a]quinoline (Compound 5-98); 4-[6-(1-Pyridin-2-yl-[1,2,4]triazolo[4,3-a]quinolin-7-ylsulfanyl)-pyridin-2-yl]-tetrahydro-pyran-4-carbonitrile (Compound 5-99); 4-[6-(1-Pyridin-2-yl-[1,2,4]triazolo[4,3-a]quinolin-7-ylsulfanyl)-pyridin-2-yl]-tetrahydro-pyran-4-carboxylic acid amide (Compound 5-100); 4-[6-([1,2,4]Triazolo[4,3-a]quinolin-7-ylsulfanyl)-pyridin-2-yl]-tetrahydro-pyran-4-carbonitrile (Compound 5-101); 4-[6-([1,2,4]Triazolo[4,3-a]quinolin-7-ylsulfanyl)-pyridin-2-yl]-tetrahydro-pyran-4-carboxylic acid amide (Compound 5-102); 4-[3-(1-Phenyl-[1,2,4]triazolo[4,3-a]quinoxalin-7-ylsulfanyl)-phenyl]-tetrahydro-pyran-4-carbonitrile (Compound 5-103); 4-[3-(1-Pyridin-2-yl-[1,2,4]triazolo[4,3-a]quinoxalin-7-ylsulfanyl)-phenyl]-tetrahydro-pyran-4-carbonitrile (Compound 5-104); 4-[3-(1-Pyridin-2-yl-[1,2,4]triazolo[4,3-a]quinoxalin-7-ylsulfanyl)-phenyl]-tetrahydro-pyran-4-ol (Compound 5-105); (2S,4R)-2-Methyl-4-[3-(1-pyridin-2-yl-[1,2,4]triazolo[4,3-a]quinoxalin-7-ylsulfanyl)-phenyl]-tetrahydro-pyran-4-ol (Compound 5-106); 4-[3-(1-Pyridin-3-yl-[1,2,4]triazolo[4,3-a]quinoxalin-7-ylsulfanyl)-phenyl]-tetrahydro-pyran-4-carbonitrile (Compound 5-107); 4-[3-(1-Pyridin-3-yl-[1,2,4]triazolo[4,3-a]quinoxalin-7-ylsulfanyl)-phenyl]-tetrahydro-pyran-4-ol (Compound 5-108); {7-[3-(4-Cyano-tetrahydro-pyran-4-yl)-phenylsulfanyl]-1-phenyl-[1,2,4]triazolo[4,3-a]quinoxalin-4-ylamino}-acetic acid methyl ester (Compound 5-109); {7-[3-(4-Cyano-tetrahydro-pyran-4-yl)-phenylsulfanyl]-1-phenyl-[1,2,4]triazolo[4,3-a]quinoxalin-4-ylamino}-acetic acid (Compound 5-110); 4-[3-(1-Pyridin-2-yl-[1,2,4]triazolo[4,3-a]quinoxalin-7-ylsulfanyl)-phenyl]-tetrahydro-pyran-4-carboxylic acid amide (Compound 5-111); 4-[3-(1-Pyridin-2-yl-[1,2,4]triazolo[4,3-a]quinoxalin-7-ylsulfanyl)-phenyl]-tetrahydro-pyran-4-carbaldehyde O-methyl-oxime (Compound 5-112); 1-{4-[3-(1-Pyridin-2-yl-[1,2,4]triazolo[4,3-a]quinoxalin-7-ylsulfanyl)-phenyl]-tetrahydro-pyran-4-yl}-ethanone (Compound 5-113); 7-[3-(4-Methoxy-tetrahydro-pyran-4-yl)-phenylsulfanyl]-4,6-dimethyl-1-pyridin-2-yl-[1,2,4]triazolo[4,3-a]quinoxaline (Compound 5-114); 4-[3-(1-Pyridin-2-yl-[1,2,4]triazolo[4,3-a]quinoxalin-7-ylsulfanyl)-phenyl]-tetrahydro-pyran-4-carbaldehyde oxime (Compound 5-115); 4-[3-Fluoro-5-(1-pyridin-2-yl-[1,2,4]triazolo[4,3-a]quinoxalin-7-ylsulfanyl)-phenyl]-tetrahydro-pyran-4-ol (Compound 5-116); 7-[3-Fluoro-5-(4-methoxy-tetrahydro-pyran-4-yl)-phenylsulfanyl]-1-pyridin-2-yl-[1,2,4]triazolo[4,3-a]quinoxaline (Compound 5-117); 4-[3-(1-Phenyl-[1,2,4]triazolo[4,3-a]quinoline-7-sulfinyl)-phenyl]-tetrahydro-pyran-4-carbonitrile (Compound 5-118); 4-[3-(1-Pyridin-2-yl-[1,2,4]triazolo[4,3-a]quinoline-7-sulfinyl)-phenyl]-tetrahydro-pyran-4-carboxylic acid amide (Compound 5-119); 4-[3-(1-Phenyl-[1,2,4]triazolo[4,3-a]quinoline-7-sulfonyl)-phenyl]-tetrahydro-pyran-4-carbonitrile (Compound 5-120); 4-[3-(1-Pyridin-2-yl-[1,2,4]triazolo[4,3-a]quinoline-7-sulfonyl)-phenyl]-tetrahydro-pyran-4-carboxylic acid amide (Compound 5-121); 8-[3-Fluoro-5-(4-methoxy-tetrahydro-pyran-4-yl)-phenoxymethyl]-[1,2,4]triazolo[4,3-a]quinoline (Compound 5-122); 5-Bromo-8-[3-fluoro-5-(4-methoxy-tetrahydro-pyran-4-yl)-phenoxymethyl]-[1,2,4]triazolo[4,3-a]quinoline (Compound 5-123); 8-[3-Fluoro-5-(4-methoxy-tetrahydro-pyran-4-yl)-phenoxymethyl]-5-furan-3-yl-[1,2,4]triazolo[4,3-a]quinoline (Compound 5-124); 5-Chloro-8-[3-fluoro-5-(4-methoxy-tetrahydro-pyran-4-yl)-phenoxymethyl]-[1,2,4]triazolo[4,3-a]quinoline (Compound 5-125); 8-[3-Fluoro-5-(4-methoxy-tetrahydro-pyran-4-yl)-phenoxymethyl]-5-phenyl-[1,2,4]triazolo[4,3-a]quinoline (Compound 5-126); 3-{8-[3-Fluoro-5-(4-methoxy-tetrahydro-pyran-4-yl)-phenoxymethyl]-[1,2,4]triazolo[4,3-a]quinolin-5-yl}-benzoic acid (Compound 5-127); 4-[3-(5-Chloro-[1,2,4]triazolo[4,3-a]quinolin-8-ylmethoxy)-5-fluoro-phenyl]-tetrahydro-pyran-4-carboxylic acid methyl ester (Compound 5-128); 4-[3-Fluoro-5-(5-methylsulfanyl-[1,2,4]triazolo[4,3-a]quinolin-8-ylmethoxy)-phenyl]-tetrahydro-pyran-4-carboxylic acid methyl ester (Compound 5-129); 4-[3-Fluoro-5-(5-methoxy-[1,2,4]triazolo[4,3-a]quinolin-8-ylmethoxy)-phenyl]-tetrahydro-pyran-4-carboxylic acid methyl ester (Compound 5-130); 4-[3-Fluoro-5-([1,2,4]triazolo[4,3-a]quinolin-8-ylmethoxy)-phenyl]-tetrahydro-pyran-4-carboxylic acid methyl ester (Compound 5-131); 4-[3-Fluoro-5-(5-pyridin-3-yl-[1,2,4]triazolo[4,3-a]quinolin-8-ylmethoxy)-phenyl]-tetrahydro-pyran-4-carboxylic acid methyl ester (Compound 5-132); 4-[3-Fluoro-5-(5-pyridin-4-yl-[1,2,4]triazolo[4,3-a]quinolin-8-ylmethoxy)-phenyl]-tetrahydro-pyran-4-carboxylic acid methyl ester (Compound 5-133); 4-[3-Fluoro-5-(5-thiophen-3-yl-[1,2,4]triazolo[4,3-a]quinolin-8-ylmethoxy)-phenyl]-tetrahydro-pyran-4-carboxylic acid methyl ester (Compound 5-134); 4-{3-[5-(3-Cyano-phenyl)-[1,2,4]triazolo[4,3-a]quinolin-8-ylmethoxy]-5-fluoro-phenyl}-tetrahydro-pyran-4-carboxylic acid methyl ester (Compound 5-135); 4-{3-Fluoro-5-[5-(3-methoxy-phenyl)-[1,2,4]triazolo[4,3-a]quinolin-8-ylmethoxy]-phenyl}-tetrahydro-pyran-4-carboxylic acid methyl ester (Compound 5-136); 4-[3-Fluoro-5-(5-m-tolyl-[1,2,4]triazolo[4,3-a]quinolin-8-ylmethoxy)-phenyl]-tetrahydro-pyran-4-carboxylic acid methyl ester (Compound 5-137); 4-[3-Fluoro-5-(5-phenyl-[1,2,4]triazolo[4,3-a]quinolin-8-ylmethoxy)-phenyl]-tetrahydro-pyran-4-carboxylic acid methyl ester (Compound 5-138); 4-[3-(5-Chloro-[1,2,4]triazolo[4,3-a]quinolin-8-ylmethoxy)-5-fluoro-phenyl]-tetrahydro-pyran-4-carboxylic acid amide (Compound 5-139); 4-{3-Fluoro-5-[5-(1-methyl-1H-pyrazol-4-yl)-[1,2,4]triazolo[4,3-a]quinolin-8-ylmethoxy]-phenyl}-tetrahydro-pyran-4-carboxylic acid amide (Compound 5-140); 4-[3-Fluoro-5-(5-m-tolyl-[1,2,4]triazolo[4,3-a]quinolin-8-ylmethoxy)-phenyl]-tetrahydro-pyran-4-carboxylic acid amide (Compound 5-141); 4-{3-Fluoro-5-[5-(4-fluoro-phenyl)-[1,2,4]triazolo[4,3-a]quinolin-8-ylmethoxy]-phenyl}-tetrahydro-pyran-4-carboxylic acid amide (Compound 5-142); 4-[3-(1-Thiazol-2-yl-[1,2,4]triazolo[4,3-a]quinolin-8-ylsulfanyl)-phenyl]-tetrahydro-pyran-4-carbonitrile (Compound 5-143); 4-[3-([1,2,4]Triazolo[4,3-a]quinolin-8-ylsulfanyl)-phenyl]-tetrahydro-pyran-4-carbonitrile (Compound 5-144); 4-[3-(5-Chloro-[1,2,4]triazolo[4,3-a]quinolin-8-ylsulfanyl)-phenyl]-tetrahydro-pyran-4-carbonitrile (Compound 5-145); 4-[3-(5-m-Tolyl-[1,2,4]triazolo[4,3-a]quinolin-8-ylsulfanyl)-phenyl]-tetrahydro-pyran-4-carbonitrile (Compound 5-146); 4-{3-[5-(1-Methyl-1H-pyrazol-4-yl)-[1,2,4]triazolo[4,3-a]quinolin-8-ylsulfanyl]-phenyl}-tetrahydro-pyran-4-carbonitrile (Compound 5-147); 4-{3-[5-(4-Fluoro-phenyl)-[1,2,4]triazolo[4,3-a]quinolin-8-ylsulfanyl]-phenyl}-tetrahydro-pyran-4-carbonitrile (Compound 5-148); 4-[3-(5-Phenyl-

[1,2,4]triazolo[4,3-a]quinolin-8-ylsulfanyl)-phenyl]-tetrahydro-pyran-4-ol (Compound 5-149); 4-[3-(5-Phenyl-[1,2,4]triazolo[4,3-a]quinolin-8-ylsulfanyl)-phenyl]-tetrahydro-pyran-4-carbonitrile (Compound 5-150); 4-[3-(5-Methyl-[1,2,4]triazolo[4,3-a]quinolin-8-ylsulfanyl)-phenyl]-tetrahydro-pyran-4-carbonitrile (Compound 5-151); 4-[6-(5-Phenyl-[1,2,4]triazolo[4,3-a]quinolin-8-ylsulfanyl)-pyridin-2-yl]-tetrahydro-pyran-4-ol (Compound 5-152); 4-[3-(1-Methyl-5-phenyl-[1,2,4]triazolo[4,3-a]quinolin-8-ylsulfanyl)-phenyl]-tetrahydro-pyran-4-carbonitrile (Compound 5-153); 4-[3-(1-Methyl-5-phenyl-[1,2,4]triazolo[4,3-a]quinolin-8-ylsulfanyl)-phenyl]-tetrahydro-pyran-4-ol (Compound 5-154); 4-[3-(1-Amino-5-phenyl-[1,2,4]triazolo[4,3-a]quinolin-8-ylsulfanyl)-phenyl]-tetrahydro-pyran-4-ol (Compound 5-155); 4-[3-(5-Phenyl-[1,2,4]triazolo[4,3-a]quinolin-8-ylsulfanyl)-phenyl]-tetrahydro-pyran-4-carboxylic acid amide (Compound 5-156); 4-[3-(5-Phenyl-1-trifluoromethyl-[1,2,4]triazolo[4,3-a]quinolin-8-ylsulfanyl)-phenyl]-tetrahydro-pyran-4-carbonitrile (Compound 5-157); 4-[3-(5-Phenyl-[1,2,4]triazolo[4,3-a]quinolin-8-ylsulfanyl)-phenyl]-tetrahydro-pyran-4-carboxylic acid (Compound 5-158); 4-[3-(5-Chloro-[1,2,4]triazolo[4,3-a]quinolin-8-ylsulfanyl)-5-fluoro-phenyl]-tetrahydro-pyran-4-carbonitrile (Compound 5-159); 8-[3-Fluoro-5-(4-methoxy-tetrahydro-pyran-4-yl)-phenylsulfanyl]-[1,2,4]triazolo[4,3-a]quinoxaline (Compound 5-160); 4-[2-Methoxy-5-(1-pyridin-2-yl-[1,2,4]triazolo[4,3-a]quinolin-7-ylsulfanyl)-phenyl]-tetrahydro-pyran-4-carboxylic acid methyl ester (Compound 5-161); 3-spiro-(4'-Tetrahydropyran)-5-(1-pyridin-2-yl-[1,2,4]triazolo[4,3-a]quinolin-7-ylsulfanyl)-3H-benzofuran-2-one (Compound 5-162).

triazolo[4,3-a]quinolin-7-ylmethoxy)-phenyl]-tetrahydro-pyran-4-ol (Compound 6-2); 7-[3-Fluoro-5-(4-methoxy-tetrahydro-pyran-4-yl)-phenoxymethyl]-1-isobutyl-1-methyl-1,2-dihydro-[1,2,4]triazolo[4,3-a]quinoline (Compound 6-3); 7-[3-Fluoro-5-(4-methoxy-tetrahydro-pyran-4-yl)-phenoxymethyl]-1-spiro-(4'-chroman)-2,3-dihydro-1H-[1,2,4]triazolo[4,3-a]quinoline (Compound 6-4); 1-Ethyl-7-[3-fluoro-5-(4-methoxy-tetrahydro-pyran-4-yl)-phenoxymethyl]-1-trifluoromethyl-2,3-dihydro-1H-[1,2,4]triazolo[4,3-a]quinoline (Compound 6-5); 7-[3-Fluoro-5-(4-methoxy-tetrahydro-pyran-4-yl)-phenoxymethyl]-1-spiro-(4'-tetrahydropyran)-2,3-dihydro-1H-[1,2,4]triazolo[4,3-a]quinoline (Compound 6-6); 7-[3-Fluoro-5-(4-methoxy-tetrahydro-pyran-4-yl)-phenoxymethyl]-1,1-dimethyl-2,3-dihydro-1H-[1,2,4]triazolo[4,3-a]quinoline (Compound 6-7); 7-[3-Fluoro-5-(4-methoxy-tetrahydro-pyran-4-yl)-phenoxymethyl]-1-spiro-(5'-Bromo-1'-indan)-2,3-dihydro-1H-[1,2,4]triazolo[4,3-a]quinoline (Compound 6-8); 7-[3-Fluoro-5-(4-methoxy-tetrahydro-pyran-4-yl)-phenoxymethyl]-1-phenyl-2,3-dihydro-1H-[1,2,4]triazolo[4,3-a]quinoline (Compound 6-9); 7-[3-Fluoro-5-(4-methoxy-tetrahydro-pyran-4-yl)-phenoxymethyl]-1-thiazol-2-yl-2,3-dihydro-1H-[1,2,4]triazolo[4,3-a]quinoline (Compound 6-10); 7-[3-Fluoro-5-(4-methoxy-tetrahydro-pyran-4-yl)-phenoxymethyl]-1-thiazol-2-yl-2,3-dihydro-1H-[1,2,4]triazolo[4,3-a]quinoline (Compound 6-11); 6-[3-Fluoro-5-(4-methoxy-tetrahydro-pyran-4-yl)-phenoxymethyl]-1-isobutyl-1-methyl-1,2-dihydro-[1,2,4]triazolo[4,3-a]quinoline (Compound 6-12).

TABLE 6

1,2-Dihydro-[1,2,4]triazolo[4,3-a]quinoline

| Compound # | $R^8$ | $R^1$ | $R^2$ | $L^1$ | M + H |
|---|---|---|---|---|---|
| 6-1 | CO$_2$Me | Methyl | iButyl | 7-OCH$_2$ | 508 |
| 6-2 | OH | Methyl | iButyl | 7-OCH$_2$ | 466 |
| 6-3 | OMe | Methyl | iButyl | 7-OCH$_2$ | 480 |
| 6-4 | OMe | Chroman-4-yl | | 7-OCH$_2$ | 528 |
| 6-5 | OMe | Trifluoromethyl | Ethyl | 7-OCH$_2$ | 506 |
| 6-6 | OMe | THP | | 7-OCH$_2$ | 480 |
| 6-7 | OMe | Methyl | Methyl | 7-OCH$_2$ | 438 |
| 6-8 | OMe | 5-Bromo-indan-1-yl | | 7-OCH$_2$ | 591 |
| 6-9 | OMe | Phenyl | H | 7-OCH$_2$ | 485 |
| 6-10 | OMe | 3-Thiazol-2-yl | H | 7-OCH$_2$ | 493 |
| 6-11 | OMe | H | 3-Thiazol-2-yl | 7-OCH$_2$ | 493 |
| 6-12 | OMe | Methyl - | iButyl | 6-OCH$_2$ | 480 |

Compounds in Table 6 are named:

4-[3-Fluoro-5-(1-isobutyl-1-methyl-1,2-dihydro-[1,2,4]triazolo[4,3-a]quinolin-7-ylmethoxy)-phenyl]-tetrahydro-pyran-4-carboxylic acid methyl ester (Compound 6-1); 4-[3-Fluoro-5-(1-isobutyl-1-methyl-1,2-dihydro-[1,2,4]

TABLE 7

[1,2,4]triazolo[4,3-a]quinoxalin-4-one

| Compound # | $R^2$ | $R^1$ | M + H |
|---|---|---|---|
| 7-1 | H | Phenyl | 480 |
| 7-2 | Me | Phenyl | 494 |
| 7-3 | H | Pyridin-2-yl | 481 |

Compounds in Table 7 are named:

4-[3-(4-Oxo-1-phenyl-4,5-dihydro-[1,2,4]triazolo[4,3-a]quinoxalin-7-ylsulfanyl)-phenyl]-tetrahydro-pyran-4-carbonitrile (Compound 7-1); 4-[3-(5-Methyl-4-oxo-1-phenyl-4,5-dihydro-[1,2,4]triazolo[4,3-a]quinoxalin-7-ylsulfanyl)-phenyl]-tetrahydro-pyran-4-carbonitrile (Compound 7-2); 4-[3-(4-Oxo-1-pyridin-2-yl-4,5-dihydro-[1,2,4]triazolo[4,3-a]quinoxalin-7-ylsulfanyl)-phenyl]-tetrahydro-pyran-4-carbonitrile (Compound 7-3).

TABLE 8

[1,2,4]Triazolo[1,5-a]quinoline

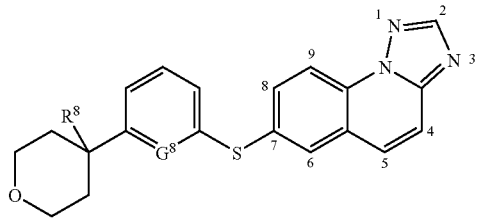

| Compound # | R8 | G8 | M + H |
|---|---|---|---|
| 8-1 | CN | C | 387 |
| 8-2 | CONH2 | C | 405 |
| 8-3 | OMe | C | 392 |
| 8-4 | OH | C | 378 |
| 8-5 | CN | N | 388 |
| 8-6 | CONH2 | N | 406 |

Compounds in Table 8 are named:
4-[3-([1,2,4]Triazolo[1,5-a]quinolin-7-ylsulfanyl)-phenyl]-tetrahydro-pyran-4-carbonitrile (Compound 8-1); 4-[3-([1,2,4]Triazolo[1,5-a]quinolin-7-ylsulfanyl)-phenyl]-tetrahydro-pyran-4-carboxylic acid amide (Compound 8-2); 7-[3-(4-Methoxy-tetrahydro-pyran-4-yl)-phenylsulfanyl]-[1,2,4]triazolo[1,5-a]quinoline (Compound 8-3); 4-[3-([1,2,4]Triazolo[1,5-a]quinolin-7-ylsulfanyl)-phenyl]-tetrahydro-pyran-4-ol (Compound 8-4); 4-[6-([1,2,4]Triazolo[1,5-a]quinolin-7-ylsulfanyl)-pyridin-2-yl]-tetrahydro-pyran-4-carbonitrile (Compound 8-5); 4-[6-([1,2,4]Triazolo[1,5-a]quinolin-7-ylsulfanyl)-pyridin-2-yl]-tetrahydro-pyran-4-carboxylic acid amide (Compound 8-6).

TABLE 9

Tetrazo[1,5-a]quinoline

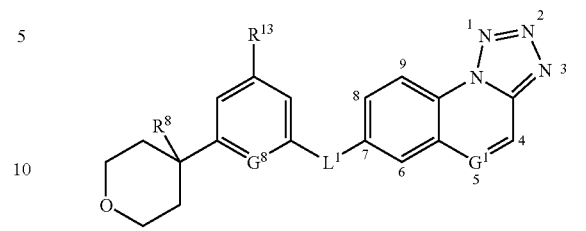

| Compound # | R8 | R13 | G8 | L1 | G1 | M + H |
|---|---|---|---|---|---|---|
| 9-1 | OMe | F | C | OCH2 | C | 409 |
| 9-2 | CO2Me | F | C | OCH2 | C | 437 |
| 9-3 | CONH2 | F | C | OCH2 | C | 422 |
| 9-4 | CO2H | F | C | OCH2 | C | 423 |
| 9-5 | CN | H | N | S | C | 389 |
| 9-6 | CONH2 | H | N | S | C | 407 |
| 9-7 | OMe | F | C | OCH2 | N | 378 [M − OMe] |

Compounds in Table 9 are named:
7-[3-Fluoro-5-(4-methoxy-tetrahydro-pyran-4-yl)-phenoxymethyl]-1,2,3,9b-tetraaza-cyclopenta[a]naphthalene (Compound 9-1); 4-[3-Fluoro-5-(1,2,3,9b-tetraaza-cyclopenta[a]naphthalen-7-ylmethoxy)-phenyl]-tetrahydro-pyran-4-carboxylic acid methyl ester (Compound 9-2); 4-[3-Fluoro-5-(1,2,3,9b-tetraaza-cyclopenta[a]naphthalen-7-ylmethoxy)-phenyl]-tetrahydro-pyran-4-carboxylic acid amide (Compound 9-3); 4-[3-Fluoro-5-(1,2,3,9b-tetraaza-cyclopenta[a]naphthalen-7-ylmethoxy)-phenyl]-tetrahydro-pyran-4-carboxylic acid (Compound 9-4); 4-[6-(1,2,3,9b-Tetraaza-cyclopenta[a]naphthalen-7-ylsulfanyl)-pyridin-2-yl]-tetrahydro-pyran-4-carbonitrile (Compound 9-5); 4-[6-(1,2,3,9b-Tetraaza-cyclopenta[a]naphthalen-7-ylsulfanyl)-pyridin-2-yl]-tetrahydro-pyran-4-carboxylic acid amide (Compound 9-6); 7-[3-Fluoro-5-(4-methoxy-tetrahydro-pyran-4-yl)-phenoxymethyl]-1,2,3,5,9b-pentaaza-cyclopenta[a]naphthalene (Compound 9-7).

TABLE 10

Non-THP or Thiazole-Linker Compounds

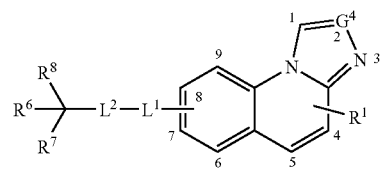

| Compound # | R8 | R6 | R7 | R1 | L2 | L1 | G4 | M + H |
|---|---|---|---|---|---|---|---|---|
| 10-1 | OH | CF3 | Et | H | 2,5-Thiazole | 7-S | N | 411 |
| 10-2 | OH | CF3 | Et | 1-Phenyl | 2,5-Thiazole | 7-S | N | 487 |
| 10-3 | OH | CF3 | Et | 1-Thiazol-2-yl | 2,5-Thiazole | 7-S | N | 494 |
| 10-4 | OH | CF3 | CH2CO2H | 1-Phenyl | 2,5-Thiazole | 7-S | N | 517 |
| 10-5 | OH | CF3 | Cyclopropyl | 1-Phenyl | 2,5-Thiazole | 7-S | N | 499 |
| 10-6 | OH | CF3 | CH2CO2Et | 1-Phenyl | 2,5-Thiazole | 7-S | N | 543 |
| 10-7 | OH | Cyclopropyl | Cyclopropyl | 1-Phenyl | 2,5-Thiazole | 7-S | N | 471 |
| 10-8 | OH | THP | | 1-Phenyl | 2,5-Thiazole | 7-S | N | 461 |
| 10-9 | H | Cyclopropyl | Cyclopropyl | 1-Phenyl | 2,5-Thiazole | 7-S | N | 455 |
| 10-10 | OH | CF3 | Et | H | 2,5-Thiazole | 7-S | C | 410 |
| 10-11 | OH | Cyclopropyl | Cyclopropyl | 1-Phenyl | 1,3-Benzene | 7-S | N | 464 |
| 10-12 | OH | Cyclopropyl | Cyclopropyl | 1-Pyridin-2-yl | 1,3-Benzene | 7-S | N | 465 |

TABLE 10-continued

Non-THP or Thiazole-Linker Compounds

| Compound # | R⁸ | R⁶ | R⁷ | R¹ | L² | L¹ | G⁴ | M + H |
|---|---|---|---|---|---|---|---|---|
| 10-13 | OH | CF₃ | CH₂CO₂H | H | 2,5-Thiazole | 8-S | N | 441 |
| 10-14 | OH | CF₃ | Et | 1-Thiazol-2-yl | 2,5-Thiazole | 8-S | N | 494 |
| 10-15 | OH | CF₃ | Et | 1-Phenyl | 2,5-Thiazole | 8-S | N | 487 |
| 10-16 | OH | CF₃ | Et | 5-Phenyl | 2,5-Thiazole | 8-S | N | 487 |
| 10-17 | OH | Cyclohexyl | | 5-Phenyl | 1,3-Benzene | 8-S | N | 452 |
| 10-18 | OH | Et | Et | 5-Phenyl | 1,3-Benzene | 8-S | N | 440 |
| 10-19 | OH | Et | Et | 5-Phenyl | 1,3-Benzene | 8-S | C | 439 |

Compounds in Table 10 are named:
1,1,1-Trifluoro-2-[2-([1,2,4]triazolo[4,3-a]quinolin-7-ylsulfanyl)-thiazol-5-yl]-butan-2-ol (Compound 10-1); 1,1,1-Trifluoro-2-[2-(1-phenyl-[1,2,4]triazolo[4,3-a]quinolin-7-ylsulfanyl)-thiazol-5-yl]-butan-2-ol (Compound 10-2); 1,1,1-Trifluoro-2-[2-(1-thiazol-2-yl-[1,2,4]triazolo[4,3-a]quinolin-7-ylsulfanyl)-thiazol-5-yl]-butan-2-ol (Compound 10-3); 4,4,4-Trifluoro-3-hydroxy-3-[2-(1-phenyl-[1,2,4]triazolo[4,3-a]quinolin-7-ylsulfanyl)-thiazol-5-yl]-butyric acid (Compound 10-4); 1-Cyclopropyl-2,2,2-trifluoro-1-[2-(1-phenyl-[1,2,4]triazolo[4,3-a]quinolin-7-ylsulfanyl)-thiazol-5-yl]-ethanol (Compound 10-5); 4,4,4-Trifluoro-3-hydroxy-3-[2-(1-phenyl-[1,2,4]triazolo[4,3-a]quinolin-7-ylsulfanyl)-thiazol-5-yl]-butyric acid ethyl ester (Compound 10-6); Dicyclopropyl-[2-(1-phenyl-[1,2,4]triazolo[4,3-a]quinolin-7-ylsulfanyl)-thiazol-5-yl]-methanol (Compound 10-7); 4-[2-(1-Phenyl-[1,2,4]triazolo[4,3-a]quinolin-7-ylsulfanyl)-thiazol-5-yl]-tetrahydro-pyran-4-ol (Compound 10-8); 7-(5-Dicyclopropylmethyl-thiazol-2-ylsulfanyl)-1-phenyl-[1,2,4]triazolo[4,3-a]quinoline (Compound 10-9); 1,1,1-Trifluoro-2-[2-(imidazo[1,2-a]quinolin-7-ylsulfanyl)-thiazol-5-yl]-butan-2-ol (Compound 10-10); Dicyclopropyl-[3-(1-phenyl-[1,2,4]triazolo[4,3-a]quinolin-7-ylsulfanyl)-phenyl]-methanol (Compound 10-11); Dicyclopropyl-[3-(1-pyridin-2-yl-[1,2,4]triazolo[4,3-a]quinolin-7-ylsulfanyl)-phenyl]-methanol (Compound 10-12); 4,4,4-Trifluoro-3-hydroxy-3-[2-([1,2,4]triazolo[4,3-a]quinolin-8-ylsulfanyl)-thiazol-5-yl]-butyric acid (Compound 10-13); 1,1,1-Trifluoro-2-[2-(1-thiazol-2-yl-[1,2,4]triazolo[4,3-a]quinolin-8-ylsulfanyl)-thiazol-5-yl]-butan-2-ol (Compound 10-14); 1,1,1-Trifluoro-2-[2-(1-phenyl-[1,2,4]triazolo[4,3-a]quinolin-8-ylsulfanyl)-thiazol-5-yl]-butan-2-ol (Compound 10-15); 1,1,1-Trifluoro-2-[2-(5-phenyl-[1,2,4]triazolo[4,3-a]quinolin-8-ylsulfanyl)-thiazol-5-yl]-butan-2-ol (Compound 10-16); 1-[3-(5-Phenyl-[1,2,4]triazolo[4,3-a]quinolin-8-ylsulfanyl)-phenyl]-cyclohexanol (Compound 10-17); 3-[3-(5-Phenyl-[1,2,4]triazolo[4,3-a]quinolin-8-ylsulfanyl)-phenyl]-pentan-3-ol (Compound 10-18); 3-[3-(5-Phenyl-imidazo[1,2-a]quinolin-8-ylsulfanyl)-phenyl]-pentan-3-ol (Compound 10-19).

TABLE 11

Sulfur Substituted Compounds

| Compound # | Z | R¹ | L¹ | M + H |
|---|---|---|---|---|
| 11-1 | Thiazol-2-yl | 1-Phenyl | 7-S | 361 |
| 11-2 | Butanoic Acid Ethyl Ester | 5-Phenyl | 8-S | 392 |
| 11-3 | Pentanoic Acid Ethyl Ester | 5-Phenyl | 8-S | 406 |
| 11-4 | Hexanoic Acid Ethyl Ester | 5-Phenyl | 8-S | 420 |
| 11-5 | Butanoic Acid | 5-Phenyl | 8-S | 364 |
| 11-6 | Pentanoic Acid | 5-Phenyl | 8-S | 378 |
| 11-7 | Hexanoic Acid | 5-Phenyl | 8-S | 392 |
| 11-8 | 3-Benzoic Acid | 5-Phenyl | 8-S | 398 |
| 11-9 | 3-Benzamide | 5-Phenyl | 8-S | 397 |
| 11-10 | 3-(N-Methylaminocarbonyl)phenyl | 5-Phenyl | 8-S | 411 |
| 11-11 | 3-(N,N,-Dimethylaminocarbonyl)phenyl | 5-Phenyl | 8-S | 425 |
| 11-12 | 3-(N-(2-Hydroxyethyl)carbonyl)phenyl | 5-Phenyl | 8-5 | 441 |
| 11-13 | 3-((Morpholin-4-yl)-carbonyl)phenyl | 5-Phenyl | 8-S | 467 |
| 11-14 | 3-(Cyclopent-1-enyl)phenyl | 5-Phenyl | 8-S | 420 |

Compounds in Table 11 are named:
1-Phenyl-7-(thiazol-2-ylsulfanyl)-[1,2,4]triazolo[4,3-a]quinoline (Compound 11-1); 4-(5-Phenyl-[1,2,4]triazolo[4,3-a]quinolin-8-ylsulfanyl)-butyric acid ethyl ester (Compound 11-2); 5-(5-Phenyl-[1,2,4]triazolo[4,3-a]quinolin-8-ylsulfanyl)-pentanoic acid ethyl ester (Compound 11-3); 6-(5-Phenyl-[1,2,4]triazolo[4,3-a]quinolin-8-ylsulfanyl)-hexanoic acid ethyl ester (Compound 11-4); 4-(5-Phenyl-[1,2,4]triazolo[4,3-a]quinolin-8-ylsulfanyl)-butyric acid (Compound 11-5); 5-(5-Phenyl-[1,2,4]triazolo[4,3-a]quinolin-8-ylsulfanyl)-pentanoic acid (Compound 11-6); 6-(5-Phenyl-[1,2,4]triazolo[4,3-a]quinolin-8-ylsulfanyl)-hexanoic acid (Compound 11-7); 3-(5-Phenyl-[1,2,4]triazolo[4,3-a]quinolin-8-ylsulfanyl)-benzoic acid (Compound 11-8); 3-(5-Phenyl-[1,2,4]triazolo[4,3-a]quinolin-8-ylsulfanyl)-benzamide (Compound 11-9); N-Methyl-3-(5-phenyl-[1,2,4]triazolo[4,3-a]quinolin-8-ylsulfanyl)-benzamide (Compound 11-10); N,N-Dimethyl-3-(5-phenyl-[1,2,4]triazolo[4,3-a]quinolin-8-ylsulfanyl)-benzamide (Compound 11-11); N-(2-Hydroxy-ethyl)-3-(5-phenyl-[1,2,4]triazolo[4,3-a]quinolin-8-ylsulfanyl)-benzamide (Compound 11-12); Morpholin-4-yl-[3-(5-phenyl-[1,2,4]triazolo[4,3-a]quinolin-8-ylsulfanyl)-phenyl]-methanone (Compound 11-13); 8-(3-Cyclopent-1-enyl-phenylsulfanyl)-5-phenyl-[1,2,4]triazolo[4,3-a]quinoline (Compound 11-14).

Throughout the specification, groups and substituents thereof can be chosen by one skilled in the field to provide stable moieties and compounds.

Further Forms of Compounds

Compounds described herein may possess one or more stereocenters and each center may exist in the R or S configuration. The compounds presented herein include all diastereomeric, enantiomeric, and epimeric forms as well as the appropriate mixtures thereof. Separation of steroisomers may be performed by chromatography. Alternatively, individual stereoisomers may be obtained by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds described herein, dissociable complexes are also possible (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chiral chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981, herein incorporated by reference in its entirety. Stereoisomers may also be obtained by stereoselective synthesis.

In some situations, compounds may exist as tautomers. All tautomers are included within the formulas described herein.

In some cases, cyclic compounds described herein may be in equilibrium with open chain forms. Closed cyclic forms as well as the corresponding open chain forms, which are in equilibrium with the closed cyclic forms, are considered part of the present disclosure.

The methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Compounds of any of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im), Formula (II), Formula (IIa), Formula (IIb), Formula (IIc), Formula (IId), Formula (III), Formula (IIIa), Formula (IIIb), Formula (IIIc), Formula (IV), Formula (V), or Formula (VI), in unoxidized form can be prepared from N-oxides of compounds of any of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im), Formula (II), Formula (IIa), Formula (IIb), Formula (IIc), Formula (IId), Formula (III), Formula (IIIa), Formula (IIIb), Formula (IIIc), Formula (IV), Formula (V), or Formula (VI), by treating with a reducing agent, such as, but not limited to, sulfur, sulfur dioxide, triphenyl phosphine, lithium borohydride, sodium borohydride, phosphorus trichloride, phosphorus tribromide, or the like in a suitable inert organic solvent, such as, but not limited to, acetonitrile, ethanol, aqueous dioxane, or the like at 0 to 80° C.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985).

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., *Am. J. Physiol.*, 269:G210-218 (1995); McLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein in their entirety.

Sites on the aromatic ring portion of compounds described herein can be susceptible to various metabolic reactions, therefore incorporation of appropriate substituents on the aromatic ring structures, such as, by way of example only, halogens can reduce, minimize or eliminate this metabolic pathway.

The compounds described herein may be labeled isotopically (e.g. with a radioisotope) or by other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2$H, $^3$H, $^{13}$C, $^{14}$C, $^{15}$N, $^{18}$O, $^{17}$O, $^{35}$S, $^{18}$F, $^{36}$Cl, respectively. Certain isotopically-labeled compounds described herein, for example those into which radioactive isotopes such as $^3$H and $^{14}$C are incorporated, are useful in drug and/or substrate tissue distribution assays. Further, substitution with isotopes such as deuterium, i.e., $^2$H, can afford certain therapeutic advantages resulting from greater metabolic stability, for example increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, nitric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, dicyclohexylamine, tris(hydroxymethyl)methylamine, and salts with amino acids such as arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Compounds described herein may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen by one skilled in the field to provide stable moieties and compounds.

Preparation of Compounds

The synthesis of compounds described herein may be accomplished using means described in the chemical literature, using the methods described herein, or by a combination thereof.

Compounds described herein may be synthesized using standard synthetic techniques known to those of skill in the art or using methods known in the art in combination with methods described herein. In addition, solvents, temperatures and other reaction conditions presented herein may vary according to those of skill in the art.

The starting material used for the synthesis of the compounds described herein may be synthesized or can be obtained from commercial sources, such as, but not limited to, Aldrich Chemical Co. (Milwaukee, Wis.), or Sigma Chemical Co. (St. Louis, Mo.). The compounds described herein, and other related compounds having different substituents can be synthesized using techniques and materials described herein as well as those that are known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

The synthesis of compounds having the general structure A-L$^1$-Z, where Z is a substituted aryl or heteroaryl group as defined herein, L$^1$ is a linking group as defined herein, and "A" is a tricyclic heterocycle as defined herein, may be accomplished using means described in the chemical literature, using the methods described herein, or by a combination thereof.

For example, when L$^1$ is —S— or —O—, compounds satisfying the formula A-L$^1$-Z (where L$^1$ is O, or S) may be prepared by reaction of a thiol of structure A-SH or a hydroxy compound of structure A-OH with a compound of formula X—Z, where X is a displaceable group such as a halide, triflate, mesylate, or tosylate. In one embodiment, treatment of A-SH or A-OH with a base, in a solvent such as THF or DMF, followed by nucleophilic displacement of the X-group form compounds of formula X—Z, forms compounds with the formula A-L$^1$-Z (where L$^1$ is O or S). In other embodiments, metal mediated coupling reactions are used to couple compounds of formula A-SH or A-OH with compounds of formula X—Z to form compounds of formula A-L$^1$-Z (where X$^1$ is O or S).

In other embodiments, compounds of formula A-L$^1$-Z (where L$^1$ is O or S) may be prepared by reacting a thiol or hydroxy containing compound of formula Z-L$^1$H (where L$^1$ is O or S) with a compound of formula X-A, where X is a displaceable group such as a halide, triflate, mesylate, or tosylate. Treatment of Z—OH or Z—SH with a base, in a solvent such as THF or DMF, followed by nucleophilic displacement of the X-group from X-A forms compounds with the formula A-L$^1$-Z (where L$^1$ is O or S). In some cases, metal mediated coupling reactions are used to couple compounds of formula A-X with compounds of formula Z—OH or Z—SH to form compounds of formula A-L$^1$-Z (where L$^1$ is O or S).

Metal mediated coupling reactions used to form diarylthioethers or diarylethers include, but are not limited to: the use of copper(I) catalysts, see for example, Bates et al., *Org. Lett.*, 2002, 4, 2803-2806; Kwong et al. *Org. Lett.*, 2002, 4, 3517-3520; Wolter et al., *Org. Lett.*, 2002, 4, 973-976; Buck et al., *Org. Lett.*, 2002, 4, p 1623-1626; the use of nickel(0) catalysts, see for example, Mano et al., *Bioorg. Med. Chem. Lett.*, 2005, 15, p 2611-2615. the use of palladium catalysts, see for example, Mano et al., *Chem. Pharm. Bull.*, 2005, 53, p 965-973; Alcaraz et al., *Org. Process Res. Dev.*, 2005, 9, p 555-569.

Coupling reactions used herein include the use of, but not limited to, Mitsunobu, S$_N$2, S$_N$AR, or metal mediated coupling reaction conditions. Metal mediated coupling reactions include, but are not limited to Suzuki reactions, Sonogashira couplings, Heck reactions, Stille cross couplings, Negishi couplings, Kumada couplings, Ullmann reactions, Buchwald-Hartwig reactions, and variants thereof (Metal-Catalyzed Cross-Coupling Reactions, Armin de Meijere (Editor), François Diederich (Editor), John Wiley & Sons; 2nd edition, 2004).

In cases where L$^1$ is —(CHR$^4$)$_n$O—, compounds with the formula A-(CHR$^4$)$_n$O—Z may be prepared by the reaction of an alcohol of structure A-(CHR$^4$)$_n$OH with a compound of X—Z where X is a displaceable group such as a halide, triflate, mesylate, or tosylate. Treatment of A-(CHR$^4$)$_n$OH with a base, in a solvent such as THF or DMF, followed by nucleophilic displacement of the X-group from X—Z forms compounds with the formula A-(CHR$^4$)$_n$O—Z. In some cases metal mediated reaction conditions may be used to couple compounds of formula A-(CHR$^4$)$_n$OH with compounds of formula X—Z. Alternatively, compounds with the formula A-(CHR$^4$)$_n$O—Z may be prepared by reaction of an aryl (or heteroaryl) compound containing a hydroxy group, such as compounds with the formula Z—OH, with compounds of formula A-(CHR$^4$)$_n$X where X is a displaceable group such as a halide, triflate, mesylate, or tosylate. Treatment of Z—OH with a base, in a solvent such as THF or DMF, followed by nucleophilic displacement of the X-group, forms A-(CHR$^4$)$_n$O—Z. Ether linkages may also be formed via a Mitsunobu reaction between Z—OH and A-(CHR$^4$)$_n$OH (see Mitsunobu, *Synthesis* 1981 p 1-28).

In embodiments where L$^1$ is —O(CHR$^4$)$_n$—, compounds with the formula A-O(CHR$^4$)$_n$—Z may be prepared by the reaction of an alcohol of structure A-OH with compounds of formula X(CHR$^4$)$_n$—Z where X is a displaceable group such as a halide, triflate, mesylate, or tosylate. Treatment of A-OH with a base, in a solvent such as THF or DMF, followed by nucleophilic displacement of the X-group forms compounds of formula A-O(CHR$^4$)$_n$—Z. Alternatively, compounds of formula A-O(CHR$^4$)$_n$—Z may be prepared by reaction of an alcohol of structure Z—(CHR$^4$)$_n$OH with tricyclic compounds of formula A-X where X is a displaceable group such as a halide, triflate, mesylate, or tosylate. Treatment of Z—(CHR$^4$)$_n$OH with a base, in a solvent such as THF or DMF, followed by nucleophilic displacement of the X-group forms A-O(CHR⁴)$_n$—Z. Ether linkages may also be formed via a Mitsunobu reaction between Z—(CHR⁴)$_n$OH and A-OH (see Mitsunobu, *Synthesis* 1981 p 1-28). In some cases, metal mediated reaction conditions may be used to couple compounds of formula Z—(CHR⁴)$_n$OH with compounds of formula X-A.

When $L^1$ is —S(=O)— or —S(=O)$_2$—, the parent thio-ether (i.e. compounds with the formula A-S—Z) may be oxidized using, for example, meta-chloroperoxybenzoic acid (mCPBA) in a solvent such as $CH_2Cl_2$. An alternative method employs magnesium monoperoxyphthalate hexahydrate in a solvent such as $CH_2Cl_2$. The stoichiometry can be controlled to favor either the sulfoxide or the sulfone. Asymmetric methods can be employed to selectively produce individual sulfoxide enantiomers (see Davis et al., *J. Am. Chem. Soc.*, 110, 8477, 1988 and Kagan et al., *J. Am. Chem. Soc.*, 106, 8188, 1984).

Phenols and heteroaryls containing a hydroxy moiety (Z—OH compounds) may be commercially available, or prepared using standard organic chemistry procedures, as described herein of known in the art, or by a combination thereof. Standard methods for the synthesis of alcohols, phenols and mercaptans are given in March "Advanced Organic Chemistry: Reactions, Mechanisms, and Structure" McGraw-Hill, 1984.

In some embodiments, phenols that can be used in the synthesis of compounds described herein, may be prepared, by way of example only, using the methods described below.

Phenols and thiophenols of structure B-1 (where $X^1$ is O or S) can be synthesized using methods described in Lambert-van der Brempt et al., *J. Med. Chem.*, 1994, 37, 113-124; Crawley et al., *J. Med. Chem.*, 1992, 35, 2600-2609; Bird et al., *J. Med. Chem.*, 1991, 34, 2176-2186; U.S. Pat. Nos. 5,552,437; 5,527,827; 5,217,977; and 5,475,009.

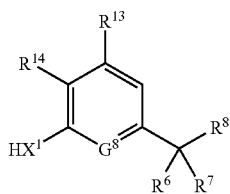

B-1

Hydroxy and thiol aromatics of structure B-2 and B-3 that include a tetrahydropyran ring can be synthesized using methods described in Lambert-van der Brempt et al., *J. Med. Chem.*, 1994, 37, 113-124; Mano et al., *Chem. Pharm. Bull.*, 2005, 53, 965-973; U.S. Pat. Nos. 5,354,865 and 5,484,786.

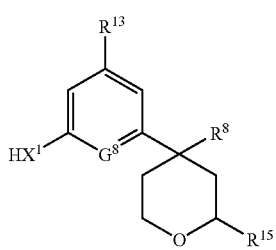

B-2

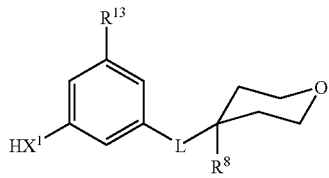

B-3

L = CH(OH), CH(OMe), C(O), CH$_2$,
C = NOMe

Phenols of structure B-4 can be synthesized using methods described in Crawley et al., *J. Med. Chem.*, 1992, 35, 2600-2609; U.S. Pat. Nos. 5,407,959 and 5,426,111.

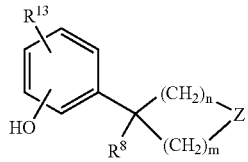

B-4 m and n = 0, 1, 2, or 3
Z = O, S, SO, SO$_2$, CH$_2$, CHOMe, CO,
  NMe, C(OMe)$_2$, NCO$_2$Et Hydroxy aromatics of structure B-5 containing a bicyclo [3,2,1]ring can be synthesized using methods described in Hamel et al., *J. Med. Chem.*, 1997, 40, 2866-2875, U.S. Pat. Nos. 5,459,271 and 5,424,320.

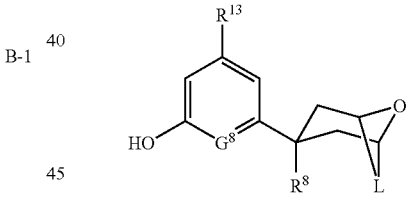

B-5

L = OCH$_2$, CH$_2$O, CH$_2$CH$_2$

Phenols of structure B-6 can be synthesized using methods described in Bird et al., *J. Med. Chem.*, 1991, 34, 2176-2186; and EP 0 623 614.

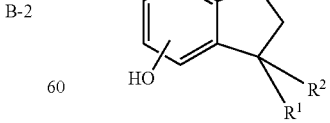

B-6

$R^1$ = OMe, H,
$R^2$ = OMe, 2-thiazolyl

Phenols or thiophenols of structure B-7 can be synthesized using methods described in U.S. Pat. No. 5,576,338.

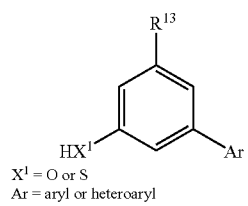

B-7

$X^1$ = O or S
Ar = aryl or heteroaryl

Aryl and heteroarylthiols of general structure Z—SH may be obtained commercially, or prepared using standard organic procedures and/or procedures described herein. Arythiols may be obtained from the corresponding hydroxyl compound by, for example, the intermediacy of dialkylthiocarbamates (Newman and Barnes, *J. Org. Chem.*, 1966, 31, 3980-3984) or the intermediacy of aryltriflates (Arnould et al., *Tet. Lett.*, 1996, 26, 4523-4524). Quenching of an aryl or heteroaryl lithium species using, for example, MeSSMe followed by deprotection also yields suitable mercapto derivatives.

Thiazole containing thiols of structure B-8 and B-9 can be synthesized using methods described herein or in International Patent Publication No. WO 2004/108720.

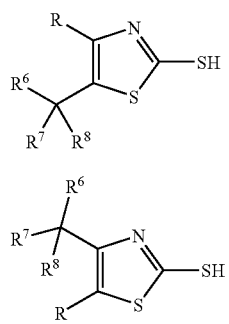

B-8

B-9

Substituted alcohols of general structure Z—(CHR$^4$)$_n$OH, may be prepared using standard organic synthetic transformations and/or procedures described herein. For example, by reduction of the corresponding ketone, aldehyde, ester, anhydrides, acid chloride, ozonide or epoxide; from addition of organometallic reagents to the corresponding ketone, aldehyde, ester, anhydrides, acid chloride or epoxide; the hydrolysis of esters, anhydrides, sulfonic esters and inorganic esters; from the hydroboration of alkenes; from the cleavage of ethers; and the like.

Non-limiting examples for the preparation of alcohols and halides that can be used in the synthesis of compounds described herein are presented below. Alcohols and halides of structure B-10 can be synthesized using methods described in Hamel et al, *J. Med. Chem.*, 1997, 40, 2866-2875; Ducharme et al., *J. Med. Chem.*, 37, 512-518, 1994; U.S. Pat. No. 5,424, 320; Cai et al., *Tet. Lett.*, 37, 2537-2540, 1996; U.S. Pat. No. 5,552,437.

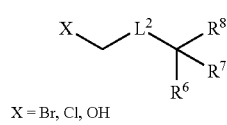

B-10

X = Br, Cl, OH

Examples of L$^2$ include, but are not limited to:

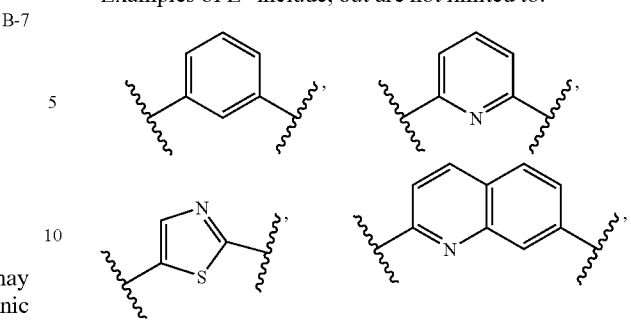

and substituted variants thereof.

Hydroxy containing aromatics of structure B-11 (G$^8$=CH or N) can be synthesized using methods described in Friesen et al, U.S. Pat. No. 5,576,338.

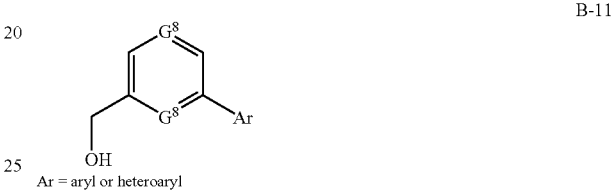

B-11

Ar = aryl or heteroaryl

Substituted thiols of general structure Z—(CHR$^4$)$_n$SH may be obtained from the corresponding alcohol using standard chemical methodologies. For example, the conversion of an alcohol to a thiol via a Mitsunobu reaction using a thiolacid followed by saponification (Volante, *Tet. Lett.*, 1981, 33, 3119-3122). An alternative method is to activate the alcohol as, for example a mesylate, and then displace with a sulfur nucleophile. Deprotection then affords the corresponding mercapto derivative.

Appropriate aryl halides, triflates, mesylates, and tosylates can be prepared, by way of example only, using the methods described below. Such aryl halides, triflates, mesylates, and tosylates can be used to prepare compounds described herein.

Aryl triflates, mesylates and tosylates can be readily derived from the corresponding phenol using standard chemical transformations.

Aromatic halides of structure B-12 can be synthesized using methods known in the art of organic synthesis or as described in Hamel et al, *J. Med. Chem.*, 40, 2866-2875, 1997; Cai et al., *Tet. Lett.*, 37, 2537-2540, 1996; Mano et al., *Bioorg. Med. Chem. Lett.*, 15, 2611-2615, 2005; Mano et al., *Chem. Pharm. Bull.*, 53, 965-973, 2005; U.S. Pat. Nos. 5,552, 437 and 5,527,827.

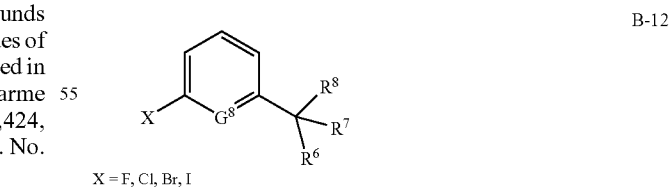

B-12

X = F, Cl, Br, I

In one embodiment, compounds described herein can be synthesized by the derivatization of chloroquinolines of general structure I-5. As shown in Scheme I, substituted chloroquinolines can be accessed by Lewis acid mediated cyclization of p-methylphenylcinnamides of structure I-1 to provide 6-methylnaphthyridones of structure I-2 (see *J. Med. Chem*, v35, 2761, 1992; *J. Med. Chem*, v35, 3607, 1992).

Scheme I

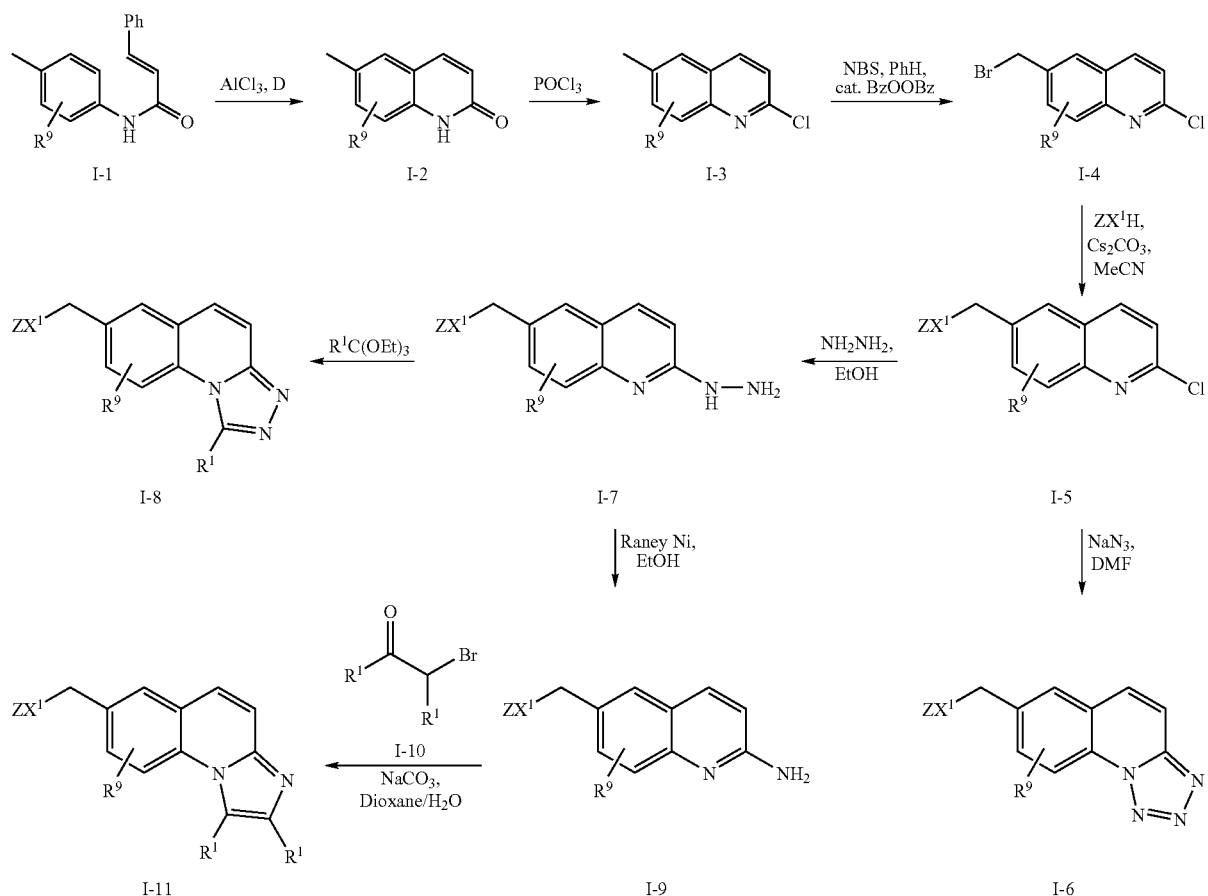

Methylnaphthyridones of structure I-2 can undergo phosphorous oxychloride-mediated chlorination to give chloroquinolines of structure I-3 followed by benzylic bromination under standard conditions to afford (bromomethyl)chloroquinolines of structure I-4. Displacement of the bromide of (bromomethyl)chloroquinolines of structure I-4 with a variety of nucleophiles (e.g. compounds of formula $ZX^1H$, where Z and $X^1$ are as defined herein) in the presence of a base, such as, for example, cesium carbonate, in aprotic solvents, such as acetonitrile, provides functionalized chloroquinolines of structure I-5. Tetrazolo[1,5-a]quinolines of structure I-6 can be prepared by reaction of chloroquinolines of structure I-5 with sodium azide in DMF solution (*J. Org. Chem.* 3755, 1990). In another embodiment, chloroquinolines of structure I-5 can be heated with hydrazine to afford hydrazinoquinolines of structure I-7. Compounds of general structure I-7 can be condensed with aliphatic and aromatic aldehydes to provide [1,2,4]triazolo[4,3-a]quinolines of structure I-8 (where $R^1$=alkyl or aryl). In some embodiments, compounds of structure I-7 are condensed with a trialkoxyorthoformate to provide compounds of structure I-8 where $R^1$=H. In other embodiments, hydrazinonaphthyridines of structure I-7 may be converted to aminonaphthyridines of structure I-9 by the action of Raney nickel and hydrogen in alcoholic solvents. Imidazo[1,2-a]quinolines of structure I-11 can be prepared from compounds of structure I-9 by modification of literature methods for the synthesis of imidazo[1,2-a]pyridines (Paudler and Blewitt, *J. Org. Chem.* vol. 30, 4081). Thus, treatment of compounds of structure I-9 with an α-halocarbonyl compound of structure I-10 (each $R^1$ may be the same, or they may be different) in the presence of inorganic bases such as sodium bicarbonate and in aqueous/organic solvent mixtures such as dioxane/water can yield compounds of general structure I-11.

As shown in Scheme II, m-methylphenylcinnamides of structure II-1 can undergo transformations similar to those shown in Scheme I to afford the isomeric tricyclic structures. Cyclization of m-methylcinnamides of structure II-1 affords a mixture of isomers of structure II-2 and II-3. These compounds may be separated, and processed using the chemistry outlined in Scheme I to afford tricyclic structures II-4 and II-5 ($G^4$ and $G^5$ can be either $CR^1$ or N).

Scheme II

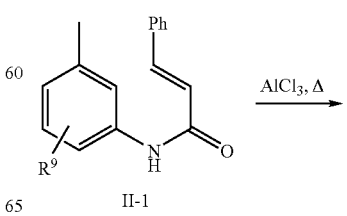

II-1

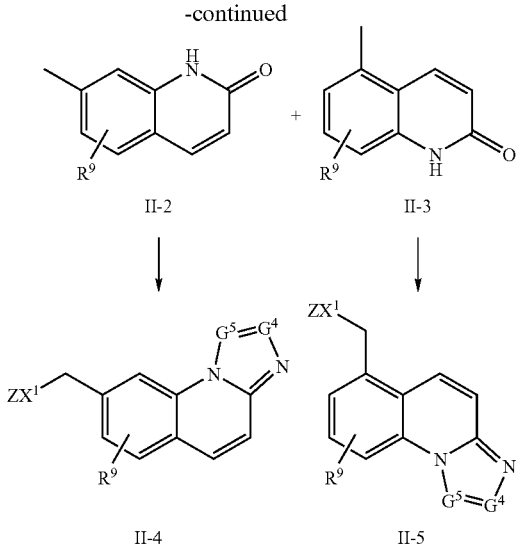

As shown in Scheme III, tricyclic structures containing a hydroxy or thiol moiety attached to the tricyclic core ("A" tricyclic heterocycle) may be synthesized utilizing the chemistry in Scheme I (see also *J. Med. Chem*, v35, 3607, 1992).

ture III-3. Compounds of structure III-3 can undergo transformation as outlined in Scheme I to provide tricyclic structures. For example, compounds of structure III-3 may be reacted with sodium azide in a polar solvent such as DMF to yield tetrazolo[1,5-a]quinolines of structure III-4. Methyl ether cleavage using, for example, boron tribromide in a chlorinated solvent such as $CH_2Cl_2$ can give phenols of structure III-5, which may be reacted with a variety of electrophiles under standard conditions, such as Mitsunobu, $S_N2$ or $S_NAR$ conditions. In other embodiments, phenols of structure III-5 may be coupled with aryl halides or triflates using standard metal mediated coupling reactions to afford compounds of structure III-6. In other embodiments, phenols of structure III-5 may be acylated with dimethylthiocarbamoyl chloride (III-7) to afford thiocarbamates of structure III-8. Thiocarbamates of structure III-8 are known to undergo a thermal rearrangement/hydrolysis protocol to afford thiols of general structure III-9. Thiols of structure III-9 may then be transformed under standard conditions (such as such as Mitsunobu, $S_N2$ or $S_NAR$, or metal mediated coupling conditions) to afford functionalized triazolo[1,5-a]quinolines of structure III-10.

As shown in Scheme IV, chloroquinolines of structure III-3 may be converted to substituted imidazo[1,2-a]quinolines of

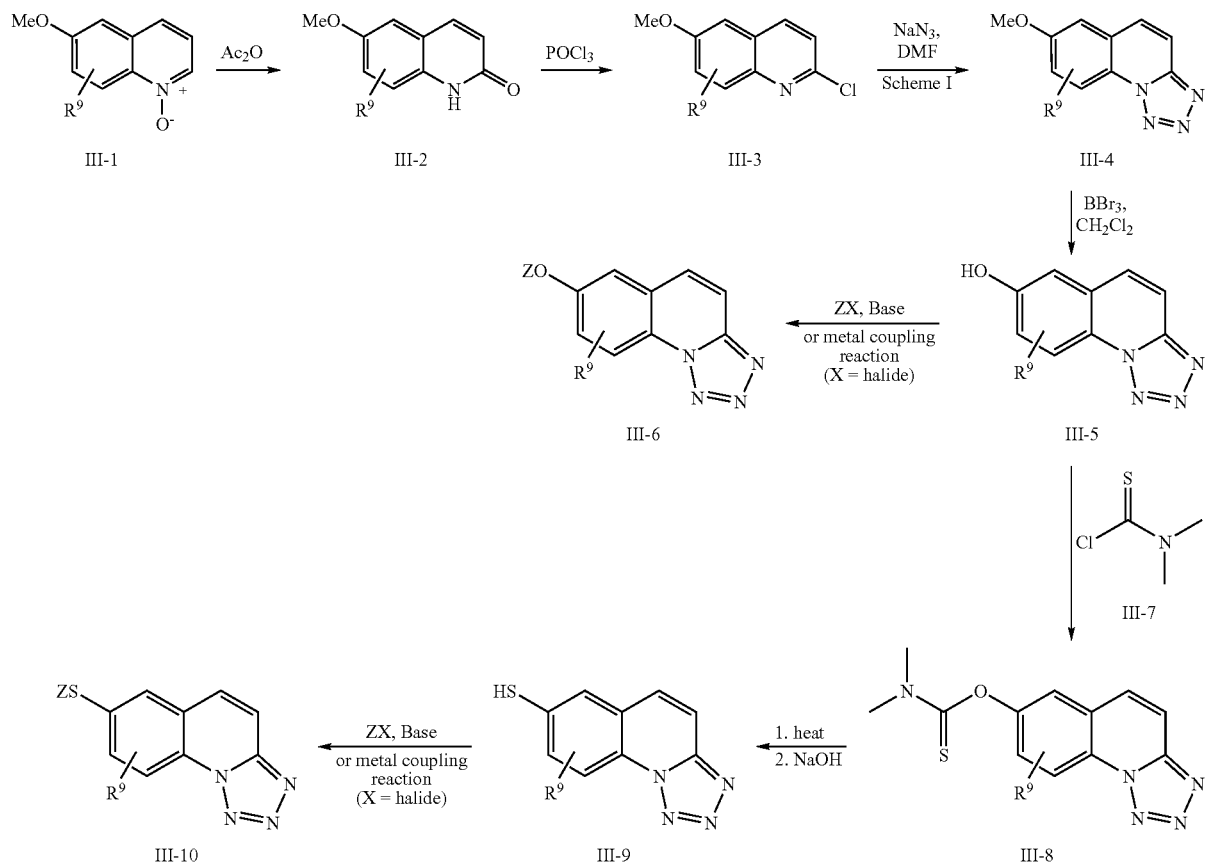

As shown in Scheme III, commercially available 6-methoxyquinoline oxide of structure III-1 may be transformed to naphthyridones of structure III-2 by treatment with acetic anhydride. Chlorination of compounds of structure III-2 under standard conditions provides chloroquinolines of structure IV-2 ($X^1$=S, O) or hydrazinoquinolines of structure IV-3 utilizing the methodology outlined in Scheme I. Transformation of compounds of structure IV-3 to [1,2,4]triazolo[4,3-a]quinolines of structure IV-4 ($X^1$=S, O) can be similarly accomplished as described herein.

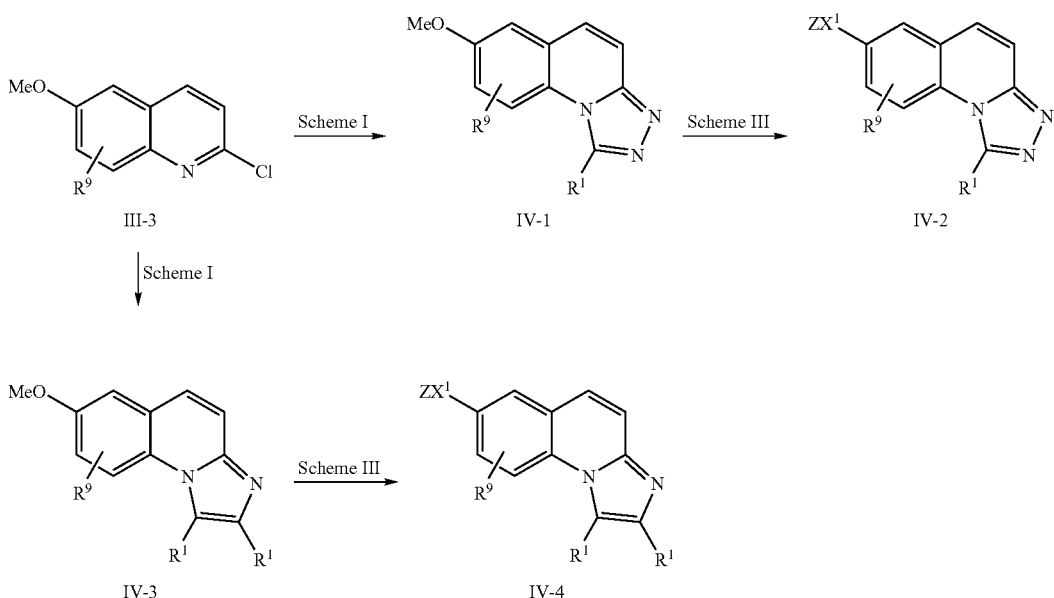

Alternative methods for the preparation of substituted 2-chloroquinolines are described in WO 2005/030774 and are shown in Schemes V and VI.

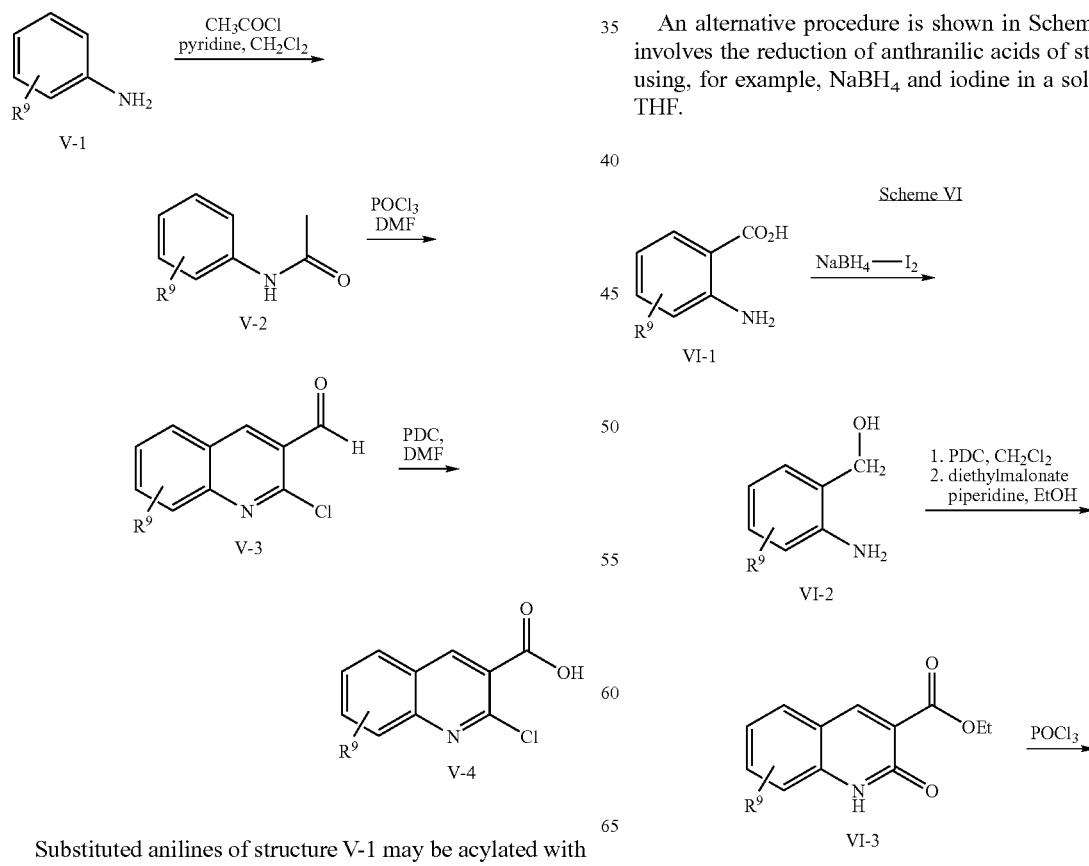

pounds of structure V-2. Compounds of structure V-2 can then be treated with $POCl_3$ in DMF to afford the 2-chloroquinolines of structure V-3, which contain a formyl moiety at C-3. Oxidation using, for example, pyridinium chlorochromate (PDC) in DMF then affords the corresponding acid derivative V-4.

An alternative procedure is shown in Scheme VI, which involves the reduction of anthranilic acids of structure VI-1 using, for example, $NaBH_4$ and iodine in a solvent such as THF.

Substituted anilines of structure V-1 may be acylated with acetyl chloride under standard conditions to afford com- -continued

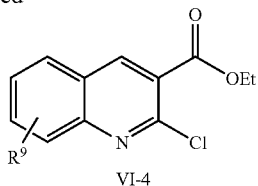

VI-4

Oxidation alcohols of structure VI-2 to the aldehyde (using PDC) is followed by condensation with diethylmalonate in the presence of a base such as piperidine then forms the quinolin-2-ones of structure VI-3. Quinolin-2-ones of structure VI-3 can be converted to 2-chloroquinolines of structure VI-4 using standard procedures (e.g. POCl$_3$).

Scheme VII outlines alternative methods for the synthesis of triazolo[4,3-a]quinolines.

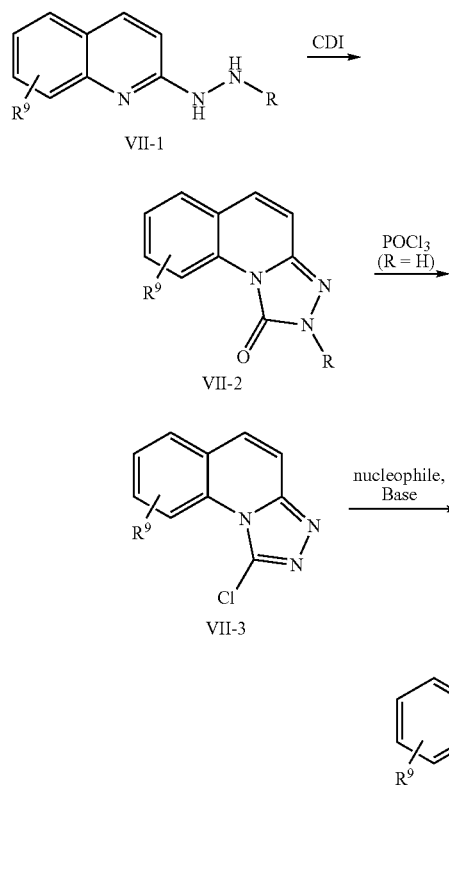

Optionally substituted 2-hyrazinoquinolines of structure VII-1 can be reacted with 1,1'-carbonyldiimidazole (CDI) to afford substituted 2H-[1,2,4]triazolo[4,3-a]quinolin-1-ones of structure VII-2. In cases where the R=H, compounds of structure VII-2 may be transformed into chlorotriazolo[4,3-a]quinolines of structure VII-3 by the action of phosphorous oxychloride. Chlorotriazolo[4,3-a]quinolines of structure VII-3 may be reacted with various nucleophiles, including, but not limited to, thiols, alcohols, amines, cyanide, etc. in the presence of a base, such as potassium carbonate, in acetonitrile to afford substituted triazolo[4,3-a]quinolines of structure VII-4.

Isomeric tricyclic structures may be synthesized by employing the chemistry in Scheme VIII.

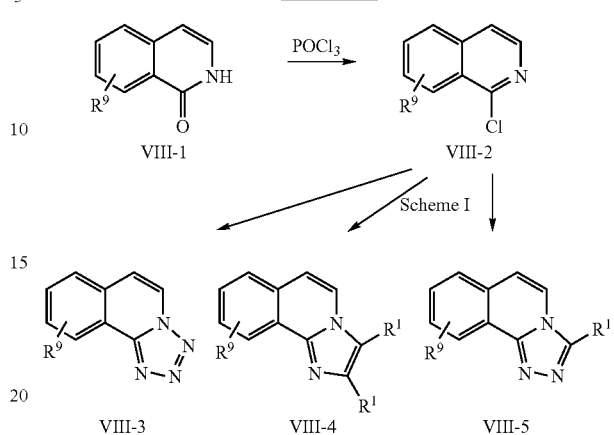

Naphthyridones of structure VIII-1 can be transformed into chloroquinolines of structure VIII-2 with phosphorous oxychloride. Utilizing the chemistry outlined in Scheme I, compounds of structure VIII-2 may be converted to tricycles of structure VIII-3, VIII-4, and VIII-5.

Scheme IX outlines the synthesis of quinoxaline-based tricycles, such as tricycles of structure IX-3, IX-4, and IX-5.

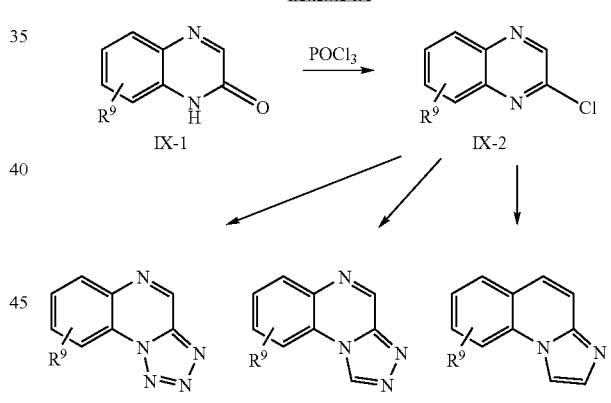

The synthesis of substituted 1H-quinoxalin-2-ones of structure IX-1 has been described in the literature (see *J. Med. Chem.*, 93, 1981). 1H-Quinoxalin-2-ones of structure IX-1 may be converted to chloroquinoxalines of structure IX-2 using, for example, POCl$_3$. Chloroquinoxalines of structure IX-2 may then be converted into the tricycles using the chemistry outlined in Scheme I. The synthesis of similar tricyclic structures has been described in the literature: for 1,2,3,5,9b-pentaaza-cyclopenta[a]naphthalenes of structure IX-3, see *J. Med. Chem.*, 3319, 1992; for [1,2,4]triazolo[4,3-a]quinoxalines of structure IX-4, see *Heterocycles*, 2025, 1985; and for imidazo[1,2-a]quinoxalines of structure IX-5, see *J. Med. Chem.*, 1088, 1988.

Scheme X outlines the synthesis of quinoxaline-based tricycles.

Scheme X

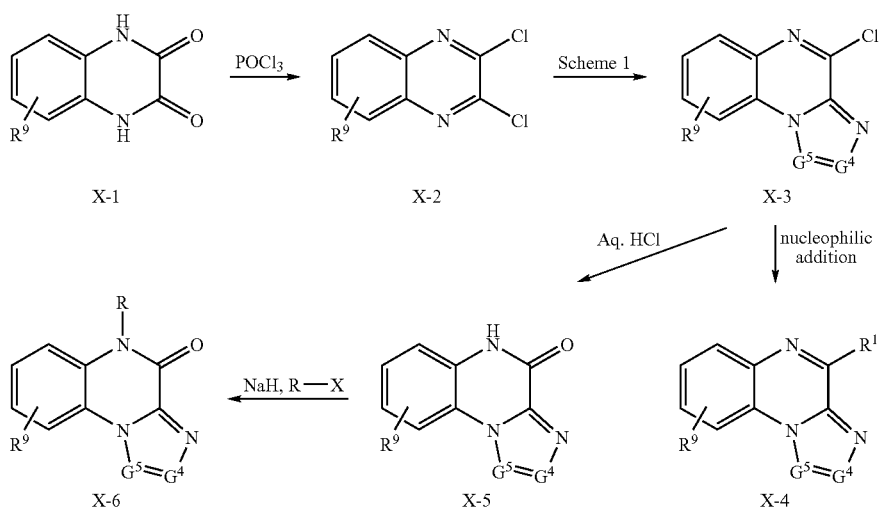

Substituted 1,4-dihydroquinoxaline-2,3-diones of structure X-1 have been described in the literature (see for example *Synth. Comm.*, 1349, 2004). Treatment of diones of structure X-1 with phosphorous oxychloride can yield dichlorides of structure X-2. Selective mono-substitution under the conditions in Scheme I can provide chlorinated tricycles of structure X-3. The remaining chloride group can then be reacted with nucleophiles, such as, but not limited to, cyanide, alkoxides, or alkyl- and arylamines in the presence of a base, such as cesium carbonate, to afford substituted quinoxaline-based tricycles of structure X-4. In some embodiments, chlorotricycles of structure X-3 may be hydrolyzed under acidic conditions to afford tricyclic quinoxalin-2-ones of structure X-5. Tricyclic quinoxalin-2-ones of structure X-5 may be alkylated with a variety of electrophiles in the presence of a base, such as sodium hydride, to afford tricyclic N-alkylquinoxalin-2-ones of structure X-6.

As shown in Scheme XI, 2-chloroquinazolines of structure XI-1 may be processed with the chemistry outlined in Scheme I to afford mixtures of regioisomeric quinazoline-based tricycles of structure XI-2 and XI-3. (see *Boll. Chim. Farm.*, 135, 1996, 585)

Scheme XI

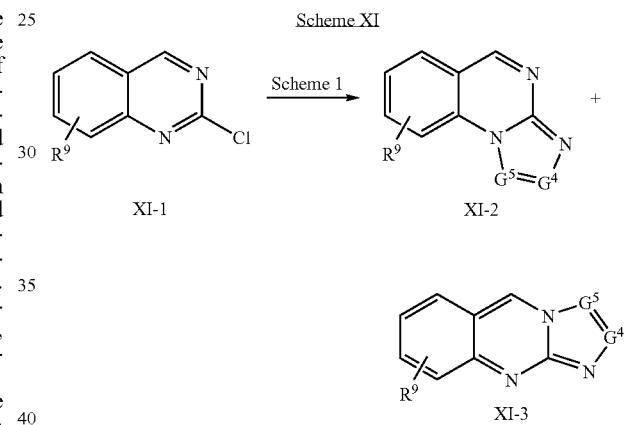

The synthesis of 3H-quinazolin-4-one based tricycles is described in Scheme XII.

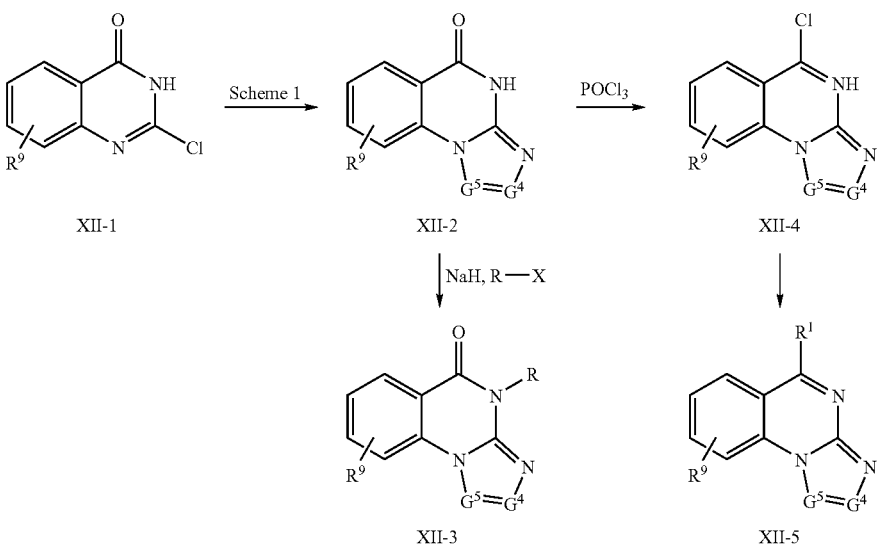

Synthetic methods towards the synthesis of 2-chloro-3H-quinazolin-4-ones have been described in the literature (see *J. Med. Chem.*, 130, 1968.) The chemistry outlined in Scheme I may be utilized to prepare 3H-quinazolin-4-one-based tricycles of structure XII-2. In one embodiment, 3H-quinazolin-4-one-based tricycles of structure XII-2 may be alkylated to afford substituted tricycles of structure XII-3. In another embodiment, treatment of compounds of structure XII-2 with phosphorous oxychloride affords chlorinated tricycles of structure XII-4. This compound may be further substituted to yield compounds of structure XII-5 by the action of various nucleophiles (such as, but not limited to, cyanide, alkoxides, and aliphatic and aromatic amines in the presence of a base, such as, for example, cesium carbonate.)

Another strategy for the synthesis of tricyclic compounds is shown in Scheme XIII.

conditions, for example, N-bromosuccinimide (NBS) and a radical initiator in a chlorinated solvent in the presence of light, affords quinolines of structure XIII-3. The benzyl halide may be displaced using a nucleophile (ZX$^1$H; Z and X$^1$ are as defined herein) in the presence of a base (for example NaH) in an aprotic solvent such as DMF to provide functionalized quinolines of structure XIII-4. The 2-halo substituent of quinolines of structure XIII-4 may be regioselectively reacted to provide substituted tricycles of structure XIII-5 using previously described chemistry (see Scheme I). Subsequently, the bromo (or chloro) substituent of compounds of structure XIII-5 may be displaced using standard organic chemistry procedures (nucleophilic displacement reactions or metal mediated coupling reactions) to give compounds of general structure XIII-6.

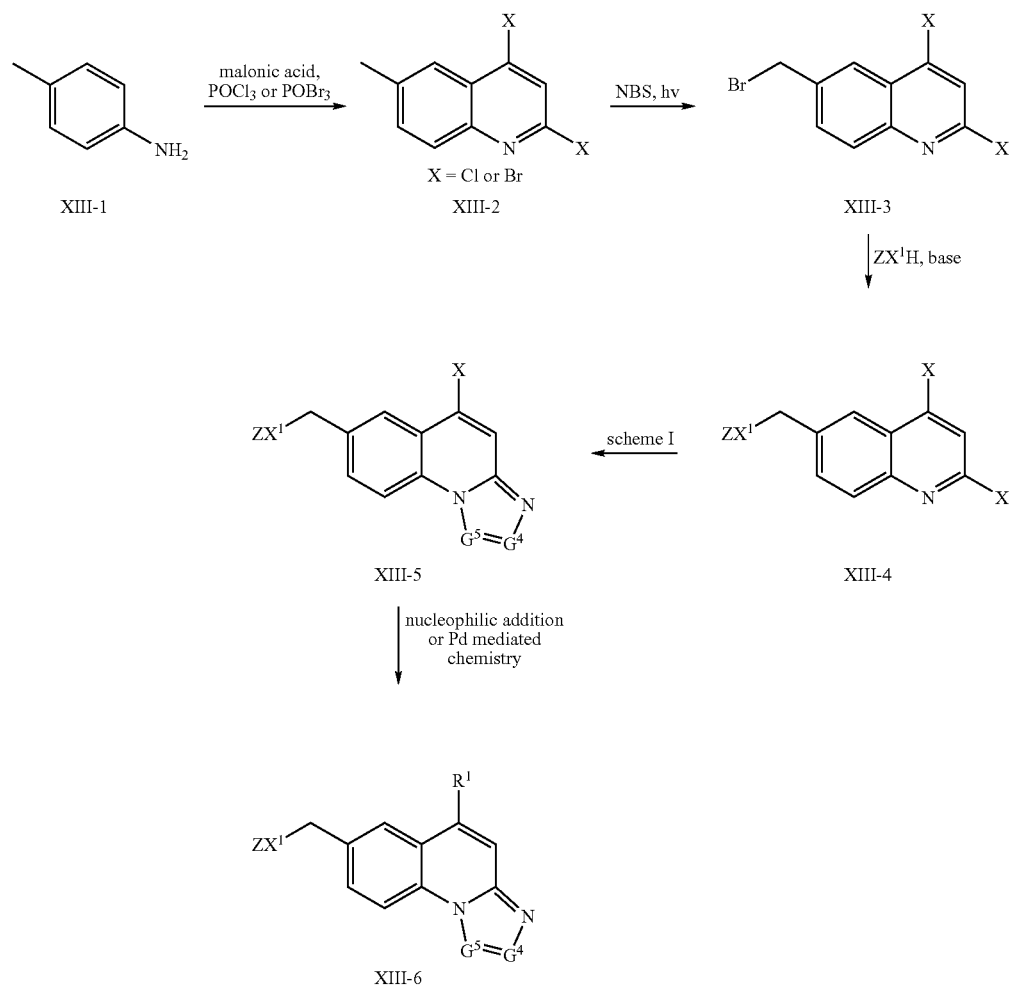

Scheme XIII

G$^4$, G$^5$ = N or CH

4-Methylaniline (XIII-I) can be treated with malonic acid in the presence of POCl$_3$ or POBr$_3$ to give dihaloquinolines of structure XIII-2, where X is Cl or Br (see *J. Chem. Soc. Perkin Trans* 1, 1994, p 2747). Benzylic bromination using standard Scheme XIV outlines a synthetic strategy for the preparation of compounds of general structure A-L$^1$-Z in which Z contains a substituted 4-aryltetrahydropyran and linker L$^1$ is CH$_2$O or CH$_2$S.

Scheme XIV

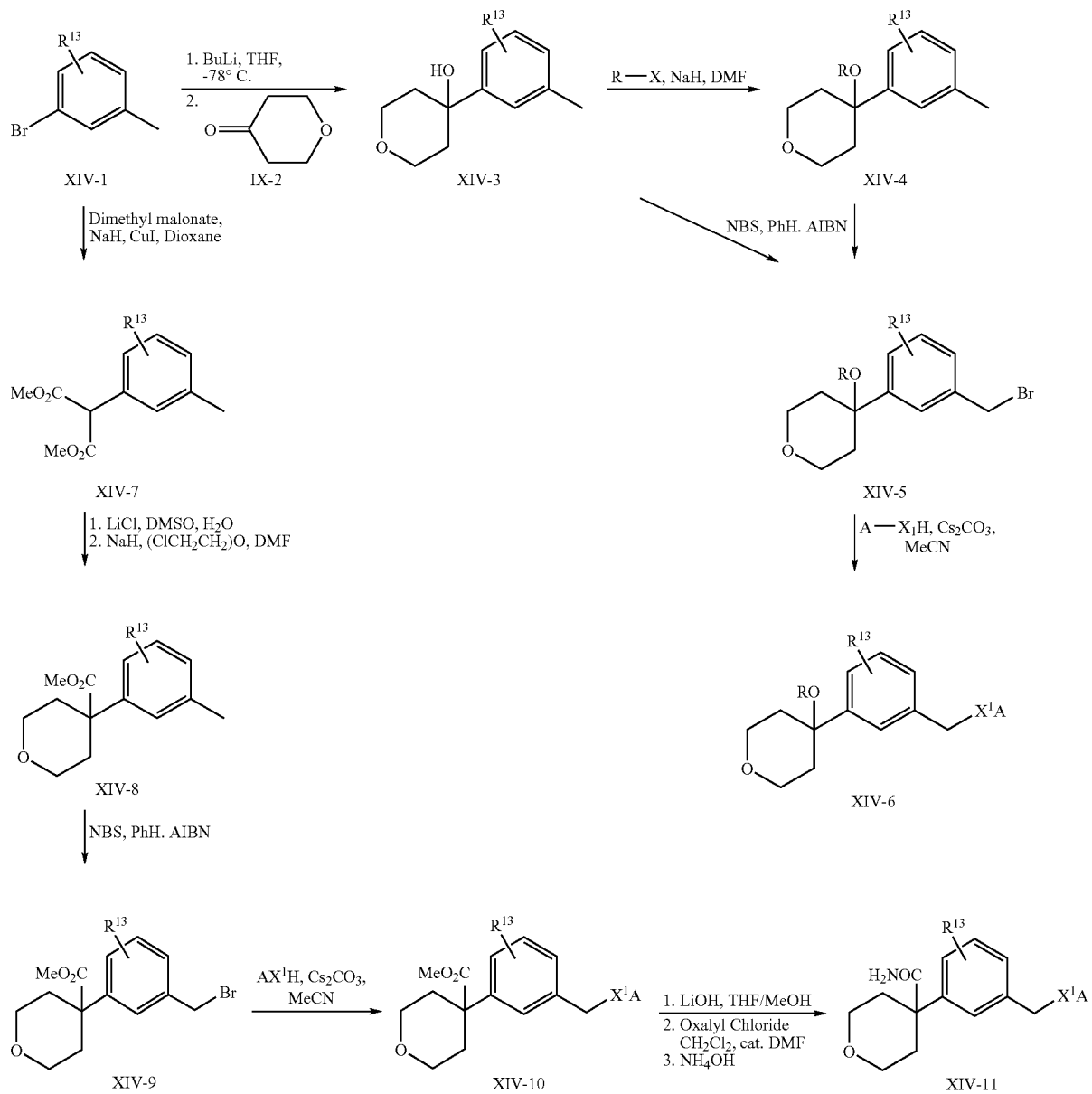

1-Bromo-3-methylbenzenes of structure XIV-1 can be metallated by the action of butyllithium in THF and reacted with 4-tetrahydropyranones of structure XIV-2 to provide alcohols of structure XIV-3. The alcohol moiety of compounds of structure XIV-3 can be alkylated with various electrophiles in the presence of NaH and solvents such as DMF to provide compounds of structure XIV-4. Aryltetrahydropyrans of structure XIV-3 or XIV-4 can be brominated under radical conditions to provide benzyl bromides of structure XIV-5. Reaction of benzylic bromides of structure XIV-5 with tricycles "A" (containing a hydroxy or thiol moiety; $AX^1H$, where $X^1$ is S or O) affords functionalized aryltetrahydropyrans of structure XIV-6. In further examples, tetrahydropyrans containing carbon substituents in the 4-position may be prepared by utilizing a copper-mediated coupling of dimethylmalonate and bromotoluenes of structure XIV-1. Decarboxylation and subsequent alkylation with bis(2-chloroethyl)ether can provide compounds of structure XIV-8. In a similar fashion, compounds of structure XIV-8 can be brominated under radical conditions (to yield compounds of structure XIV-9) and subsequently reacted with a suitable tricycle ("A" group containing a nucleophilic moiety such as, for example, a hydroxy or thiol moiety; $AX^1H$, where $X^1$ is S or O) to afford compounds of structure XIV-10. The ester functionality of compounds of structure XIV-10 may be converted to the carboxamide using standard conditions for amide synthesis to provide compounds of structure XIV-11.

Scheme XV describes the synthesis of compounds of Formula $A-L^1-Z$, wherein Z contains a substituted 4-aryltetrahydropyran and linker $L^1$ is $OCH_2$ or $SCH_2$.

Scheme XV

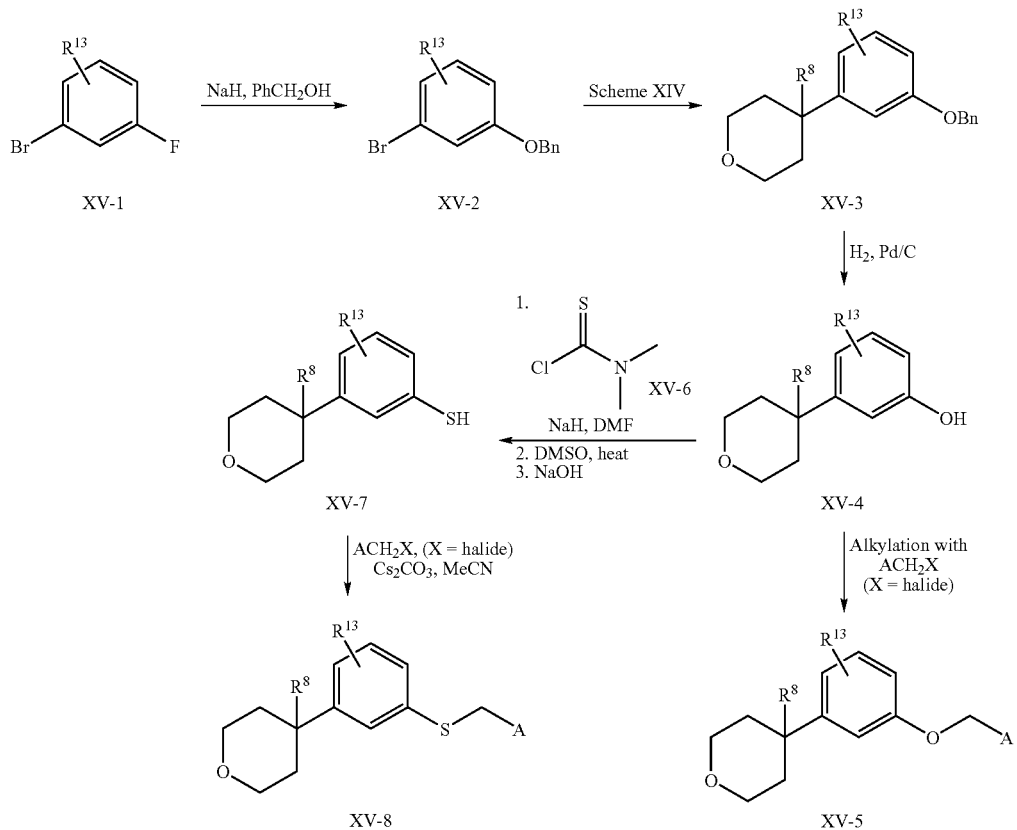

1,3-Bromofluorobenzenes of structure XV-1 can be transformed to benzyl ethers of structure XV-2 under $S_NAr$ conditions. Following the protocols outlined in Scheme XIV, an optionally substituted tetrahydropyran can be installed to afford compounds of structure XV-3. The benzyl ether may be selectively cleaved under the action of hydrogen with palladium catalysis to yield phenols of structure XV-4. This intermediate can be alkylated with a suitable bromomethyl-containing tricycle ("A" group) to afford compounds of structure XV-5. Alternatively, phenols of structure XV-4 may be transformed to the corresponding thiophenols of structure XV-7 by standard methodology (for example by treatment with dimethylthiocarbamoyl chloride (XV-6), rearrangement and deprotection; Newman and Barnes, *J. Org. Chem.*, 1966, 31, 3980-3984). Similarly, thiophenols of structure XV-7 can be alkylated with a bromomethyl-containing tricycle ("A" group) to give compounds of structure XV-8.

Scheme XVI describes the synthesis of compounds of Formula A-L$^1$-Z, wherein Z contains a substituted 4-aryltetrahydropyran and linker L$^1$ is S or O.

Scheme XVI

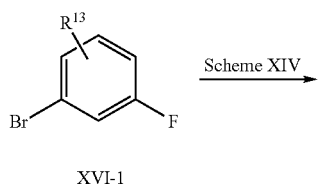

-continued

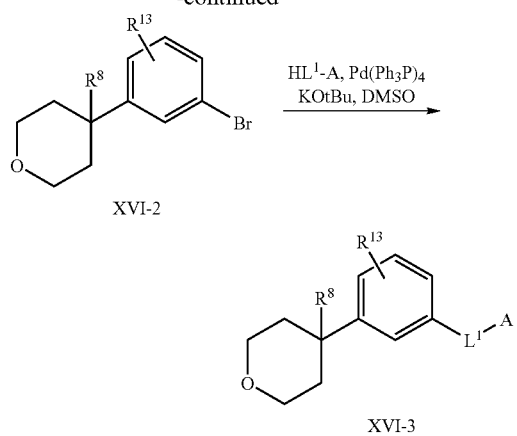

Utilizing the chemistry shown in Scheme XVI, an optionally substituted 1,3-dibromobenzene of structure XVI-1 can be transformed into aryltetrahydrofurans of structure XVI-2. A palladium-catalyzed coupling between bromides of structure XVI-2 and a phenolic or thiophenolic tricycle ("A" group) (*Org. Proc. Res. Dev.*, 2005, 9, 555-559) can yield compounds of structure XVI-3.

Scheme XVII describes a non-limiting example of the synthesis of compounds described herein where the linker group L$^1$ is a substituted ether or thioether moiety (—CH(R$^4$)O—, —CH(R$^4$)S—, —OCH(R$^4$)—, or —SCH(R$^4$)—).

Scheme XVII

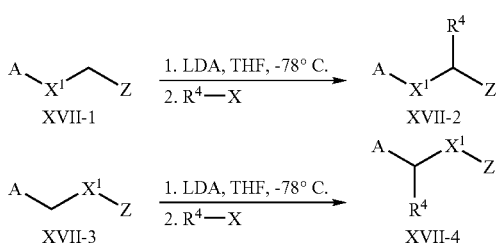

Compounds of structure XVII-1 or compounds of structure XVII-3 (where $X^1=S, O$) can be metallated by the action of a strong base such as LDA at low temperature. The resultant anion can be reacted with electrophiles including, but not limited to, alkyl halides, aldehydes, and ketones to provide methylene-substituted analogs of structure XVII-2 or XVII-3.

Scheme XVIII outlines the synthesis of compounds described herein where Z is a 2,5-disubstituted thiazole.

above, this intermediate can be transformed to alcohols and ethers of structure XVIII-6 and XVIII-7.

Throughout the specification, groups and substituents thereof can be chosen by one skilled in the field to provide stable moieties and compounds.

Certain Terminology

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be

Scheme XVIII

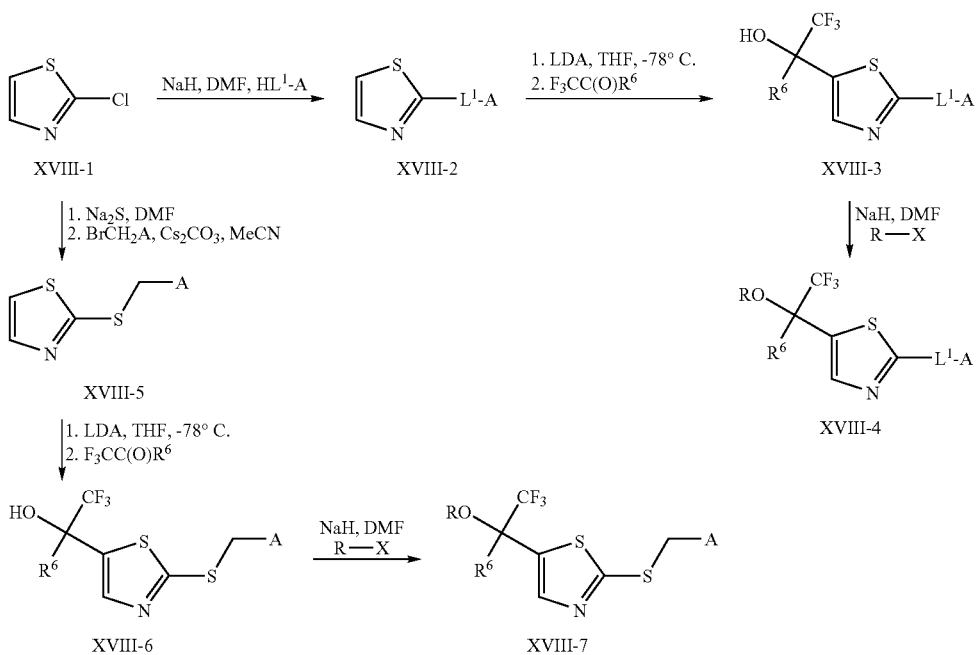

2-Chlorothiazoles of structure XVIII-1 can be coupled with a hydroxy or thiol containing tricycle ("A" group) to afford compounds of structure XVIII-2, where $L^1$ is O or S. Metallation of the 5-position of the thiazole affords an anion which may be quenched with trifluoromethyl ketones to give alcohols of structure XVIII-3. In some embodiments, alcohols of structure XVIII-3 can be further alkylated with alkyl halides in the presence of sodium hydride in DMF to afford ethers of structure XVIII-4. In cases where the linker group $L^1$ is $SCH_2$, 2-chlorothiazoles of structure XVIII-1 may first be transformed to the corresponding mercaptothiazole with sodium sulfide and subsequently alkylated with tricycles bromomethyl containing tricycles ("A" group) to provide compounds of structure XVIII-5. Using the chemistry described noted that, as used in the specification and the appended claims, the singular forms "a," "an" and "the" include plural referents unless the context clearly dictates otherwise. In this application, the use of "or" means "and/or" unless otherwise stated. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein.

As used herein, $C_1$-$C_x$ includes $C_1$-$C_2$, $C_1$-$C_3$ . . . $C_1$-$C_x$.

An "alkyl" group refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic. Depending on the structure, an alkyl group can be a monoradical or a diradical (i.e., an alkylene group).

The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group could also be a "lower alkyl" having 1 to 6 carbon atoms. The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

An "alkoxy" group refers to a (alkyl)O— group, where alkyl is as defined herein. A "lower alkoxy" has 1 to 6 carbon atoms.

The term "alkenyl" refers to a type of alkyl group in which the first two atoms of the alkyl group form a double bond that is not part of an aromatic group. That is, an alkenyl group begins with the atoms —C(R)=CR$_2$, wherein R refers to the remaining portions of the alkenyl group, which may be the same or different. Non-limiting examples of an alkenyl group include —CH=CH$_2$, —C(CH$_3$)=CH$_2$, —CH=CHCH$_3$ and —C(CH$_3$)=CHCH$_3$. The alkenyl moiety may be branched, straight chain, or cyclic (in which case, it would also be known as a "cycloalkenyl" group). Depending on the structure, an alkenyl group can be a monoradical or a diradical (i.e., an alkenylene group). A "lower alkenyl" has 2 to 6 carbon atoms in the chain.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which may be the same or different. Non-limiting examples of an alkynyl group include —C≡CH, —C≡CCH$_3$ and —C≡CCH$_2$CH$_3$. The "R" portion of the alkynyl moiety may be branched, straight chain, or cyclic. Depending on the structure, an alkynyl group can be a monoradical or a diradical (i.e., an alkynylene group). A "lower alkynyl" has 2 to 6 carbon atoms in the chain.

The term "alkylamine" refers to the —N(alkyl)$_x$H$_y$, group, where alkyl is as defined herein and x and y are selected from the group x=1, y=1 and x=2, y=0. When x=2, the alkyl groups taken together with the nitrogen atom to which they are attached can optionally form a heterocyclic ring system.

An "amide" is a chemical moiety with formula —C(=O)NHR or —NHC(=O)R, where R is selected from the group consisting of alkyl, cycloalkyl, aryl, heteroaryl (bonded through a ring carbon) and heteroalicyclic (bonded through a ring carbon). An amide may be an amino acid or a peptide molecule attached to a compound described herein, such as, for example, a compound of Formula (I), thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

The term "ester" refers to a chemical moiety with formula —COOR, where R is selected from the group consisting of alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e a heteroatom). Heterocycle includes heteroaryl and heterocycloalkyl. Carbocycles and heterocycles can be optionally substituted.

The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyl groups include groups having from 3 to 10 ring atoms. Illustrative examples of cycloalkyl groups include the following moieties:

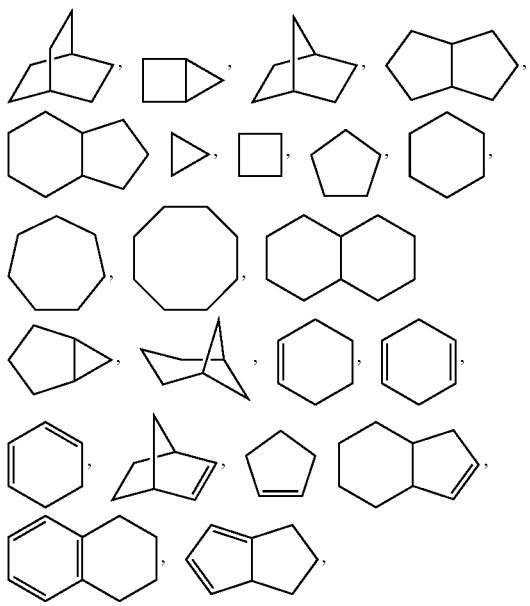

and the like. Depending on the structure, a cycloalkyl group can be a monoradical or a diradical (e.g., an cycloalkylene group). Monocyclic cycloalkyls include, but are not limited to, cyclopropyl, cyclobutyl, cyclopentyl, cyclohexyl, cycloheptyl, and cyclooctyl. A "lower cycloalkyl" has 3 to 8 ring carbon atoms.

A "cycloalkylalkyl" refers to an alkyl, as defined herein, substituted with a cycloalkyl, as defined herein. Cycloalkylalkyls include, but are not limited to, cyclopropylmethyl, cyclobutylmethyl, cyclopentylmethyl, cyclohexylmethyl, cycloheptylmethyl, and cyclooctylmethyl.

A "cycloalkoxy" refers to —O-(cycloalkyl), where cycloalkyl is as defined herein. A lower cycloalkoxy has 3 to 8 carbons.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. The polycyclic heteroaryl group may be fused or non-fused. Illustrative examples of heteroaryl groups include the following moieties:

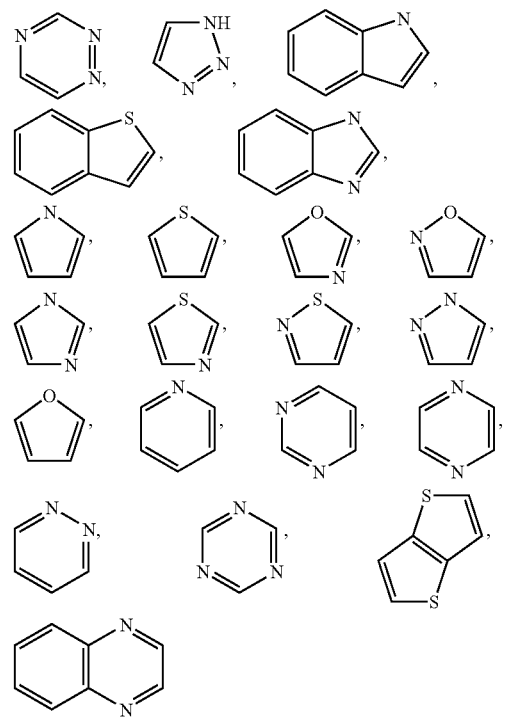

and the like. Depending on the structure, a heteroaryl group can be a monoradical or a diradical (i.e., a heteroarylene group).

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

A "heteroalicyclic" or "heterocycloalkyl" group refers to a cycloalkyl group that includes at least one ring atom that is not a carbon, i.e. at least one ring atom is a heteroatom selected from nitrogen, oxygen and sulfur. The heterocycloalkyl radicals may be fused with an aryl or heteroaryl. Illustrative examples of heterocycloalkyl groups, also referred to as non-aromatic heterocycles, include:

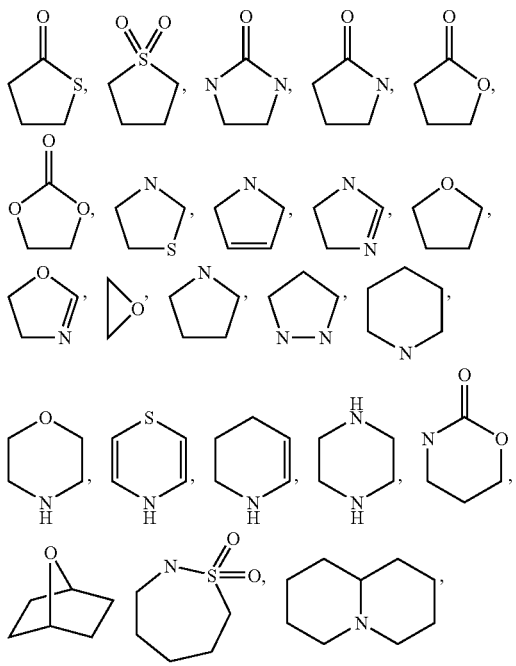

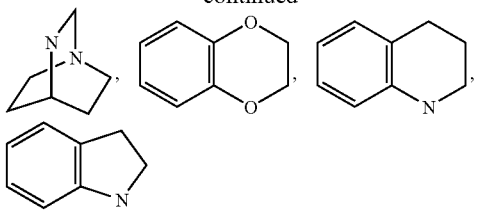

and the like. The term heteroalicyclic also includes all ring forms of the carbohydrates, including but not limited to the monosaccharides, the disaccharides and the oligosaccharides. Heterocycloalkyls have from 2 to 10 carbons in the ring. A "lower heterocycloalkyl" has 2 to 8 ring carbon atoms. It is understood that when referring to the number of carbon atoms in a heterocycloalkyl, the number of carbon atoms in the heterocycloalkyl is not the same at the total number of atoms (including the heteroatoms) that make up the heterocycloalkyl (i.e skeletal atoms of the heterocycloalkyl ring).

The terms "halo", "halide", and "halogen" mean fluoro, chloro, bromo and iodo.

The terms "haloalkyl," "haloalkenyl," "haloalkynyl" and "haloalkoxy" include alkyl, alkenyl, alkynyl and alkoxy structures that are substituted with one or more halogens. The halogens may the same or they may be different. A "lower haloalkyl" has 1 to 6 carbon atoms in the chain. A "lower haloalkenyl" has 2 to 6 carbon atoms in the chain. A "lower haloalkynyl" has 2 to 6 carbon atoms in the chain. A "lower haloalkoxy" has 1 to 6 carbon atoms in the chain.

The terms "fluoroalkyl" and "fluoroalkoxy" include haloalkyl and haloalkoxy groups, respectively, in which the halo is fluorine. A "lower fluoroalkyl" and a "lower fluoroalkoxy" have 1 to 6 carbon atoms in the chain.

The terms "heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. In addition, up to two heteroatoms may be consecutive, such as, by way of example, —CH$_2$—NH—OCH$_3$ and —CH$_2$—O—Si(CH$_3$)$_3$. A "lower heteroalkyl" has 1 to 6 carbon atoms in the chain. A "lower heteroalkenyl" has 2 to 6 carbon atoms in the chain. A "lower heteroalkynyl" has 2 to 6 carbon atoms in the chain.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

A "cyano" group refers to a —CN group.

An "isocyanato" group refers to a —NCO group.

An "isothiocyanato" group refers to a —NCS group.

"Acyl" refers to a RC(=O)— group.

"Acyloxy" refers to a RC(=O)O— group.

"Sulfanyl" refers to a —S— moiety.

"Sulfinyl" or "sulfoxide" refers to a —S(=O)— moiety.

"Sulfonyl" refers to a —S(=O)$_2$— moiety.

A "mercaptyl" group or "thioalkoxy" or "alkylthio" refers to a (alkyl)S— group.

A "thiocyanato" group refers to a —CNS group.

As used herein, the substituent "R" appearing by itself and without a number designation refers to a substituent selected from among from alkyl, cycloalkyl, aryl, heteroaryl (bonded through a ring carbon) and non-aromatic heterocycle (bonded through a ring carbon).

The term "optionally substituted" or "substituted" means that the referenced group may be substituted with one or more additional group(s) individually and independently selected from $C_1$-$C_6$alkyl, $C_3$-$C_8$cycloalkyl, aryl, heteroaryl, $C_2$-$C_6$heteroalicyclic, hydroxy, $C_1$-$C_6$alkoxy, aryloxy, $C_1$-$C_6$alkylthio, arylthio, $C_1$-$C_6$alkylsulfoxide, arylsulfoxide, $C_1$-$C_6$alkylsulfone, arylsulfone, cyano, halo, $C_2$-$C_8$acyl, $C_2$-$C_8$acyloxy, nitro, $C_1$-$C_6$haloalkyl, $C_1$-$C_6$fluoroalkyl, and amino, including $C_1$-$C_6$alkylamino, and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(=O)—, —C(=O)NH—, S(=O)$_2$NH—, —NHS(=O)$_2$—, —OC(=O)NH—, —NHC(=O)O—, —($C_1$-$C_6$alkyl)-, or —($C_2$-$C_6$alkenyl)-; and each $R^s$ is independently selected from H, ($C_1$-$C_4$alkyl), ($C_3$-$C_8$cycloalkyl), heteroaryl, aryl, and $C_1$-$C_6$heteroalkyl. Optionally substituted non-aromatic groups may be substituted with one or more oxo (=O). The protecting groups that may form the protective derivatives of the above substituents are known to those of skill in the art and may be found in references such as Greene and Wuts, above.

The compounds presented herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods known in the art such as, for example, the separation of individual stereoisomers by chiral chromatographic columns or by stereoselective synthesis.

The methods and formulations described herein include the use of N-oxides, crystalline forms (also known as polymorphs), or pharmaceutically acceptable salts of compounds having the structure of any of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im), Formula (II), Formula (IIa), Formula (IIb), Formula (IIc), Formula (IId), Formula (III), Formula (IIIa), Formula (IIIb), Formula (IIIc), Formula (IV), Formula (V), or Formula (VI), as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

The term "acceptable" with respect to a formulation, composition or ingredient, as used herein, means having no persistent detrimental effect on the general health of the subject being treated.

As used herein, the term "target protein" refers to a protein or a portion of a protein capable of being bound by a selective binding compound. In certain embodiments, a target protein is 5-LO.

As used herein, the term "selective binding compound" refers to a compound that selectively binds to any portion of one or more target proteins.

As used herein, the term "selectively binds" refers to the ability of a selective binding compound to bind to a target protein, such as, for example, 5-LO, with greater affinity than it binds to a non-target protein. In certain embodiments, specific binding refers to binding to a target with an affinity that is at least 10, 50, 100, 250, 500, 1000 or more times greater than the affinity for a non-target.

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "agonist" refers to a compound, the presence of which results in a biological activity of a protein that is the same as the biological activity resulting from the presence of a naturally occurring ligand for the protein, such as, for example, 5-LO.

As used herein, the term "antagonist" refers to a compound, the presence of which results in a decrease in the magnitude of a biological activity of a protein. In certain embodiments, the presence of an antagonist results in complete inhibition of a biological activity of a protein, such as, for example, 5-LO. In certain embodiments, an antagonist is an inhibitor.

The terms "inhibits", "inhibiting", or "inhibitor" of 5-LO, as used herein, refer to inhibition of 5-lipoxygenase activity.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

The term "bone disease," as used herein, refers to a disease or condition of the bone, including, but not limited to, inappropriate bone remodeling, loss or gain, osteopenia, osteomalacia, osteofibrosis, and Paget's disease [Garcia, "Leukotriene B4 stimulates osteoclastic bone resorption both in intro and in vivo", *J Bone Miner Res.* 1996; 11:1619-27].

The term "cardiovascular disease," as used herein refers to diseases affecting the heart or blood vessels or both, including but not limited to: arrhythmia; atherosclerosis and its sequelae; angina; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue. Lotzer K et al., "The 5-lipoxygenase pathway in arterial wall biology and atherosclerosis", *Biochim. Biophys. Acta,* 1736:30-7, 2005; Helgadottir, A, et al., *Nat. Genet.,* 233-9, 2004; Heise C E, Evans J F et al., *J Biol Chem.* 30531-30536, 2000].

The term "cancer," as used herein refers to an abnormal growth of cells, which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias) [Ding X Z et al., *Anticancer Drugs.* 2005 June; 16(5):467-73. Review; Chen X et al., *Clin Cancer Res.* 2004 Oct. 1; 10(19): 6703-9].

The term "dermatological disorder," as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, urticaria [Wedi, B, et al., *BioDrugs,* 2001, 15(11): 729-43].

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis [Charbeneau R P et al., *Clin Sci* (Lond). 2005 June; 108(6):479-91].

The term "iatrogenic" means a leukotriene-dependent or leukotriene-mediated condition, disorder, or disease created or worsened by medical or surgical therapy.

The term "inflammatory disorders" refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arteritis); joints (arthritis: crystalline, osteo-, psoriatic, reactive, rheumatoid, Reiter's); gastrointestinal tract (Crohn's Disease, ulcerative colitis); skin (dermatitis); or multiple organs and tissues (systemic lupus erythematosus) [Harrison's Principles of Internal Medicine, 16$^{th}$ Edition, Kasper D L, et al., Editors; McGraw-Hill, publishers].

The term "interstitial cystitis" refers to a disorder characterized by lower abdominal discomfort, frequent and sometimes painful urination that is not caused by anatomical abnormalities, infection, toxins, trauma or tumors [Bouchelouche K et al., *J. Urol.* 166:1734, 2001].

The terms "neurogenerative disease" or "nervous system disorder," as used herein, refers to conditions that alter the structure or function of the brain, spinal cord or peripheral nervous system, including but not limited to Alzheimer's Disease, cerebral edema, cerebral ischemia, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica. The acronym "CNS" refers to disorders of the central nervous system, i.e., brain and spinal cord [Sugaya K, et al., *Jpn. J. Pharmacol.,* 2000, February, 82(2): 85-94; Yu, G L, et al., *Pharmacology,* 2005, January, 73(1):31-40. Epub 2004 Sep. 27; Zhang W P, et al., *Acta Pharmacol. Sin.,* 2002, October, 23(10): 871-7].

The terms "ocular disease" or "ophthalmic disease," as used herein, refer to diseases which affect the eye or eyes and potentially the surrounding tissues as well. Ocular or ophthalmic diseases include, but are not limited to, conjunctivitis, retinitis, scleritis, uveitis, allergic conjunctivitis, vernal conjunctivitis, papillary conjunctivitis [Toriyama S., *Nippon Ganka Gakkai Zasshi.* 2000 June; 104(6):396-40; [Chen F, et al., *Ophthalmic Res.* 1991; 23(2):84-91].

The term "respiratory disease," as used herein, refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia [Evans J F, "The Cysteinyl Leukotriene (CysLT) Pathway in Allergic Rhinitis", *Allergology International* 2005; 54: 187-90); Kemp J P., "Leukotriene receptor antagonists for the treatment of asthma", *IDrugs.* 2000 April; 3(4): 430-41; Riccioni G, et al., *Allergy Asthma Proc.* 2004 November-December; 25(6):445-8].

The term "leukotriene-driven mediators," as used herein, refers to molecules able to be produced in a patient that may result from excessive production of leukotriene stimulation of cells, such as, by way of example only, $LTB_4$, $LTC_4$, $LTE_4$, cysteinyl leukotrienes, monocyte inflammatory protein (MIP-1α), interleukin-8 (IL-8), interleukin-4 (IL-4), interleukin-13 (IL-13), monocyte chemoattractant protein (MCP-1), soluble intracellular adhesion molecule (sICAM; soluble ICAM), myeloperoxidase (MPO), eosinophil peroxidase (EPO), and general inflammation molecules such as interleukin-6 (Il-6), C-reactive protein (CRP), and serum amyloid A protein (SAA).

The term "leukotriene-dependent", as used herein, refers to conditions or disorders that would not occur, or would not occur to the same extent, in the absence of one or more leukotrienes.

The term "leukotriene-mediated", as used herein, refers to refers to conditions or disorders that might occur in the absence of leukotrienes but can occur in the presence of one or more leukotrienes.

The term "leukotriene-responsive patient," as used herein, refers to a patient who has been identified by either genotyping of FLAP haplotypes, or genotyping of $LTA_4$ hydrolase haplotypes or genotyping of one or more other genes in the leukotriene pathway and/or, by phenotyping of patients either by previous positive clinical response to another leukotriene modulator, including, by way of example only, zileuton (Zyflo®), montelukast (Singulair®), pranlukast, zafirlukast (Accolate®), and/or by their profile of leukotriene-driven mediators that indicate excessive leukotriene stimulation of inflammatory cells, as likely to respond favorably to leukotriene modulator therapy.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "enzymatically cleavable linker," as used herein refers to unstable or degradable linkages which may be degraded by one or more enzymes.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

By "pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of any of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im), Formula (II), Formula (IIa), Formula (IIb), Formula (IIc), Formula (IId), Formula (III), Formula (IIIa), Formula (IIIb), Formula (IIIc), Formula (IV), Formula (V), or Formula (VI), and a co-agent, are both administered to a patient simultaneously in the form of a single entity or dosage. The term "non-fixed combination" means that the active ingredients, e.g. a compound of any of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im), Formula (II), Formula (IIa), Formula (IIb), Formula (IIc), Formula (IId), Formula (III), Formula (IIIa), Formula (IIIb), Formula (IIIc), Formula (IV), Formula (V), or Formula (VI), and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound of any of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im), Formula (II), Formula (IIa), Formula (IIb), Formula (IIc), Formula (IId), Formula (III), Formula (IIIa), Formula (IIIb), Formula (IIIc), Formula (IV), Formula (V), or Formula (VI), with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Composition/Formulation

For convenience, the pharmaceutical compositions and formulations described in this section and other parts herein use a single formula, such as "Formula (I)," by way of example. In addition, the pharmaceutical compositions and formulations described herein apply equally well to all formulae presented herein that fall within the scope of Formula (I). For example, the pharmaceutical compositions and formulations described herein can be applied to compounds having the structure of any of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im), Formula (II), Formula (IIa), Formula (IIb), Formula (IIc), Formula (IId), Formula (III), Formula (IIIa), Formula (IIIb), Formula (IIIc), Formula (IV), Formula (V), or Formula (VI), as well as to all of the specific compounds that fall within the scope of these generic formulae.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

Provided herein are pharmaceutical compositions that include a compound described herein, such as a compound of Formula (I) and a pharmaceutically acceptable diluent(s), excipient(s), and/or carrier(s). In addition, the compounds described herein can be administered as pharmaceutical compositions in which compounds described herein, such as compounds of Formula (I), are mixed with other active ingredients, as in combination therapy.

A pharmaceutical composition, as used herein, refers to a mixture of a compound described herein, such as a compound of Formula (I) with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein, such as compounds of Formula (I) provided herein are administered in a pharmaceutical composition to a mammal having a disease or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

For oral administration, compounds described herein can be formulated readily by combining the active compounds with pharmaceutically acceptable carriers or excipients well known in the art. Such carriers enable the compounds described herein to be formulated as tablets, powders, pills, dragees, capsules, liquids, gels, syrups, elixirs, slurries, suspensions and the like, for oral ingestion by a patient to be treated.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, but not limited to, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in a conventional manner. Parental injections may involve bolus injection or continuous infusion. Formulations for injection may be presented in unit dosage form, e.g., in ampoules or in multi-dose containers, with an added preservative. The pharmaceutical composition of the compounds described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compound(s) in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds described herein, such as compounds of Formula (I), can be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds described herein. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

For administration by inhalation, the compounds described herein may be in a form as an aerosol, a mist, or a powder. Pharmaceutical compositions of compounds described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, such as, by way of example only, gelatin for use in an inhaler or insufflator may be formulated containing a powder mix of the compound and a suitable powder base such as lactose or starch.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Pharmaceutical compositions may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. Pharmaceutical compositions that include a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one pharmaceutically acceptable carrier, diluent and/or excipient and a compound described herein, such as a compound of Formula (I) as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. In some embodiments, cyclic compounds described herein may exist in equilibrium with open chain forms. Both forms, cyclic and open form, are included. Additionally, the compounds described herein can exist in unsolvated as well as solvated forms with pharmaceutically acceptable solvents such as water, ethanol, and the like. The solvated forms of the compounds presented herein are also considered to be disclosed herein. In addition, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions can also contain other therapeutically valuable substances.

Methods for the preparation of compositions that include the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions that include a compound described herein, or a solution containing liposomes, micelles, or nanoparticles that include a compound as disclosed herein. Semi-solid compositions include, but are not limited to, gels, suspensions and creams. The compositions may be in liquid solutions or suspensions, solid forms suitable for solution or suspension in a liquid prior to use, or as emulsions. These compositions may also contain minor amounts of nontoxic, auxiliary substances, such as wetting or emulsifying agents, pH buffering agents, and so forth.

A composition that includes a compound described herein, such as a compound of Formula (I) can illustratively take the form of a liquid where the agents are present in solution, in suspension, or both. Typically when the composition is administered as a solution or suspension, a first portion of the compound is present in solution and a second portion of the compound is present in particulate form, in suspension in a liquid matrix. In some embodiments, a liquid composition may include a gel formulation. In other embodiments, the liquid composition is aqueous.

Aqueous suspensions can also contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful compositions can also include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate, and dextran.

Compositions may also include solubilizing agents to aid in the solubility of a compound described herein, such as a compound of Formula (I). The term "solubilizing agent" generally includes agents that result in formation of a micellar solution or a true solution of the agent. Certain acceptable nonionic surfactants, for example polysorbate 80, can be useful as solubilizing agents, as can ophthalmically acceptable glycols, polyglycols, e.g., polyethylene glycol 400, and glycol ethers.

Compositions may also include one or more pH adjusting agents or buffering agents, including acids such as acetic acid, boric acid, citric acid, lactic acid, phosphoric acid and hydrochloric acid; bases such as sodium hydroxide, sodium carbonate, sodium bicarbonate, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other compositions may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other compositions may include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other compositions may include one or more antioxidants to enhance chemical stability where required. Suitable antioxidants include, by way of example only, ascorbic acid and sodium metabisulfite.

Aqueous suspension compositions can be packaged in single-dose non-reclosable containers. Alternatively, multiple-dose reclosable containers can be used, in which case it is typical to include a preservative in the composition.

Alternatively, other delivery systems for hydrophobic pharmaceutical compounds may be employed. Liposomes and emulsions are well known examples of delivery vehicles or carriers for hydrophobic drugs. Certain organic solvents such as N-methylpyrrolidone also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds over the course of 4-24 hours. Depending on the chemical nature and the biological stability of the therapeutic reagent, additional strategies for protein stabilization may be employed.

All of the formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Methods of Dosing and Treatment Regimens

For convenience, the methods of dosing and treatment regimens described in this section and other parts herein use a single formula, such as "Formula (I)," by way of example. In addition, the methods of dosing and treatment regimens described herein apply equally well to all formulae presented herein that fall within the scope of Formula (I). For example, the methods of dosing and treatment regimens described herein can be applied to compounds having the structure of any of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im), Formula (II), Formula (IIa), Formula (IIb), Formula (IIc), Formula (IId), Formula (III), Formula (IIIa), Formula (IIIb), Formula (IIIc), Formula (IV), Formula (V), or Formula (VI), as well as to all of the specific compounds that fall within the scope of these generic formulae.

The compounds described herein, such as compounds of Formula (I), can be used in the preparation of medicaments for the treatment of leukotriene-dependent or leukotriene mediated diseases or conditions. In addition, a method for treating any of the diseases or conditions described herein in a subject in need of such treatment, involves administration of pharmaceutical compositions containing at least one compound described herein, such as a compound of Formula (I), or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds described herein may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds described herein may be given continuously; alternatively, the dose of the compounds described herein being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, the dosage or the frequency of administration, or both, can be reduced, as a function of the symptoms, to a level at which the improved state of the disease, disorder or condition is maintained. Patients can, however, require intermittent treatment on a long-term basis upon any recurrence of symptoms.

The amount of a given agent that will correspond to such an amount will vary depending upon factors such as the particular compound, disease condition and its severity, the identity (e.g., age, weight, gender, etc.) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, in some embodiments 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein are from about 0.01 to 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended release form. Suitable unit dosage forms for oral administration include from about 1 mg to about 50 mg active ingredient. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

For convenience, the combination treatments described in this section and other parts herein use a single formula, such as "Formula (I)," by way of example. In addition, the combination treatments described herein apply equally well to all formulae presented herein that fall within the scope of Formula (I). For example, the combination treatments described herein can be applied to compounds having the structure of any of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im), Formula (II), Formula (IIa), Formula (IIb), Formula (IIc), Formula (IId), Formula (III), Formula (IIIa), Formula (IIIb), Formula (IIIc), Formula (IV), Formula (V), or Formula (VI), as well as to all of the specific compounds that fall within the scope of these generic formulae.

In certain instances, it may be appropriate to administer at least one compound of Formula (I) in combination with another therapeutic agent. By way of example only, if one of the side effects experienced by a patient upon receiving one of the compounds herein is inflammation, then it may be appropriate to administer an anti-inflammatory agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. By way of example only, in a treatment for asthma involving administration of one of the compounds described herein, increased therapeutic benefit may result by also providing the patient with other therapeutic agents or therapies for asthma. In any case, regardless of the disease, disorder or condition being treated, the overall benefit experienced by the patient may simply be additive of the two therapeutic agents or the patient may experience a synergistic benefit.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature.

A combination treatment regimen may encompasses treatment regimens in which administration of a 5-lipoxygenase inhibitor described herein is initiated prior to, during, or after treatment with a second agent described above, and continues until any time during treatment with the second agent or after termination of treatment with the second agent. It also includes treatments in which a 5-lipoxygenase inhibitor described herein and the second agent being used in combination are administered simultaneously or at different times and/or at decreasing or increasing intervals during the treatment period. Combination treatment further includes periodic treatments that start and stop at various times to assist with the clinical management of the patient. For example, a 5-lipoxygenase inhibitor described herein in the combination treatment can be administered weekly at the onset of treatment, decreasing to biweekly, and decreasing further as appropriate.

Compositions and methods for combination therapy are provided herein. In accordance with one aspect, the pharmaceutical compositions disclosed herein are used to treat leukotriene-dependent or leukotriene mediated conditions. In accordance with another aspect, the pharmaceutical compositions disclosed herein are used to treat respiratory diseases, where treatment with a 5-lipoxygenase inhibitor is indicated, in particular asthma, and to induce bronchodilation in a subject. In one embodiment, pharmaceutical compositions disclosed herein are used to treat a subject suffering from a vascular inflammation-driven disorder. In one embodiment, the pharmaceutical compositions disclosed herein are used to treat a subject susceptible to myocardial infarction (MI).

Combination therapies described herein can be used as part of a specific treatment regimen intended to provide a beneficial effect from the co-action of a 5-lipoxygenase inhibitors described herein and a concurrent treatment. It is understood that the dosage regimen to treat, prevent, or ameliorate the condition(s) for which relief is sought, can be modified in accordance with a variety of factors. These factors include the type of respiratory disorder and the type of bronchodilation from which the subject suffers, as well as the age, weight, sex, diet, and medical condition of the subject. Thus, the dosage regimen actually employed can vary widely and therefore can deviate from the dosage regimens set forth herein.

For combination therapies described herein, dosages of the co-administered compounds will of course vary depending on the type of co-drug employed, on the specific compound employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering the compound described herein, such as a compound of Formula (I), in combination with the biologically active agent(s).

In any case, the multiple therapeutic agents (one of which is one of the compounds described herein, such as a compound of Formula (I) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

In addition, the compounds described herein, such as compounds of Formula (I), may also be used in combination with procedures that may provide additional or synergistic benefit to the patient. By way of example only, patients are expected to find therapeutic and/or prophylactic benefit in the methods described herein, wherein pharmaceutical composition of Formula (I) and/or combinations with other therapeutics are combined with genetic testing to determine whether that individual is a carrier of a mutant gene that is known to be correlated with certain diseases or conditions.

The compounds described herein, such as compounds of Formula (I), and combination therapies can be administered before, during or after the occurrence of a disease or condition, and the timing of administering the composition(s) containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, in some embodiments within the first 48 hours of the onset of the symptoms, in other embodiments within the first 6 hours of the onset of the symptoms, and yet in other embodiments within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, a solution, suspension, and the like, or combination thereof. A compound is preferably administered as soon as is practicable after the onset of a disease or condition is detected or suspected, and for a length of time necessary for the treatment of the disease, such as, for example, from about 1 day to about 3 months. The length of treatment can vary for each subject, and the length can be determined using known criteria. For example, the compound or a formulation containing the compound can be administered for at least 2 weeks, in some embodiments from about 1 month to about 5 years, and in other embodiments from about 1 month to about 3 years.

By way of example, therapies which combine compounds of Formula (I) with inhibitors of leukotriene synthesis or leukotriene receptor antagonists, either acting at the same or other points in the leukotriene synthesis pathway, could prove to be particularly useful for treating leukotriene-dependent or leukotriene mediated diseases or conditions. In addition, by way of example, therapies which combine compounds of Formula (I) with inhibitors of inflammation could prove to be particularly useful for treating leukotriene-dependent or leukotriene mediated diseases or conditions.

Anti-Inflammatory Agents

In another embodiment described herein, methods for treatment of leukotriene-dependent or leukotriene mediated conditions or diseases include administering to a patient compounds, pharmaceutical compositions, or medicaments described herein in combination with an anti-inflammatory agent including, but not limited to, non-steroidal anti-inflammatory drugs (NSAIDs) and corticosteroids (glucocorticoids).

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, CS-502, JTE-522, L-745,337 and NS398).

Corticosteroids, include, but are not limited to: betamethasone (Celestone), prednisone (Deltasone), alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

Corticosteroids do not directly inhibit leukotriene production, therefore co-dosing with steroids could provide additional anti-inflammatory benefit.

Some commercially available anti-inflammatories include, but are not limited to: diclofenac and misoprostol (Arthrotec®), 5-aminosalicyclic acid (Asacol®, Salofalk®), antipyrine and benzocaine (Auralgan®), sulfasalazine (Azulfidine®), oxaprozin (Daypro®), etodolac (Lodine®), mefenamic acid (Ponstan®), methylprednisolone (Solumedrol®), aspirin (Bayer®, Bufferin®), indomethacin (Indocin®), rofecoxib (Vioxx®), celecoxib (Celebrex®), valdecoxib (Bextra®), etoricoxib (Arcoxia®), lumiracoxib (Prexige®), ibuprofen (Advil®, Motrin®), diclofenac (Voltaren®), ketoprofen (Orudis®), meloxicam (Mobic®), nabumetone (Relafen®), naproxen (Aleve®, Naprosyn®), piroxicam (Feldene®).

By way of example, asthma is a chronic inflammatory disease characterized by pulmonary eosinophilia and airway hyperresponsiveness. Zhao et al., *Proteomics*, Jul. 4, 2005. In patients with asthma, leukotrienes may be released from mast cells, eosinophils, and basophils. The leukotrienes are involved in contraction of airway smooth muscle, an increase in vascular permeability and mucus secretions, and have been reported to attract and activate inflammatory cells in the airways of asthmatics (Siegel et al., ed., Basic Neurochemistry, Molecular, Cellular and Medical Aspects, Sixth Ed., Lippincott Williams & Wilkins, 1999). Thus, in another embodiment described herein, the methods for treatment of respiratory diseases include administering to a patient compounds, pharmaceutical compositions, or medicaments described herein in combination with an anti-inflammatory agent.

Leukotriene Receptor Antagonists

In another embodiment described herein, methods for treatment of leukotriene-dependent or leukotriene mediated conditions or diseases include administering to a patient compounds, pharmaceutical compositions, or medicaments described herein in combination with leukotriene receptor antagonists including, but are not limited to, $CysLT_1/CysLT_2$ dual receptor antagonists and $CysLT_1$ receptor antagonists. In another embodiment described herein, methods for treatment of leukotriene-dependent or leukotriene mediated conditions or diseases include administering to a patient compounds, pharmaceutical compositions, or medicaments described herein in combination with a $CysLT_1/CysLT_2$ dual receptor antagonist. $CysLT_1/CysLT_2$ dual receptor antagonists include, but are not limited to, BAY u9773 (4-((4S,5R,6E,8E,10Z,13Z)-1-carboxy-4-hydroxynonadeca-6,8,10,13-tetraen-5-ylthio)benzoic acid) (EP 00791576), DUO-LT (6-((4-(2-carbamoylacetyl)phenyl)sulfanyl)-6-(4-nonylphenyl)-5-oxohexanoic acid) (Galczenski et al, D38, Poster F4 presented at American Thoracic Society, May 2002, Tsuji et al, *Org. Biomol. Chem.*, 3139-3141, 2003). For a particular patient, the most appropriate formulation or method of use of such combination treatments may depend on the type of leukotriene-dependent or leukotriene mediated disorder, the time period in which the 5-lipoxygenase inhibitor acts to treat the disorder and the time period in which the $CysLT_1/CysLT_2$ dual receptor antagonist acts to inhibit CysLT receptor activity. By way of example only, such combination treatments may be used for treating a patient suffering from a respiratory disorder.

In another embodiment described herein, methods for treatment of leukotriene-dependent or leukotriene mediated conditions or diseases include administering to a patient compounds, pharmaceutical compositions, or medicaments described herein in combination with a $CysLT_1$ receptor antagonist. $CysLT_1$ receptor antagonists include, but are not limited to, zafirlukast (Accolate®), montelukast (Singulair®), prankulast (ONO-1078), and derivatives or analogs thereof. Such combinations may be used to treat leukotriene-dependent or leukotriene mediated disorder, including respiratory disorders.

The co-administration of a 5-lipoxygenase or FLAP inhibitor described herein with a $CysLT_1$ receptor antagonist or a dual $CysLT_1/CysLT_2$ receptor antagonist may have therapeutic benefit over and above the benefit derived from the administration of a either a 5-lipoxygenase or FLAP inhibitor or a $CysLT_1R$ antagonist alone. In the case that substantial inhibition of leukotriene production has undesired effects, partial inhibition of this pathway through the amelioration of the effects of the proinflammatory $LTB_4$ and cysteinyl leukotrienes combined with the block of the $CysLT_1$ receptor and/or dual $CysLT_1/CysLT_2$ receptor block may afford substantial therapeutic benefits, particularly for respiratory diseases.

Other Combination Therapies

In another embodiment described herein, methods for treatment of leukotriene-dependent or leukotriene mediated conditions or diseases, such as proliferative disorders, including cancer, include administration to a patient compounds, pharmaceutical compositions, or medicaments described herein in combination with at least one additional agent selected from among: alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, paclitaxel (Taxol), temozolomide, thioguanine, or classes of drugs including hormones (an antiestrogen, an antiandrogen, or gonadotropin releasing hormone analogues), interferons such as, but not limited to, alpha interferon; nitrogen mustards such as, but not limited to, busulfan, melphalan, and mechlorethamine; retinoids such as, but not limited to, tretinoin; topoisomerase inhibitors such as, but not limited to, irinotecan, and topotecan; tyrosine kinase inhibitors such as, but not limited to, gefinitinib, and imatinib; or agents to treat signs or symptoms induced by such therapy including, but not limited to, allopurinol, filgrastim, granisetron/ondansetron/palonosetron, and dronabinol.

In another embodiment described herein, methods for treatment of leukotriene-dependent or leukotriene mediated conditions or diseases, such as the therapy of transplanted organs or tissues or cells, include administration to a patient compounds, pharmaceutical compositions, or medicaments described herein in combination with at least one additional agent selected from among azathioprine, a corticosteroid, cyclophosphamide, cyclosporin, dacluzimab, mycophenolate mofetil, OKT3, rapamycin, tacrolimus, and thymoglobulin.

In another embodiment described herein, methods for treatment of leukotriene-dependent or leukotriene mediated conditions or diseases, such as atherosclerosis, include administration to a patient compounds, pharmaceutical compositions, or medicaments described herein in combination with at least one additional agent selected from among HMG-CoA reductase inhibitors (e.g., statins in their lactonized or dihydroxy open acid forms and pharmaceutically acceptable salts and esters thereof, including but not limited to lovastatin; simvastatin; dihydroxy open-acid simvastatin, particularly the ammonium or calcium salts thereof; pravastatin, particularly the sodium salt thereof; fluvastatin, particularly the sodium salt thereof; atorvastatin, particularly the calcium salt thereof; nisvastatin, also referred to as NK-104; rosuvastatin); agents that have both lipid-altering effects and other pharmaceutical activities; HMG-CoA synthase inhibitors; cholesterol absorption inhibitors such as ezetimibe; cholesterol ester transfer protein (CETP) inhibitors, for example JTT-705 and CP529, 414; squalene epoxidase inhibitors; squalene synthetase inhibitors (also known as squalene synthase inhibitors); acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; bile acid sequestrants; LDL (low density lipoprotein) receptor inducers; platelet aggregation inhibitors, for example adenosine diphosphate (ADP) receptor (P2Y12 receptor) inhibitors such as clopidogrel (Plavix®), glycoprotein IIb/IIIa fibrinogen receptor antagonists and aspirin; human peroxisome proliferator activated receptor gamma (PPARγ) agonists, including the compounds commonly referred to as glitazones, for example troglitazone, pioglitazone and rosiglitazone and including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists such as 5-[(2,4-dioxo-5-thiazolidinyl)methyl]-2-methoxy-N-[[4-(trifluoromethyl) phenyl]methyl]-benzamide, known as KRP-297; vitamin B6 (also known as pyridoxine) and the pharmaceutically acceptable salts thereof such as the HCl salt; vitamin B12 (also known as cyancobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABC1 gene expression; FXR and LXR ligands including both inhibitors and agonists; bisphosphonate compounds such as alendronate sodium; and cyclooxygenase-2 inhibitors, such as, for example, rofecoxib, celecoxib, etoricoxib, and lumiracoxib.

In another embodiment described herein, methods for treatment of leukotriene-dependent or leukotriene mediated conditions or diseases, such as the therapy of stroke, include administration to a patient compounds, pharmaceutical compositions, or medicaments described herein in combination with at least one additional agent selected from COX-2 inhibitors; nitric oxide synthase inhibitors, such as, but not limited to, N-(3-(aminomethyl)benzyl)acetamidine; Rho kinase inhibitors, such as, but not limited to, fasudil; angiotensin II type-1 receptor antagonists, including, but not limited to, candesartan, losartan, irbesartan, eprosartan, temisartan, and valsartan; glycogen synthase kinase 3 inhibitors; sodium or calcium channel blockers, including, but not limited to, crobenetine; p38 MAP kinase inhibitors, including, but not limited to, SKB 239063; thromboxane A X-synthetase inhibitors, including, but not limited to, isbogrel, ozagrel, ridogrel and dazoxiben; statins (HMG CoA reductase inhibitors), including, but not limited to, lovastatin, simvastatin, dihydroxy open-acid simvastatin, pravastatin, fluvastatin, atorvastatin, nisvastatin, and rosuvastatin; neuroprotectants, including free radical scavengers, calcium channel blockers, excitatory amino acid antagonists, growth factors, antioxidants, such as edaravone, vitamin C, vitamin E, 6-hydroxy-2,5,7,8-tetramethylchroman-2-carboxylic acid (TROLOX™), citicoline and minicycline, and reactive astrocyte inhibitors, such as (2R)-2-propyloctanoic acid; beta andrenergic blockers, such as, but not limited to, propranolol, nadolol, timolol, pindolol, labetalol, metoprolol, atenolol, esmolol and acebutolol; NMDA receptor antagonists, including memantine; NR2B antagonists, such as traxoprodil; 5-HT1A agonists; adenosine diphosphate (ADP) receptor (P2Y12 receptor) inhibitors such as clopidogrel (Plavix®); aspirin; receptor platelet fibrinogen receptor antagonists, including tirofiban and lamifiban; thrombin inhibitors; antithrombotics, such as argatroban; antihypertensive agents, such as enalapril; vasodilators, such as cyclandelate; nociceptin antagonists; DPIV antagonists; GABA 5 inverse agonists; and selective androgen receptor modulators.

In another embodiment described herein, methods for treatment of leukotriene-dependent or leukotriene mediated conditions or diseases, such as the therapy of pulmonary fibrosis, include administration to a patient compounds, pharmaceutical compositions, or medicaments described herein in combination with at least one additional agent selected from among anti-inflammatory agents, such as corticosteroids, azathioprine, and cyclophosphamide.

In another embodiment described herein, methods for treatment of leukotriene-dependent or leukotriene mediated conditions or diseases, such as the therapy of interstitial cystitis, include administration to a patient compounds, pharmaceutical compositions, or medicaments described herein in combination with at least one additional agent selected from among dimethylsulfoxide, omalizumab, and pentosan polysulfate.

In another embodiment described herein, methods for treatment of leukotriene-dependent or leukotriene mediated conditions or diseases, such as the therapy of disorders of bone, include administration to a patient compounds, pharmaceutical compositions, or medicaments described herein in combination with at least one additional agent selected from among minerals, vitamins, bisphosphonates, anabolic steroids, parathyroid hormone or analogs, and cathepsin K inhibitors.

Diagnostic Methods for Patient Identification

For convenience, the diagnostic and/or patient identification methods and treatment methods resulting therefrom that are described in this section and other parts herein use a single formula, such as "Formula (I)," by way of example. In addition, the diagnostic and/or patient identification methods and treatment methods resulting therefrom that are described herein apply equally well to all formulae presented herein that fall within the scope of Formula (I). For example, the diagnostic and/or patient identification methods and treatment methods resulting therefrom that are described herein can be applied to compounds having the structure of any of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im), Formula (II), Formula (IIa), Formula (IIb), Formula (IIc), Formula (IId), Formula (III), Formula (IIIa), Formula (IIIb), Formula (IIIc), Formula (IV), Formula (V), or Formula (VI), as well as to all of the specific compounds that fall within the scope of these generic formulae.

The screening of "leukotriene-responsive patients" which may be selected for treatment with compounds described herein, such as compounds of Formula (I), or pharmaceutical compositions or medicaments described herein which include compounds of Formula (I), or other 5-lipoxygenase modulators, may be accomplished using techniques and methods described herein. Such techniques and methods include, by way of example, evaluation of gene haplotypes (genotype analysis), monitoring/measurement of biomarkers (phenotype analysis), monitoring/measurement of functional markers (phenotype analysis), which indicate patient response to known modulators of the leukotriene pathway, or any combination thereof.

Phenotype Analysis: Biomarkers

Patients who are under consideration for treatment with compounds described herein, such as compounds of Formula (I), or drug combinations described herein that include compounds described herein, such as compounds of Formula (I), may be screened for potential responsiveness to treatment based on leukotriene-driven inflammatory biomarker phenotypes.

Patient screening based on leukotriene-driven inflammatory biomarker phenotypes may be used as an alternative to, or it may be complimentary with, patient screening by leukotriene pathway gene haplotype detection. The term "biomarker" as used herein refers to a characteristic which can be measured and evaluated as an indicator of normal biological processes, pathological processes, or pharmacological responses to therapeutic intervention. Thus a biomarker may be any substance, structure or process which can be measured in the body, or its products, and which may influence or predict the incidence of outcome or disease. Biomarkers may be classified into markers of exposure, effect, and susceptibility. Biomarkers can be physiologic endpoints, by way of example blood pressure, or they can be analytical endpoints, by way of example, blood glucose, or cholesterol concentrations. Techniques, used to monitor and/or measure biomarkers include, but are not limited to, NMR, LC-MS, LC-MS/MS, GC-MS, GC-MS/MS, HPLC-MS, HPLC-MS/MS, FT-MS, FT-MS/MS, ICP-MS, ICP-MS/MS, peptide/protein sequencing, nucleic acid sequencing, electrophoresis techniques, immuno-assays, immuno-blotting, in-situ hybridization, fluorescence in-situ hybridization, PCR, radio-immuno assays, and enzyme-immuno assays. Single nucleotide polymorphisms (SNPs) have also been useful for the identification of biomarkers for propensity to certain diseases and also susceptibility or responsiveness to drugs such as chemotherapeutic agents and antiviral agents. These techniques, or any combination thereof, may be used to screen patients for leukotriene-dependent or leukotriene mediated diseases or conditions, wherein such patients may be beneficially treated with compounds described herein, such as compounds of Formula (I), or drug combinations described herein that include compounds described herein, such as compounds of Formula (I).

By way of example only, patients may be selected for treatment with compounds described herein, such as compounds of Formula (I), or drug combinations described herein that include compounds described herein, such as compounds of Formula (I), by screening for enhanced inflammatory blood biomarkers such as, but not limited to, stimulated $LTB_4$, $LTC_4$, $LTE_4$, myeloperoxidase (MPO), eosinophil peroxidase (EPO), C-reactive protein (CRP), soluble intracellular adhesion molecule (sICAM), monocyte chemoattractant protein (MCP-1), monocyte inflammatory protein (MIP-1α), interleukin-6 (IL-6), the TH2 T cell activators interleukin 4 (IL-4), and 13 (IL-13) and other inflammatory cytokines. In certain embodiments, patients with inflammatory respiratory diseases, including but not limited to, asthma and COPD, or with cardiovascular diseases, are selected as those most likely to be responsive to leukotriene synthesis inhibition using compounds described herein, such as compounds of Formula (I), by using a panel of leukotriene driven inflammatory biomarkers.

Phenotype Analysis: Functional Markers

Patients who are under consideration for treatment with compounds described herein, such as compounds of Formula (I), or drug combinations described herein that include compounds described herein, such as compounds of Formula (I), may be screened for response to known modulators of the leukotriene pathway. Patient screening by evaluation of functional markers as indicators of a patient's response to known modulators of the leukotriene pathway may be used as an alternative to, or it may be complimentary with, patient screening by leukotriene pathway gene haplotype detection (genotype analysis) and/or monitoring/measurement of leukotriene-driven inflammatory biomarker phenotypes. Functional markers may include, but are not limited to, any physical characteristics associated with a leukotriene dependent condition or disease, or knowledge of current or past drug treatment regimens.

By way of example only, the evaluation of lung volume and/or function may be used as a functional marker for leukotriene-dependent or leukotriene mediated diseases or conditions, such as respiratory diseases. Lung function tests may be used to screen patients, with such leukotriene-dependent or leukotriene mediated diseases or conditions, for treatment using compounds described herein, such as compounds of Formula (I) or pharmaceutical compositions or medicaments which include compounds of Formula (I). Such tests include, but are not limited to, evaluation of lung volumes and capacities, such as tidal volume, inspiratory reserve volume, expiratory reserve volume, residual volume, inspiratory capacity, functional residual capacity, vital capacity, total lung capacity, respiratory minute volume, alveolar ventilation, timed vital capacity, and ventilatory capacity. Method of measurement of lung volumes and capacities include, but are not limited to, maximum expiratory flow volume curve, forced expiratory volume in 1 sec. (FEV1), peak expiratory flow rate. In addition, other lung function tests used as functional markers for patient evaluation described herein include, but are not limited to, respiratory muscle power, maximum inspiratory pressure, maximum expiratory pressure, transdiaphragmatic pressure, distribution of ventilation, single breath nitrogen test, pulmonary nitrogen washout, and gas transfer.

Additionally, the knowledge of a patients past or current treatment regimen may be used as a functional marker to assist in screening patients for treatment of leukotriene dependent conditions or diseases using compounds of Formula (I) or pharmaceutical compositions or medicaments that include compounds of Formula (I). By way of example only, such treatment regimens may include past or current treatment using zileuton (Zyflo®), montelukast (Singulair®), pranlukast, zafirlukast (Accolate®).

Also, patients who are under consideration for treatment with compounds described herein, such as compounds of Formula (I), or drug combinations described herein that include compounds described herein, such as compounds of Formula (I), may be screened for functional markers which include, but are not limited to, reduced eosinophil and/or basophil, and/or neutrophil, and/or monocyte and/or dendritic cell and/or lymphocyte recruitment, decreased mucosal secretion, decreased mucosal edema, and/or increased bronchodilation.

Figure 6:
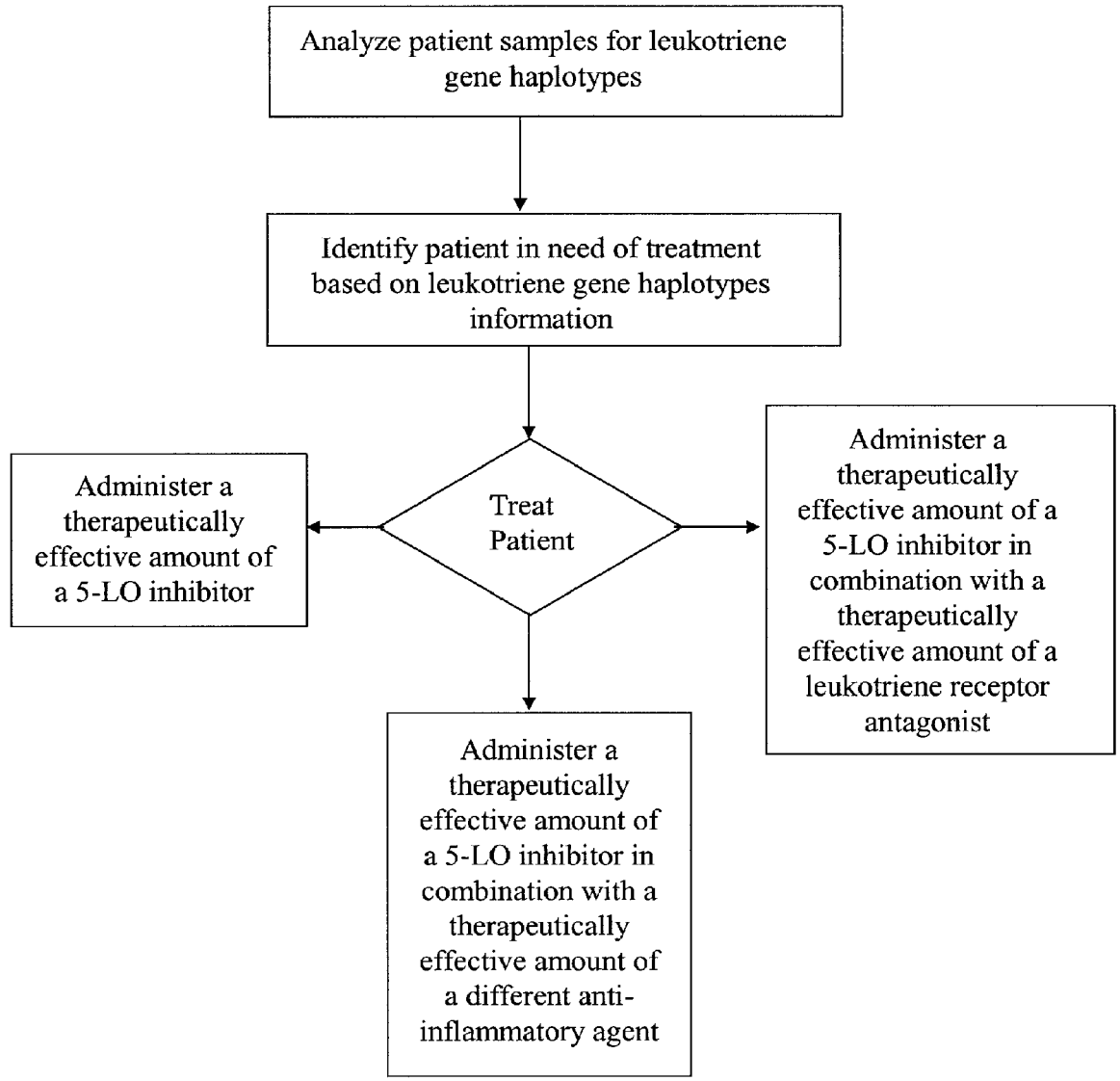
FIG. 6 present an illustrative scheme for the treatment of patients using the compounds and methods described herein.
Figure 7:
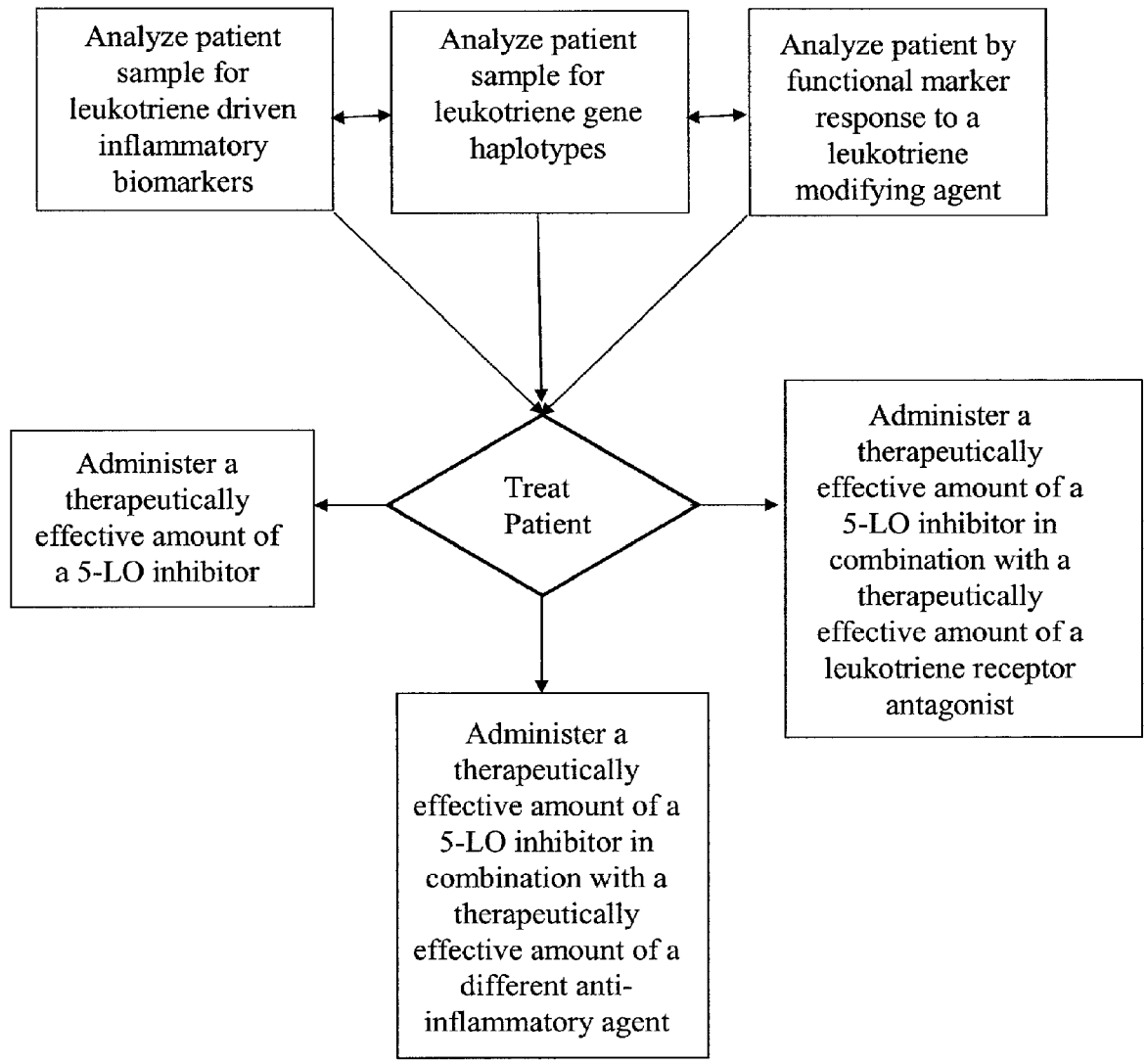
FIG. 7 present an illustrative scheme for the treatment of patients using the compounds and methods described herein.
Figure 8:
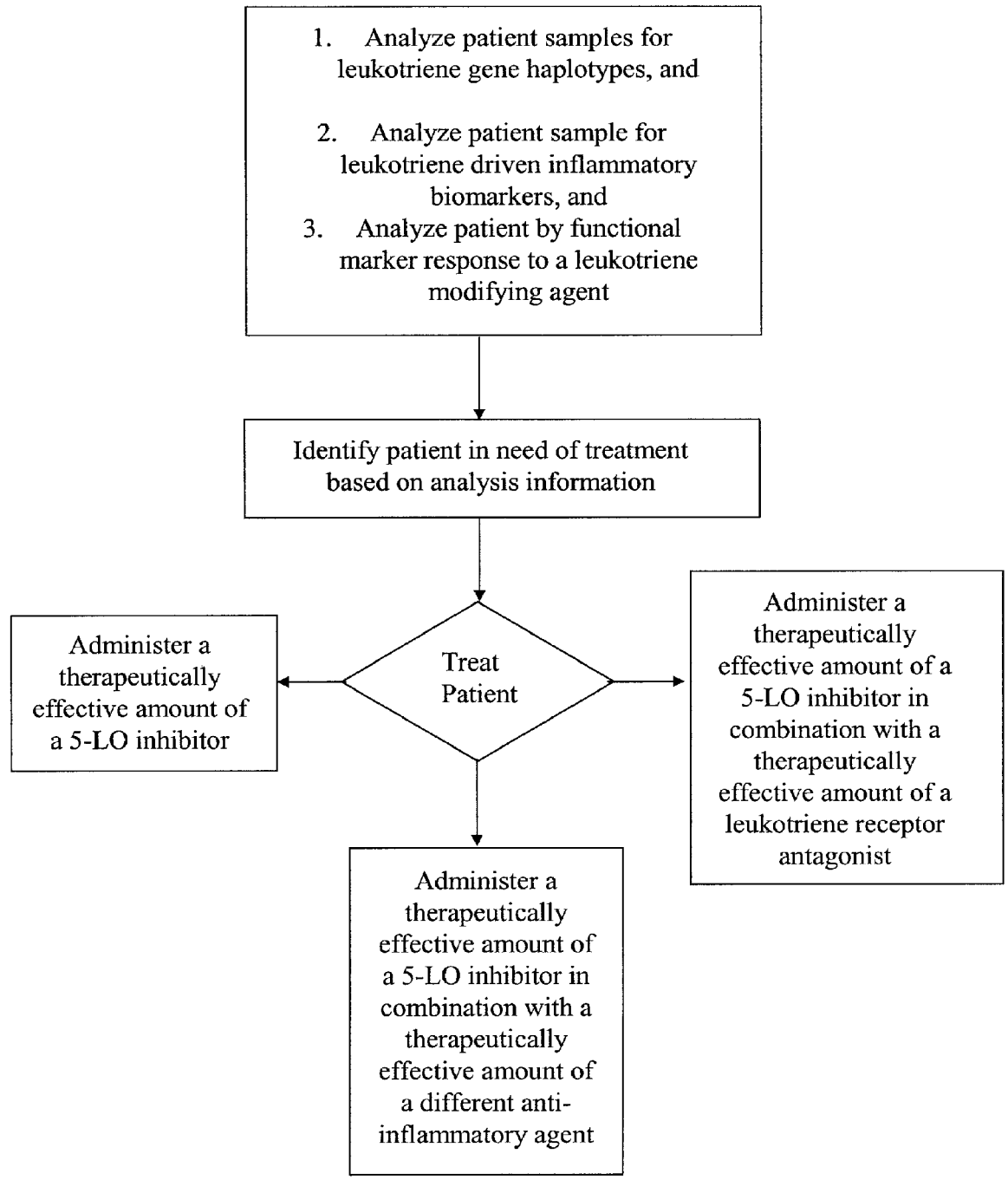
FIG. 8 present an illustrative scheme for the treatment of patients using the compounds and methods described herein.

Methods for the identification of a patient in need of treatment for leukotriene-dependent or leukotriene mediated conditions or diseases, and exemplary, non-limiting treatment methods are shown in FIGS. 5-8, wherein a patient sample is analyzed and the information obtained is used to identify possible treatment methods. It is expected that one skilled in the art will use this information in conjunction with other patient information, including, but not limited to age, weight, sex, diet, and medical condition, to choose a treatment method. It is also expected that each piece of information will be given a particular weight in the decision process. In certain embodiments, the information obtained from the diagnostic methods described above and any other patient information, including, but not limited to age, weight, sex, diet, and medical condition, are incorporated into an algorithm used to elucidate a treatment method, wherein each piece of information will be given a particular weight in the decision process.

In certain embodiments a patient sample is analyzed for leukotriene gene haplotypes and the information obtained identifies a patient in need of treatment using various treatment methods. Such treatment methods include, but are not limited to, administering a therapeutic effective amount of a compound of Formula (I) or pharmaceutical composition or medicament which includes a compound of Formula (I), administering a therapeutic effective amount of a compound of Formula (I) or pharmaceutical composition or medicament which includes a compound of Formula (I), in combination with a therapeutic effective amount of a leukotriene receptor antagonist (by way of example, $CysLT_1/CysLT_2$ antagonist or $CysLT_1$ antagonist), or administering a therapeutic effective amount of a compound of Formula (I) or pharmaceutical composition or medicament which includes a compound of Formula (I), in combination with a therapeutic effective amount of another anti-inflammatory agent. In other embodiments a patient sample is analyzed for leukotriene gene haplotypes, and/or phenotype biomarkers, and/or phenotype functional marker responses to leukotriene modifying agents. The patient may then be treated using various treatment methods. Such treatment methods include, but are not limited to, administering a therapeutic effective amount of a compound of Formula (I) or pharmaceutical composition or medicament which includes a compound of Formula (I), administering a therapeutic effective amount of a compound of Formula (I) or pharmaceutical composition or medicament which includes a compound of Formula (I), in combination with a therapeutic effective amount of a leukotriene receptor antagonist (by way of example, $CysLT_1/CysLT_2$ antagonist or $CysLT_1$ antagonist), or administering a therapeutic effective amount of a compound of Formula (I) or pharmaceutical composition or medicament which includes a compound of Formula (I), in combination with a therapeutic effective amount of another anti-inflammatory agent. In still other embodiments a patient sample is analyzed for leukotriene gene haplotypes, and phenotype biomarkers, and phenotype functional marker responses to leukotriene modifying agents. The patient may then be treated using various treatment methods. Such treatment methods include, but are not limited to, administering a therapeutic effective amount of a 5-lipoxygenase inhibitor, or pharmaceutical composition or medicament that includes a 5-lipoxygenase inhibitor, administering a therapeutic effective amount of a 5-lipoxygenase inhibitor, or pharmaceutical composition or medicament which includes a 5-lipoxygenase inhibitor, in combination with a therapeutic effective amount of a leukotriene receptor antagonist (by way of example, $CysLT_1/CysLT_2$ antagonist or $CysLT_1$ antagonist), or administering a therapeutic effective amount of a 5-lipoxygenase inhibitor, or pharmaceutical composition or medicament that includes a 5-lipoxygenase inhibitor in combination with a therapeutic effective amount of another anti-inflammatory agent.

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of 5-LO or in which 5-LO activity is a mediator or contributor to the symptoms or cause.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally include an identifying description or label or instructions relating to its use in the methods described herein.

A kit may include one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The person skilled in the art may further appreciate various aspects and advantages of the present disclosure upon review of the following illustrative and non-limiting examples:

The starting material used for the synthesis of the compounds described herein may be synthesized or can be obtained from commercial sources, such as, but not limited to, Aldrich Chemical Co. (Milwaukee, Wis.), or Sigma Chemical Co. (St. Louis, Mo.). The compounds described herein, and other related compounds having different substituents can be synthesized using techniques and materials described herein as well as those that are known to those of skill in the art.

Preparation of Intermediates:

Scheme A:

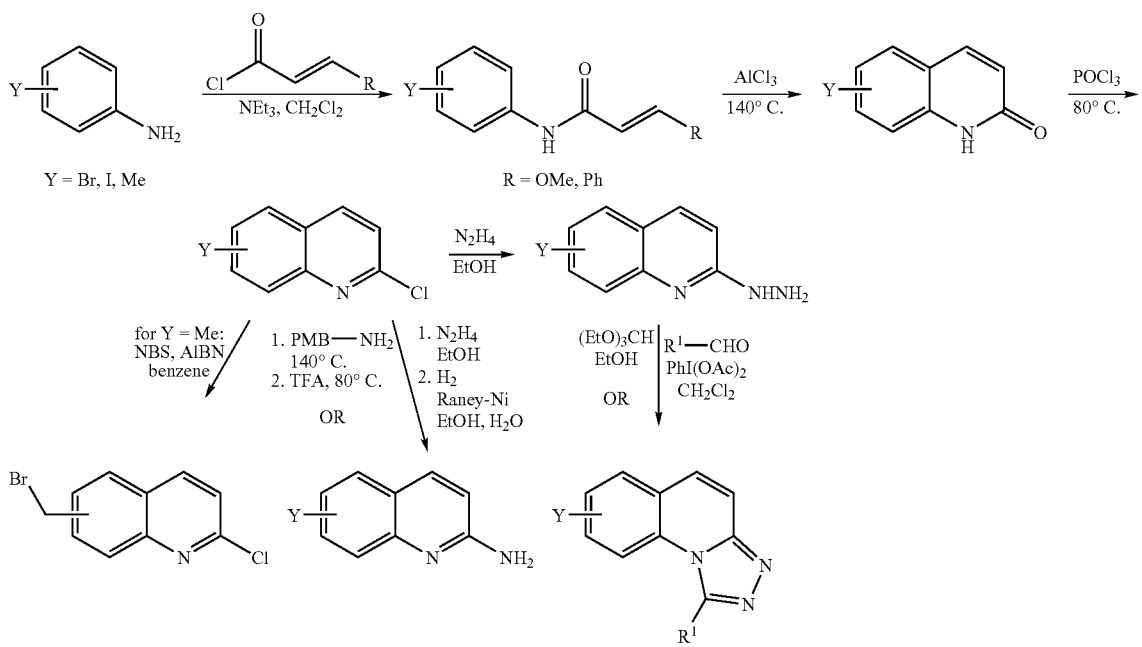

The following compounds were prepared as outlined in Scheme A:
6-Iodo-1H-quinolin-2-one (Alabaster, C. et al., *J. Med. Chem.*, 1988, 2048-2056); 5-Bromomethyl-2-chloro-quinoline (Inglis, S. et al., *Org. Biomol. Chem.*, 2005, 2543-2557); 6-Bromomethyl-2-chloro-quinoline (Warner, P. et al., *J. Med. Chem.*, 1992, 2761-2768); 7-Bromomethyl-2-chloro-quinoline (Inglis, S. et al., *Org. Biomol. Chem.*, 2005, 2543-2557); 6-Bromo-2-chloro-quinoline (Alabaster, C. et al., *J. Med. Chem.*, 1988, 2048-2056); 2-Chloro-6-iodo-quinoline (Lee, B. S. et al., *Bioorg. Med. Chem. Lett.*, 2000, 1559-1562); 6-Bromo-quinolin-2-ylamine (Inglis, S. et al., *J. Med. Chem.*, 2004, 5405-5417); 6-Iodo-quinolin-2-ylamine (MS (ES) M+H: 271); (6-Iodo-quinolin-2-yl)-hydrazine (MS (ES) M+H: 286); (7-Iodo-quinolin-2-yl)-hydrazine (MS (ES) M+H: 286); 7-Iodo-[1,2,4]triazolo[4,3-a]quinoline (MS (ES) M+H: 296); 8-Iodo-[1,2,4]triazolo[4,3-a]quinoline (MS (ES) M+H: 296); 7-Iodo-1-phenyl-[1,2,4]triazolo[4,3-a]quinoline (MS (ES) M+H: 372); 8-Iodo-1-phenyl-[1,2,4]triazolo[4,3-a]quinoline (MS (ES) M+H: 372); 7-Iodo-1-pyridin-2-yl-[1,2,4]triazolo[4,3-a]quinoline (MS (ES) M+H: 373); 7-Iodo-1-thiazol-2-yl-[1,2,4]triazolo[4,3-a]quinoline (MS (ES) M+H: 379); and 8-Iodo-1-thiazol-2-yl-[1,2,4]triazolo[4,3-a]quinoline (MS (ES) M+H: 379).

Scheme B:

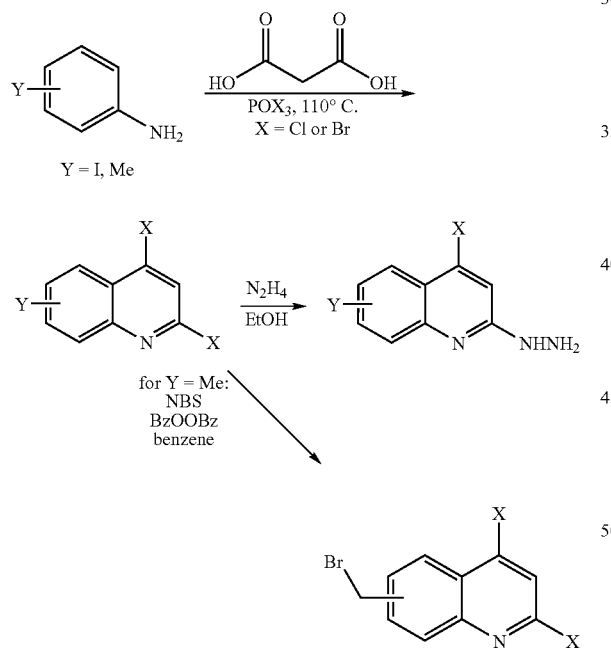

The following compounds were prepared as outlined in Scheme B:
6-Bromomethyl-2,4-dichloro-quinoline (Warner, P. et al., *J. Med. Chem.*, 1992, 2761-2768); 7-Bromomethyl-2,4-dichloro-quinoline (MS (ES) M+H: 292); 2,4-Dibromo-6-bromomethyl-quinoline (MS (ES) M+H: 382); 2,4-Dibromo-7-bromomethyl-quinoline (MS (ES) M+H: 381); 2,4-Dichloro-7-iodo-quinoline ($^1$H NMR (CDCl$_3$) δ 8.47 (s, 1H), 7.91 (s, 2H), 7.26 (s, 1H)); and (4-Chloro-7-iodo-quinolin-2-yl)-hydrazine (prepared in situ from 2,4-Dichloro-7-iodo-quinoline and used without further characterization).

Scheme C:

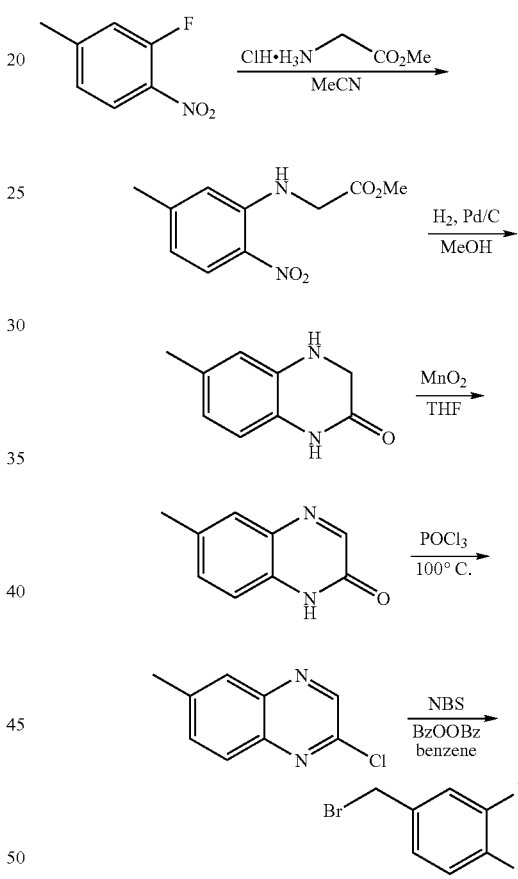

The following compound was prepared as outlined in Scheme C:
6-Bromomethyl-2-chloro-quinoxaline (MS (ES) M+H: 258).

Scheme D:

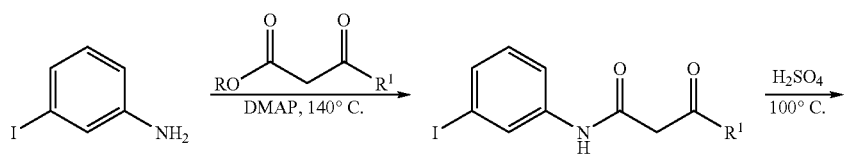

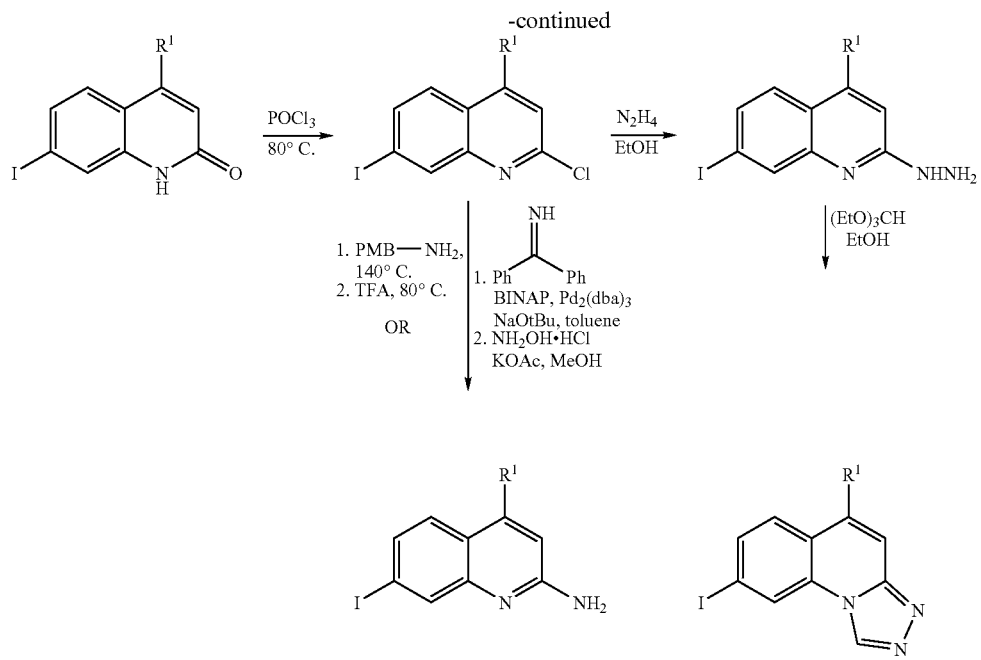

The following compounds were prepared as outlined in Scheme D:

2-Chloro-7-iodo-4-methyl-quinoline (MS (ES) M+H: 304); 2-Chloro-7-iodo-4-isopropyl-quinoline (MS (ES) M+H: 332); 2-Chloro-7-iodo-4-phenyl-quinoline (MS (ES) M+H: 366); 2-Chloro-4-(4-fluoro-phenyl)-7-iodo-quinoline (MS (ES) M+H: 384); 7-Iodo-4-methyl-quinolin-2-ylamine (MS (ES) M+H: 285); 7-Iodo-4-isopropyl-quinolin-2-ylamine (MS (ES) M+H: 313); 7-Iodo-4-phenyl-quinolin-2-ylamine (MS (ES) M+H: 347); (7-Iodo-4-phenyl-quinolin-2-yl)-hydrazine (MS (ES) M+H: 362); and 8-Iodo-5-phenyl-[1,2,4]triazolo[4,3-a]quinoline (MS (ES) M+H: 372).

Scheme E:

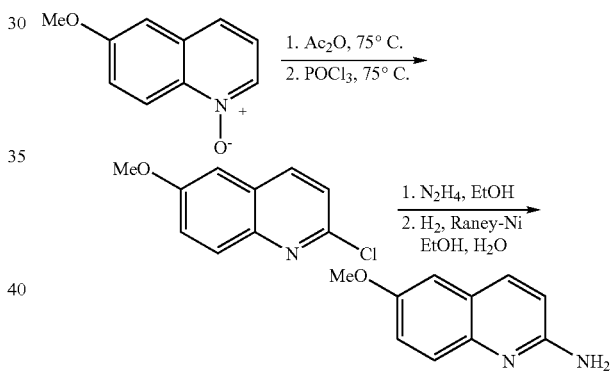

The following compound was prepared as outlined in Scheme E:
6-Methoxy-quinolin-2-ylamine (Inglis, S. et al., J. Med. Chem., 2004, 5405-5417).

Scheme F:

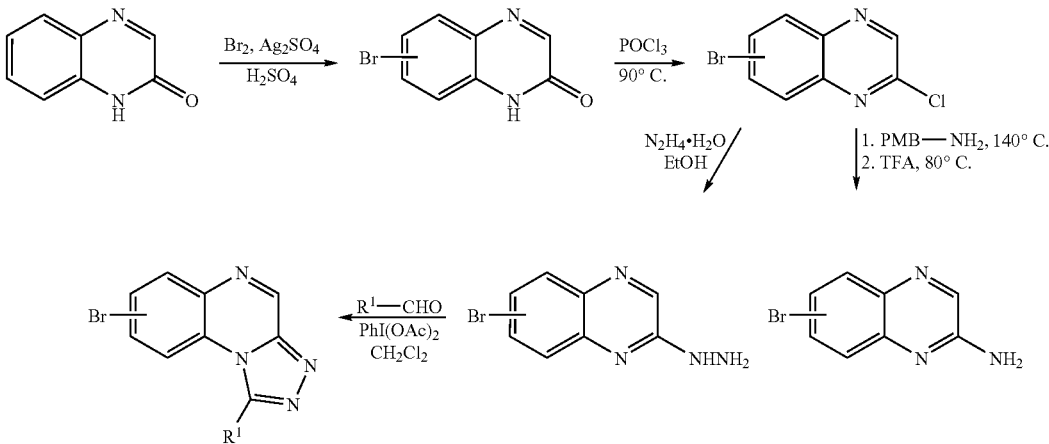

The following compounds were prepared as outlined in Scheme F:

6-Bromo-quinoxalin-2-ylamine (Wolf, F. J. et al., *J. Am. Chem. Soc.*, 1949, 6-10); 7-Bromo-quinoxalin-2-ylamine (Wolf, F. J. et al., *J. Am. Chem. Soc.*, 1949, 6-10); (6-Bromo-quinoxalin-2-yl)-hydrazine (MS (ES) M+H: 240); (7-Bromo-quinoxalin-2-yl)-hydrazine (MS (ES) M+H: 240); 7-Bromo-1-phenyl-[1,2,4]triazolo[4,3-a]quinoxaline (MS (ES) M+H: 326); and 7-Bromo-1-pyridin-2-yl-[1,2,4]triazolo[4,3-a]quinoxaline (MS (ES) M+H: 327).

Scheme G:

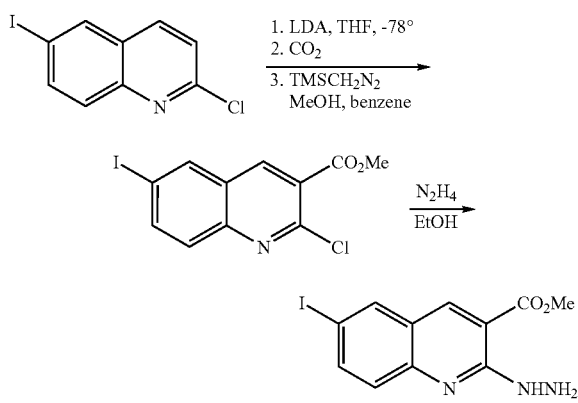

The following compound was prepared as outlined in Scheme G:

2-Hydrazino-6-iodo-quinoline-3-carboxylic acid methyl ester (MS (ES) M+H: 344).

Scheme H:

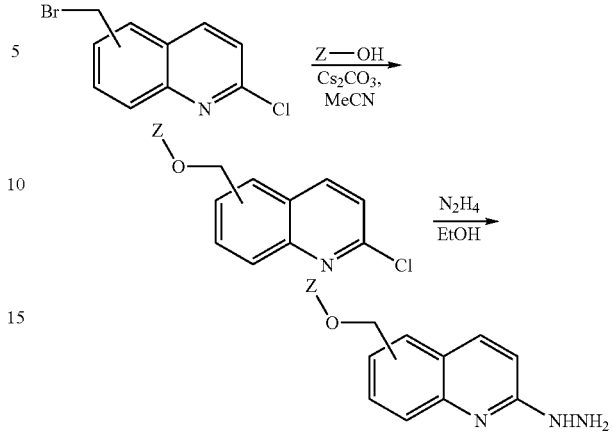

The following compounds were prepared as outlined in Scheme H:

{5-[3-Fluoro-5-(4-methoxy-tetrahydro-pyran-4-yl)-phenoxymethyl]-quinolin-2-yl}-hydrazine (prepared from 5-Bromomethyl-2-chloro-quinoline and 3-Fluoro-5-(4-methoxy-tetrahydro-pyran-4-yl)-phenol and used without further characterization); 4-[3-Fluoro-5-(2-hydrazino-quinolin-6-ylmethoxy)-phenyl]-tetrahydro-pyran-4-ol (prepared from 6-Bromomethyl-2-chloro-quinoline and 4-(3-Fluoro-5-hydroxy-phenyl)-tetrahydro-pyran-4-ol and used without further characterization); {6-[3-Fluoro-5-(4-methoxy-tetrahydro-pyran-4-yl)-phenoxymethyl]-quinolin-2-yl}-hydrazine (MS (ES) M+H: 398); and 4-[3-Fluoro-5-(2-hydrazino-quinolin-6-ylmethoxy)-phenyl]-tetrahydro-pyran-4-carboxylic acid methyl ester (MS (ES) M+H: 426).

Scheme I:

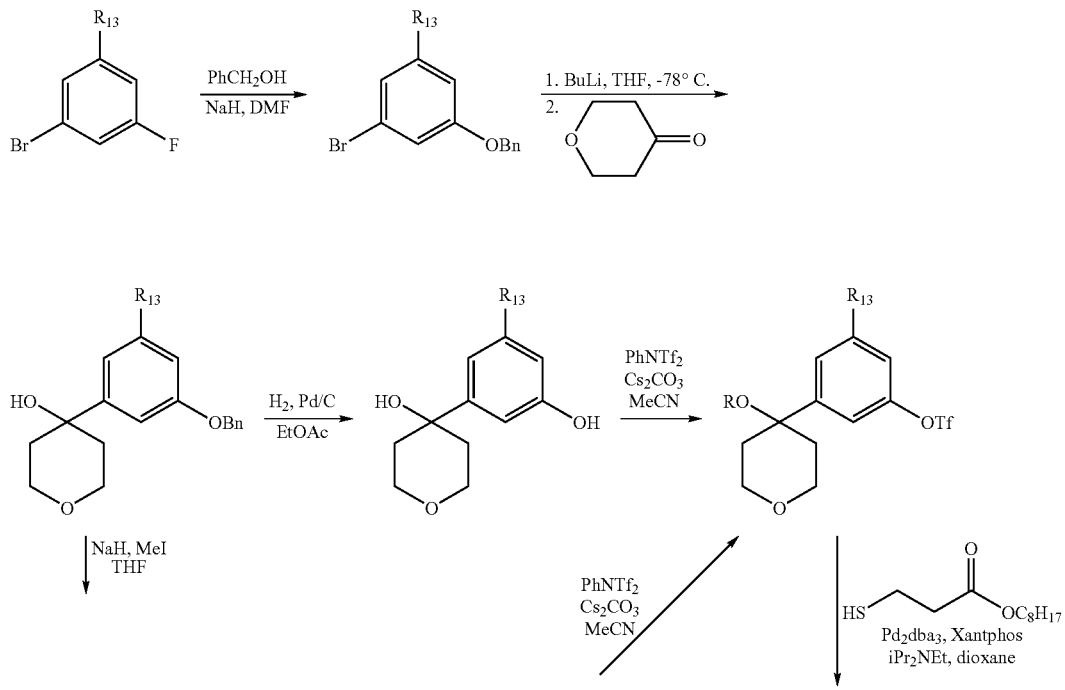

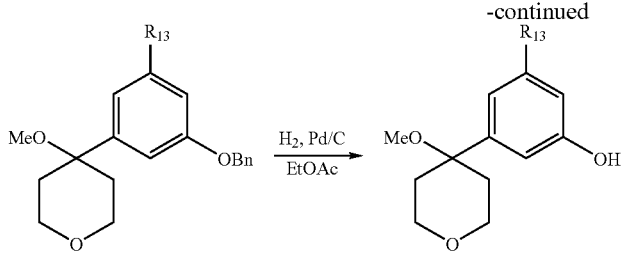
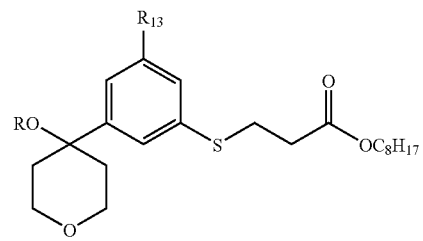

The following compounds were prepared as outlined in Scheme I:

3-(4-Methoxy-tetrahydro-pyran-4-yl)-phenol (Crawley, G. et al., *J. Med. Chem.*, 1992, 2600-2609); 4-(3-Fluoro-5-hydroxy-phenyl)-tetrahydro-pyran-4-ol (Lambert-van der Brempt, C. et al., *J. Med. Chem.*, 1994, 113-124); 3-Fluoro-5-(4-methoxy-tetrahydro-pyran-4-yl)-phenol (Crawley, G. et al., *J. Med. Chem.*, 1992, 2600-2609); 3-[3-Fluoro-5-(4-hydroxy-tetrahydro-pyran-4-yl)-phenylsulfanyl]-propionic acid 2-ethyl-hexyl ester ($^1$H NMR (CDCl$_3$) δ 7.25 (s, 1H), 7.01 (d, 1H), 6.94 (d, 1H), 4.01 (d, 2H), 3.92-3.88 (m, 4H), 3.20 (t, 2H), 2.66 (t, 2H), 2.18-2.05 (m, 2H), 1.69-1.48 (m, 3H), 1.49-1.29 (m, 9H), 0.91 (t, 6H)); and 3-[3-Fluoro-5-(4-methoxy-tetrahydro-pyran-4-yl)-phenylsulfanyl]-propionic acid 2-ethyl-hexyl ester ($^1$H NMR (CDCl$_3$) δ 7.12 (s, 1H), 6.94 (t, 2H), 4.03 (d, 2H), 3.83 (d, 4H), 3.20 (t, 2H), 2.99 (s, 3H), 2.66 (t, 2H), 2.00-1.88 (m, 4H), 1.40-1.26 (m, 9H), 0.89 (t, 6H)).

Scheme J:

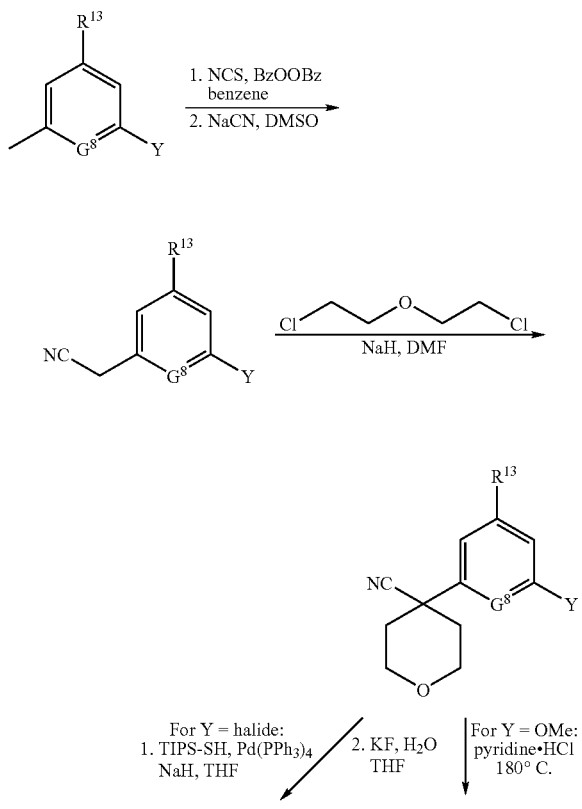

-continued

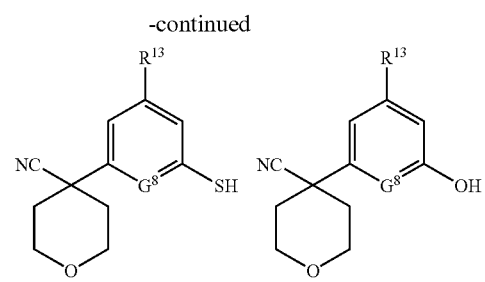

The following compounds were prepared as outlined in Scheme J:

4-(3-Hydroxy-phenyl)-tetrahydro-pyran-4-carbonitrile (Mano, T. et al., *Chem. Pharm. Bull.*, 2005, 965-973); 4-(3-Mercapto-phenyl)-tetrahydro-pyran-4-carbonitrile ($^1$H NMR (CDCl$_3$) δ 7.41-7.38 (m, 1H), 7.29-7.25 (m, 3H), 4.11-4.06 (m, 2H), 3.94-3.85 (m, 2H), 3.55 (s, 1H), 2.16-2.00 (m, 4H)); 4-(3-Fluoro-5-mercapto-phenyl)-tetrahydro-pyran-4-carbonitrile (Mano, T. et al., *Chem. Pharm. Bull.*, 2005, 965-973); and 4-(6-Fluoro-pyridin-2-yl)-tetrahydro-pyran-4-carbonitrile.

Scheme K:

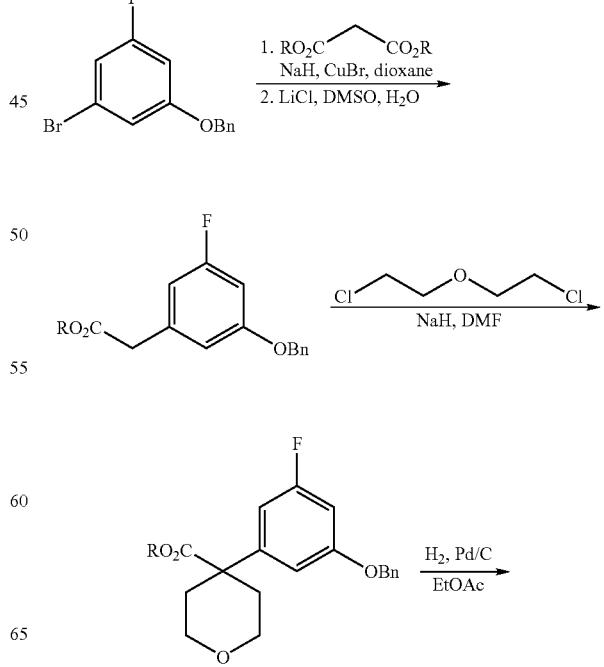

159

-continued

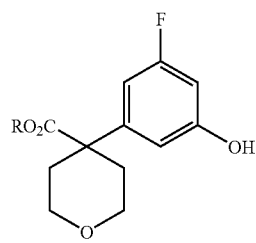

The following compounds were prepared as outlined in Scheme K:

4-(3-Fluoro-5-hydroxy-phenyl)-tetrahydro-pyran-4-carboxylic acid methyl ester ($^1$H NMR (CDCl$_3$) δ 6.70-6.66 (m, 2H), 6.54-6.48 (m, 1H), 5.62 (s, 1H), 3.91-3.82 (m, 4H), 3.05 (s, 3H), 2.21-1.92 (m, 4H)); and 4-(3-Fluoro-5-hydroxy-phenyl)-tetrahydro-pyran-4-carboxylic acid ethyl ester (Mano, T. et al., *Synthesis*, 2004, 2625-2628).

Scheme L:

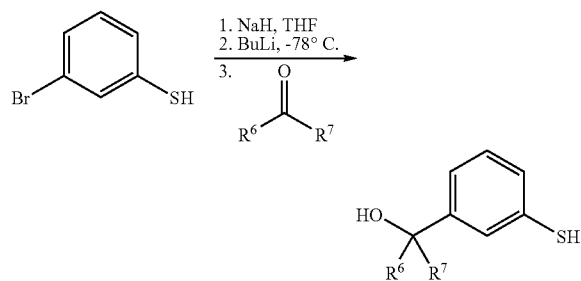

The following compounds were prepared as outlined in Scheme L:

4-(3-Mercapto-phenyl)-tetrahydro-pyran-4-ol (MS (ES) M−H: 209); 1-(3-Mercapto-phenyl)-cyclopentanol (MS (ES) M−H: 193); and 1,1,1-Trifluoro-2-(3-mercapto-phenyl)-butan-2-ol MS (ES) M−H: 236):

Scheme M:

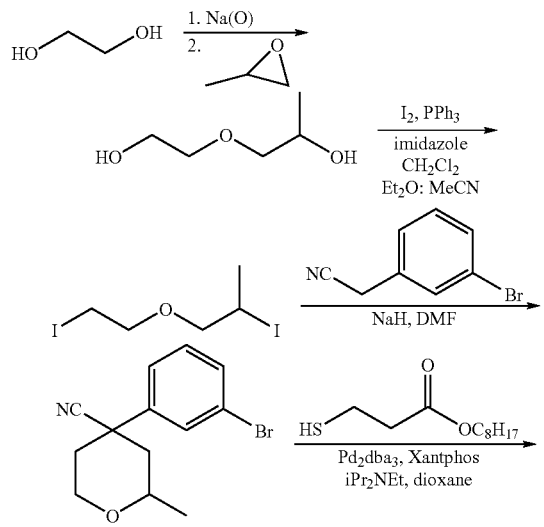

160

-continued

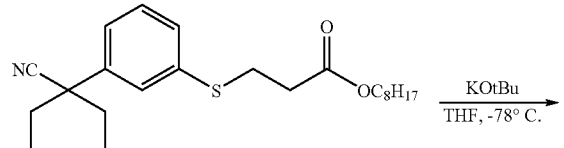

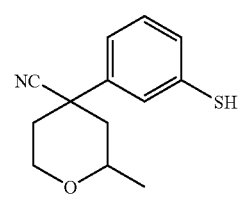

The following compound was prepared as outlined in Scheme M:

4-(3-Mercapto-phenyl)-2-methyl-tetrahydro-pyran-4-carbonitrile.

Scheme N:

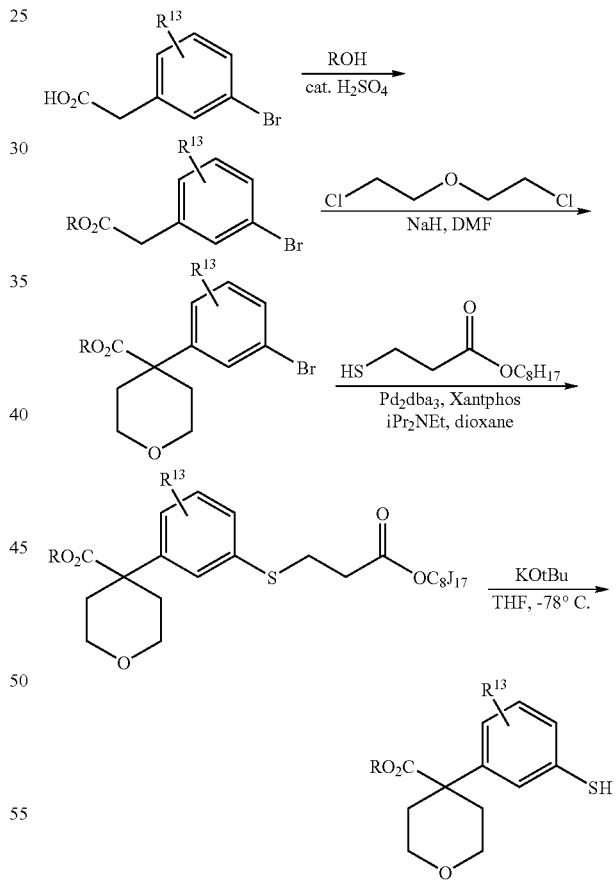

The following compounds were prepared as outlined in Scheme N:

4-(5-Mercapto-2-methoxy-phenyl)-tetrahydro-pyran-4-carboxylic acid methyl ester; and 4-(3-Bromo-phenyl)-tetrahydro-pyran-4-carboxylic acid methyl ester ($^1$H NMR (CDCl$_3$) δ 7.50 (s, 1H), 7.40 (d, 1H), 7.32 (d, 1H), 7.31-7.19 (m, 1H), 3.97-3.90 (m, 2H), 3.69 (s, 3H), 3.50-3.59 (m, 2H), 2.50 (d, 2H), 1.95 (dt, 2H)).

Scheme O:

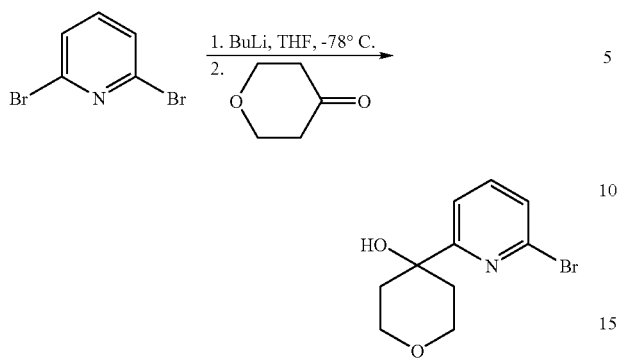

The following compound was prepared as outlined in Scheme O:
4-(6-Bromo-pyridin-2-yl)-tetrahydro-pyran-4-ol (Hamel, P. et al., *J. Med. Chem.*, 1997, 2866-2875).

The following compounds were prepared as outlined in Scheme P:
[4-(3-Bromo-phenyl)-tetrahydro-pyran-4-yl]-methanol ($^1$H NMR (CDCl$_3$) δ 7.55-7.26 (m, 4H), 3.94-3.49 (m, 6H), 2.21-2.04 (m, 2H), 2.01-1.84 (m, 2H)); 1-[4-(3-Bromo-phenyl)-tetrahydro-pyran-4-yl]-ethanol ($^1$H NMR (CDCl$_3$) δ 7.47-7.40 (m, 2H), 7.30-7.26 (m, 2H), 3.91-3.79 (m, 2H), 3.74-3.67 (m, 1H), 3.51-3.29 (m, 2H), 2.33 (d, 1H), 2.11 (d, 1H), 2.08-1.84 (m, 2H), 1.19 (d, 1H), 0.94 (d, 3H)); 3-[3-(4-Acetyl-tetrahydro-pyran-4-yl)-phenylsulfanyl]-propionic acid 2-ethyl-hexyl ester ($^1$H NMR (CDCl$_3$) δ 7.34-7.25 (m, 3H), 7.13 (d, 1H), 4.02 (d, 2H), 3.92-3.81 (m, 2H), 3.63 (t, 2H), 3.18 (t, 2H), 2.62 (t, 2H), 2.38 (d, 2H), 2.14-2.00 (m, 2H), 1.93 (s, 3H), 1.45-1.22 (m, 9H), 0.91 (t, 6H)); 3-{3-[4-(Hydroxyimino-methyl)-tetrahydro-pyran-4-yl]-phenylsulfanyl}-propionic acid octyl ester (MS (ES) M+H: 422); 3-{3-[4-(Methoxyimino-methyl)-tetrahydro-pyran-4-yl]-phenylsulfanyl}-propionic acid 2-ethyl-hexyl ester (MS (ES) M+H: 436); and 3-[3-(4-Vinyl-tetrahydro-pyran-4-yl)-phenylsulfanyl]-propionic acid 2-ethyl-hexyl ester ($^1$H NMR (CDCl$_3$) δ 7.41-7.12 (m, 4H), 5.84 (dd, Scheme P:

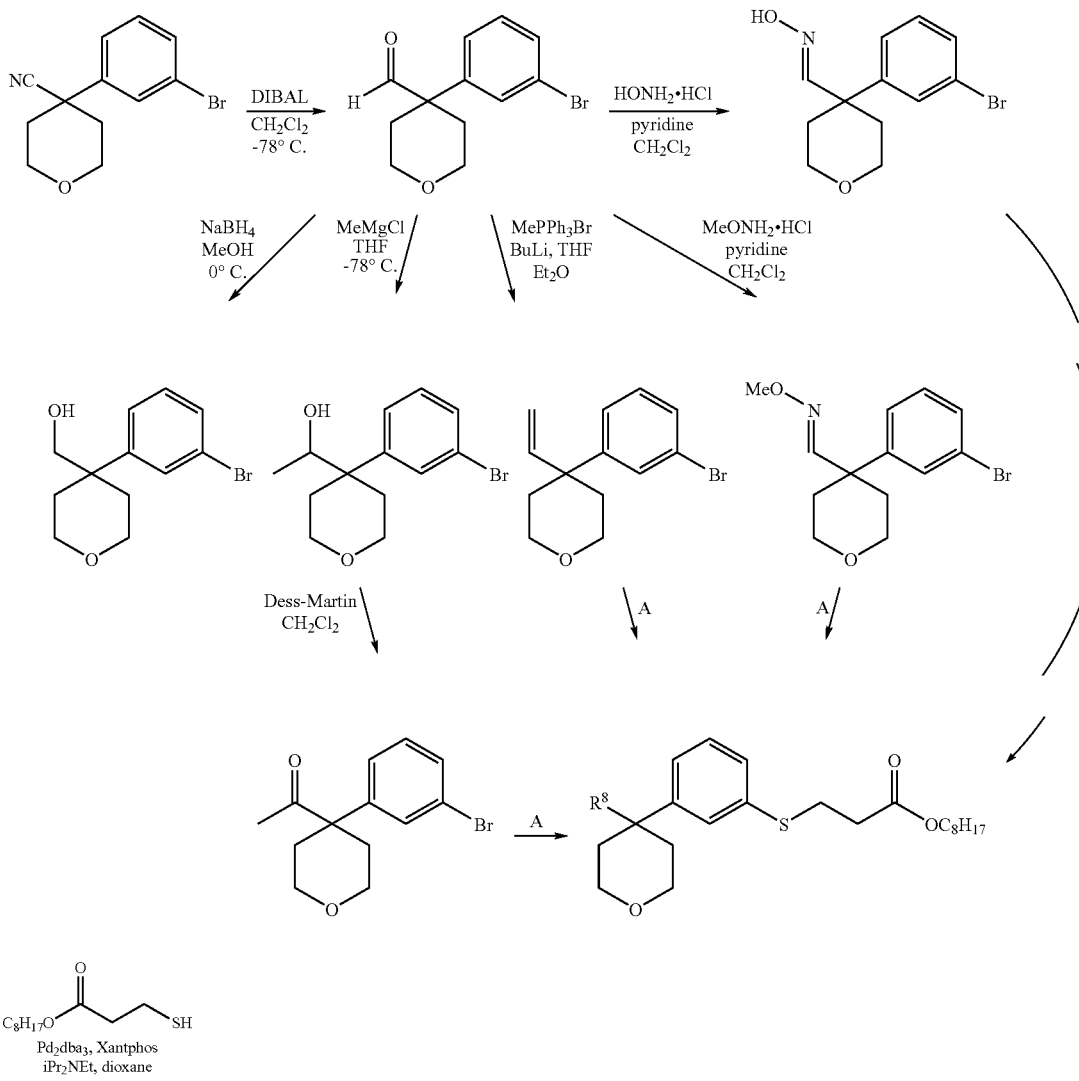

1H), 5.20 (d, 1H), 4.97 (d, 1H, 4.01 (d, 2H), 3.79-3.68 (m, 4H), 3.16 (t, 2H), 2.63 (t, 2H), 2.19-2.07 (m, 2H), 2.03-1.96 (m, 2H), 1.40-1.28 (m, 9H), 0.89 (t, 6H)).

Scheme Q:

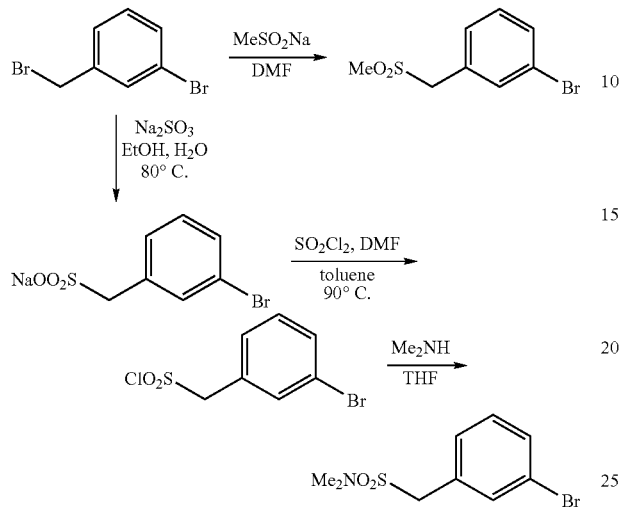

The following compounds were prepared as outlined in Scheme Q:

4-(3-Bromo-phenyl)-4-methanesulfonyl-tetrahydro-pyran (¹H NMR (CDCl₃) δ 7.69 (s, 1H), 7.61-7.49 (m, 2H), 7.39-7.31 (m, 1H), 4.08-3.97 (m, 2H), 3.39 (t, 2H), 2.66-2.36 (m, 7H)); and 4-(3-Bromo-phenyl)-tetrahydro-pyran-4-sulfonic acid dimethylamide (¹H NMR δ 7.67 (s, 1H), 7.56-7.49 (m, 2H), 7.34 (t, 1H), 3.98-3.92 (m, 2H), 3.35 (t, 2H), 2.61 (s, 6H), 2.59-2.46 (m, 4H)).

Scheme R:

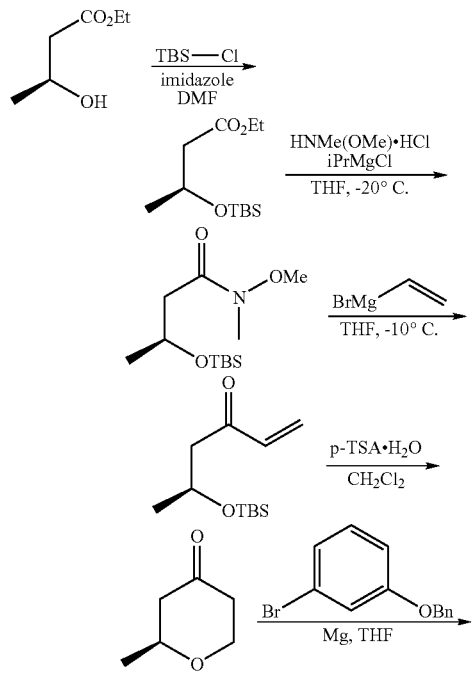

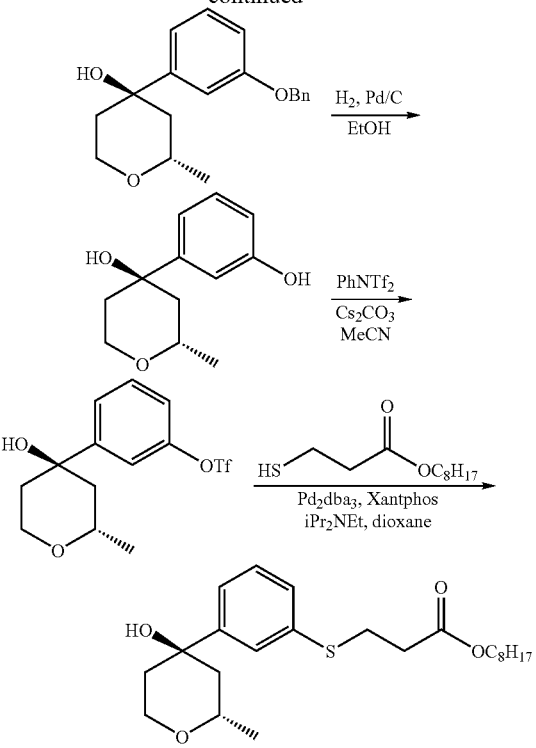

The following compound was prepared as outlined in Scheme R:

3-[3-((2S,4R)-4-Hydroxy-2-methyl-tetrahydro-pyran-4-yl)-phenylsulfanyl]-propionic acid 2-ethyl-hexyl ester (¹H NMR (CDCl₃) δ 7.51 (s, 1H), 7.32-7.25 (m, 3H), 4.04-3.92 (m, 5H), 3.19 (t, 2H), 2.65 (t, 2H), 2.16-2.05 (m, 1H), 1.78-1.51 (m, 6H), 1.39-1.21 (m, 7H), 1.19 (d, 3H), 0.89 (t, 6H)).

Scheme S:

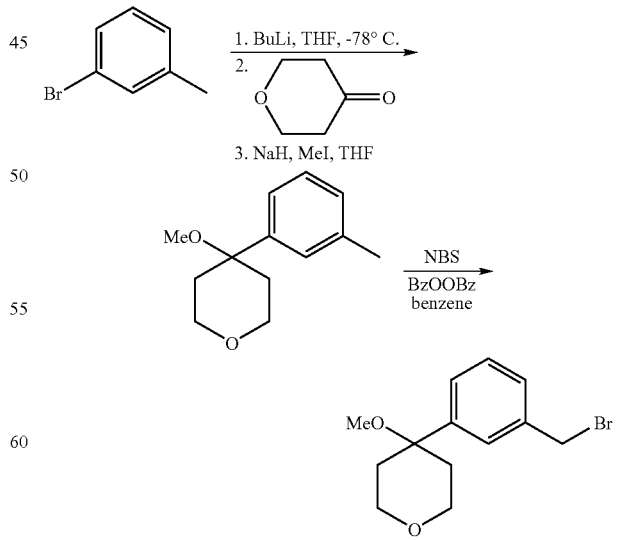

The following compound was prepared as outlined in Scheme S:

4-(3-Bromomethyl-phenyl)-4-methoxy-tetrahydro-pyran (Ducharme, Y. et al., *J. Med. Chem.*, 1994, 512-518).

Scheme T:

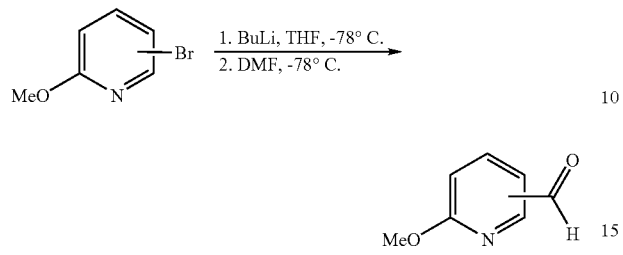

The following compounds were prepared as outlined in Scheme T:

6-Methoxy-pyridine-2-carbaldehyde (Comins, D. et al., *J. Org. Chem.*, 1990, 69-73); 6-Methoxy-pyridine-3-carbaldehyde (Comins, D. et al., *J. Org. Chem.*, 1990, 69-73); and 2-Methoxy-pyridine-4-carbaldehyde (Subramanyam, C. et al., *J. Org. Chem.*, 1989, 5580-5585).

Synthesis of Compounds.

Scheme 1A:

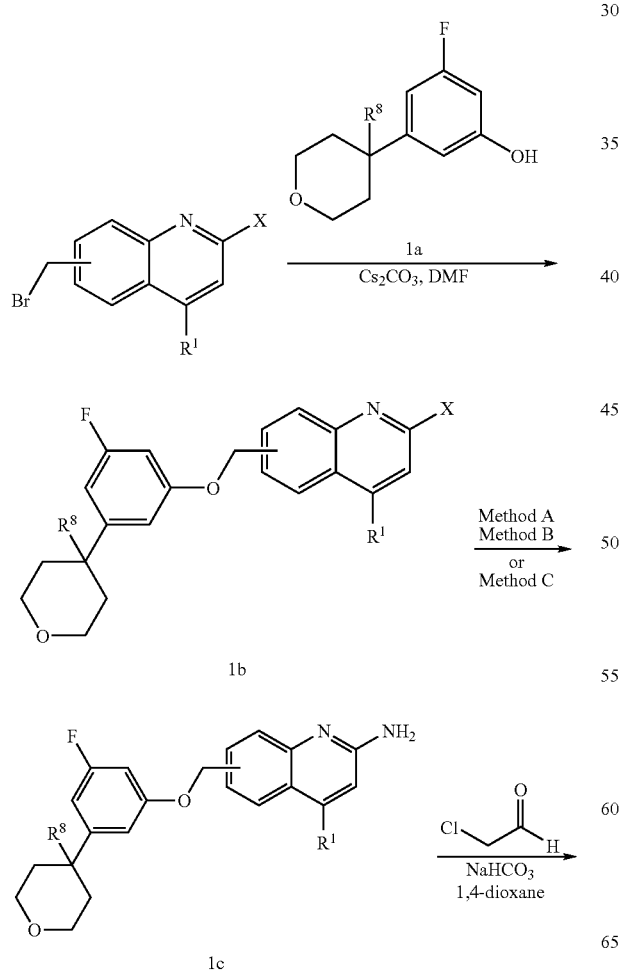

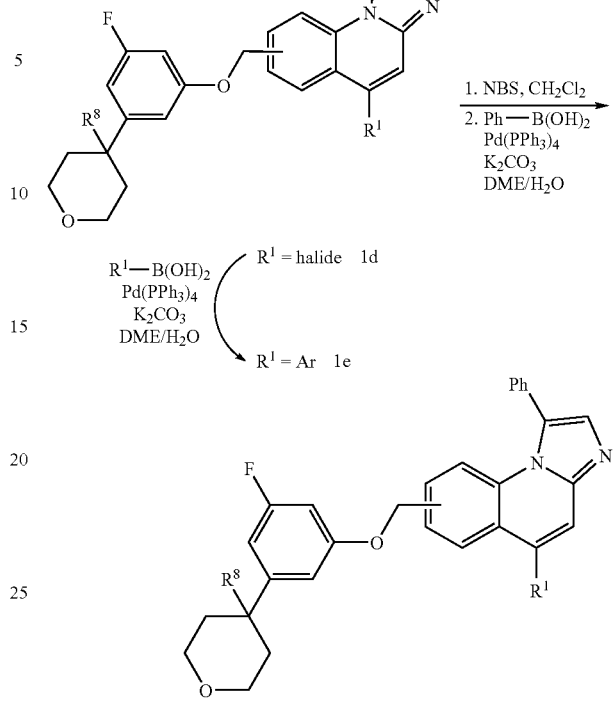

Example 1A

Preparation of Compound 1-2, Compound 1-3, Compound 1-4, Compound 1-5, Compound 1-6, Compound 1-7, Compound 1-8, Compound 1-25, Compound 1-26, Compound 1-27, Compound 1-28, Compound 1-29, Compound 1-30, Compound 1-31, Compound 1-32, Compound 1-33, Compound 1-34, Compound 1-35, Compound 1-36, Compound 1-37, Compound 1-38, Compound 1-39, Compound 1-40, Compound 1-41, Compound 1-42, Compound 1-43, Compound 1-44, Compound 1-45, Compound 1-46, Compound 1-47, Compound 1-48, and Compound 1-49

Compound 1-2, Compound 1-3, Compound 1-4, Compound 1-5, Compound 1-6, Compound 1-7, Compound 1-8, Compound 1-25, Compound 1-26, Compound 1-27, Compound 1-28, Compound 1-29, Compound 1-30, Compound 1-31, Compound 1-32, Compound 1-33, Compound 1-34, Compound 1-35, Compound 1-36, Compound 1-37, Compound 1-38, Compound 1-39, Compound 1-40, Compound 1-41, Compound 1-42, Compound 1-43, Compound 1-44, Compound 1-45, Compound 1-46, Compound 1-47, Compound 1-48, and Compound 1-49 were prepared as outlined in Scheme 1A. A detailed illustrative example of the reaction conditions shown in Scheme 1A is described for the synthesis of 4-[3-Fluoro-5-(5-phenyl-imidazo[1,2-a]quinolin-8-ylmethoxy)-phenyl]-tetrahydro-pyran-4-carboxylic acid amide.

Step 1: 4-[3-(2,4-Dibromo-quinolin-7-ylmethoxy)-5-fluoro-phenyl]-tetrahydro-pyran-4-carboxylic acid methyl ester (1b)

2,4-Dibromo-7-bromomethyl-quinoline (1.0 g, 2.6 mmol), 4-(3-fluoro-5-hydroxy-phenyl)-tetrahydro-pyran-4-carboxylic acid methyl ester (1a, 670 mg, 2.6 mmol), and cesium carbonate (1.7 g, 5.3 mmol) were suspended in DMF (15 mL) and stirred overnight at room temperature. The mixture was diluted with EtOAc and saturated aqueous NH₄Cl, and the aqueous layer was extracted with EtOAc. The combined organic layers were dried over MgSO₄, filtered, and concentrated. The residue was purified by silica gel chromatography to give the desired product, 1b.

Step 2:

Method A—4-[3-(2-Amino-quinolin-6-ylmethoxy)-5-fluoro-phenyl]-tetrahydro-pyran-4-carboxylic acid methyl ester (1c)

4-[3-(2-Chloro-quinolin-6-ylmethoxy)-5-fluoro-phenyl]-tetrahydro-pyran-4-carboxylic acid methyl ester (200 mg, 0.46 mmol) was dissolved in EtOH (20 mL). Hydrazine, anhydrous (1 mL) was added, and the mixture was heated to 80° C. for 12 hours. The reaction was poured into water, and the aqueous layer was extracted with CH₂Cl₂ 4 times, and with EtOAc once. The combined organic layers were dried over MgSO₄, filtered, and concentrated. The residue was purified by silica gel chromatography to give the desired product, 1c.

Method B—4-[3-(2-Amino-4-chloro-quinolin-7-ylmethoxy)-5-fluoro-phenyl]-tetrahydro-pyran-4-carboxylic acid methyl ester (1c)

4-[3-(2,4-Dichloro-quinolin-7-ylmethoxy)-5-fluoro-phenyl]-tetrahydro-pyran-4-carboxylic acid methyl ester (200 mg, 0.43 mmol), sodium tert-butoxide (62 mg, 0.65 mmol), Pd₂dba₃ (10 mg, 0.01 mmol), and BINAP (27 mg, 0.04 mmol) were suspended in toluene (5 mL) and degassed with N₂ for 5 minutes. Benzophenone imine (0.07 mL, 0.43 mmol) was added, and the reaction was heated to 100° C. for 2 hours. After cooling to room temperature, the mixture was diluted with EtOAc and water, and the aqueous layer was extracted with EtOAc. The combined organic layers were dried over MgSO₄, filtered, and concentrated. The residue was treated with hydroxylamine hydrochloride (60 mg, 0.86 mmol) and potassium acetate (110 mg, 1.2 mmol) in MeOH (30 mL), and stirred at room temperature for 2 hours. The reaction was concentrated and diluted with EtOAc and water. The aqueous layer was extracted with EtOAc, and the combined organic layers were dried over MgSO₄, filtered, and concentrated. The crude material was purified by silica gel chromatography to give the desired product, 1c.

Method C—4-[3-(2-Amino-4-bromo-quinolin-7-ylmethoxy)-5-fluoro-phenyl]-tetrahydro-pyran-4-carboxylic acid methyl ester (1c)

To 1b (100 mg, 0.18 mmol) in toluene (2 mL) was added 4-methoxybenzylamine (0.16 mL, 1.2 mmol), and the reaction was heated to 100° C. overnight. The mixture was concentrated and purified by silica gel chromatography. The residue was then treated with TFA at 70° C. for 1 hour and concentrated to dryness to give the amine product, 1c.

Step 3: 4-[3-(5-Bromo-imidazo[1,2-a]quinolin-8-ylmethoxy)-5-fluoro-phenyl]-tetrahydro-pyran-4-carboxylic acid methyl ester (1d)

1c (1.0 g, 1.7 mmol) was dissolved in 1,4-dioxane (10 mL). Chloroacetaldehyde (50 wt %, 290 mg, 1.8 mmol), sodium bicarbonate (700 mg, 8.3 mmol), and water (2 mL) were added, and the mixture was heated at 80° C. for 2.5 hours. Additional chloroacetaldehyde (0.5 eq) was added, and the heated was continued for 2 hours. The mixture was then cooled to room temperature and concentrated. The residue was purified by silica gel chromatography (60% EtOAc in hexanes) to give the desired product, 1d.

Step 3a: 4-[3-Fluoro-5-(5-phenyl-imidazo[1,2-a]quinolin-8-ylmethoxy)-phenyl]-tetrahydro-pyran-4-carboxylic acid amide (1e)

The amide equivalent of ester 1d (30 mg, 0.06 mmol), phenylboronic acid (11 mg, 0.09 mmol), and potassium carbonate (21 mg, 0.15 mmol) were dissolved in DME:H₂O (2:1, 3 mL) and degassed with N₂ for 2 minutes. Pd(PPh₃)₄ (7 mg, 0.01 mmol) was added, and the mixture was degassed with N₂ for an additional 2 minutes. The reaction was then heated to 80° C. for 2 hours. After cooled to room temperature, the mixture was diluted with EtOAc and brine, and the aqueous layer was extracted with EtOAc. The combined organic layers were dried over MgSO₄, filtered, concentrated, and the residue was purified by preparative HPLC to give the desired product, 1e.

Step 4: 4-[3-Fluoro-5-(1-phenyl-imidazo[1,2-a]quinolin-7-ylmethoxy)-phenyl]-tetrahydro-pyran-4-carboxylic acid methyl ester (1f)

4-[3-Fluoro-5-(imidazo[1,2-a]quinolin-7-ylmethoxy)-phenyl]-tetrahydro-pyran-4-carboxylic acid methyl ester (50 mg, 0.12 mmol) and NBS (20 mg, 0.12 mmol) were dissolved in CH₂Cl₂ (10 mL) and stirred at room temperature for 30 minutes. The reaction was concentrated and purified by silica gel chromatography to give the 1-bromo intermediate. The bromide (30 mg, 0.06 mmol), phenylboronic acid (15 mg, 0.12 mmol), potassium carbonate (41 mg, 0.3 mmol), and catalytic Pd(PPh₃)₄ were suspended in DME:H₂O (3:1, 4 mL) and degassed with N₂ for 20 minutes. The reaction was heated to 80° C. overnight, then cooled to room temperature and concentrated. The residue was purified by silica gel chromatography to give the desired product, 1f.

Mass spectrometry data for Compound 1-2, Compound 1-3, Compound 1-4, Compound 1-5, Compound 1-6, Compound 1-7, Compound 1-8, Compound 1-25, Compound 1-26, Compound 1-27, Compound 1-28, Compound 1-29, Compound 1-30, Compound 1-31, Compound 1-32, Compound 1-33, Compound 1-34, Compound 1-35, Compound 1-36, Compound 1-37, Compound 1-38, Compound 1-39, Compound 1-40, Compound 1-41, Compound 1-42, Compound 1-43, Compound 1-44, Compound 1-45, Compound 1-46, Compound 1-47, Compound 1-48, and Compound 1-49 is shown in Table 1.

Notes: For Compound 1-2, Compound 1-3, Compound 1-4, Compound 1-5, Compound 1-6, Compound 1-7, and Compound 1-8, 6-Bromomethyl-2-chloro-quinoline was used as the starting material. For Compound 1-25, Compound 1-26, Compound 1-27, Compound 1-28, Compound 1-29, Compound 1-30, Compound 1-31, Compound 1-32, Compound 1-33, Compound 1-34, Compound 1-35, Compound 1-36, Compound 1-37, Compound 1-38, Compound 1-39, Compound 1-40, Compound 1-41, Compound 1-42, Compound 1-43, Compound 1-44, Compound 1-45, Compound 1-46, Compound 1-47, Compound 1-48, and Compound 1-49, substituted 7-Bromomethylquinolines were used as the starting materials. For Compound 1-2, Compound 1-3, Compound 1-4, Compound 1-5, Compound 1-6, Compound 1-7, Compound 1-8, and Compound 1-25, Method A was used for Step 2. For Compound 1-26, Compound 1-27, Compound 1-28, Compound 1-29, Compound 1-30, Compound 1-31, and Compound 1-32, Method B was used for Step 2. For Compound 1-33, Compound 1-34, Compound 1-35, Compound 1-36, Compound 1-37, Compound 1-38, Compound 1-39, Compound 1-40, Compound 1-41, Compound 1-42, Compound 1-43, Compound 1-44, Compound 1-45, Compound 1-46, Compound 1-47, Compound 1-48, and Compound 1-49, Method C was used for Step 2. For Compound 1-4, Compound 1-28, Compound 1-31, and Compound 1-34, the ester in 1d was hydrolyzed to give the acid in the product. For Compound 1-5, Compound 1-27, Compound 1-29, Compound 1-32, Compound 1-35, Compound 1-36, Compound 1-37, Compound 1-38, Compound 1-39, Compound 1-40, Compound 1-41, Compound 1-42, Compound 1-43, Compound 1-44, Compound 1-45, Compound 1-46, Compound 1-47, Compound 1-48, and Compound 1-49 was hydrolyzed, and the resulting acid was reacted with oxalyl chloride, followed by ammonium hydroxide, to give the amide in the product. For Compound 1-7, Step 4 was also performed, stopping after the bromide was introduced in 1f. For Compound 1-8, Step 4 was also performed to give the phenyl in 1f. For Compound 1-30, Compound 1-36, Compound 1-37, Compound 1-38, Compound 1-39, Compound 1-40, Compound 1-41, Compound 1-42, Compound 1-43, Compound 1-44, Compound 1-45, Compound 1-46, Compound 1-47, Compound 1-48, and Compound 1-49, Step 3a was performed. For Compound 1-28, Compound 1-29, Compound 1-31, and Compound 1-32, Step 3a was performed, but using NaS(alkyl) in DMF to introduce the alkylsulfanyl group as $R^1$ in the product.

Scheme 1B:

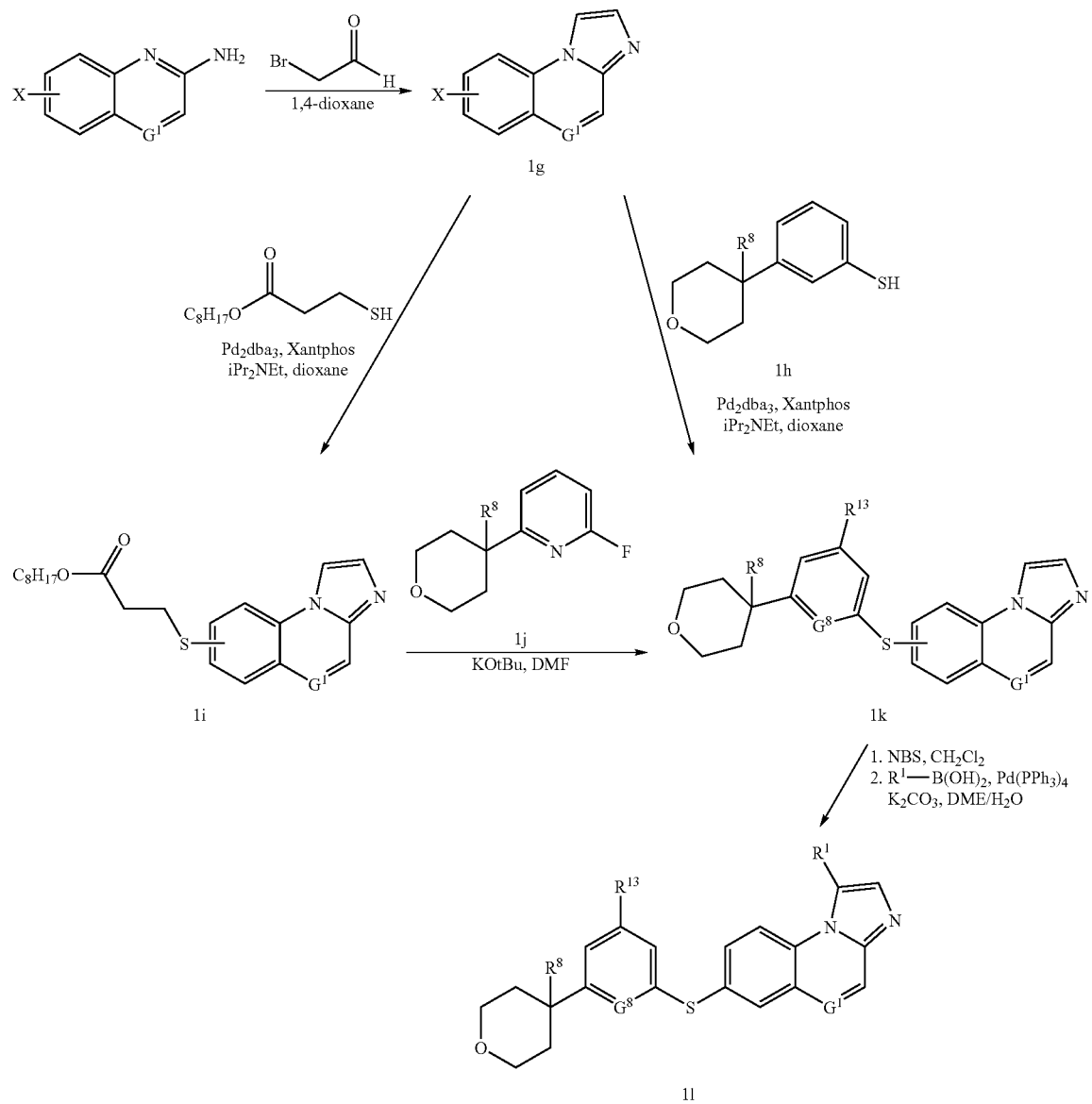

Example 1B

Compound 1-1, Compound 1-9, Compound 1-10, Compound 1-11, Compound 1-13, Compound 1-14, Compound 1-15, Compound 1-16, Compound 1-17, Compound 1-18, Compound 1-22, Compound 1-23, Compound 1-24, Compound 1-86, Compound 1-87, Compound 1-88, Compound 1-89, and Compound 1-90

Compound 1-1, Compound 1-9, Compound 1-10, Compound 1-11, Compound 1-13, Compound 1-14, Compound 1-15, Compound 1-16, Compound 1-17, Compound 1-18, Compound 1-22, Compound 1-23, Compound 1-24, Compound 1-86, Compound 1-87, Compound 1-88, Compound 1-89, and Compound 1-90 were prepared as outlined in Scheme 1B. A detailed illustrative example of the reaction conditions shown in Scheme 1B is described for the synthesis of 4-[3-Fluoro-5-(1-phenyl-imidazo[1,2-a]quinolin-7-ylsulfanyl)-phenyl]-tetrahydro-pyran-4-carbonitrile and 4-[6-(Imidazo[1,2-a]quinolin-7-ylsulfanyl)-pyridin-2-yl]-tetrahydro-pyran-4-carbonitrile.

Step 1: 7-Iodo-imidazo[1,2-a]quinoline (1g)

To chloroacetaldehyde (50 wt %, 460 mg, 2.92 mmol) and sodium bicarbonate (613 mg, 7.3 mmol) was added 6-Iodo-quinolin-2-ylamine (390 mg, 1.46 mmol) in 1,4-dioxane (5 mL). The mixture was heated to 80° C. overnight, and then cooled to room temperature. The solvent was removed in vacuo, and the residue was purified by silica gel chromatography (50-100% EtOAc in hexanes) to obtain the desired product, 1g.

Step 2: 4-[3-Fluoro-5-(imidazo[1,2-a]quinolin-7-ylsulfanyl)-phenyl]-tetrahydro-pyran-4-carbonitrile (1k)

1g (230 mg, 0.82 mmol) and 4-(3-Fluoro-5-mercapto-phenyl)-tetrahydro-pyran-4-carbonitrile (1h, 230 mg, 0.99 mmol) were dissolved in 1,4-dioxane (10 mL) and degassed with $N_2$ for 10 minutes. $iPr_2NEt$ (0.35 mL, 2.0 mmol), $Pd_2dba_3$ (20 mg, 0.02 mmol), and 4,5-bis(diphenylphosphino)-9,9-dimethylxanthene (24 mg, 0.04 mmol) were added, and the mixture was degassed with $N_2$ for an additional 10 minutes. The reaction was heated to 80° C. overnight, then cooled to room temperature, concentrated, and purified by silica gel chromatography to give the desired product, 1k.

Step 2a: 3-(Imidazo[1,2-a]quinolin-7-ylsulfanyl)-propionic acid 2-ethyl-hexyl ester (1i)

1g (120 mg, 0.5 mmol) and 3-mercaptopropionic acid 2-ethylhexyl ester (110 mg, 0.5 mmol) were dissolved in 1,4-dioxane (5 mL) and degassed with $N_2$ for 10 minutes. $iPr_2NEt$ (0.15 mL, 0.84 mmol), $Pd_2dba_3$ (10 mg, 0.01 mmol), and 4,5-bis(diphenylphosphino)-9,9-dimethylxanthene (12 mg, 0.02 mmol) were added, and the mixture was degassed with $N_2$ for an additional 10 minutes. The reaction was heated to 80° C. overnight, then cooled to room temperature, concentrated, and purified by silica gel chromatography to give the desired product, 1i.

Step 2b: 4-[6-(Imidazo[1,2-a]quinolin-7-ylsulfanyl)-pyridin-2-yl]-tetrahydro-pyran-4-carbonitrile (1k)

1i (261 mg, 0.6 mmol) and 4-(6-Fluoro-pyridin-2-yl)-tetrahydro-pyran-4-carbonitrile (1j, 123 mg, 0.6 mmol) were dissolved in DMF and degassed with $N_2$ for 10 minutes. Potassium tert-butoxide (81 mg, 0.72 μmmol) was added, and the mixture was degassed with $N_2$ for an additional 10 minutes. The reaction was heated to 90° C. for 24 hours, then cooled to room temperature. The solution was diluted with EtOAc and water, and the aqueous layer was extracted with EtOAc. The combined organic layers were dried over $MgSO_4$, filtered, and concentrated, and the residue was purified by silica gel chromatography to obtain the desired product, 1k.

Step 3: 4-[3-Fluoro-5-(1-phenyl-imidazo[1,2-a]quinolin-7-ylsulfanyl)-phenyl]-tetrahydro-pyran-4-carbonitrile (1l)

1k (84 mg, 0.21 mmol) and NBS (37 mg, 0.21 mmol) were dissolved in $CH_2Cl_2$ (5 mL) and stirred at room temperature for 30 minutes. The reaction was concentrated and purified by silica gel chromatography (50% EtOAc in hexanes) to give the 1-bromo intermediate. The bromide (70 mg, 0.14 mmol), phenylboronic acid (21 mg, 0.17 mmol), potassium carbonate (200 mg, 1.5 mmol), and catalytic $Pd(PPh_3)_4$ were suspended in $DME:H_2O$ (3:1, 4 mL) and degassed with $N_2$ for 20 minutes. The reaction was heated to 80° C. overnight, then cooled to room temperature and concentrated. The residue was purified by silica gel chromatography (50% EtOAc in hexanes) to give the desired product, 1l.

Mass spectrometry data for Compound 1-1, Compound 1-9, Compound 1-10, Compound 1-11, Compound 1-13, Compound 1-14, Compound 1-15, Compound 1-16, Compound 1-17, Compound 1-18, Compound 1-22, Compound 1-23, Compound 1-24, Compound 1-86, Compound 1-87, Compound 1-88, Compound 1-89, and Compound 1-90 is shown in Table 1.

Notes: For Compound 1-1, 6-Methoxy-quinolin-2-ylamine was used as the starting material. For Compound 1-9, Compound 1-10, Compound 1-11, Compound 1-13, Compound 1-14, Compound 1-15, Compound 1-16, Compound 1-17, Compound 1-18, Compound 1-22, and Compound 1-23, 6-Bromo-quinolin-2-ylamine was used as the starting material. For Compound 1-24, 6-Bromo-quinoxalin-2-ylamine was used as the starting material. For Compound 1-86, Compound 1-87, Compound 1-88, Compound 1-89, and Compound 1-90, 7-Bromo-quinoxalin-2-ylamine was used as the starting material. For Compound 1-1, the methoxy group in 1g was hydrolyzed to a hydroxy group with HBr following Step 1. Step 2 was then performed using 4-(3-Bromomethyl-phenyl)-4-methoxy-tetrahydro-pyran as 1h, and $Cs_2CO_3$ in MeCN in place of $Pd_2dba_3$, Xanthphos, and $iPr_2NEt$ in 1,4-dioxane. For Compound 1-9, Compound 1-10, Compound 1-11, Compound 1-13, Compound 1-14, Compound 1-15, Compound 1-16, Compound 1-17, Compound 1-18, Compound 1-24, Compound 1-86, Compound 1-87, Compound 1-88, Compound 1-89, and Compound 1-90, Step 2 was performed. For Compound 1-22 and Compound 1-23, Steps 2a and 2b were performed. For Compound 1-9, Compound 1-10, and Compound 1-11, KOtBu and $Pd(PPh_3)_4$ in DMSO was used in place of $Pd_2dba_3$, Xanthphos, and $iPr_2NEt$ in 1,4-dioxane for Step 2. For Compound 1-10, the hydroxy group in 1k was methylated to give the methoxy group in the product. For Compound 1-11, Compound 1-23, and Compound 1-88, the nitrile in 1k was reduced to give the amide in the product. For Compound 1-1, Compound 1-9, Compound 1-10, Compound 1-11, Compound 1-13, Compound 1-16, Compound 1-22, Compound 1-23, Compound 1-24, Compound 1-86, Compound 1-87, Compound 1-88, Compound 1-89, and Compound 1-90, Step 3 was not performed. For Compound 1-14, Step 3 was performed, but using BuLi and MeI to introduce the $R^1$ group in 1l. For Compound 1-17, Step 3 was performed, stopping after the bromide was introduced in 1l. For Compound 1-15 and Compound 1-18, Step 3 was performed to give the $R^1$ group in 1l. For Compound 1-24, Compound 1-89, and Compound 1-90, substituted 3-[3-(Tetrahydro-pyran-4-yl)-phenylsulfanyl]-propionic acid 2-ethyl-hexyl esters were used as 1h.

Scheme 1C:

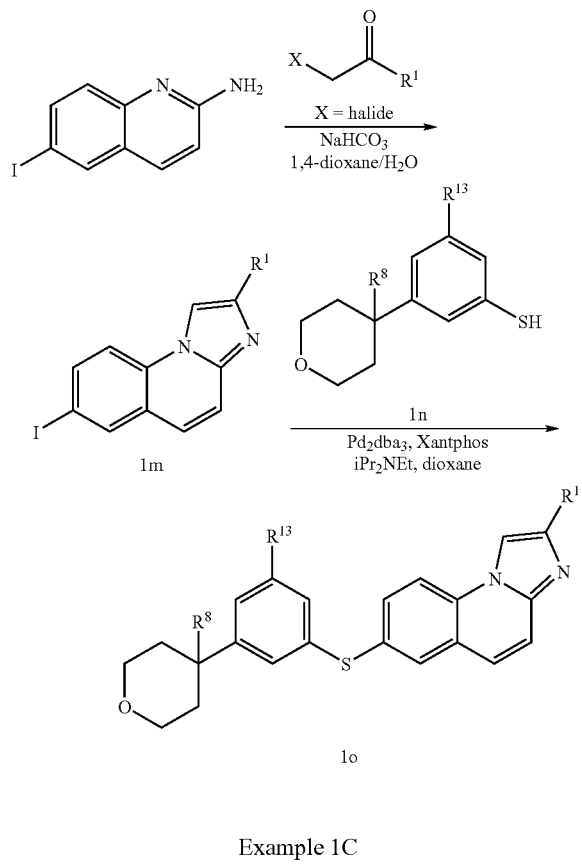

Example 1C

Compound 1-12, Compound 1-19, Compound 1-20, and Compound 1-21

Compound 1-12, Compound 1-19, Compound 1-20, and Compound 1-21 were prepared as outlined in Scheme 1C. A detailed illustrative example of the reaction conditions shown in Scheme 1C is described for the synthesis of 4-[3-(2-Methyl-imidazo[1,2-a]quinolin-7-ylsulfanyl)-phenyl]-tetrahydro-pyran-4-carbonitrile.

Step 1: 7-Iodo-2-methyl-imidazo[1,2-a]quinoline (1m)

6-Iodo-quinolin-2-ylamine (270 mg, 1.0 mmol), chloroacetone (111 mg, 1.2 mmol), sodium bicarbonate (252 mg, 3.0 mmol), and catalytic tetrabutylammonium iodide were dissolved in 1,4-dioxane and water, and stirred at 80° C. overnight. The reaction was cooled to room temperature and concentrated, and the residue was purified by preparative HPLC to give the desired compound, 1m.

Step 2: 4-[3-(2-Methyl-imidazo[1,2-a]quinolin-7-ylsulfanyl)-phenyl]-tetrahydro-pyran-4-carbonitrile (1o)

1m (30 mg, 0.13 mmol) and 4-(3-mercapto-phenyl)-tetrahydro-pyran-4-carbonitrile (1n, 35 mg, 0.11 mmol) were dissolved in 1,4-dioxane (4 mL) and degassed with $N_2$ for 10 minutes. $iPr_2NEt$ (0.04 mL, 0.22 mmol), $Pd_2dba_3$ (catalytic), and 4,5-bis(diphenylphosphino)-9,9-dimethylxanthene (catalytic) were added, and the mixture was degassed with $N_2$ for an additional 10 minutes. The reaction was heated to 80° C. overnight, then cooled to room temperature, concentrated, and purified by preparative HPLC to give the desired product, 1o.

Mass spectrometry data for Compound 1-12, Compound 1-19, Compound 1-20, and Compound 1-21 is shown in Table 1.

Scheme 1D:

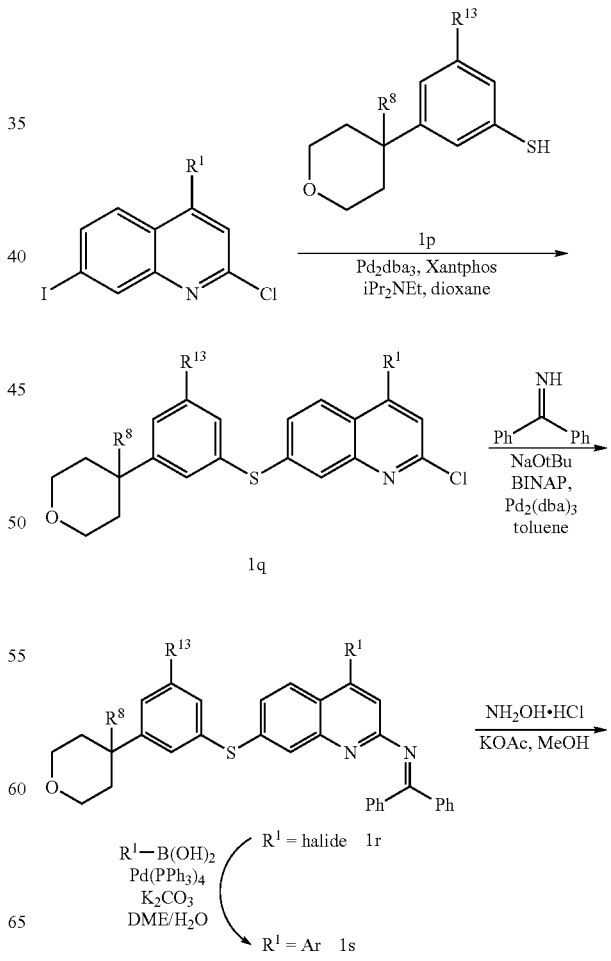

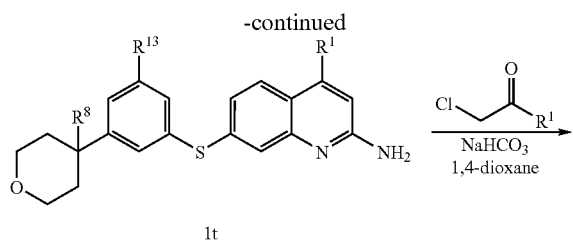

1t

1u

Example 1D

Compound 1-50, Compound 1-51, Compound 1-52, Compound 1-53, Compound 1-54, Compound 1-56, Compound 1-57, Compound 1-59, Compound 1-60, Compound 1-68, Compound 1-69, Compound 1-70, Compound 1-72, Compound 1-73, and Compound 1-85

Compound 1-50, Compound 1-51, Compound 1-52, Compound 1-53, Compound 1-54, Compound 1-56, Compound 1-57, Compound 1-59, Compound 1-60, Compound 1-68, Compound 1-69, Compound 1-70, Compound 1-72, Compound 1-73, and Compound 1-85 were prepared as outlined in Scheme 1D. A detailed illustrative example of the reaction conditions shown in Scheme 1D is described for the synthesis of 4-[3-(5-Phenyl-imidazo[1,2-a]quinolin-8-ylsulfanyl)-phenyl]-tetrahydro-pyran-4-ol.

Step 1: 4-[3-(2,4-Dichloro-quinolin-7-ylsulfanyl)-phenyl]-tetrahydro-pyran-4-carbonitrile (1q)

2,4-Dichloro-7-iodo-quinoline (1.7 g, 5.26 mmol) and 4-(3-mercapto-phenyl)-tetrahydro-pyran-4-carbonitrile (1p, 1.27 g, 5.79 mmol) were dissolved in 1,4-dioxane (50 mL) and degassed with $N_2$ for 10 minutes. $Pd_2dba_3$ (120 mg, 0.13 mmol) and 4,5-bis(diphenylphosphino)-9,9-dimethylxanthene (150 mg, 0.27 mmol) were added, followed by $iPr_2NEt$ (1.4 mL, 7.9 mmol), and the reaction was heated to 70° C. for 2 hours. The mixture was diluted with EtOAc and water, and the aqueous layer was extracted with EtOAc. The combined organic layers were dried over $MgSO_4$, filtered, and concentrated, and the residue was purified by silica gel chromatography to give the desired product, 1q.

Step 2: 4-{3-[2-(Benzhydrylidene-amino)-4-chloro-quinolin-7-ylsulfanyl]-phenyl}-tetrahydro-pyran-4-carbonitrile (1r)

1q (2.2 g, 5.3 mmol), benzophenone imine (1.1 g, 5.8 mmol), and sodium tert-butoxide (620 mg, 6.5 mmol) were dissolved in toluene (50 mL). $Pd_2dba_3$ (98 mg, 0.11 mmol) and BINAP (270 mg, 0.43 mmol) were added, and the reaction was heated to 80° C. for 2 hours. After cooling to room temperature, the mixture was diluted with EtOAc and water, and the aqueous layer was extracted with EtOAc. The combined organic layers were washed with water, dried over $MgSO_4$, filtered, and concentrated to give the desired product, 1r.

Step 2a: 4-{3-[2-(Benzhydrylidene-amino)-4-phenyl-quinolin-7-ylsulfanyl]-phenyl}-tetrahydro-pyran-4-carbonitrile (1s)

1r (100 mg, 0.18 mmol), phenylboronic acid (26 mg, 0.21 mmol), $Pd(PPh_3)_4$ (20 mg, 0.02 mmol), and potassium carbonate (50 mg, 0.36 mmol) was dissolved in 1,4-dioxane and water and degassed with $N_2$. The mixture was heated to 90° C. until no starting material was seen by tlc analysis. The reaction was cooled to room temperature, and the aqueous layer was extracted with EtOAc. The combined organic layers were dried over $MgSO_4$, filtered, and concentrated, and the residue was purified by silica gel chromatography to give the desired product, 1s.

Step 3: 4-[3-(2-Amino-4-phenyl-quinolin-7-ylsulfanyl)-phenyl]-tetrahydro-pyran-4-carbonitrile (1t)

1s (110 mg, 0.18 mmol), hydroxylamine hydrochloride (25 mg, 0.36 mmol), and potassium acetate (44 mg, 0.45 mmol) were dissolved in MeOH (10 mL) and stirred at room temperature for 30 minutes. The reaction was concentrated and diluted with EtOAc and water. The aqueous layer was extracted with EtOAc, and the combined organic layers were dried over $MgSO_4$, filtered, and concentrated to give 1t.

Step 4: 4-[3-(5-Phenyl-imidazo[1,2-a]quinolin-8-ylsulfanyl)-phenyl]-tetrahydro-pyran-4-ol (1u)

To 1t (78 mg, 0.18 mmol) in 1,4-dioxane (3 mL) and water (1 mL) was added chloroacetaldehyde (50 wt %, 0.04 mL, 0.27 mmol) and saturated aqueous $NaHCO_3$ (2 drops), and the reaction was heated to 70° C. until no starting material was seen by tlc analysis. The mixture was concentrated and purified by preparative HPLC to give the desired product, 1u.

Mass spectrometry data for Compound 1-50, Compound 1-51, Compound 1-52, Compound 1-53, Compound 1-54, Compound 1-56, Compound 1-57, Compound 1-59, Compound 1-60, Compound 1-68, Compound 1-69, Compound 1-70, Compound 1-72, Compound 1-73, and Compound 1-85 is shown in Table 1.

Notes: For Compound 1-50 and Compound 1-51, Step 2a was performed. For Compound 1-51, Compound 1-68, and Compound 1-69, the nitrile in 1u was reduced to give the amide in the product. For Compound 1-53, the ester in 1u was hydrolyzed to give the acid in the product. For Compound 1-54, the ester in 1u was hydrolyzed, and the resulting acid was reacted with oxalyl chloride, followed by ammonium hydroxide, to give the amide in the product. For Compound 1-70, Compound 1-72, and Compound 1-73, the ester in 1u was hydrolyzed, and the resulting acid was reacted with oxalyl chloride, followed by ammonium hydroxide, to give an amide, which was then reacted with $POCl_3$ to give the nitrile in the product.

Scheme 1E:

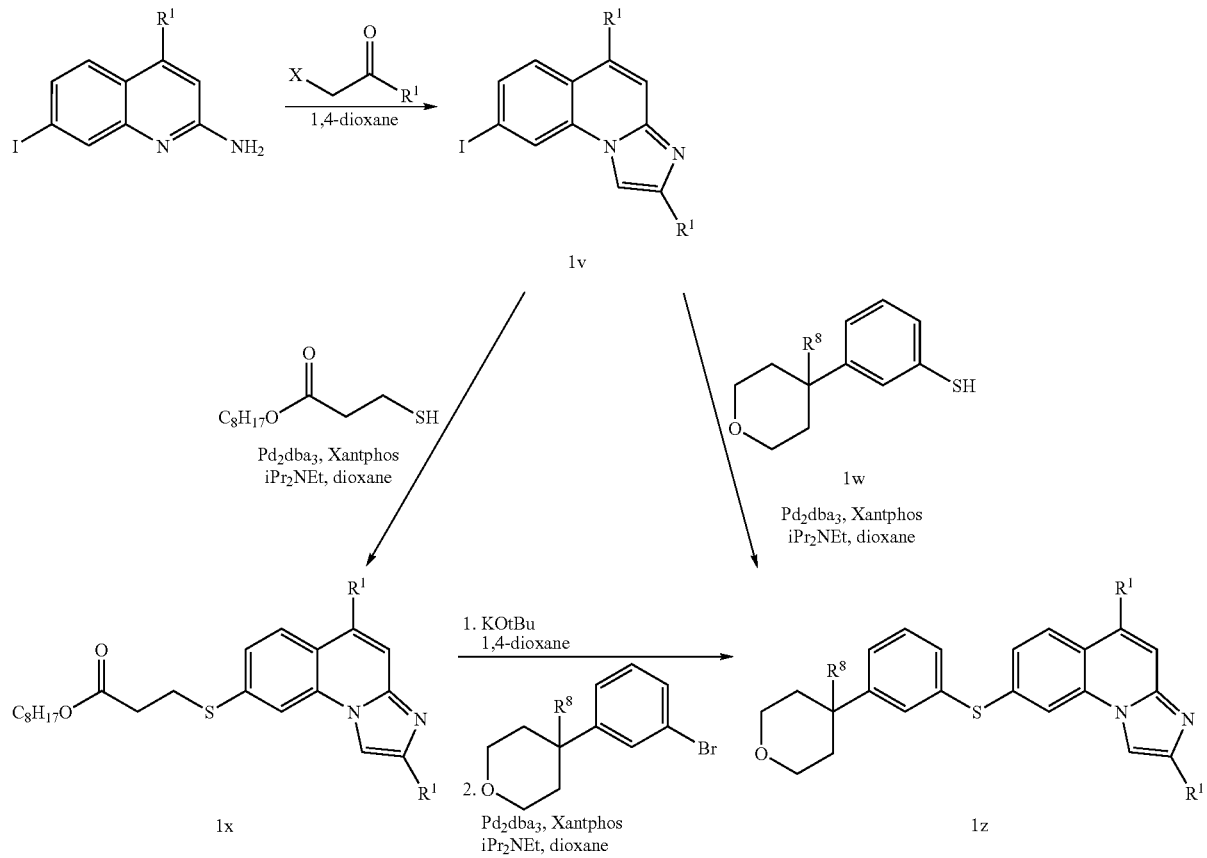

Example 1E

Compound 1-55, Compound 1-58, Compound 1-61, Compound 1-62, Compound 1-63, Compound 1-64, Compound 1-65, Compound 1-66, Compound 1-67, Compound 1-71, Compound 1-74, Compound 1-75, Compound 1-76, Compound 1-77, Compound 1-78, Compound 1-79, Compound 1-80, Compound 1-81, Compound 1-82, Compound 1-83, and Compound 1-84

Compound 1-55, Compound 1-58, Compound 1-61, Compound 1-62, Compound 1-63, Compound 1-64, Compound 1-65, Compound 1-66, Compound 1-67, Compound 1-71, Compound 1-74, Compound 1-75, Compound 1-76, Compound 1-77, Compound 1-78, Compound 1-79, Compound 1-80, Compound 1-81, Compound 1-82, Compound 1-83, and Compound 1-84 were prepared as outlined in Scheme 1E. A detailed illustrative example of the reaction conditions shown in Scheme 1E is described for the synthesis of 8-[3-(4-Cyano-tetrahydro-pyran-4-yl)-phenylsulfanyl]-5-phenyl-imidazo[1,2-a]quinoline-2-carboxylic acid ethyl ester and 4-[3-(5-Phenyl-imidazo[1,2-a]quinolin-8-ylsulfanyl)-phenyl]-tetrahydro-pyran-4-carboxylic acid methyl ester.

Step 1: 8-Iodo-5-phenyl-imidazo[1,2-a]quinoline-2-carboxylic acid ethyl ester (1v)

7-Iodo-4-phenyl-quinolin-2-ylamine (100 mg, 0.29 mmol), ethyl bromopyruvate (0.05 mL, 0.43 mmol), and sodium bicarbonate (22 mg, 0.58 mmol) were dissolved in EtOH (2 mL) and heated to 80° C. for 3 hours. The mixture was concentrated and purified by silica gel chromatography (30% EtOAc in hexanes) to give the desired product, 1v.

Step 2: 8-[3-(4-Cyano-tetrahydro-pyran-4-yl)-phenylsulfanyl]-5-phenyl-imidazo[1,2-a]quinoline-2-carboxylic acid ethyl ester (1z)

1v (262 mg, 0.59 mmol), 4-(3-Mercapto-phenyl)-tetrahydro-pyran-4-carbonitrile (1w, 130 mg, 0.59 mmol), Pd$_2$dba$_3$ (14 mg, 0.01 mmol), 4,5-bis(diphenylphosphino)-9,9-dimethylxanthene (17 mg, 0.03 mmol), and iPr$_2$NEt (0.27 mL, 1.9 mmol) were dissolved in 1,4-dioxane (2 mL) and degassed with N$_2$ for 10 minutes. The mixture was heated at 60° C. for 2 hours, then cooled to room temperature and concentrated. The residue was purified by silica gel chromatography to give the desired product, 1z.

Step 2a: 3-(5-Phenyl-imidazo[1,2-a]quinolin-8-ylsulfanyl)-propionic acid 2-ethyl-hexyl ester (1x)

1v (900 mg, 2.4 mmol), 3-mercaptopropionic acid 2-ethylhexyl ester (660 mg, 3.0 mmol), Pd$_2$dba$_3$ (69 mg, 0.08 mmol), 4,5-bis(diphenylphosphino)-9,9-dimethylxanthene (87 mg, 0.15 mmol), and iPr$_2$NEt (1.1 mL, 6.0 mmol) were dissolved in 1,4-dioxane (15 mL) and degassed with N$_2$ for 10 minutes. The mixture was heated at 60° C. for 1.5 hours, then cooled to room temperature and concentrated. The residue was purified by silica gel chromatography (0-100% EtOAc in hexanes) to give the desired product, 1x.

Step 2b: 4-[3-(5-Phenyl-imidazo[1,2-a]quinolin-8-ylsulfanyl)-phenyl]-tetrahydro-pyran-4-carboxylic acid methyl ester (1z)

1x (200 mg, 0.43 mmol) in 1,4-dioxane (5 mL) was degassed with N₂ for 10 minutes and cooled to 0° C. Potassium tert-butoxide (73 mg, 0.65 mmol) was added, and the mixture was stirred at room temperature for 5 minutes. The solution was degassed with N₂ for another 5 minutes while 4-(3-bromo-phenyl)-tetrahydro-pyran-4-carboxylic acid methyl ester (1y, 130 mg, 0.43 mmol), Pd₂dba₃ (10 mg, 0.01 mmol), 4,5-bis(diphenylphosphino)-9,9-dimethylxanthene (11 mg, 0.02 mmol), and iPr₂NEt (0.15 mL, 0.87 mmol) were added. The reaction was heated to 60° C. overnight, and then cooled to room temperature and concentrated. The residue was purified by silica gel chromatography (0-100% EtOAc in hexanes) to give the desired product, 1z.

Mass spectrometry data for Compound 1-55, Compound 1-58, Compound 1-61, Compound 1-62, Compound 1-63, Compound 1-64, Compound 1-65, Compound 1-66, Compound 1-67, Compound 1-71, Compound 1-74, Compound 1-75, Compound 1-76, Compound 1-77, Compound 1-78, Compound 1-79, Compound 1-80, Compound 1-81, Compound 1-82, Compound 1-83, and Compound 1-84 is shown in Table 1.

Notes: For Compound 1-55, Compound 1-58, Compound 1-61, Compound 1-62, Compound 1-65, Compound 1-66, Compound 1-67, Compound 1-71, Compound 1-74, Compound 1-75, Compound 1-76, Compound 1-77, Compound 1-78, Compound 1-79, Compound 1-80, Compound 1-81, Compound 1-82, Compound 1-83, and Compound 1-84, Step 2 was performed. For Compound 1-63 and Compound 1-64, Steps 2a and 2b were performed. For Compound 1-58, Compound 1-65, Compound 1-71, and Compound 1-74, the hydroxy group in 1t was reacted with POCl₃ to give the chloride in the product. For Compound 1-62, Compound 1-64, Compound 1-66, Compound 1-67, and Compound 1-79, the ester in 1x was hydrolyzed to give the acid in the product. For Compound 1-74, the nitrile in 1x was reduced to give the amide in the product. For Compound 1-75, the ester in it was reduced to give the hydroxy group in the product. For Compound 1-76, the ester in 1t was reduced with MeMgCl to give the tertiary alcohol in the product. For Compound 1-77, the ester in 1x was reduced to give the hydroxy group in the product. For Compound 1-78, the ester in 1x was reduced with MeMgCl to give the tertiary alcohol in the product. For Compound 1-80, the ester in 1x was reduced, and the resulting alcohol was then reacted with (bis(2-methoxyethyl) amino)sulfurtrifluoride to give the fluoromethyl group in the product. For Compound 1-81, the ester in 1x was reduced, and the resulting alcohol was then reacted with succinic anhydride to give the succinic ester in the product. For Compound 1-83, the ester in 1x was hydrolyzed, and the resulting acid was then reacted with MeLi to give the ketone in the product. For Compound 1-84, the ester in it was hydrolyzed, and the resulting acid was then reacted with N,O-dimethylhydroxylamine to give a Weinreb amide. For Compound 1-84, the Weinreb amide in 1x was reduced to give the aldehyde in the product.

Scheme 2:

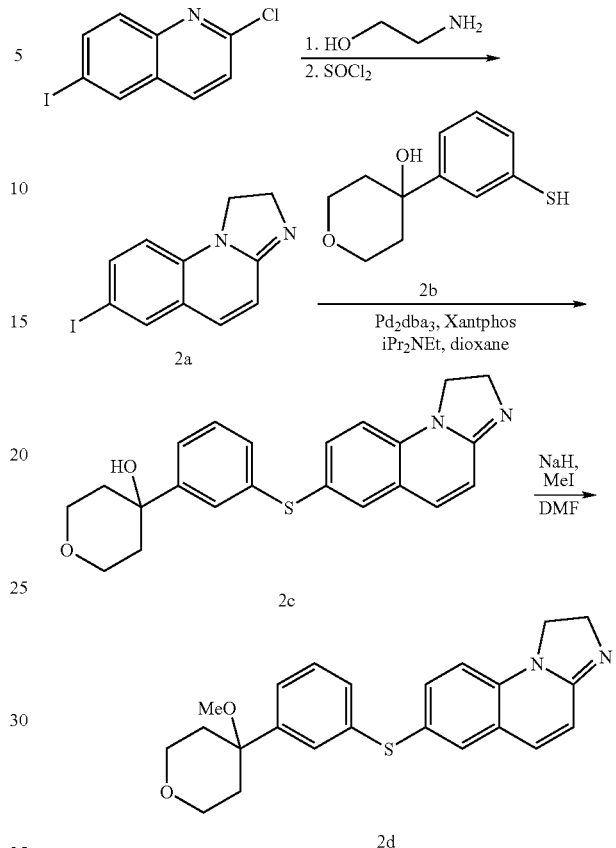

Example 2

Preparation of Compound 2-1 and Compound 2-2

Compound 2-1 and Compound 2-2 were prepared as outlined in Scheme 2. A detailed illustrative example of the reaction conditions shown in Scheme 2 is described for the synthesis of 7-[3-(4-Methoxy-tetrahydro-pyran-4-yl)-phenylsulfanyl]-1,2-dihydro-imidazo[1,2-a]quinoline.

Step 1: 7-Iodo-1,2-dihydro-imidazo[1,2-a]quinoline (2a)

2-Chloro-6-iodo-quinoline (200 mg, 0.69 mmol) and ethanolamine (1 mL) were heated at 130° C. for 1 hour. The reaction was cooled and purified by silica gel chromatography (4:1 EtOAc:Hex), and the isolated product was dissolved in CHCl₃. Thionyl chloride (0.12 mL, 1.65 mmol) was added, and the reaction was heated at 50° C. for 1 hour. The reaction was quenched with methanol and basified with saturated aqueous Na₂CO₃. The mixture was extracted with CH₂Cl₂, and the combined organic layers were combined, dried, filtered, and concentrated to give the desired product, 2a.

Step 2: 4-[3-(1,2-Dihydro-imidazo[1,2-a]quinolin-7-ylsulfanyl)-phenyl]-tetrahydro-pyran-4-ol (2c)

2a (175 mg, 0.59 mmol) and 4-(3-mercapto-phenyl)-tetrahydro-pyran-4-ol (2b, 150 mg, 0.71 mmol) were combined in 1,4-dioxane (6 mL) and degassed with N₂ for 10 minutes.

iPr₂NEt (0.33 mL, 1.8 mmol) was added, followed by Pd₂dba₃ (14 mg, 0.02 mmol) and 4,5-bis(diphenylphosphino)-9,9-dimethylxanthene (16 mg, 0.03 mmol). The mixture was degassed with N₂ for an additional 10 minutes, and then heated to 80° C. for 24 hours. The reaction was cooled to room temperature, concentrated, and purified by silica gel chromatography (0-20% MeOH in EtOAc) to give the desired product, 2c.

Step 3: 7-[3-(4-Methoxy-tetrahydro-pyran-4-yl)-phenylsulfanyl]-1,2-dihydro-imidazo[1,2-a]quinoline (2d)

To a solution of 2c (42 mg, 0.11 mmol) in DMF was added sodium hydride (5 mg, 0.12 mmol). Iodomethane (one drop) was added, and the mixture was stirred at room temperature for 5 hours. The reaction was quenched with water, extracted with EtOAc, and purified by preparative HPLC to give the desired product, 2d.

Mass spectrometry data for Compound 2-1 and Compound 2-2 is shown in Table 2.

Notes: For Compound 2-1, Step 3 was not performed.

Scheme 3:

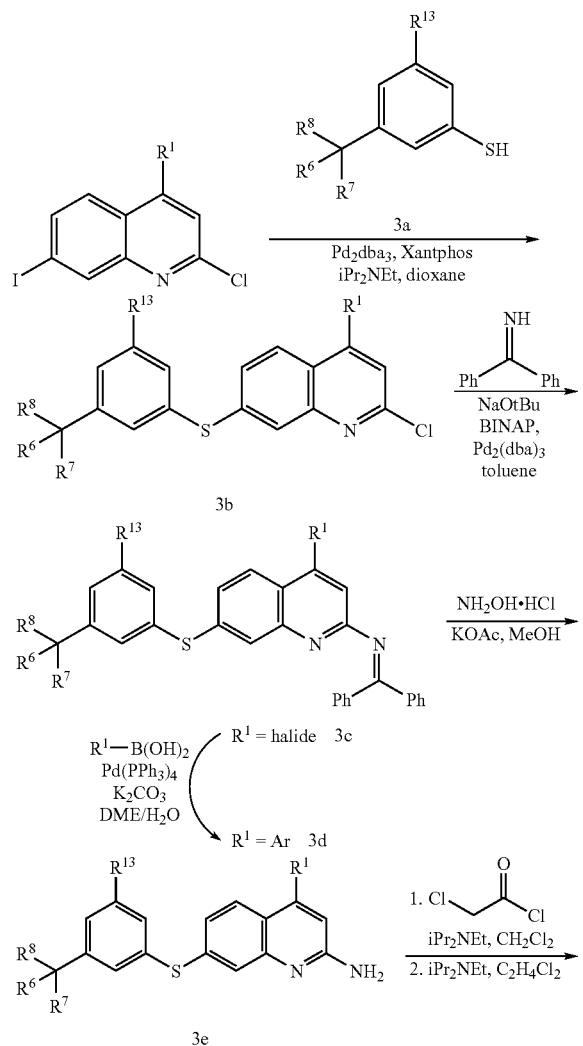

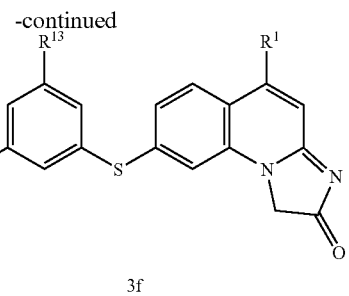

3f

Example 3

Preparation of Compound 3-1, Compound 3-2, Compound 3-3, Compound 3-4, Compound 3-5, and Compound 3-6

Compound 3-1, Compound 3-2, Compound 3-3, Compound 3-4, Compound 3-5, and Compound 3-6 were prepared as outlined in Scheme 3. A detailed illustrative example of the reaction conditions shown in Scheme 3 is described for the synthesis of 4-{3-[5-(4-Fluoro-phenyl)-2-oxo-1,2-dihydro-imidazo[1,2-a]quinolin-8-ylsulfanyl]-phenyl}-tetrahydro-pyran-4-carbonitrile.

Step 1: 4-[3-(2,4-Dichloro-quinolin-7-ylsulfanyl)-phenyl]-tetrahydro-pyran-4-carbonitrile (3b)

2,4-Dichloro-7-iodo-quinoline (3.4 g, 10.5 mmol), 4-(3-mercapto-phenyl)-tetrahydro-pyran-4-carbonitrile (3a, 2.3 g, 10.5 mmol), iPr₂NEt (3.67 mL, 21.0 mmol), Pd₂dba₃ (240 mg, 0.26 mmol), and 4,5-bis(diphenylphosphino)-9,9-dimethylxanthene (303 mg, 0.52 mmol) were dissolved in 1,4-dioxane (50 mL) and degassed for 10 minutes with N₂. The reaction was then sealed and heated to 60° C. for 1 hour. After cooling to room temperature, the reaction was diluted with EtOAc and saturated aqueous NH₄Cl. The aqueous layer was extracted with EtOAc, and the combined organic layers were dried over MgSO₄, filtered, and concentration. The residue was purified by silica gel chromatography (30% EtOAc in hexanes) to give the desired product, 3b.

Step 2: 4-{3-[2-(Benzhydrylidene-amino)-4-chloro-quinolin-7-ylsulfanyl]-phenyl}-tetrahydro-pyran-4-carbonitrile (3c)

3b (1.0 g, 2.4 mmol), benzophenone imine (0.4 mL, 2.4 mmol), sodium tert-butoxide (350 mg, 3.6 mmol), BINAP (150 mg, 0.27 mmol), and Pd₂dba₃ (55 mg, 0.06 mmol) were dissolved in toluene (10 mL) and degassed for 10 minutes with N₂. The reaction was then sealed and heated to 80° C. for 2 hours. After cooling to room temperature, the reaction was diluted with EtOAc and brine, and the aqueous layer was extracted with EtOAc. The combined organic layers were dried over MgSO₄, filtered, and concentrated, and the residue was purified by silica gel chromatography (30% EtOAc in hexanes) to give the desired product, 3c.

Step 2a: 4-{3-[2-(Benzhydrylidene-amino)-4-(4-fluoro-phenyl)-quinolin-7-ylsulfanyl]-phenyl}-tetrahydro-pyran-4-carbonitrile (3d)

3c (400 mg, 0.72 mmol), 4-fluorobenzeneboronic acid (150 mg, 1.07 mmol), potassium carbonate (247 mg, 1.79 mmol), and Pd(PPh₃)₄ (82 mg, 0.07 mmol) were dissolved in 2:1 DME:H₂O (10 mL) at degassed for 5 minutes with N₂. The reaction was then sealed and heated to 80° C. overnight. After cooling to room temperature, the reaction was concentrated and purified by silica gel chromatography (10% MeOH in CH₂Cl₂) to give the desired product, 3d.

Step 3: 4-{3-[2-Amino-4-(4-fluoro-phenyl)-quinolin-7-ylsulfanyl]-phenyl}-tetrahydro-pyran-4-carbonitrile (3e)

3d (300 mg, 0.48 mmol), hydroxylamine hydrochloride (67 mg, 0.97 mmol), and potassium acetate (92 mg, 0.97 mmol) was dissolved in MeOH (10 mL) and stirred overnight at room temperature. The reaction was concentrated and purified by silica gel chromatography (30% EtOAc in hexanes) to obtain the desired product, 3e.

Step 4: 4-{3-[5-(4-Fluoro-phenyl)-2-oxo-1,2-dihydro-imidazo[1,2-a]quinolin-8-ylsulfanyl]-phenyl}-tetrahydro-pyran-4-carbonitrile (3f)

To 3e (120 mg, 0.26 mmol) in CH₂Cl₂ (3 mL) was added iPr₂NEt (0.12 mL, 0.66 mmol), followed by chloroacetyl chloride (0.03 mL, 0.40 mmol), and the reaction was stirred at room temperature. Once complete, the reaction was diluted with water, and the aqueous layer was extracted with CH₂Cl₂. The combined organic layers were dried over MgSO₄, filtered, and concentrated, and the residue was dissolved in C₂H₄Cl₂. iPr₂NEt (0.12 mL, 0.66 mol) was added, and the reaction was sealed and heated to 80° C. overnight. After cooling to room temperature, the reaction was concentrated and purified by preparative HPLC to give the desired product.

Mass spectrometry data for Compound 3-1, Compound 3-2, Compound 3-3, Compound 3-4, Compound 3-5, and Compound 3-6 is shown in Table 3.

Notes: For Compound 3-1, Compound 3-2, Compound 3-3, and Compound 3-4, Step 2a was performed. For Compound 3-6, Step 1 was performed last; Step 2 used p-methoxybenzylamine in place of benzophenone imine.

Scheme 4:

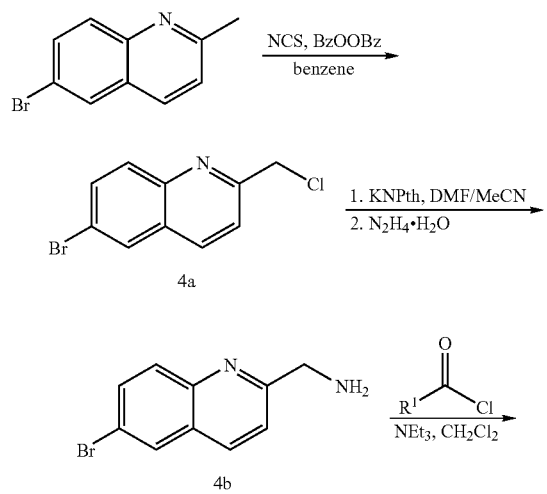

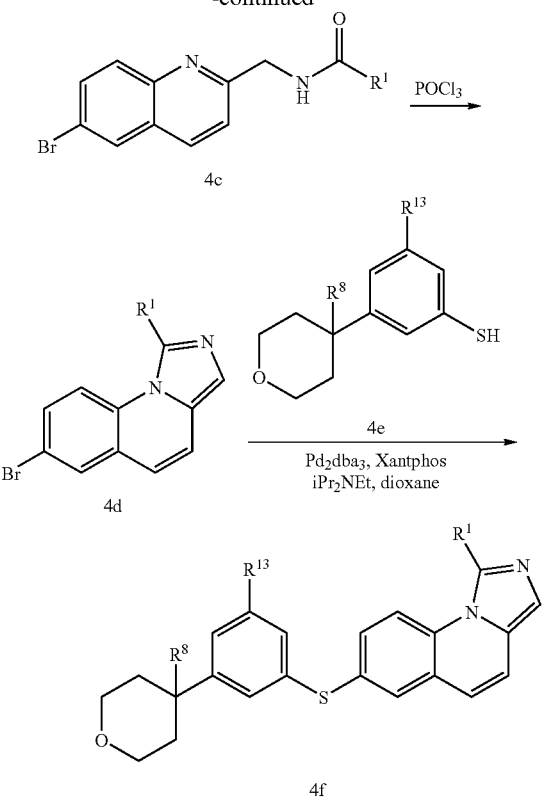

Example 4

Preparation of Compound 4-1, Compound 4-2, Compound 4-3, Compound 4-4, and Compound 4-5

Compound 4-1, Compound 4-2, Compound 4-3, Compound 4-4, and Compound 4-5 were prepared as outlined in Scheme 4. A detailed illustrative example of the reaction conditions shown in Scheme 4 is described for the synthesis of 4-[3-Fluoro-5-(1-methyl-imidazo[1,5-a]quinolin-7-ylsulfanyl)-phenyl]-tetrahydro-pyran-4-carbonitrile.

Step 1: 6-Bromo-2-chloromethyl-quinoline (4a)

To 6-Bromo-2-methyl-quinoline (2.4 g, 11.0 mmol) in benzene (20 mL) at room temperature was added NCS (1.44 g, 11.0 mmol) and catalytic benzoyl peroxide, and the reaction was heated to 80° C. for 1 hour. After cooling to room temperature, the mixture was concentrated and purified by silica gel chromatography (0-50% EtOAc in hexanes) to give the desired product, 4a.

Step 2: C-(6-Bromo-quinolin-2-yl)-methylamine (4b)

To 4a (440 mg, 1.7 mmol) in 1:1 DMF/MeCN (3 mL) at room temperature was added potassium phthalimide (350 mg, 1.9 mmol), and the reaction was heated to 60° C. overnight. The mixture was poured into water and filtered, and the solid was suspended in EtOH (10 mL). Hydrazine (82 mg, 2.5 mmol) was added, and the mixture was heated to 70° C. for 30 minutes. The reaction was then concentrated, and the crude material, 4b, was used directly in the next step.

185

Step 3: N-(6-Bromo-quinolin-2-ylmethyl)-acetamide (4c)

To a slurry of 4b (401 mg, 1.7 mmol) in CH$_2$Cl$_2$ at room temperature was added NEt$_3$ (0.47 mL, 3.4 mmol), followed by acetyl chloride (0.18 mL, 2.6 mmol). Once the reaction was complete by LCMS analysis, the mixture was concentrated and purified by silica gel chromatography (0-100% EtOAc in hexanes, followed by 10% MeOH in EtOAc) to give the desired product, 4c.

Step 4: 7-Bromo-1-methyl-imidazo[1,5-a]quinoline (4d)

4c (213 mg, 0.82 mmol) was refluxed in phosphorus oxychloride (5 mL) for 1 hour. The mixture was cooled to room temperature, concentrated, and diluted with saturated aqueous NaHCO$_3$ and EtOAc. The aqueous layer was extracted with EtOAc, and the combined organic layers were dried over MgSO$_4$, filtered, and concentrated. The residue was purified by silica gel chromatography (50-100% EtOAc in hexanes) to give the desired product, 4d.

Step 5: 4-{3-Fluoro-5-(1-methyl-imidazo[1,5-a]quinolin-7-ylsulfanyl)-phenyl}-tetrahydro-pyran-4-carbonitrile (4f)

4d (80 mg, 0.3 mmol) and 4-(3-Fluoro-5-mercapto-phenyl)-tetrahydro-pyran-4-carbonitrile (4e, 88 mg, 0.37 mmol) were dissolved in 1,4-dioxane (3 mL) and degassed for 10 minutes with N$_2$. iPr$_2$NEt (0.10 mL, 0.6 mmol), Pd$_2$dba$_3$ (14 mg, 0.02 mmol), and 4,5-bis(diphenylphosphino)-9,9-dimethylxanthene (17 mg, 0.03 mmol) were added, and the reaction was degassed for another 10 minutes with N$_2$. The reaction was then sealed and heated to 80° C. overnight. After cooling to room temperature, the reaction was concentrated and purified by silica gel chromatography (0-20% MeOH in EtOAc) to give the desired product, 4f.

Mass spectrometry data for Compound 4-1, Compound 4-2, Compound 4-3, Compound 4-4, and Compound 4-5 is shown in Table 4.

Notes: For Compound 4-3, the hydroxy group in 4f was alkylated to give the methoxy group in the product. For Compound 4-5, the nitrile in 4f was reduced to give the amide in the product.

Scheme 5A:

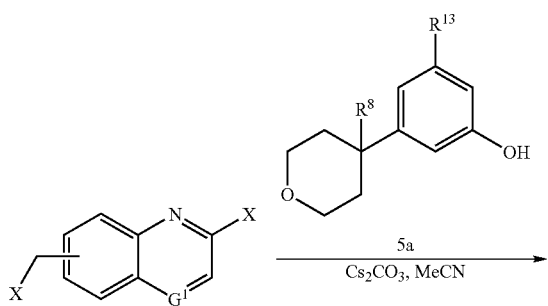

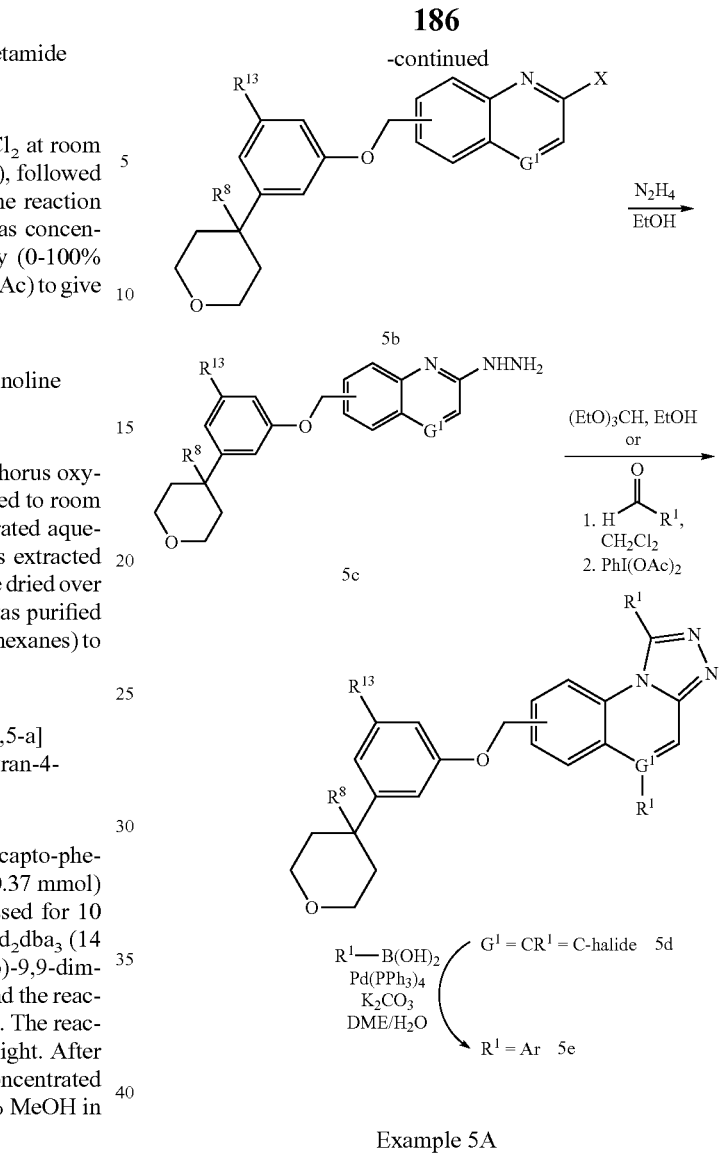

Example 5A

Compound 5-1, Compound 5-2, Compound 5-3, Compound 5-4, Compound 5-5, Compound 5-6 Compound 5-7, Compound 5-8, Compound 5-9, Compound 5-10, Compound 5-11, Compound 5-12, Compound 5-13, Compound 5-14, Compound 5-15, Compound 5-16, Compound 5-17, Compound 5-18, Compound 5-19, Compound 5-20, Compound 5-122, Compound 5-123, Compound 5-124, Compound 5-125, Compound 5-126, Compound 5-127, Compound 5-128, Compound 5-129, Compound 5-130, Compound 5-131, Compound 5-132, Compound 5-133, Compound 5-134, Compound 5-135, Compound 5-136, Compound 5-137, Compound 5-138, Compound 5-139, Compound 5-140, Compound 5-141, and Compound 5-142

Compound 5-1, Compound 5-2, Compound 5-3, Compound 5-4, Compound 5-5, Compound 5-6, Compound 5-7, Compound 5-8, Compound 5-9, Compound 5-10, Compound 5-11, Compound 5-12, Compound 5-13, Compound 5-14, Compound 5-15, Compound 5-16, Compound 5-17, Compound 5-18, Compound 5-19, Compound 5-20, Compound 5-122, Compound 5-123, Compound 5-124, Compound 5-125, Compound 5-126, Compound 5-127, Compound 5-128, Compound 5-129, Compound 5-130, Compound 5-131, Compound 5-132, Compound 5-133, Compound 5-134, Compound 5-135, Compound 5-136, Compound 5-137, Compound 5-138, Compound 5-139, Compound 5-140, Compound 5-141, and Compound 5-142 were prepared as outlined in Scheme 5A. A detailed illustrative example of the reaction conditions shown in Scheme 5A is described for the synthesis of 4-[3-Fluoro-5-(5-pyridin-3-yl-[1,2,4]triazolo[4,3-a]quinolin-8-ylmethoxy)-phenyl]-tetrahydro-pyran-4-carboxylic acid methyl ester.

Step 1: 4-[3-(2,4-Dichloro-quinolin-7-ylmethoxy)-5-fluoro-phenyl]-tetrahydro-pyran-4-carboxylic acid methyl ester (5b)

7-Bromomethyl-2,4-dichloro-quinoline (1.4 g, 4.8 mmol), 4-(3-Fluoro-5-hydroxy-phenyl)-tetrahydro-pyran-4-carboxylic acid methyl ester (5a, 1.2 g, 4.8 mmol), and cesium carbonate (3.1 g, 9.6 mmol) were suspended in DMF (20 mL) and stirred overnight at room temperature. The mixture was diluted with EtOAc and saturated $NH_4Cl$, and the aqueous layer was extracted with EtOAc. The combined organic layers were dried over $MgSO_4$, filtered, and concentrated, and the residue was purified by silica gel chromatography (30% EtOAc in hexanes) to give the desired product, 5b.

Step 2: 4-[3-(4-Chloro-2-hydrazino-quinolin-7-ylmethoxy)-5-fluoro-phenyl]-tetrahydro-pyran-4-carboxylic acid methyl ester (5c)

To 5b (1.7 g, 3.7 mmol) in EtOH (60 mL) was added hydrazine, anhydrous (10 mL), and the reaction was heated to 60° C. for 2 hours. After cooling to room temperature, the mixture was concentrated, and the residue was diluted with $CH_2Cl_2$ and water. The aqueous layer was extracted with $CH_2Cl_2$, and the combined organic layers were dried over $MgSO_4$, filtered, and concentrated to give the desired product, 5c.

Step 3: 4-[3-(5-Chloro-[1,2,4]triazolo[4,3-a]quinolin-8-ylmethoxy)-5-fluoro-phenyl]-tetrahydro-pyran-4-carboxylic acid methyl ester (5d)

To 5c (3.7 mmol) in EtOH (60 mL) was added triethyl orthoformate (10 mL), and the reaction was heated to 65° C. overnight. After cooling to room temperature, the mixture was concentrated, and the residue was purified by silica gel chromatography (100% EtOAc) to give the desired product, 5d.

Step 3a: 4-[3-Fluoro-5-(5-pyridin-3-yl-[1,2,4]triazolo[4,3-a]quinolin-8-ylmethoxy)-phenyl]-tetrahydro-pyran-4-carboxylic acid methyl ester (5e)

To 5d (50 mg, 0.11 mmol) in $DME:H_2O$ (2:1, 2 mL) was added 3-pyridineboronic acid (20 mg, 0.16 mmol) and potassium carbonate (37 mg, 0.27 mmol). The mixture was degassed with $N_2$ for 5 minutes, and then $Pd(PPh_3)_4$ (12 mg, 0.01 mmol) was added, and the mixture was degassed with $N_2$ for an additional 5 minutes. The reaction was then heated to 80° C. overnight. After cooling to room temperature, the reaction was concentrated and purified by silica gel chromatography (10% MeOH in EtOAc) to give the desired product, 5e.

Mass spectrometry data for Compound 5-1, Compound 5-2, Compound 5-3, Compound 5-4, Compound 5-5, Compound 5-6, Compound 5-7, Compound 5-8, Compound 5-9, Compound 5-10, Compound 5-11, Compound 5-12, Compound 5-13, Compound 5-14, Compound 5-15, Compound 5-16, Compound 5-17, Compound 5-18, Compound 5-19, Compound 5-20, Compound 5-122, Compound 5-123, Compound 5-124, Compound 5-125, Compound 5-126, Compound 5-127, Compound 5-128, Compound 5-129, Compound 5-130, Compound 5-131, Compound 5-132, Compound 5-133, Compound 5-134, Compound 5-135, Compound 5-136, Compound 5-137, Compound 5-138, Compound 5-139, Compound 5-140, Compound 5-141, and Compound 5-142 is shown in Table 5.

Notes: For Compound 5-1 and Compound 5-2, 5-Bromomethyl-2-chloro-quinoline was used as the starting material. For Compound 5-3, Compound 5-4, Compound 5-5, Compound 5-6, Compound 5-7, Compound 5-8, Compound 5-9, Compound 5-10, Compound 5-11, Compound 5-12, Compound 5-13, Compound 5-14, Compound 5-15, Compound 5-16, Compound 5-17, Compound 5-18, and Compound 5-19, substituted 6-Halomethylquinolines were used as the starting materials. For Compound 5-20, 6-Bromomethyl-2-chloro-quinoxaline was used as the starting material. For Compound 5-122, Compound 5-123, Compound 5-124, Compound 5-125, Compound 5-126, Compound 5-127, Compound 5-128, Compound 5-129, Compound 5-130, Compound 5-131, Compound 5-132, Compound 5-133, Compound 5-134, Compound 5-135, Compound 5-136, Compound 5-137, Compound 5-138, Compound 5-139, Compound 5-140, Compound 5-141, and Compound 5-142, substituted 7-Bromomethylquinolines were used as the starting materials. For Compound 5-8, Compound 5-124, Compound 5-126, Compound 5-127, Compound 5-132, Compound 5-133, Compound 5-134, Compound 5-135, Compound 5-136, Compound 5-137, Compound 5-138, Compound 5-140, Compound 5-141, and Compound 5-142, Step 3a was performed. For Compound 5-4, the nitrile in 5d was reduced to give the amide in the product. For Compound 5-15, the ester in 5d was hydrolyzed to give the acid in the product. For Compound 5-16, Compound 5-139, Compound 5-140, Compound 5-141, and Compound 5-142, the ester in 5d was hydrolyzed, and the resulting acid was reacted with oxalyl chloride, followed by ammonium hydroxide, to give the amide in the product. For Compound 5-129 and Compound 5-130, Step 3a was performed, but using NaSMe or NaOMe to introduce the methylsulfanyl group or methoxy group as $R^1$ in the product.

Scheme 5B:

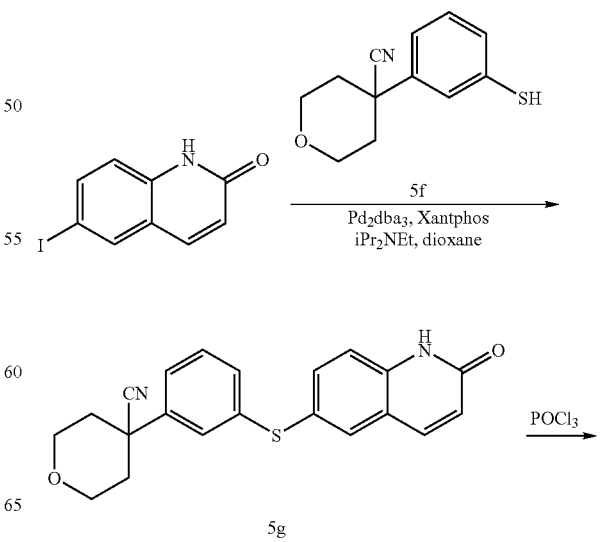

-continued

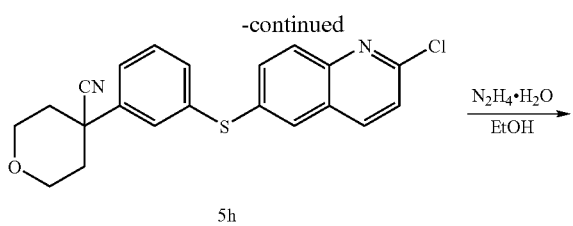

5h

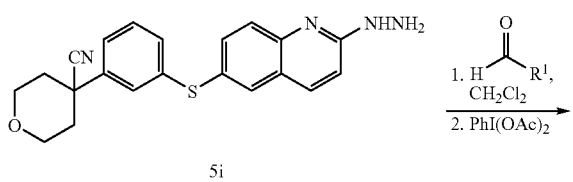

5i

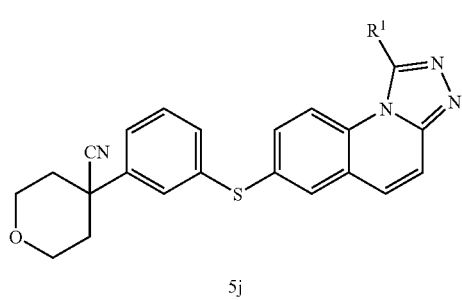

5j

Example 5B

Compound 5-28, Compound 5-29, Compound 5-30, Compound 5-31, Compound 5-32, Compound 5-33, Compound 5-34, Compound 5-35, Compound 5-36, Compound 5-37, Compound 5-38, Compound 5-39, Compound 5-40, Compound 5-41, Compound 5-42, Compound 5-47, Compound 5-48, Compound 5-49, Compound 5-50, Compound 5-51, Compound 5-55, Compound 5-56, Compound 5-57, Compound 5-58, Compound 5-59, Compound 5-60, Compound 5-61, Compound 5-62, Compound 5-63, Compound 5-64, Compound 5-65, Compound 5-66, Compound 5-67, Compound 5-68, Compound 5-69, Compound 5-70, Compound 5-71, Compound 5-72, Compound 5-73, Compound 5-74, Compound 5-75, Compound 5-79, and Compound 5-94

Compound 5-28, Compound 5-29, Compound 5-30, Compound 5-31, Compound 5-32, Compound 5-33, Compound 5-34, Compound 5-35, Compound 5-36, Compound 5-37, Compound 5-38, Compound 5-39, Compound 5-40, Compound 5-41, Compound 5-42, Compound 5-47, Compound 5-48, Compound 5-49, Compound 5-50, Compound 5-51, Compound 5-55, Compound 5-56, Compound 5-57, Compound 5-58, Compound 5-59, Compound 5-60, Compound 5-61, Compound 5-62, Compound 5-63, Compound 5-64, Compound 5-65, Compound 5-66, Compound 5-67, Compound 5-68, Compound 5-69, Compound 5-70, Compound 5-71, Compound 5-72, Compound 5-73, Compound 5-74, Compound 5-75, Compound 5-79, and Compound 5-94 were prepared as outlined in Scheme 5B. A detailed illustrative example of the reaction conditions shown in Scheme 5B is described for the synthesis of 4-[3-(1-Pyridin-2-yl-[1,2,4]azolo[4,3-a]quinolin-7-ylsulfanyl)-phenyl]-tetrahydro-pyran-4-carbonitrile.

Step 1: 4-[3-(2-Oxo-1,2-dihydro-quinolin-6-ylsulfanyl)-phenyl]-tetrahydro-pyran-4-carbonitrile (5g)

6-Iodo-1H-quinolin-2-one (5.13 g, 18.9 mmol) and 4-(3-Mercapto-phenyl)-tetrahydro-pyran-4-carbonitrile (5f, 4.57 g, 20.8 mmol) were dissolved in 1,4-dioxane (160 mL) and degassed for 10 minutes with $N_2$. $iPr_2NEt$ (6.6 mL, 37.9 mmol) was added, followed by $Pd_2dba_3$ (434 mg, 0.47 mmol), and 4,5-bis(diphenylphosphino)-9,9-dimethylxanthene (548 mg, 0.95 mmol), and the reaction was degassed for another 10 minutes with $N_2$. The reaction was then sealed and heated to 80° C. overnight. After cooling to room temperature, the reaction was filtered and concentrated, and the residue was purified by silica gel chromatography (0-100% MeOH in EtOAc) to give the desired product, 5g.

Step 2: 4-[3-(2-Chloro-quinolin-6-ylsulfanyl)-phenyl]-tetrahydro-pyran-4-carbonitrile (5h)

5g (4.52 g, 12.5 mmol) was dissolved in phosphorus oxychloride (23 mL) and heated to 90° C. for 1 hour. The reaction was cooled to room temperature, and ice was added slowly, followed by EtOAc and $NaHCO_3$. The aqueous layer was extracted with $CH_2Cl_2$ twice, and the combined organic layers were dried over $MgSO_4$, filtered, and concentrated to give the desired product, 5h.

Step 3: 4-[3-(2-Hydrazino-quinolin-6-ylsulfanyl)-phenyl]-tetrahydro-pyran-4-carbonitrile (5i)

5h (4.4 g, 11.6 mmol) was suspended in hydrazine hydrate (11 mL) and EtOH (45 mL) and heated to 80° C. overnight. The reaction was cooled to room temperature and concentrated, and then diluted with EtOAc and water. The aqueous layer was extracted with EtOAc twice, and the combined organic layers were washed with brine, dried over $MgSO_4$, filtered, and concentrated. The residue was dissolved in $CH_2Cl_2$ (15 mL) and heated to dissolve as much of the material as possible. Hexanes (45 mL) was added slowly, and the mixture was stirred for 30 minutes. The precipitate was filtered, rinsed with hexanes, and dried to give the desired product, 5i.

Step 4: 4-{3-[1-(4-Fluoro-phenyl)-[1,2,4]triazolo[4,3-a]quinolin-7-ylsulfanyl]-phenyl}-tetrahydro-pyran-4-carbonitrile (5j)

5i (203 mg, 0.54 mmol) was suspended in $CH_2Cl_2$. 4-Fluorobenzaldehyde (0.07 mL, 0.65 mmol) was added, and the reaction was stirred at room temperature for 4 hours. Iodobenzene diacetate (176 mg, 0.54 mmol) was added, and the reaction was stirred overnight at room temperature. The reaction was adsorbed onto silica gel and concentrated, and then purified by silica gel chromatography (20-100% EtOAc in hexanes, followed by 0-10% MeOH in EtOAc) to give the desired product, 5j.

Mass spectrometry data for Compound 5-28, Compound 5-29, Compound 5-30, Compound 5-31, Compound 5-32, Compound 5-33, Compound 5-34, Compound 5-35, Compound 5-36, Compound 5-37, Compound 5-38, Compound 5-39, Compound 5-40, Compound 5-41, Compound 5-42, Compound 5-47, Compound 5-48, Compound 5-49, Compound 5-50, Compound 5-51, Compound 5-55, Compound 5-56, Compound 5-57, Compound 5-58, Compound 5-59, Compound 5-60, Compound 5-61, Compound 5-62, Compound 5-63, Compound 5-64, Compound 5-65, Compound 5-66, Compound 5-67, Compound 5-68, Compound 5-69, Compound 5-70, Compound 5-71, Compound 5-72, Compound 5-73, Compound 5-74, Compound 5-75, Compound 5-79, and Compound 5-94 is shown in Table 5.

Notes: For Compound 5-49, the 1H-imidazole in 5j was alkylated to give the 1-methyl-1H-imidazole in the product. For Compound 5-50 and Compound 5-51, the nitrile in 5j was reduced to give the amide in the product. For Compound 5-55, the acid in 5j was activated with CDI and then reacted with ammonia in MeOH to give the amide in the product. For Compound 5-61, Compound 5-62, and Compound 5-63, the protected amine in 5j was deprotected to give the unprotected amine in the product. For Compound 5-65, Compound 5-69, and Compound 5-70, the amine in 5j was acetylated to give the amide in the product. For Compound 5-66, Compound 5-67, and Compound 5-68, the amine in 5j was alkylated to give the substituted amine in the product. For Compound 5-75, the ester in 5j was hydrolyzed to give the acid in the product. For Compound 5-79, the nitrile in 5j was reduced to give an aldehyde, which was then reacted with MeONH$_2$ to give the imine in the product.

Scheme 5C:

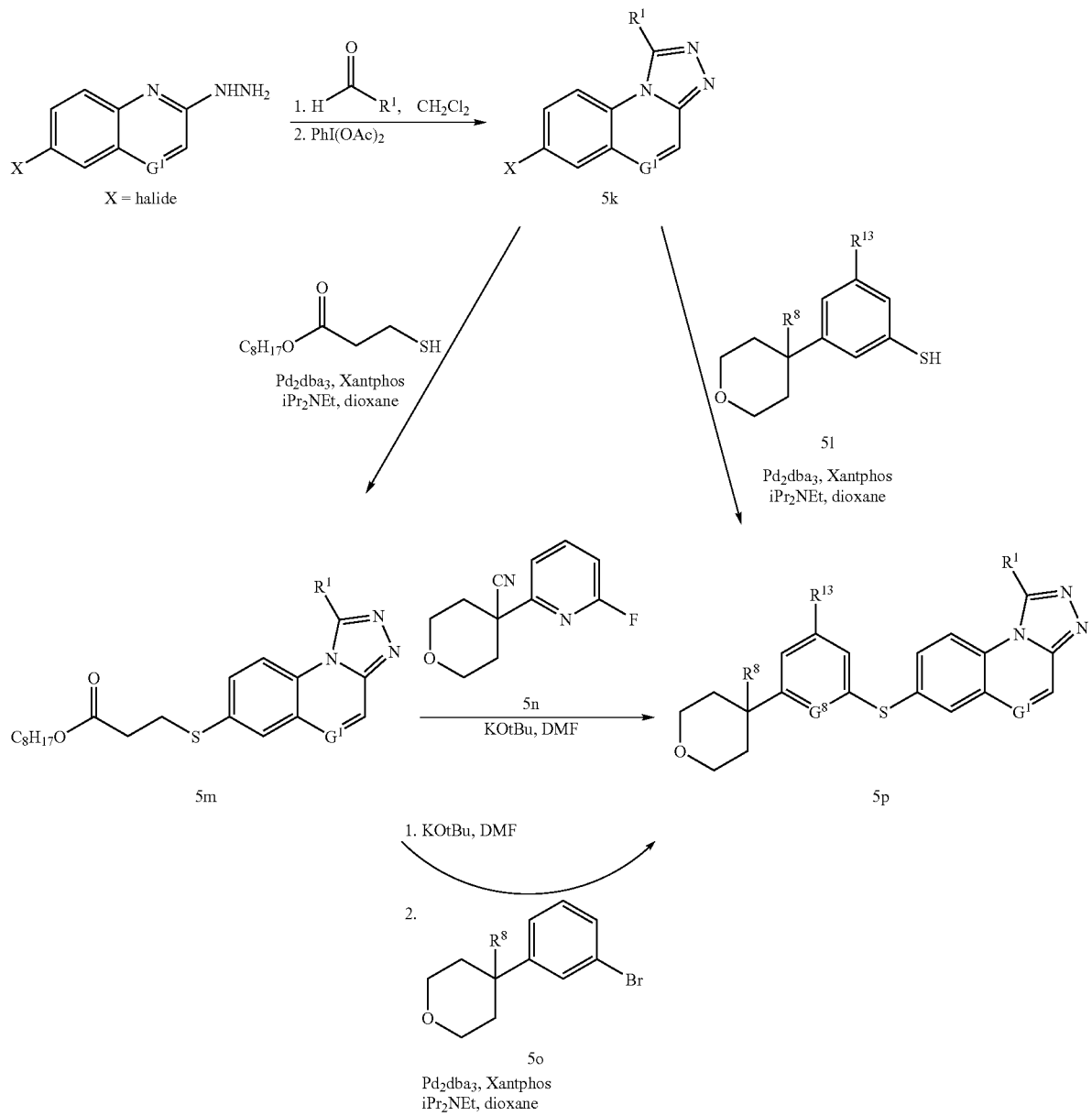

Example 5C

Compound 5-21, Compound 5-22, Compound 5-23, Compound 5-24, Compound 5-25, Compound 5-26, Compound 5-27, Compound 5-43, Compound 5-44, Compound 5-45, Compound 5-46, Compound 5-52, Compound 5-53, Compound 5-54, Compound 5-76, Compound 5-77, Compound 5-78, Compound 5-80, Compound 5-81, Compound 5-82, Compound 5-83, Compound 5-84, Compound 5-85, Compound 5-86, Compound 5-87, Compound 5-88, Compound 5-89, Compound 5-90, Compound 5-91, Compound 5-92, Compound 5-93, Compound 5-95, Compound 5-96, Compound 5-97, Compound 5-98, Compound 5-99, Compound 5-100, Compound 5-101, Compound 5-102, Compound 5-103, Compound 5-104, Compound 5-105, Compound 5-106, Compound 5-107, Compound 5-108, Compound 5-111, Compound 5-112, Compound 5-113, Compound 5-114, Compound 5-115, Compound 5-116, Compound 5-117, Compound 5-118, Compound 5-119, Compound 5-120, Compound 5-121, Compound 5-160, Compound 5-161, and Compound 5-162

Compound 5-21, Compound 5-22, Compound 5-23, Compound 5-24, Compound 5-25, Compound 5-26, Compound 5-27, Compound 5-43, Compound 5-44, Compound 5-45, Compound 5-46, Compound 5-52, Compound 5-53, Compound 5-54, Compound 5-76, Compound 5-77, Compound 5-78, Compound 5-80, Compound 5-81, Compound 5-82, Compound 5-83, Compound 5-84, Compound 5-85, Compound 5-86, Compound 5-87, Compound 5-88, Compound 5-89, Compound 5-90, Compound 5-91, Compound 5-92, Compound 5-93, Compound 5-95, Compound 5-96, Compound 5-97, Compound 5-98, Compound 5-99, Compound 5-100, Compound 5-101, Compound 5-102, Compound 5-103, Compound 5-104, Compound 5-105, Compound 5-106, Compound 5-107, Compound 5-108, Compound 5-111, Compound 5-112, Compound 5-113, Compound 5-114, Compound 5-115, Compound 5-116, Compound 5-117, Compound 5-118, Compound 5-119, Compound 5-120, Compound 5-121, Compound 5-160, Compound 5-161, and Compound 5-162 were prepared as outlined in Scheme 5C. A detailed illustrative example of the reaction conditions shown in Scheme 5C is described for the synthesis of 4-[3-(1-Pyridin-2-yl-[1,2,4]triazolo[4,3-a]quinolin-7-ylsulfanyl)-phenyl]-tetrahydro-pyran-4-ol, 4-[6-(1-Pyridin-2-yl-[1,2,4]triazolo[4,3-a]quinolin-7-ylsulfanyl)-pyridin-2-yl]-tetrahydro-pyran-4-carbonitrile, and 4-[3-(1-Pyridin-2-yl-[1,2,4]triazolo[4,3-a]quinolin-7-ylsulfanyl)-phenyl]-tetrahydro-pyran-4-carboxylic acid methyl ester.

Step 1: 7-Iodo-1-pyridin-2-yl-[1,2,4]triazolo[4,3-a]quinoline (5k)

To (6-Iodo-quinolin-2-yl)-hydrazine (2.99 g, 10.5 mmol) suspended in $CH_2Cl_2$ (30 mL) was added 2-pyridinecarboxaldehyde (1.2 mL, 12.6 mmol). The reaction was stirred at room temperature for 2 hours, followed by the addition of iodobenzene diacetate (3.39 g, 10.5 mmol). The reaction was stirred overnight at room temperature, during which time a precipitate formed. The mixture was concentrated to half the volume, and the precipitate was filtered and washed with minimal $CH_2Cl_2$ to give the desired product, 5k. The filtrate was concentrated and suspended in EtOH. After stirring overnight at room temperature, the mixture was filtered and rinsed with EtOH to obtain additional product, 5k.

Step 2: 4-[3-(1-Pyridin-2-yl-[1,2,4]triazolo[4,3-a]quinolin-7-ylsulfanyl)-phenyl]-tetrahydro-pyran-4-ol (5p)

5k (201 mg, 0.54 mmol) was suspended in 1,4-dioxane (4.5 mL) and degassed with $N_2$ for 5 minutes. $iPr_2NEt$ (0.19 mL, 1.08 mmol) was added, followed by 4-(3-Mercapto-phenyl)-tetrahydro-pyran-4-ol (5l, 131 mg, 0.60 mmol) in 1,4-dioxane (1 mL). $Pd_2dba_3$ (13 mg, 0.01 mmol) and 4,5-bis(diphenylphosphino)-9,9-dimethylxanthene (16 mg, 0.03 mmol) were added, and the reaction was sealed and heated to 90° C. overnight. After cooling to room temperature, the mixture was concentrated and purified by silica gel chromatography (20-100% EtOAc in hexanes, followed by 0-10% MeOH in EtOAc) to obtain the desired product, 5p. Further purification by preparative HPLC was required, followed by standard aqueous workup of the combined fractions using EtOAc and saturated aqueous $NaHCO_3$ to give clean product.

Step 2a: 3-(1-Pyridin-2-yl-[1,2,4]triazolo[4,3-a]quinolin-7-ylsulfanyl)-propionic acid 2-ethyl-hexyl ester (5m)

5k (890 mg, 2.4 mmol) and 3-mercaptopropionic acid 2-ethylhexyl ester (630 mg, 2.9 mmol) were dissolved in 1,4-dioxane (20 mL) and degassed with $N_2$ for 10 minutes. $iPr_2NEt$ (0.86 mL, 4.8 mmol), $Pd_2dba_3$ (54 mg, 0.06 mmol), and 4,5-bis(diphenylphosphino)-9,9-dimethylxanthene (69 mg, 0.12 mmol) were added, and the mixture was degassed with $N_2$ for an additional 10 minutes. The reaction was heated to 90° C. until no starting material was seen by tlc analysis, and then the mixture was concentrated and purified by silica gel chromatography to give the desired product, 5m.

Step 2b: 4-[6-(1-Pyridin-2-yl-[1,2,4]triazolo[4,3-a]quinolin-7-ylsulfanyl)-pyridin-2-yl]-tetrahydro-pyran-4-carbonitrile (5p)

5m (93 mg, 0.2 mmol) and 4-(6-Fluoro-pyridin-2-yl)-tetrahydro-pyran-4-carbonitrile (5n, 41 mg, 0.2 mmol) were dissolved in DMF (2 mL) and degassed with $N_2$. Potassium tert-butoxide (22 mg, 0.2 mmol) was added, and the reaction was sealed and heated to 80° C. overnight. After cooling to room temperature, the mixture was diluted with EtOAc and water, and the aqueous phase was extracted with EtOAc. The combined organic layers were dried over $MgSO_4$, filtered, and concentrated, and the residue was purified by silica gel chromatography to obtain the desired product, 5p.

Step 2c: 4-[3-(1-Pyridin-2-yl-[1,2,4]triazolo[4,3-a]quinolin-7-ylsulfanyl)-phenyl]-tetrahydro-pyran-4-carboxylic acid methyl ester (5p)

5m (216 mg, 0.47 mmol) was dissolved in 1,4-dioxane (5 mL) and degassed with $N_2$ for 20 minutes. Potassium tert-butoxide (55 mg, 0.49 mmol) was added, and the reaction was stirred at room temperature overnight. The mixture was degassed with $N_2$ for an additional 20 minutes, and then 4-(3-Bromo-phenyl)-tetrahydro-pyran-4-carboxylic acid methyl ester (5o, 141 mg, 0.47 mmol) in 1,4-dioxane (1 mL) was added, followed by $iPr_2NEt$ (0.18 mL, 1.03 mmol), $Pd_2dba_3$ (11 mg, 0.01 mmol), and 4,5-bis(diphenylphosphino)-9,9-dimethylxanthene (15 mg, 0.02 mmol). The reaction was sealed and heated to 110° C. for 1.5 hours. The mixture was cooled to room temperature and concentrated, and the residue was purified by silica gel chromatography (20-100% EtOAc in hexanes, followed by 0-10% MeOH in EtOAc) to give the desired product, 5p.

Mass spectrometry data for Compound 5-21, Compound 5-22, Compound 5-23, Compound 5-24, Compound 5-25, Compound 5-26, Compound 5-27, Compound 5-43, Compound 5-44, Compound 5-45, Compound 5-46, Compound 5-52, Compound 5-53, Compound 5-54, Compound 5-76, Compound 5-77, Compound 5-78, Compound 5-80, Compound 5-81, Compound 5-82, Compound 5-83, Compound 5-84, Compound 5-85, Compound 5-86, Compound 5-87, Compound 5-88, Compound 5-89, Compound 5-90, Compound 5-91, Compound 5-92, Compound 5-93, Compound 5-95, Compound 5-96, Compound 5-97, Compound 5-98, Compound 5-99, Compound 5-100, Compound 5-101, Compound 5-102, Compound 5-103, Compound 5-104, Compound 5-105, Compound 5-106, Compound 5-107, Compound 5-108, Compound 5-111, Compound 5-112, Compound 5-113, Compound 5-114, Compound 5-115, Compound 5-116, Compound 5-117, Compound 5-118, Compound 5-119, Compound 5-120, Compound 5-121, Compound 5-160, Compound 5-161, and Compound 5-162 is shown in Table 5.

Notes: For Compound 5-21, Compound 5-22, Compound 5-23, Compound 5-24, Compound 5-25, Compound 5-26, Compound 5-27, Compound 5-43, Compound 5-44, Compound 5-45, Compound 5-46, Compound 5-52, Compound 5-53, Compound 5-54, Compound 5-76, Compound 5-77, Compound 5-78, Compound 5-80, Compound 5-81, Compound 5-82, Compound 5-83, Compound 5-84, Compound 5-85, Compound 5-86, Compound 5-87, Compound 5-88, Compound 5-89, Compound 5-90, Compound 5-91, Compound 5-92, Compound 5-93, Compound 5-95, Compound 5-96, Compound 5-97, Compound 5-98, Compound 5-99, Compound 5-100, Compound 5-101, Compound 5-102, Compound 5-118, Compound 5-119, Compound 5-120, Compound 5-121, Compound 5-161, and Compound 5-162, (6-Iodo-quinolin-2-yl)-hydrazine was used as the starting material. For Compound 5-77, 2-Hydrazino-6-iodo-quinoline-3-carboxylic acid methyl ester was used as the starting material. For Compound 5-103, Compound 5-104, Compound 5-105, Compound 5-106, Compound 5-107, Compound 5-108, Compound 5-111, Compound 5-112, Compound 5-113, Compound 5-114, Compound 5-115, Compound 5-116, and Compound 5-117, 6-Bromo-quinoxalin-2-ylamine was used as the starting material. For Compound 5-160, 7-Bromo-quinoxalin-2-ylamine was used as the starting material. For Compound 5-21, Compound 5-22, Compound 5-23, Compound 5-24, Compound 5-25, Compound 5-26, Compound 5-27, Compound 5-43, Compound 5-44, Compound 5-45, Compound 5-46, Compound 5-52, Compound 5-53, Compound 5-54, Compound 5-76, Compound 5-77, Compound 5-78, Compound 5-91, Compound 5-92, Compound 5-93, Compound 5-95, Compound 5-96, Compound 5-97, Compound 5-98, Compound 5-103, Compound 5-104, Compound 5-105, Compound 5-106, Compound 5-107, Compound 5-108, Compound 5-111, Compound 5-112, Compound 5-113, Compound 5-114, Compound 5-115, Compound 5-116, Compound 5-117, Compound 5-118, Compound 5-119, Compound 5-120, Compound 5-121, Compound 5-160, Compound 5-161, and Compound 5-162, Step 2 was performed. For Compound 5-99, Compound 5-100, Compound 5-101, and Compound 5-102, Steps 2a and 2b were performed. For Compound 5-80, Compound 5-81, Compound 5-82, Compound 5-83, Compound 5-84, Compound 5-85, Compound 5-86, Compound 5-87, Compound 5-88, Compound 5-89, and Compound 5-90, Step 2a and 2c were performed. For Compound 5-22, Compound 5-25, Compound 5-26, Compound 5-78, Compound 5-96, Compound 5-100, Compound 5-102, Compound 5-111, Compound 1-119, and Compound 1-121, the nitrile in 5p was reduced to give the amide in the product. For Compound 5-43, Compound 5-53, Compound 5-91, Compound 5-98, Compound 5-106, Compound 5-112, Compound 5-113, Compound 5-116, Compound 5-117, Compound 5-160, substituted 3-[3-(Tetrahydro-pyran-4-yl)-phenylsulfanyl]-propionic acid 2-ethyl-hexyl esters were used as 5l. For Compound 5-45 and Compound 5-46, the hydroxy group in 5p was alkylated to give the alkoxy group in the product. For Compound 5-85, the ester in 5p was hydrolyzed to give the acid in the product. For Compound 5-86, Compound 5-87, and Compound 5-88, the ester in 5p was hydrolyzed, and the resulting acid was activated with CDI and then reacted with an amine to give the amide in the product. For Compound 5-89, the hydroxy group in 5p was oxidized to give the ketone in the product. For Compound 5-90, the hydroxy group in 5p was oxidized, and the resulting ketone was reduced with MeMgCl to give the tertiary alcohol in the product. For Compound 5-92, the vinyl group in 5p was reduced to give the ethyl group in the product. For Compound 5-114, the hydroxy group in 5p was methylated, which resulted in the addition of methyl groups at the 4 and 6 positions, and gave the desired methoxy group in the product. For Compound 5-118 and Compound 5-119, the sulfanyl in 5p was oxidized to the sulfinyl in the product. For Compound 5-120 and Compound 5-121, the sulfanyl in 5p was oxidized to the sulfonyl in the product. For Compound 5-161 and Compound 5-162, 4-(5-Mercapto-2-methoxy-phenyl)-tetrahydro-pyran-4-carboxylic acid methyl ester was used as 5l. For Compound 5-162, Compound 5-161 was reacted with pyridine hydrochloride at 180° C. to form the lactone in the product.

Scheme 5D:

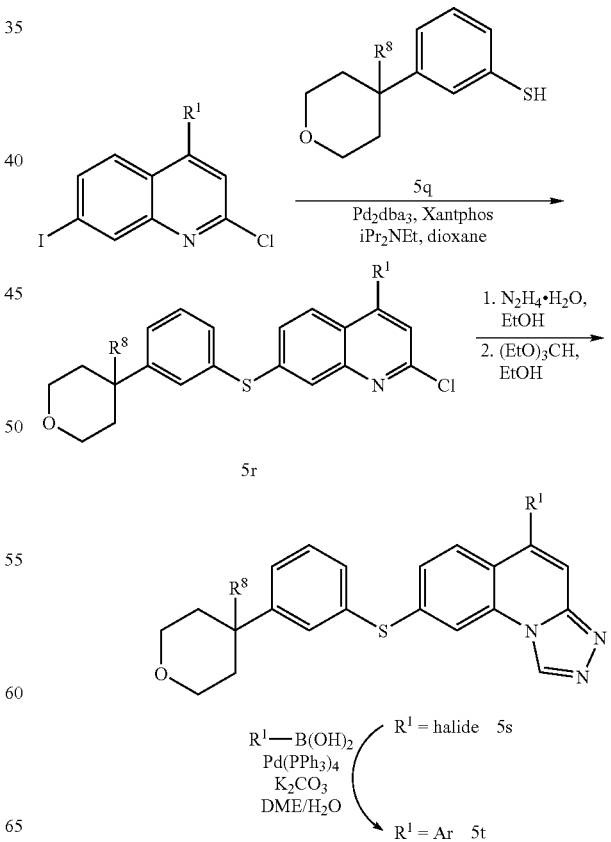

Example 5D

Compound 5-145, Compound 5-146, Compound 5-147, Compound 5-148, Compound 5-149, Compound 5-150, Compound 5-151, and Compound 5-156

Compound 5-145, Compound 5-146, Compound 5-147, Compound 5-148, Compound 5-149, Compound 5-150, and Compound 5-156 were prepared as outlined in Scheme 5D. A detailed illustrative example of the reaction conditions shown in Scheme 5D is described for the synthesis of 4-[3-(5-m-Tolyl-[1,2,4]triazolo[4,3-a]quinolin-8-ylsulfanyl)-phenyl]-tetrahydro-pyran-4-carbonitrile.

Step 1: 4-[3-(2,4-Dichloro-quinolin-7-ylsulfanyl)-phenyl]-tetrahydro-pyran-4-carbonitrile (5r)

2,4-Dichloro-7-iodo-quinoline (3.4 g, 10.5 mmol), 4-(3-Mercapto-phenyl)-tetrahydro-pyran-4-carbonitrile (5q, 2.3 g, 10.5 mmol), iPr$_2$NEt (3.67 mL, 21.0 mmol), Pd$_2$dba$_3$ (240 mg, 0.26 mmol), and 4,5-bis(diphenylphosphino)-9,9-dimethylxanthene (303 mg, 0.52 mmol) were dissolved in 1,4-dioxane (50 mL) and degassed with N$_2$ for 10 minutes. The reaction was heated at 60° C. for 1 hour, and then cooled to room temperature and diluted with EtOAc and saturated aqueous NH$_4$Cl. The aqueous layer was extracted with EtOAc, and the combined organic layers were dried over MgSO$_4$, filtered, and concentrated. The residue was purified by silica gel chromatography (30% EtOAc in hexanes) to give the desired product, 5r.

Step 2: 4-[3-(5-Chloro-[1,2,4]triazolo[4,3-a]quinolin-8-ylsulfanyl)-phenyl]-tetrahydro-pyran-4-carbonitrile (5s)

5r (1 g, 2.4 mmol) was treated with hydrazine, anhydrous (6.6 mL) in EtOH (60 mL) at 60° C. for 1 hour. The reaction was cooled to room temperature and concentrated, and then diluted with CH$_2$Cl$_2$ and water. The organic layer was dried over MgSO$_4$, filtered, and concentrated to give the hydrazino intermediate. The hydrazine was then treated with triethyl orthoformate (6.6 mL) in EtOH (30 mL) at 65° C. overnight. The reaction was cooled to room temperature, concentrated, and purified by silica gel chromatography (0-10% MeOH in CH$_2$Cl$_2$) to give the desired product, 5s.

Step 2a: 4-[3-(5-m-Tolyl-[1,2,4]triazolo[4,3-a]quinolin-8-ylsulfanyl)-phenyl]-tetrahydro-pyran-4-carbonitrile (5t)

5s (70 mg, 0.17 mmol), m-tolylboronic acid (34 mg, 0.25 mmol), Pd$_2$dba$_3$ (4 mg, 0.01 mmol), potassium fluoride (29 mg, 0.50 mmol), and 2-(di-tert-butylphosphino)biphenyl (5 mg, 0.02 mmol) were dissolved in THF (5 mL) and degassed with N$_2$ for 5 minutes. The reaction was heated to 80° C. for 5 hours, then cooled to room temperature and concentrated. The residue was purified by preparative HPLC to give the desired product, 5t.

Mass spectrometry data for Compound 5-145, Compound 5-146, Compound 5-147, Compound 5-148, Compound 5-149, Compound 5-150, Compound 5-151, and Compound 5-156 is shown in Table 5.

Notes: For Compound 5-146, Compound 5-147, and Compound 5-148, Step 2a was performed. For Compound 5-156, the nitrile in 5s was reduced to give the amide in the product.

Scheme 5E:

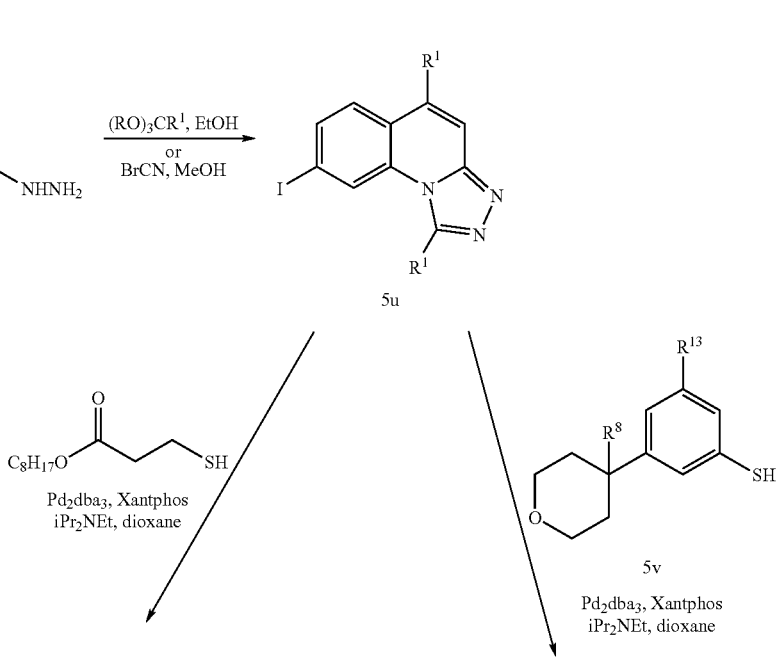

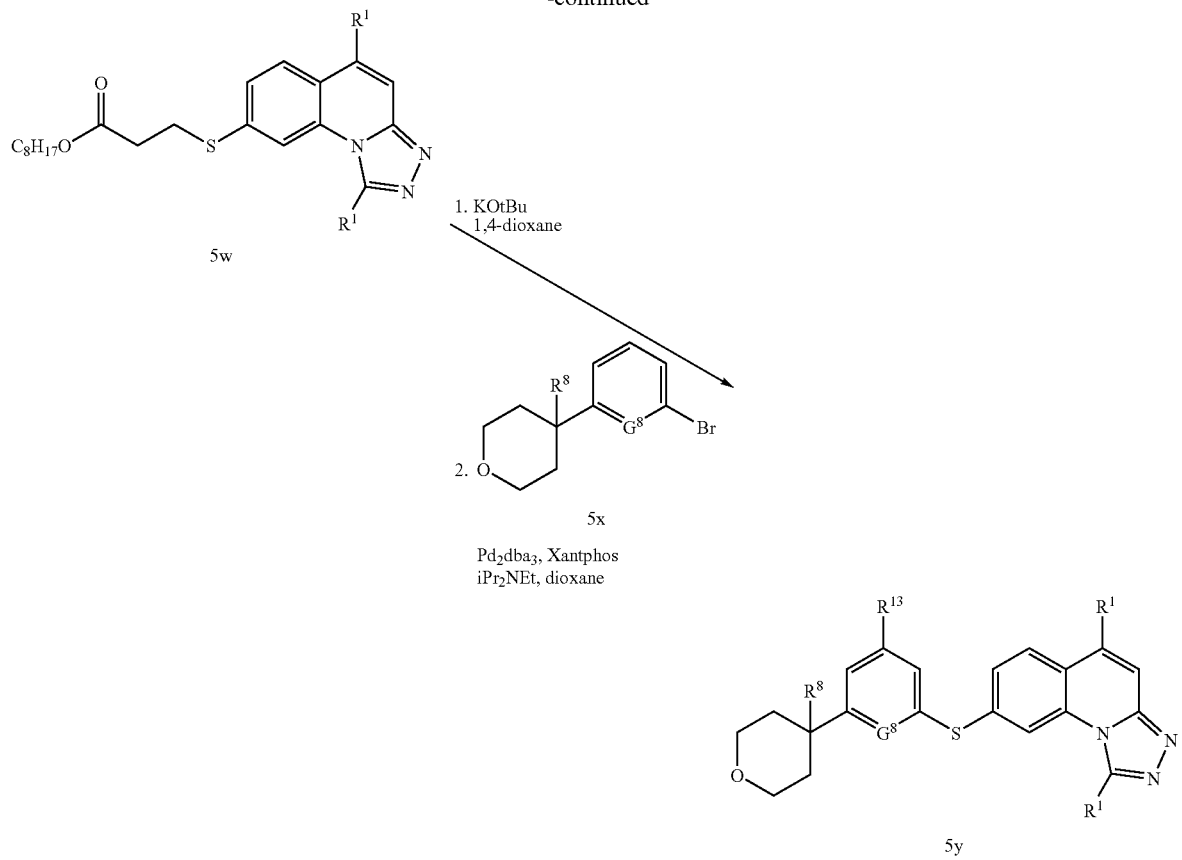

Example 5E

Compound 5-143, Compound 5-144, Compound 5-152, Compound 5-153, Compound 5-154, Compound 5-155, Compound 5-157, Compound 5-158, and Compound 5-159

Compound 5-143, Compound 5-144, Compound 5-151, Compound 5-152, Compound 5-153, Compound 5-154, Compound 5-155, Compound 5-157, Compound 5-158, and Compound 5-159 were prepared as outlined in Scheme 5E. A detailed illustrative example of the reaction conditions shown in Scheme 5E is described for the synthesis of 4-[3-(1-Methyl-5-phenyl-[1,2,4]triazolo[4,3-a]quinolin-8-ylsulfanyl)-phenyl]-tetrahydro-pyran-4-ol and 4-[6-(5-Phenyl-[1,2,4]triazolo[4,3-a]quinolin-8-ylsulfanyl)-pyridin-2-yl]-tetrahydro-pyran-4-ol.

Step 1: 8-Iodo-1-methyl-5-phenyl-[1,2,4]triazolo[4,3-a]quinoline (5u)

To (7-Iodo-4-phenyl-quinolin-2-yl)-hydrazine (400 mg, 1.1 mmol) in EtOH (5 mL) was added trimethyl orthoacetate (2 mL), and the reaction was heated to 80° C. overnight. After cooling to room temperature, the mixture was concentrated and purified by silica gel chromatography (40-100% EtOAc in hexanes) to give the desired product, 5u.

Step 2: 4-[3-(1-Methyl-5-phenyl-[1,2,4]triazolo[4,3-a]quinolin-8-ylsulfanyl)-phenyl]-tetrahydro-pyran-4-ol (5y)

5u (100 mg, 0.26 mmol), 4-(3-Mercapto-phenyl)-tetrahydro-pyran-4-ol (5v, 65 mg, 0.31 mmol), iPr$_2$NEt (0.1 mL, 0.52 mmol), Pd$_2$dba$_3$ (6 mg, 0.01 mmol), and 4,5-bis(diphenylphosphino)-9,9-dimethylxanthene (8 mg, 0.01 mmol) were dissolved in 1,4-dioxane (4 mL) and degassed with N$_2$ for 5 minutes. The mixture was heated to 70° C. until no starting material was seen by tlc analysis. The reaction was cooled to room temperature and concentrated, and the residue was purified by silica gel chromatography to give the desired product, 5y.

Step 2a: 3-(5-Phenyl-[1,2,4]triazolo[4,3-a]quinolin-8-ylsulfanyl)-propionic acid 2-ethyl-hexyl ester (5w)

8-Iodo-5-phenyl-[1,2,4]triazolo[4,3-a]quinoline (900 mg, 3.0 mmol), 3-mercaptopropionic acid 2-ethylhexyl ester (660 mg, 3.0 mmol), iPr$_2$NEt (1.05 mL, 6.0 mmol), Pd$_2$dba$_3$ (69 mg, 0.08 mmol), and 4,5-bis(diphenylphosphino)-9,9-dimethylxanthene (87 mg, 0.15 mmol) were dissolved in 1,4-dioxane (15 mL) and degassed with N$_2$ for 10 minutes. The reaction was heated to 60° C. for 1.5 hours, and then cooled to room temperature and concentrated. The residue was purified by silica gel chromatography (0-100% EtOAc in hexanes) to give the desired product, 5w.

Step 2b: 4-[6-(5-Phenyl-[1,2,4]triazolo[4,3-a]quinolin-8-ylsulfanyl)-pyridin-2-yl]-tetrahydro-pyran-4-ol (5y)

5w (300 mg, 0.87 mmol) was dissolved in DMF (5 mL) and degassed with N$_2$ for 10 minutes, and then cooled to 0° C. Potassium tert-butoxide (146 mg, 1.3 mmol) was added, and the reaction was stirred at room temperature for 10 minutes. 10% aqueous HCl was added to the mixture to obtain pH~2, and the solution was extracted with EtOAc. The combined organic layers were dried over MgSO$_4$, filtered, and concentrated, and the residue was triturated with hexane 3 times to give the thiol intermediate. The thiol (60 mg, 0.22 mol), 4-(6-Bromo-pyridin-2-yl)-tetrahydro-pyran-4-ol (5x, 56 mg, 0.22 mmol), iPr$_2$NEt (0.08 mL, 0.43 mmol), Pd$_2$dba$_3$ (5 mg, 0.01 mmol), and 4,5-bis(diphenylphosphino)-9,9-dimethylx- anthene (6 mg, 0.01 mmol) were dissolved in 1,4-dioxane (2 mL) and degassed with N$_2$ for 10 minutes. The reaction was heated to 60° C. for 2 hours, and then concentrated and purified by silica gel chromatography (0-100% EtOAc in hexanes) to give the desired product, 5y.

Mass spectrometry data for Compound 5-143, Compound 5-144, Compound 5-152, Compound 5-153, Compound 5-154, Compound 5-155, Compound 5-157, Compound 5-158, and Compound 5-159 is shown in Table 5.

Notes: For Compound 5-143, Compound 5-144, Compound 5-153, Compound 5-154, Compound 5-155, Compound 5-157, and Compound 5-159, Step 2 was performed. For Compound 5-152 and Compound 5-158, Steps 2a and 2b were performed. For Compound 5-158, the ester in 5y was hydrolyzed to give the acid in the product.

Scheme 5F:

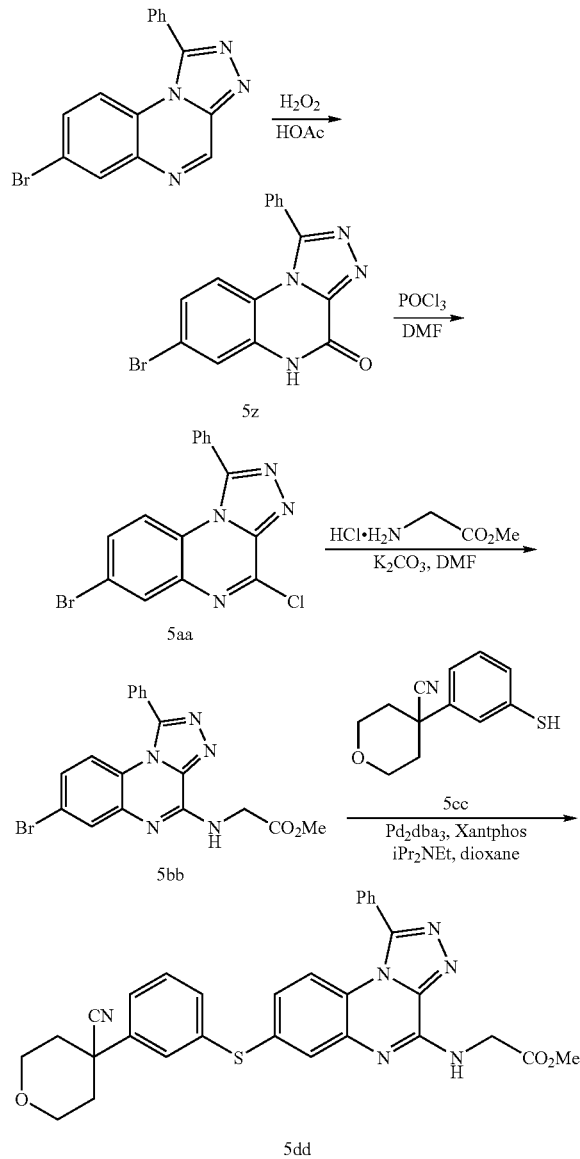

Example 5F

Compound 5-109 and Compound 5-110

Compound 5-109 and Compound 5-110 were prepared as outlined in Scheme 5F. A detailed illustrative example of the reaction conditions shown in Scheme 5F is described for the synthesis of {7-[3-(4-Cyano-tetrahydro-pyran-4-yl)-phenyl-sulfanyl]-1-phenyl-[1,2,4]triazolo[4,3-a]quinoxalin-4-ylamino}-acetic acid methyl ester.

Step 1: 7-Bromo-1-phenyl-5H-[1,2,4]triazolo[4,3-a] quinoxalin-4-one (5z)

7-Bromo-1-phenyl-[1,2,4]triazolo[4,3-a]quinoxaline (279 mg, 0.86 mmol) was dissolved in acetic acid (7.5 mL). Hydrogen peroxide (30%, 2.5 mL) was added, and the reaction was heated to 50° C. overnight. The reaction was poured into water (25 mL) and stirred at room temperature for 2 hours. The precipitate was filtered, washed with water, and dried to obtain the desired product, 5z.

Step 2: 7-Bromo-4-chloro-1-phenyl-[1,2,4]triazolo [4,3-a]quinoxaline (5aa)

5z (197 mg, 0.58 mmol) was dissolved in DMF (3 mL) with heating, and then phosphorus oxychloride (0.27 mL, 2.9 mmol) was added, and the reaction was heated to 80° C. for 1.5 hours. After cooling to room temperature, the mixture was quenched with NaHCO$_3$, and the resulting slurry was stirred at room temperature for 30 minutes and filtered. The solid material was washed with water and dried to obtain the desired product, 5aa.

Step 3: (7-Bromo-1-phenyl-[1,2,4]triazolo[4,3-a] quinoxalin-4-ylamino)-acetic acid methyl ester (5bb)

5aa (193 mg, 0.54 mmol), glycine methyl ester hydrochloride (69 mg, 0.54 mmol), and potassium carbonate (152 mg, 1.1 mmol) were suspended in DMF (2 mL) and heated to 70° C. overnight. After cooling to room temperature, water was added and a precipitate formed. The mixture was stirred overnight and filtered, and the solid material was washed with water to obtain the desired product, 5bb.

Step 4: {7-[3-(4-Cyano-tetrahydro-pyran-4-yl)-phenylsulfanyl]-1 phenyl-[1,2,4]triazolo[4,3-a]quinoxalin-4-ylamino}-acetic acid methyl ester (5dd)

5bb (132 mg, 0.32 mmol) and 4-(3-Mercapto-phenyl)-tetrahydro-pyran-4-carbonitrile (5 cc, 83 mg, 0.35 mmol) were suspended in 1,4-dioxane (3.2 mL) and degassed with N$_2$ for 5 minutes. iPr$_2$NEt (0.13 mL, 0.70 mmol), Pd$_2$dba$_3$ (24 mg, 0.02 mmol), and 4,5-bis(diphenylphosphino)-9,9-dimethylxanthene (30 mg, 0.05 mmol) were added, and the reaction was sealed and heated to 110° C. overnight. Starting material still remained, so the mixture was degassed with N$_2$ for 10 minutes and additional 5cc (105 mg), Pd$_2$dba$_3$ (22 mg), and 4,5-bis(diphenylphosphino)-9,9-dimethylxanthene (29 mg) was added. After heating for 3 days at 110° C., the reaction was cooled to room temperature and concentrated. The residue was diluted with CH$_2$Cl$_2$ and water, and the aqueous layer was extracted with CH$_2$Cl$_2$. The combined organic fractions were dried over MgSO$_4$, filtered, adsorbed on silica gel, and concentrated. The crude material was purified by silica gel chromatography (20-100% EtOAc in hexanes, followed by 0-10% MeOH in EtOAc) to give the desired product, 5dd.

Mass spectrometry data for Compound 5-109 and Compound 5-110 is shown in Table 5.

Notes: For Compound 5-110, the ester in 5dd was hydrolyzed to give the acid in the product.

Scheme 6:

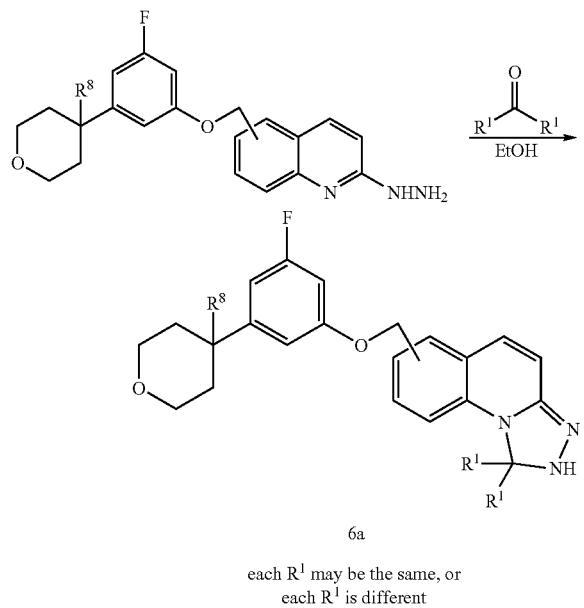

each R¹ may be the same, or
each R¹ is different

Example 6

Preparation of Compound 6-1, Compound 6-2, Compound 6-3, Compound 6-4, Compound 6-5, Compound 6-6, Compound 6-7, Compound 6-8, Compound 6-9, Compound 6-10, Compound 6-11, and Compound 6-12

Compound 6-1, Compound 6-2, Compound 6-3, Compound 6-4, Compound 6-5, Compound 6-6, Compound 6-7, Compound 6-8, Compound 6-9, Compound 6-10, Compound 6-11, and Compound 6-12 were prepared as outlined in Scheme 6. A detailed illustrative example of the reaction conditions shown in Scheme 6 is described for the synthesis of 7-[3-Fluoro-5-(4-methoxy-tetrahydro-pyran-4-yl)-phenoxymethyl]-1,1-dimethyl-1,2-dihydro-[1,2,4]triazolo[4,3-a]quinoline.

Step 1: 7-[3-Fluoro-5-(4-methoxy-tetrahydro-pyran-4-yl)-phenoxymethyl]-1,1-dimethyl-1,2-dihydro-[1,2,4]triazolo[4,3-a]quinoline (6a)

{6-[3-Fluoro-5-(4-methoxy-tetrahydro-pyran-4-yl)-phenoxymethyl]-quinolin-2-yl}-hydrazine (36 mg, 0.09 mmol) was suspended in EtOH (2 mL). Acetone (0.01 mL, 0.18 mmol) was added, and the reaction was heated at 75° C. overnight. The mixture was concentrated and purified by silica gel chromatography to give the desired product, 6a.

Mass spectrometry data for Compound 6-1, Compound 6-2, Compound 6-3, Compound 6-4, Compound 6-5, Compound 6-6, Compound 6-7, Compound 6-8, Compound 6-9, Compound 6-10, Compound 6-11, and Compound 6-12 is shown in Table 6.

Scheme 7:

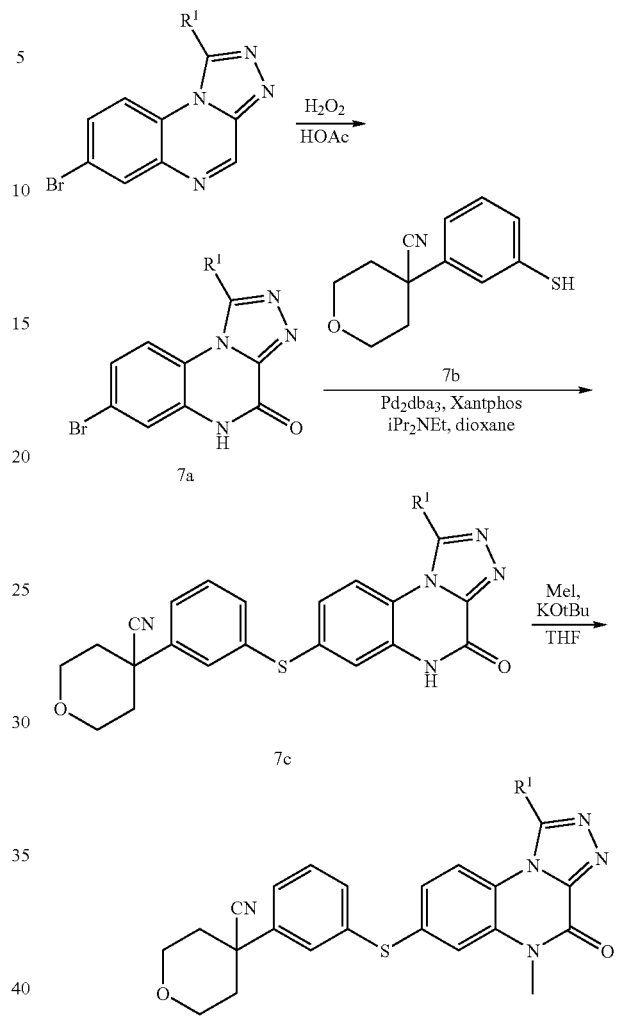

Example 7

Preparation of Compound 7-1, Compound 7-2, and Compound 7-3

Compound 7-1, Compound 7-2, and Compound 7-3 were prepared as outlined in Scheme 7. A detailed illustrative example of the reaction conditions shown in Scheme 7 is described for the synthesis of 4-[3-(5-Methyl-4-oxo-1-phenyl-4,5-dihydro-[1,2,4]triazolo[4,3-a]quinoxalin-7-ylsulfanyl)-phenyl]-tetrahydro-pyran-4-carbonitrile.

Step 1: 7-Bromo-1-phenyl-5H-[1,2,4]triazolo[4,3-a]quinoxalin-4-one (7a)

7-Bromo-1-phenyl-[1,2,4]triazolo[4,3-a]quinoxaline (7.4 g, 22.7 mmol), hydrogen peroxide (30%, 59 mL), and acetic acid (185 mL) were combined and heated at 50° C. overnight. Additional hydrogen peroxide (30%, 15 mL) was added to push the reaction to completion, and the mixture was stirred overnight at room temperature. The reaction was added to water (550 mL) and the precipitate was filtered and rinsed with water to give the desired product, 7a.

Step 2: 4-[3-(4-Oxo-1-phenyl-4,5-dihydro-[1,2,4]triazolo[4,3-a]quinoxalin-7-ylsulfanyl)-phenyl]-tetrahydro-pyran-4-carbonitrile (7c)

7a (108 mg, 0.32 mmol) and 4-(3-mercapto-phenyl)-tetrahydro-pyran-4-carbonitrile (7b, 86 mg, 0.38 mmol) were dissolved in NMP (3.2 mL) and degassed with $N_2$ for 20 minutes. $iPr_2NEt$ (0.12 mL, 0.70 mmol) was added, followed by $Pd_2dba_3$ (15 mg, 0.02 mmol) and 4,5-bis(diphenylphosphino)-9,9-dimethylxanthene (19 mg, 0.03 mmol). The reaction was sealed and heated overnight at 130° C., and then cooled to room temperature and diluted with EtOAc and water. The organic layer was washed with water and brine, dried over $MgSO_4$, filtered, and concentrated. The residue was purified by silica gel chromatography (25-100% EtOAc in hexanes, followed by 10% MeOH in EtOAc) to give the desired product, 7c.

Step 3: 4-[3-(5-Methyl-4-oxo-1-phenyl-4,5-dihydro-[1,2,4]triazolo[4,3-a]quinoxalin-7-ylsulfanyl)-phenyl]-tetrahydro-pyran-4-carbonitrile (7d)

7c (58 mg, 0.12 mmol) was dissolved in THF (1.2 μL) and cooled to 0° C. Potassium tert-butoxide (18 mg, 0.16 mmol) was added, followed by iodomethane (0.01 mL, 0.18 mmol), and the reaction was warmed to room temperature and stirred overnight. The reaction was diluted with EtOAc and water, and the aqueous layer was extracted with EtOAc. The combined organics were washed with brine, dried over $MgSO_4$, filtered, and concentrated. The residue was purified by silica gel chromatography (20-100% EtOAc, followed by 10% MeOH in EtOAc) to give the desired product, 7d.

Mass spectrometry data for Compound 7-1, Compound 7-2, and Compound 7-3 is shown in Table 7.

Notes: For Compound 7-1, Step 3 was not performed. For Compound 7-3, Step 1 and Step 2 were reversed; Step 3 was not performed.

Scheme 8:

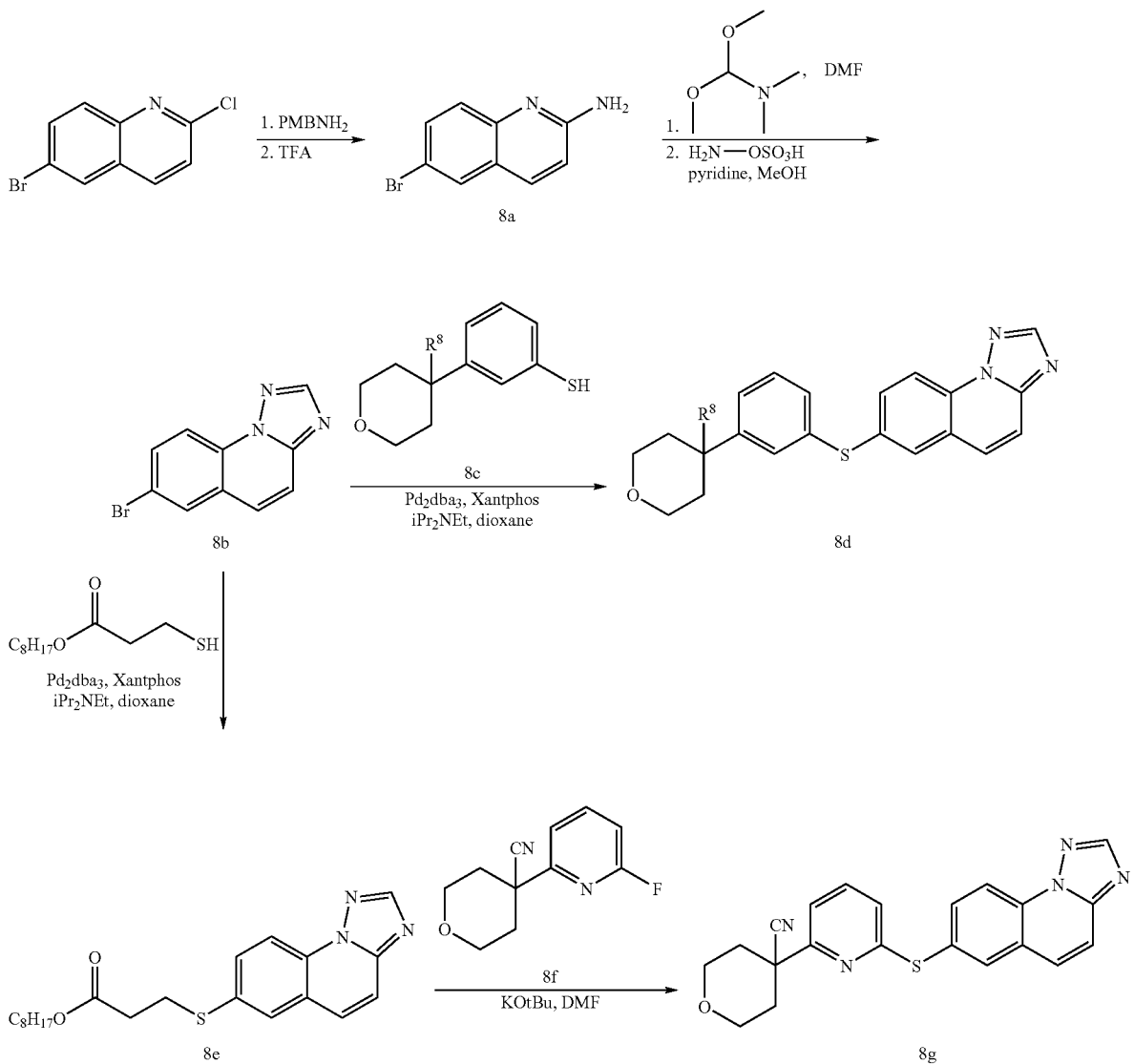

207

Example 8

Preparation of Compound 8-1, Compound 8-2, Compound 8-3, Compound 8-4, Compound 8-5, and Compound 8-6

Compound 8-1, Compound 8-2, Compound 8-3, Compound 8-4, Compound 8-5, and Compound 8-6 were prepared as outlined in Scheme 8. A detailed illustrative example of the reaction conditions shown in Scheme 8 is described for the synthesis of 4-[6-([1,2,4]Triazolo[1,5-a]quinolin-7-ylsulfanyl)-pyridin-2-yl]-tetrahydro-pyran-4-carbonitrile.

Step 1: 6-Bromo-quinolin-2-ylamine (8a)

6-Bromo-2-chloro-quinoline (3.34 g, 13.8 mmol) was dissolved in p-methoxybenzylamine (5 mL) and heated to 140° C. for 1 hour. The mixture was cooled to room temperature, filtered, and concentrated. The residue was purified by silica gel chromatography, and the isolated material was refluxed in TFA (6 mL) for 1 hour. The mixture was concentrated and purified by silica gel chromatography to give the desired product, 8a.

Step 2: 7-Bromo-[1,2,4]triazolo[1,5-a]quinoline (8b)

8a (497 mg, 2.46 mmol) and dimethoxymethyldimethylamine (1 mL) were combined in DMF (5 mL) and heated to 130° C. for 1 hour. The reaction was concentrated and redissolved in MeOH (5 mL) and pyridine (400 mg). Hydroxylamine-O-sulfonic acid (282 mg, 2.49 mmol) was added, and the mixture was stirred at room temperature for 3 days. The solution was concentrated and poured into water, and the resulting solid was filtered and dried to give the desired product, 8b.

Step 3: 4-[3-([1,2,4]Triazolo[1,5-a]quinolin-7-ylsulfanyl)-phenyl]-tetrahydro-pyran-4-carbonitrile (8d)

8b (66 mg, 0.25 mmol) and 4-(3-Mercapto-phenyl)-tetrahydro-pyran-4-carbonitrile (8c, 90 mg, 0.32 mmol) were dissolved in 1,4-dioxane (5 mL) and degassed for 10 minutes with $N_2$. $iPr_2NEt$ (0.15 mL, 0.80 mmol) was added, followed by $Pd_2dba_3$ (10 mg, 0.01 mmol) and 4,5-bis(diphenylphosphino)-9,9-dimethylxanthene (12 mg, 0.02 mmol), and the mixture was degassed with $N_2$ for an additional 10 minutes. The reaction was sealed and heated overnight at 110° C. Additional catalyst was added after 24 hours to push the reaction to completion, and the mixture was heated at 110° C. for another 2 hours. The reaction was cooled to room temperature and purified by silica gel chromatography (25-100% EtOAc in hexanes) to give the desired product, 8d.

Step 4: 3-([1,2,4]Triazolo[1,5-a]quinolin-7-ylsulfanyl)-propionic acid 2-ethyl-hexyl ester (8e)

8b (120 mg, 0.48 mmol) and 3-mercaptopropionic acid 2-ethylhexyl ester (110 mg, 0.55 mmol) were dissolved in 1,4-dioxane (5 mL) and degassed for 10 minutes with $N_2$. $iPr_2NEt$ (0.16 mL, 0.89 mmol) was added, followed by $Pd_2dba_3$ (10 mg, 0.01 mmol) and 4,5-bis(diphenylphosphino)-9,9-dimethylxanthene (12 mg, 0.02 mmol), and the mixture was degassed with $N_2$ for an additional 10 minutes. The reaction was sealed and heated at 110° C. for 4 hours. The reaction was cooled to room temperature and purified by silica gel chromatography (25-100% EtOAc in hexanes) to give the desired product, 8e.

208

Step 5: 4-[6-([1,2,4]Triazolo[1,5-a]quinolin-7-ylsulfanyl)-pyridin-2-yl]-tetrahydro-pyran-4-carbonitrile (8g)

8e (201 mg, 0.50 mmol) and 4-(6-Fluoro-pyridin-2-yl)-tetrahydro-pyran-4-carbonitrile (8f, 105 mg, 0.51 mmol) were dissolved in DMF at room temperature and degassed for 10 minutes with $N_2$. Potassium tert-butoxide (67 mg, 0.60 mmol) was added, and the mixture was degassed with $N_2$ for another 10 minutes. The reaction was heated to 90° C. for 12 hours, and then concentrated and purified by silica gel chromatography (25-50% EtOAc in hexanes) to give the desired product, 8g.

Mass spectrometry data for Compound 8-1, Compound 8-2, Compound 8-3, Compound 8-4, Compound 8-5, and Compound 8-6 is shown in Table 8.

Notes: For Compound 8-1, Compound 8-2, Compound 8-3, and Compound 8-4, Steps 1-5 were performed. For Compound 8-2, the nitrile in 8d was reduced to give the amide in the product. For Compound 8-3, the hydroxy group in 8d was alkylated to give the methoxy group in the product. For Compound 8-5 and Compound 8-6, Steps 1-4 and Steps 6-7 were performed. For Compound 8-6, the nitrile in 8g was reduced to give the amide in the product.

Scheme 9A:

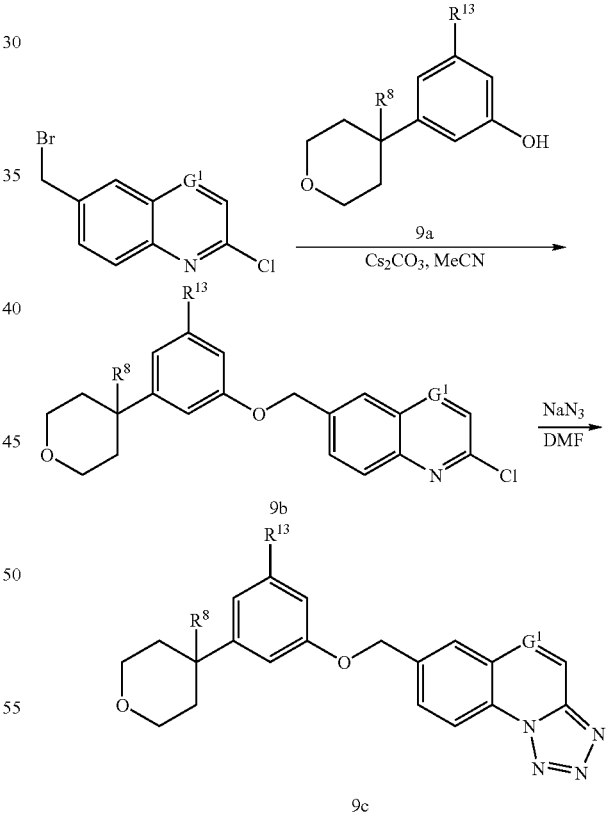

Example 9A

Preparation of Compound 9-1, Compound 9-2, Compound 9-3, Compound 9-4, and Compound 9-7

Compound 9-1, Compound 9-2, Compound 9-3, Compound 9-4, and Compound 9-7 were prepared as outlined in

209

Scheme 9A. A detailed illustrative example of the reaction conditions shown in Scheme 9A is described for the synthesis of 7-[3-Fluoro-5-(4-methoxy-tetrahydro-pyran-4-yl)-phenoxymethyl]-1,2,3,9b-tetraaza-cyclopenta[a]naphthalene.

Step 1: 2-Chloro-6-[3-fluoro-5-(4-methoxy-tetrahydro-pyran-4-yl)-phenoxymethyl]-quinoline (9b)

6-Bromomethyl-2-chloro-quinoline (2.5 g, 9.7 mmol), 3-fluoro-5-(4-methoxy-tetrahydro-pyran-4-yl)-phenol (9a, 2.2 g, 9.7 mmol), and cesium carbonate (4.7 g, 14.6 mmol) were combined in MeCN (25 mL) and stirred at room temperature for 2 hours. The reaction was diluted with EtOAc and water, and the aqueous layer was extracted with EtOAc. The combined organic layers were washed with brine, dried over MgSO$_4$, filtered, and concentrated to give the desired product, 9b.

Step 2: 7-[3-Fluoro-5-(4-methoxy-tetrahydro-pyran-4-yl)-phenoxymethyl]-1,2,3,9b-tetraaza-cyclopenta[a]naphthalene (9c)

To 9b (29 mg, 0.07 mmol) in DMF (1 mL) was added sodium azide (9 mg, 0.09 mmol). The reaction was heated at 130° C. overnight, then cooled to room temperature and diluted with EtOAc and water. The aqueous layer was extracted with EtOAc, and the combined organic layers were dried over MgSO$_4$, filtered, and concentrated. The crude material was purified by silica gel chromatography (50% EtOAc in hexanes) to give the desired product, 9c.

Mass spectrometry data for Compound 9-1, Compound 9-2, Compound 9-3, Compound 9-4, and Compound 9-7 is shown in Table 9.

Notes: For Compound 9-3 and Compound 9-4, the ester in 9c was hydrolyzed to give the acid in the product.

Scheme 9B:

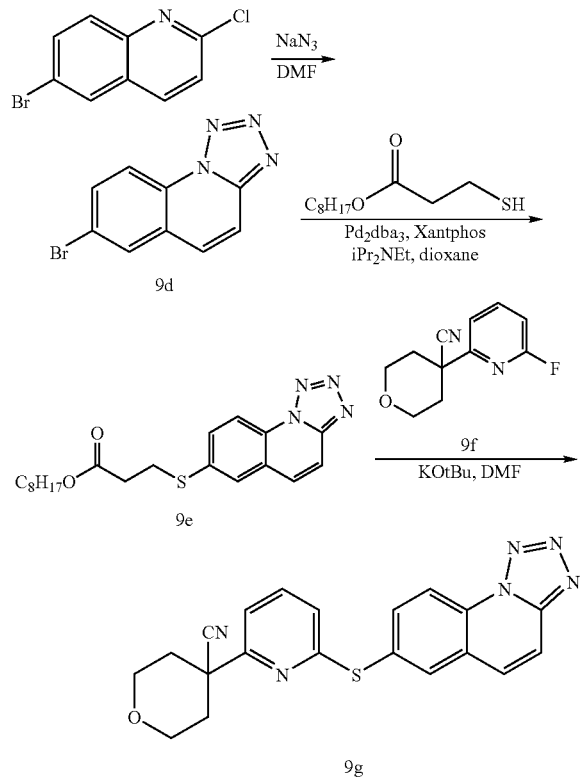

210

Example 9B

Preparation of Compound 9-5 and Compound 9-6

Compound 9-5 and Compound 9-6 were prepared as outlined in Scheme 9B. A detailed illustrative example of the reaction conditions shown in Scheme 9B is described for the synthesis of 4-[6-(1,2,3,9b-Tetraaza-cyclopenta[a]naphthalen-7-ylsulfanyl)-pyridin-2-yl]-tetrahydro-pyran-4-carbonitrile.

Step 1: 7-Bromo-1,2,3,9b-tetraaza-cyclopenta[a]naphthalene (9d)

To 6-Bromo-2-chloro-quinoline (223 mg, 1.0 mmol) in DMF (10 mL) was added sodium azide (65 mg, 1.0 mmol). The reaction was heated at 130° C. for 1 hour, then cooled to room temperature and diluted with EtOAc and water. The aqueous layer was extracted with EtOAc, and the combined organic layers were dried over MgSO$_4$, filtered, and concentrated. The crude material was purified by silica gel chromatography (50% EtOAc in hexanes) to give the desired product, 9d.

Step 2: 3-(1,2,3,9b-Tetraaza-cyclopenta[a]naphthalen-7-ylsulfanyl)-propionic acid 2-ethyl-hexyl ester (9e)

9d (233 mg, 0.88 mmol) and 3-mercaptopropionic acid 2-ethylhexyl ester (86 mg, 0.38 mmol) were dissolved in 1,4-dioxane (10 mL) and degassed with N$_2$ for 10 minutes. iPr$_2$NEt (0.33 mL, 1.80 mmol) was added, followed by Pd$_2$dba$_3$ (20 mg, 0.02 mmol) and 4,5-bis(diphenylphosphino)-9,9-dimethylxanthene (23 mg, 0.04 mmol). The reaction was sealed and heated overnight at 130° C., and then cooled to room temperature and diluted with EtOAc and water. The organic layer was washed with water and brine, dried over MgSO$_4$, filtered, and concentrated. The residue was purified by silica gel chromatography (0-20% MeOH in EtOAc) to give the desired product, 9e.

Step 3: 4-[6-(1,2,3,9b-Tetraaza-cyclopenta[a]naphthalen-7-ylsulfanyl)-pyridin-2-yl]-tetrahydro-pyran-4-carbonitrile (9g)

9e (110 mg, 0.28 mmol) and 4-(6-fluoro-pyridin-2-yl)-tetrahydro-pyran-4-carbonitrile (9f, 60 mg, 0.28 mmol) were dissolved in DMF and degassed with N$_2$ for 10 minutes. Potassium tert-butoxide (38 mg, 0.34 mmol) was added, and the reaction was degassed with N$_2$ for another 10 minutes, and then heated to 90° C. for 2 hours. After cooling to room temperature, the mixture was concentrated and purified by silica gel chromatography to obtain the desired product, 9g.

Mass spectrometry data for Compound 9-5 and Compound 9-6 is shown in Table 9.

Notes: For Compound 9-6, the nitrile in 9g was reduced to give the amide in the product.

Scheme 10A:

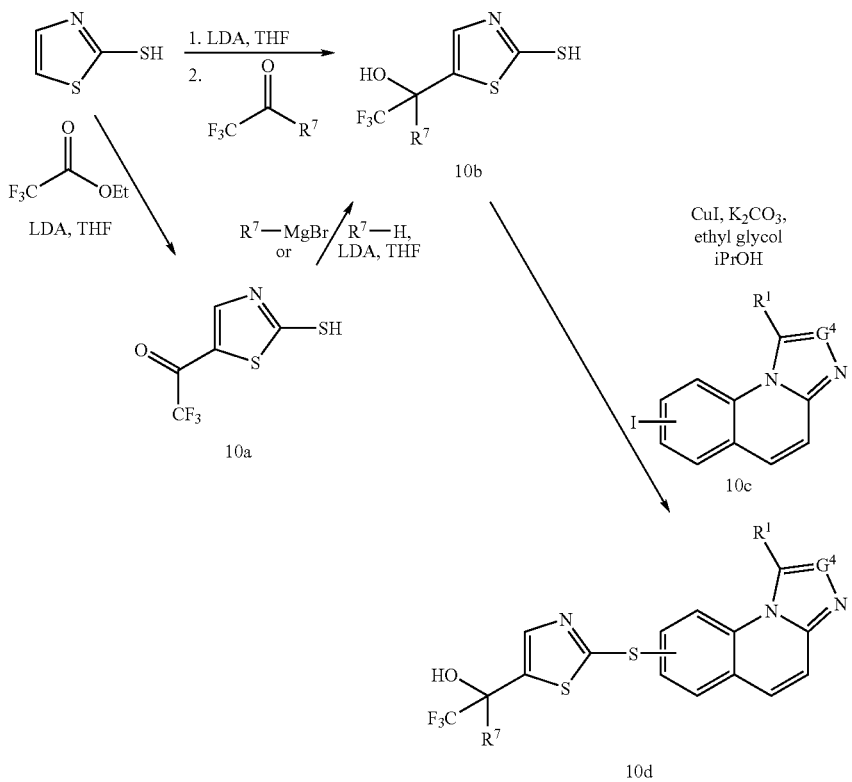

Example 10A

Preparation of Compound 10-1, Compound 10-2, Compound 10-3, Compound 10-4, Compound 10-5, Compound 10-6, Compound 10-10, Compound 10-13, Compound 10-14, Compound 10-15, and Compound 10-16

Compound 10-1, Compound 10-2, Compound 10-3, Compound 10-4, Compound 10-5, Compound 10-6, Compound 10-10, Compound 10-13, Compound 10-14, Compound 10-15, and Compound 10-16 were prepared as outlined in Scheme 10A. A detailed illustrative example of the reaction conditions shown in Scheme 10A is described for the synthesis of 1,1,1-Trifluoro-2-[2-(1-phenyl-[1,2,4]triazolo[4,3-a]quinolin-7-ylsulfanyl)-thiazol-5-yl]-butan-2-ol.

Step 1: 1,1,1-Trifluoro-2-(2-mercapto-thiazol-5-yl)-butan-2-ol (10b)

iPr$_2$NH (2.0 g, 19.9 mmol) was dissolved in THF (23 mL) and cooled to −78° C. n-Butyllithium (2.5M, 8.0 mL, 19.9 mmol) was added dropwise, followed by thiazole-2-thiol (0.9 g, 7.9 mmol) in THF (5 mL). After 10 minutes, trifluoro-2-butanone (0.5 g, 4.0 mmol) was added and the reaction was stirred at −78° C. for 6 hours. The reaction was warmed to room temperature and quenched with 5% aqueous NH$_4$Cl (20 mL). The aqueous layer was acidified and extracted with EtOAc, and the combined organic layers were dried over MgSO$_4$, filtered, and concentrated. The residue was purified by silica gel chromatography (50% EtOAc in hexanes) to give the desired product, 10b.

Step 1a: 2,2,2-Trifluoro-1-(2-mercapto-thiazol-5-yl)-ethanone (10a)

iPr$_2$NH (1.0 g, 9.4 mmol) was dissolved in THF (12 mL) and cooled to −10° C. n-Butyllithium (2.5M, 3.8 mL, 9.4 mmol) was added dropwise, and the reaction was cooled to −78° C. Thiazole-2-thiol (1.0 g, 8.5 mmol) in THF (2.5 mL) was added, followed by ethyl trifluoroacetate (1.3 mL, 11.1 mmol), and the reaction was stirred at −78° C. for 1 hours. The reaction was warmed to −10° C. and quenched with 5% aqueous NH$_4$Cl (10 mL). The aqueous layer was acidified and extracted with EtOAc, and the combined organic layers were dried over MgSO$_4$, filtered, and concentrated. The residue was purified by silica gel chromatography (50% EtOAc in hexanes) to give the desired product, 10a.

Step 1b: 4,4,4-Trifluoro-3-hydroxy-3-(2-mercapto-thiazol-5-yl)-butyric acid ethyl ester (10b)

iPr$_2$NH (205 mg, 2.0 mmol) was dissolved in THF (3.5 mL) and cooled to −10° C. n-Butyllithium (2.5M, 0.81 mL, 2.0 mmol) was added dropwise, and the reaction was cooled to −78° C. EtOAc (179 mg, 2.0 µmmol) in THF (0.5 mL) was added, followed by 10a (188 mg, 0.9 mmol) in THF (10.5 mL), and the reaction was stirred at −78° C. for 1 hour. The reaction was warmed to −10° C. and quenched with 5% aqueous NH$_4$Cl (10 mL). The aqueous layer was extracted with EtOAc, and the combined organic layers were washed with 1N HCl and brine, dried over MgSO$_4$, filtered, and concentrated. The residue was purified by silica gel chromatography (50% Et$_2$O in hexanes) to give the desired product, 10b.

Step 2: 1,1,1-Trifluoro-2-[2-(1-phenyl-[1,2,4]triazolo[4,3-a]quinolin-7-ylsulfanyl)-thiazol-5-yl]-butan-2-ol (10d)

7-Iodo-1-phenyl-[1,2,4]triazolo[4,3-a]quinoline (10c, 140 mg, 0.38 mmol), copper iodide (14 mg, 0.08 mmol), and potassium carbonate (105 mg, 0.76 mmol) were suspended in iPrOH (1 mL). 10b (92 mg, 0.38 mmol) in iPrOH (1 mL) was added, followed by ethyl glycol (0.04 mL, 0.76 mmol), and the reaction was heated to 90° C. overnight. The reaction was diluted with EtOAc and water, and the aqueous layer was extracted with EtOAc. The combined organic layers were dried over MgSO$_4$, filtered, and concentrated. The residue was purified by silica gel chromatography (5% MeOH in CH$_2$Cl$_2$), and the isolated product was precipitated from CH$_2$Cl$_2$ to give the desired product, 10d.

Mass spectrometry data for Compound 10-1, Compound 10-2, Compound 10-3, Compound 10-4, Compound 10-5, Compound 10-6, Compound 10-10, Compound 10-13, Compound 10-14, Compound 10-15, and Compound 10-16 is shown in Table 10.

Notes: For Compound 10-1, Compound 10-2, Compound 10-3, Compound 10-10, Compound 10-13, Compound 10-14, Compound 10-15, and Compound 10-16, Step 1 was performed. For Compound 10-4, Compound 10-5, and Compound 10-6, Steps 1a and 1b were performed. For Compound 10-1, Compound 10-2, Compound 10-3, Compound 10-4, Compound 10-5, and Compound 10-6, substituted 7-iodo-[1,2,4]triazolo[4,3-a]quinolines were used as 10c. For Compound 10-10, 7-iodo-imidazo[1,2-a]quinoline was used as 10c. For Compound 10-13, Compound 10-14, Compound 10-15, and Compound 10-16, substituted 8-iodo-[1,2,4]triazolo[4,3-a]quinolines were used as 10c. For Compound 10-16, R$^1$ is substituted at the 5 position, not the 1 position.

Scheme 10B:

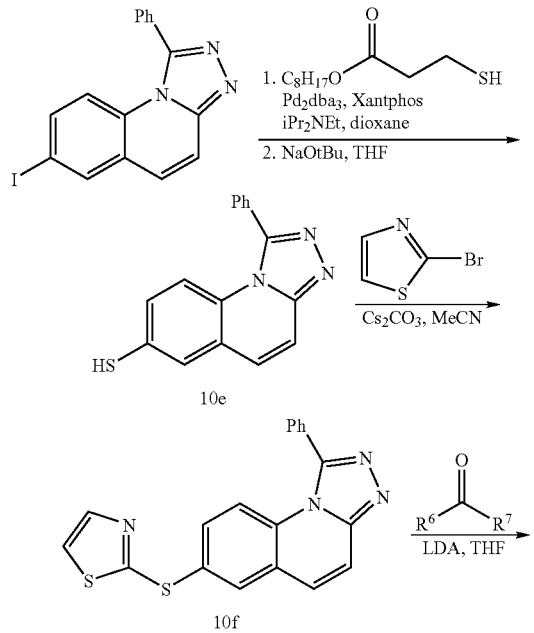

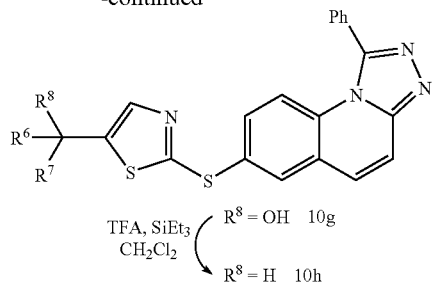

Example 10B

Preparation of Compound 10-7, Compound 10-8, and Compound 10-9

Compound 10-7, Compound 10-8, and Compound 10-9 were prepared as outlined in Scheme 10B. A detailed illustrative example of the reaction conditions shown in Scheme 10B is described for the synthesis of 7-(5-Dicyclopropylmethyl-thiazol-2-ylsulfanyl)-1-phenyl-[1,2,4]triazolo[4,3-a]quinoline.

Step 1: 1-Phenyl-[1,2,4]triazolo[4,3-a]quinoline-7-thiol (10e)

To 7-Iodo-1-phenyl-[1,2,4]triazolo[4,3-a]quinoline (1.5 g, 4.0 mmol) in 1,4-dioxane (15 mL) was added iPr$_2$NEt (1.4 mL, 8.1 mmol), and the reaction was degassed with N$_2$ for 10 minutes. 3-Mercapto-propionic acid 2-ethylhexyl ester (975 mg, 4.5 mmol) was added, followed by Pd$_2$dba$_3$ (93 mg, 0.1 mmol) and 4,5-bis(diphenylphosphino)-9,9-dimethylxanthene (117 mg, 0.2 mmol). The reaction was sealed and heated overnight at 80° C., and then cooled to room temperature and concentrated. The residue was purified by silica gel chromatography (60-100% EtOAc in hexanes) to give the thiol intermediate as an oil. The oil was dissolved in THF (9 mL) and cooled to −78° C. Sodium tert-butoxide (780 mg, 8.1 mmol) was added, and the reaction was stirred at room temperature overnight. The mixture was diluted with 1N NaOH, and the aqueous layer was washed with Et$_2$O. The aqueous layer was acidified with 1N HCl and extracted with EtOAc. The combined organic layers were dried over MgSO$_4$, filtered, and concentrated, and the crude material was purified by silica gel chromatography (60-100% EtOAc in hexanes) to give the desired product, 10e.

Step 2: 1-Phenyl-7-(thiazol-2-ylsulfanyl)-[1,2,4]triazolo[4,3-a]quinoline (10f)

To 2-Bromothiazole (0.27 mL, 3.0 mmol) in 1,4-dioxane (20 mL) was added iPr$_2$NEt (0.96 mL, 5.5 mmol), and the reaction was degassed with N$_2$ for 10 minutes. 10e (765 mg, 2.8 mmol) was added, followed by Pd$_2$dba$_3$ (63 mg, 0.07 mmol) and 4,5-bis(diphenylphosphino)-9,9-dimethylxanthene (81 mg, 0.14 mmol). The reaction was sealed and heated overnight at 80° C., and then cooled to room temperature and concentrated. The residue was diluted with EtOAc and water, and the aqueous layer was extracted with EtOAc. The combined organic layers were dried over MgSO$_4$, filtered, and concentrated, and the crude material was purified by silica gel chromatography (60-100% EtOAc in hexanes) to give the desired product, 10f.

Step 3: Dicyclopropyl-[2-(1-phenyl-[1,2,4]triazolo[4,3-a]quinolin-7-ylsulfanyl)-thiazol-5-yl]-methanol (10g)

iPr$_2$NH (0.12 g, 0.84 mmol) was dissolved in THF (2 mL) and cooled to −78° C. n-Butyllithium (2.5M, 0.37 mL, 0.84 mmol) was added dropwise, followed by 10f (150 mg, 0.42 mmol) in THF (5 mL). Dicyclopropylmethanone (53 mg, 0.46 mmol) in THF (0.25 mL) was added, and the reaction was stirred overnight at room temperature. The reaction was quenched with 5% aqueous NH$_4$Cl (10 mL). The aqueous layer was extracted with EtOAc, and the combined organic layers were dried over MgSO$_4$, filtered, and concentrated. The residue was purified by preparative HPLC to give the desired product, 10g.

Step 3a: 7-(5-Dicyclopropylmethyl-thiazol-2-ylsulfanyl)-1-phenyl-[1,2,4]triazolo[4,3-a]quinoline (10h)

To 10g (23 mg, 0.05 mmol) in CH$_2$Cl$_2$ (3 mL) was added triethylsilane (0.04 mL, 0.24 mmol) and TFA (0.04 mL, 0.49 mmol) at 0° C. After 4 hours at room temperature, additional triethylsilane (0.02 mL, 0.12 mmol) and TFA (0.02 mL, 0.25 mmol) as added at 0° C., and the reaction was stirred for another 3 hours at room temperature. The reaction was washed with saturated aqueous NaHCO$_3$, and the aqueous layer was extracted with EtOAc. The combined organic layers were dried over MgSO$_4$, filtered, and concentrated. The crude material was purified by silica gel chromatography to give the desired product, 10h.

Mass spectrometry data for Compound 10-7, Compound 10-8, and Compound 10-9 is shown in Table 10.

Notes: For Compound 10-9, Step 3a was performed.

Scheme 10C:

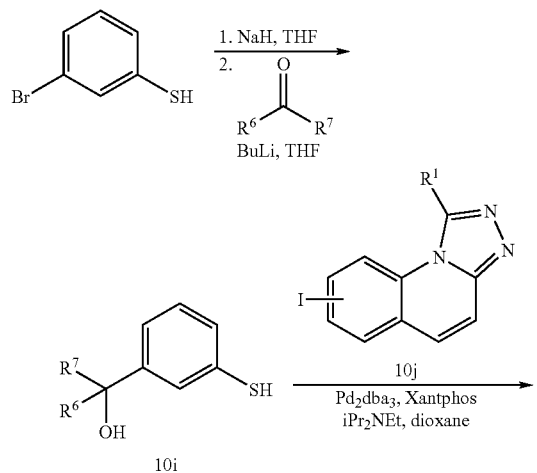

-continued

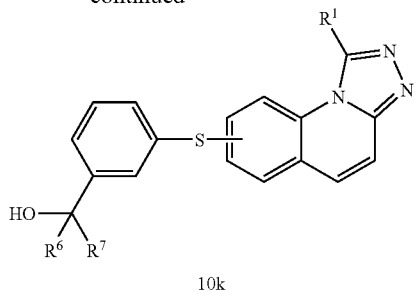

10k

Example 10C

Preparation of Compound 10-11, Compound 10-12, and Compound 10-17

Compound 10-11, Compound 10-12, and Compound 10-17 were prepared as outlined in Scheme 10C. A detailed illustrative example of the reaction conditions shown in Scheme 10C is described for the synthesis of Dicyclopropyl-[3-(1-phenyl-[1,2,4]triazolo[4,3-a]quinolin-7-ylsulfanyl)-phenyl]-methanol.

Step 1: Dicyclopropyl-(3-mercapto-phenyl)-methanol (10i)

3-Bromobenzenethiol (2.0 g, 10.6 mmol) was dissolved in THF (20 mL) and cooled to −5° C. under N$_2$. Sodium hydride (60 wt %, 477 mg, 11.6 mmol) was added portionwise, and the reaction was then cooled to −78° C. n-Butyllithium (2.5M, 4.7 mL, 11.6 mmol) was added over 20 minutes, followed by dicyclopropylmethanone (1.2 mL, 10.6 mmol), and the reaction was slowly warmed to room temperature over 3 hours. The reaction was acidified with 1N aqueous HCl to pH 2, and the reaction mixture was extracted with EtOAc three times. The combined organic layers were dried over MgSO$_4$, filtered, and concentrated. The residue was purified by silica gel chromatography (0-80% EtOAc in hexanes) to give the desired product, 10i.

Step 2: Dicyclopropyl-[3-(1-phenyl-[1,2,4]triazolo[4,3-a]quinolin-7-ylsulfanyl)-phenyl]-methanol (10k)

To 7-iodo-1-phenyl-[1,2,4]triazolo[4,3-a]quinoline (10j, 176 mg, 0.47 μmmol) in 1,4-dioxane (4.5 mL) was added iPr$_2$NEt (0.16 mL, 0.94 mmol), and the reaction was degassed with N$_2$ for 5 minutes. 10i (174 mg, 0.47 mmol) was added, followed by Pd$_2$dba$_3$ (22 mg, 0.02 mmol) and 4,5-bis(diphenylphosphino)-9,9-dimethylxanthene (28 mg, 0.05 mmol). The reaction was sealed and heated at 100° C. for 6 hours, and then cooled to room temperature and concentrated. The residue was purified by silica gel chromatography (60-80% EtOAc in hexanes) to give the desired product, 10k.

Mass spectrometry data for Compound 10-11, Compound 10-12, and Compound 10-17 is shown in Table 10.

Notes: For Compound 10-11 and Compound 10-12, substituted 7-iodo-[1,2,4]triazolo[4,3-a]quinolines were used as 10j. For Compound 10-17, 8-iodo-5-phenyl-[1,2,4]triazolo[4,3-a]quinoline was used as 10j; R$^1$ is substituted at the 5 position, not the 1 position.

Scheme 10D:

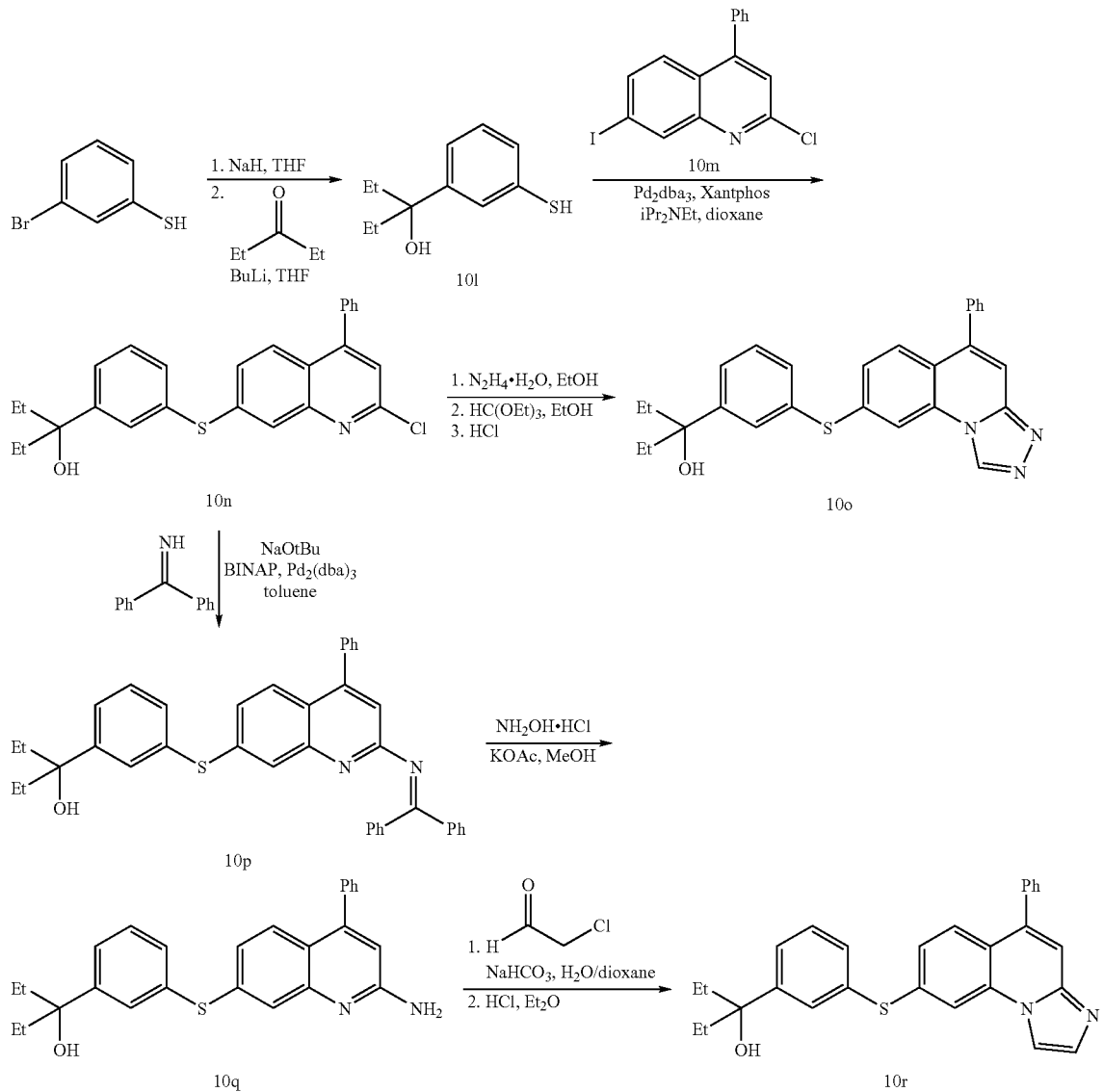

Example 10D

Preparation of Compound 10-18 and Compound 10-19

Compound 10-18 and Compound 10-19 were prepared as outlined in Scheme 10D. A detailed illustrative example of the reaction conditions shown in Scheme 10D is described for the synthesis of 3-[3-(5-Phenyl-[1,2,4]triazolo[4,3-a]quinolin-8-ylsulfanyl)-phenyl]-pentan-3-ol and 3-[3-(5-Phenyl-imidazo[1,2-a]quinolin-8-ylsulfanyl)-phenyl]-pentan-3-ol.

Step 1: 3-(3-Mercapto-phenyl)-pentan-3-ol (10l)

To 3-Bromobenzenethiol (1.6 mL, 13.5 mmol) in THF (10 mL) at 0° C. was added sodium hydride (60 wt %, 600 mg, 14.9 mmol). After stirring for 10 minutes, the reaction was cooled to −78° C. and n-butyllithium (7.4 mL, 14.9 mmol) was added dropwise. After stirring for 20 minutes, 3-pentanone (1.6 mL, 14.9 mmol) was added, and the reaction was slowly warmed to room temperature and immediately acidified with 1N aqueous HCl to pH 3. The reaction mixture was extracted with EtOAc, and the combined organic layers were dried over MgSO$_4$, filtered, and concentrated. The residue was purified by silica gel chromatography (5% EtOAc in hexanes) to give the desired product, 10l.

Step 2: 3-[3-(2-Chloro-4-phenyl-quinolin-7-ylsulfanyl)-phenyl]-pentan-3-ol (10n)

10l (900 mg, 4.6 mmol), 2-chloro-7-iodo-4-phenyl-quinoline (10m, 1.6 g, 4.6 mmol), iPr$_2$NEt (1.6 mL, 9.2 mmol), Pd$_2$dba$_3$ (104 mg, 0.1 mmol), and 4,5-bis(diphenylphosphino)-9,9-dimethylxanthene (132 mg, 0.2 mmol) were dissolved in 1,4-dioxane (15 mL) and degassed with N$_2$ for 10 minutes. The reaction was heated to 60° C. for 1 hour, and then diluted with saturated aqueous NH₄Cl and EtOAc. The aqueous layer was extracted with EtOAc, and the combined organic layers were dried over MgSO₄, filtered, and concentrated. The residue was purified by silica gel chromatography (30% EtOAc in hexanes) to give the desired product, 10n.

Step 3: 3-[3-(5-Phenyl-[1,2,4]triazolo[4,3-a]quinolin-8-ylsulfanyl)-phenyl]-pentan-3-ol (10o)

10n (200 mg, 0.46 mmol) was treated with anhydrous hydrazine (2 mL) in EtOH (2 mL) at 60° C. for 1 hour. The reaction was concentrated and diluted with CH₂Cl₂ and water. The organic layer was dried over MgSO₄, filtered, and concentrated. The residue was then treated with ethyl orthoformate (2.5 mL) in EtOH (5 mL) at 65° C. overnight. The mixture was concentrated and diluted with EtOAc and water. The aqueous layer was extracted with EtOAc, and the combined organic layers were dried over MgSO₄, filtered, and concentrated. The residue was purified by silica gel chromatography to give the desired product, 10o. The hydrochloride salt was prepared by dissolving the product in CH₂Cl₂, adding 1N HCl in ether, and concentrating the mixture.

Step 4: 3-[3-[2-(Benzhydrylidene-amino)-4-phenyl-quinolin-7-ylsulfanyl]-phenyl]-pentan-3-ol (10p)

10n (500 mg, 1.8 mmol), benzophenone imine (0.31 mL, 1.8 mmol), sodium tert-butoxide (265 mg, 2.8 mmol), BINAP (115 mg, 0.2 mmol), and Pd₂dba₃ (42 mg, 0.05 mmol) were dissolved in toluene (10 mL) and degassed for 10 minutes with N₂. The reaction was then sealed and heated to 80° C. for 2 hours. After cooling to room temperature, the mixture was diluted with EtOAc and brine, and the aqueous layer was extracted with EtOAc. The combined organic layers were dried over MgSO₄, filtered, and concentrated, and the residue was purified by silica gel chromatography (30% EtOAc in hexanes) to give the desired product, 10p.

Step 5: 3-[3-(2-Amino-4-phenyl-quinolin-7-ylsulfanyl)-phenyl]-pentan-3-ol (10q)

10p (990 mg, 15.5 mmol), hydroxylamine hydrochloride (220 mg, 31.1 mmol), and potassium acetate (310 mg, 31.1 mmol) were dissolved in MeOH (1.5 mL) and stirred overnight at room temperature. The reaction was concentrated and purified by silica gel chromatography (30% EtOAc in hexanes) to give the desired product, 10q.

Step 6: 3-[3-(5-Phenyl-imidazo[1,2-a]quinolin-8-ylsulfanyl)-phenyl]-pentan-3-ol (10r)

To 10q (200 mg, 0.48 mmol) in 1,4-dioxane (4 mL) was added chloroacetaldehyde (0.07 mL, 0.53 mmol), sodium bicarbonate (243 mg, 2.89 mmol), and water (2 mL). The mixture was heated to 80° C. for 5 hours, and then cooled to room temperature and concentrated. The residue was purified by silica gel chromatography (30% EtOAc in hexanes) to give the desired product, 10r.

Mass spectrometry data for Compound 10-18 and Compound 10-19 is shown in Table 10.

Notes: For Compound 10-18, Steps 1-3 were performed. For Compound 10-19, Steps 1-2 and Steps 4-6 were performed.

Scheme 11:

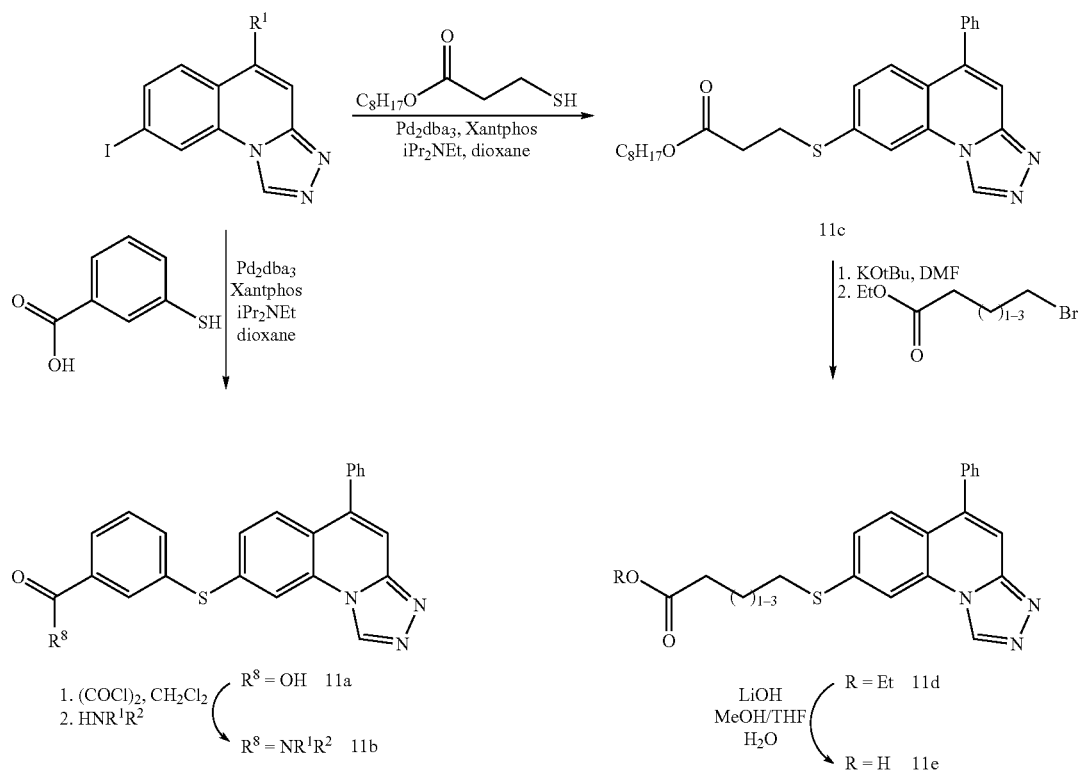

Example 11

Preparation of Compound 11-1, Compound 11-2, Compound 11-3, Compound 114, Compound 11-5, Compound 11-6, Compound 11-7, Compound 11-8, Compound 11-9, Compound 11-10, Compound 11-11, Compound 11-12, Compound 11-13, and Compound 11-14

Compound 11-1, Compound 11-2, Compound 11-3, Compound 11-4, Compound 11-5, Compound 11-6, Compound 11-7, Compound 11-8, Compound 11-9, Compound 11-10, Compound 11-11, Compound 11-12, Compound 11-13, and Compound 11-14 were prepared as outlined in Scheme 11. A detailed illustrative example of the reaction conditions shown in Scheme 11 is described for the synthesis of N,N-Dimethyl-3-(5-phenyl-[1,2,4]triazolo[4,3-a]quinolin-8-ylsulfanyl)-benzamide and 4-(5-Phenyl-[1,2,4]triazolo[4,3-a]quinolin-8-ylsulfanyl)-butyric acid.

Step 1: 3-(5-Phenyl-[1,2,4]triazolo[4,3-a]quinolin-8-ylsulfanyl)-benzoic acid (11a)

8-Iodo-5-phenyl-[1,2,4]triazolo[4,3-a]quinoline (250 mg, 0.67 mmol), 3-mercaptobenzoic acid (120 mg, 0.81 mmol), iPr$_2$NEt (0.36 mL, 2.1 mmol), Pd$_2$dba$_3$ (15 mg, 0.02 mmol), and 4,5-bis(diphenylphosphino)-9,9-dimethylxanthene (19 mg, 0.03 mmol) were dissolved in 1,4-dioxane and degassed with N$_2$. The reaction was then sealed and heated to 70° C. for 30 minutes, followed by cooling to room temperature, filtration, and concentration to give the desired product, 11a.

Step 1a: N,N-Dimethyl-3-(5-phenyl-[1,2,4]triazolo[4,3-a]quinolin-8-ylsulfanyl)-benzamide (11b)

To 11a (219 mg, 0.67 mmol) in CH$_2$Cl$_2$ (30 mL) was added oxalyl chloride (0.07 mL, 0.80 mmol) and a drop of DMF. The mixture was then concentrated, and the residue was redissolved in CH$_2$Cl$_2$ and divided into 5 portions. To one portion, dimethylamine (2.0M, 0.3 mL, 0.54 mmol) was added, and the mixture was stirred at room temperature until no SM was observed by LCMS analysis. The reaction was concentrated and purified by preparative HPLC to give the desired product, 11b.

Step 2: 3-(5-Phenyl-[1,2,4]triazolo[4,3-a]quinolin-8-ylsulfanyl)-propionic acid 2-ethyl-hexyl ester (11c)

8-Iodo-5-phenyl-[1,2,4]triazolo[4,3-a]quinoline (900 mg, 3.0 mmol), 3-mercaptopropionic acid 2-ethylhexyl ester (660 mg, 3.0 mmol), iPr$_2$NEt (1.1 mL, 6.3 mmol), Pd$_2$dba$_3$ (69 mg, 0.05 mmol), and 4,5-bis(diphenylphosphino)-9,9-dimethylxanthene (87 mg, 0.15 mmol) were dissolved in 1,4-dioxane (15 mL) and degassed for 10 minutes with N$_2$. The reaction was then sealed and heated to 60° C. for 1.5 hours, followed by cooling to room temperature and concentration. The residue was purified by silica gel chromatography (30% EtOAc in hexanes) to give the desired product, 11c.

Step 3: 4-(5-Phenyl-[1,2,4]triazolo[4,3-a]quinolin-8-ylsulfanyl)-butyric acid ethyl ester (11d)

11c (100 mg, 0.21 mmol) in DMF (1 mL) was degassed for 5 minutes with N$_2$, and then cooled to 0° C. under N$_2$. Potassium tert-butoxide (29 mg, 0.26 mmol) in DMF (1 mL) was degassed for 5 minutes with N$_2$, and then added to the solution of 11c. The reaction was warmed to room temperature, and LCMS analysis showed no starting material remained after 10 minutes. Ethyl 4-bromobutyrate (0.04 mL, 0.24 mmol) was added, and the mixture was stirred for 20 minutes. The reaction was diluted with EtOAc and water, and the aqueous layer was extracted with EtOAc. The combined organic layers were dried over MgSO$_4$, filtered, and concentrated, and the residue was purified by silica gel chromatography (0-100% EtOAc in hexanes) to give the desired product, 11d.

Step 3a: 4-(5-Phenyl-[1,2,4]triazolo[4,3-a]quinolin-8-ylsulfanyl)-butyric acid (11e)

11d (40 mg, 0.10 mmol) was treated with 1N aqueous LiOH (2 mL) in 3:3:1 THF:MeOH:H$_2$O (2 mL) overnight at room temperature. 1N aqueous HCl was added to adjust to pH 4, and the aqueous layer was extracted with EtOAc. The combined organic layers were dried over MgSO$_4$, filtered, and concentrated to give the desired product, 11e.

Mass spectrometry data for Compound 11-1, Compound 11-2, Compound 11-3, Compound 11-4, Compound 11-5, Compound 11-6, Compound 11-7, Compound 11-8, Compound 11-9, Compound 11-10, Compound 11-11, Compound 11-12, Compound 11-13, and Compound 11-14 is shown in Table 11.

Notes: For Compound 1, 2-bromothiazol was used in place of ethyl 4-bromobutyrate. For Compound 11-5, Compound 11-6, and Compound 11-7, Step 3a was performed. For Compound 11-9, Compound 11-10, Compound 11-11, Compound 11-12, and Compound 11-13, Step 1a was performed. For Compound 11-14, 1-(3-mercapto-phenyl)-cyclopentanol was used in place of 3-mercaptobenzoic acid; following the coupling reaction, dehydration occurred to give the final product.

Example 12

Human 5-Lipoxygenase Activity Inhibition Assay

A non-limiting example of a 5-lipoxygenase activity inhibition assay is as follows:
Human polymorphonuclear leukocytes are prepared from blood by Ficoll-Hypaque separation, lysed and centrifuged at 100,000×g. The 100,000×g supernatant containing 5-lipoxygenase is added to tubes, containing 100 mM Tris Cl pH 8.0, 2 mM ATP, 2 mM calcium and incubated with 20-200 µM arachidonic acid in a final volume of 100 µL for 1-10 minutes at 37° C. Reaction is terminated by the addition of an equal volume of ice cold methanol, centrifuged at 10,000×g for 10 minutes and supernatant analyzed by reverse phase HPLC for formation of 5-HETE/5HPETE monitoring absorbance at 235 nm.

Example 13

Human Leukocyte LTB$_4$ Inhibition Assay

A non-limiting example of a human leukocyte inhibition assay is as follows;
Blood was drawn from consenting human volunteers into heparinized tubes and 3% dextran 0.9% saline equal volume added. After sedimentation of red blood cells a hypotonic lysis of remaining red blood cells was performed and leukocytes sedimented at 1000 rpm. The pellet was resuspended at 1.25×10$^5$ cells/ml and aliquoted into wells containing 2.5 µL 20% DMSO (vehicle) or 2.5 µL drug in 20% DMSO. Samples were incubated for 5 minutes at 37° C. and 2 µL calcium ionophore A23817 (from a 50 mM DMSO stock diluted just prior to the assay in Hanks balanced salt solution (Invitrogen)) to 1.25 mM) was added, solutions mixed and incubated for 30 minutes at 37° C. Samples were centrifuged at 1,000 rpm (~200×g) for 10 minutes at 4° C., plasma removed and a 1:4 dilution assayed for $LTB_4$ concentration using ELISA (Assay Designs). Drug concentrations to achieve 50% inhibition ($IC_{50}$'s) of vehicle $LTB_4$ were determined by nonlinear regression (Graphpad Prism) of % inhibition versus log drug concentration.

Example 14

Human Blood $LTB_4$ Inhibition Assay

A non-limiting example of such a human blood $LTB_4$ inhibition assay is as follows:
Blood was drawn from consenting human volunteers into heparinized tubes and 125 µL aliquots added to wells containing 2.5 µL 50% DMSO (vehicle) or 2.5 µL drug in 50% DMSO. Samples were incubated for 15 minutes at 37° C. 2 µL calcium ionophore A23817 (from a 50 mM DMSO stock diluted just prior to the assay in Hanks balanced salt solution (Invitrogen)) to 1.25 mM) was added, solutions mixed and incubated for 30 minutes at 37° C. Samples were centrifuged at 1,000 rpm (~200×g) for 10 minutes at 4° C., plasma removed and a 1:100 dilution assayed for $LTB_4$ concentration using ELISA (Assay Designs). Drug concentrations to achieve 50% inhibition ($IC_{50}$'s) of vehicle $LTB_4$ were determined by nonlinear regression (Graphpad Prism) of % inhibition versus log drug concentration.

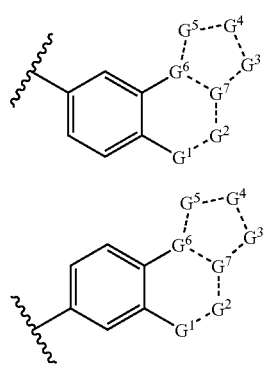

A1

A2

Compound A1: (a) $G^3$ and $G^6$=N; $G^1$, $G^2$, $G^4$, $G^5$+CH and $G^7$=C; $IC_{50}$=a
(b) $G^3$, $G^4$ and $G^6$=N; $G^1$, $G^2$, $G^5$=CH and $G^7$=C; $IC_{50}$=b
(c) $G^3$, $G^4$, $G^5$ and $G^6$=N; $G^1$, $G^2$=CH and $G^7$=C; $IC_{50}$=a
Compound A2: (a) $G^3$ and $G^6$=N; $G^1$, $G^2$, $G^4$, $G^5$=CH and $G^7$=C; $IC_{50}$=a
(b) $G^3$, $G^4$ and $G^6$=N; $G^1$, $G^2$, $G^5$=CH and $G^7$=C; $IC_{50}$=c
Key: a is <200 nM; b is between 200 and 1000 nm; c is greater than 1000 nm.

Example 15

Rat Peritoneal Inflammation and Edema Assay

A non-limiting example of such a rat peritoneal inflammation and edema assay is as follows:
The in vivo efficacy of leukotriene biosynthesis inhibitors against inflammation and vascular edema was assessed using a rat model of peritoneal inflammation. Male Sprague-Dawley rats (weighing 200-300 grams) received a single intraperitoneal (i.p.) injection of 3 ml saline containing zymosan (5 mg/mL) followed immediately by an intravenous (i.v.) injection of Evans blue dye (2 mL of 1.5% solution). Compounds were administered orally (3 mL/kg in 0.5% methylcellulose vehicle) 2 to 4 hours prior to zymosan injection. One to two hours after zymosan injection, rats were euthanized, and the peritoneal cavity was flushed with 10 mL phosphate buffered saline solution (PBS). The resulting fluid was centrifuged at 1,200 rpm for 10 minutes. Vascular edema was assesses by quantifying the amount of Evans blue dye in the supernatant using a spectrophotometer (Absorbance 610 nm). $LTB_4$ and cysteinyl leukotriene concentrations in the supernatant were determined by ELISA. Drug concentrations to achieve 50% inhibition of plasma leakage (Evans blue dye) and inhibition of peritoneal $LTB_4$ and cysteinyl leukotrienes could be calculated by nonlinear regression (Graphpad Prism) of % inhibition versus log drug concentration.

In Vivo Activity: Rat Peritoneal Assay (@ 30 mpk PO)

A1

(a) $G^3$ and $G^6$=N; $G^1$, $G^2$, $G^4$, $G^5$=CH and $G^7$=C; 90% inhibition of $LTB_4$
(b) $G^3$, $G^4$ and $G^6$=N; $G^1$, $G^2$, $G^5$=CH and $G^7$=C; 85% inhibition of $LTB_4$ Example 16

Rat Ionophore Lung Lavage

A non-limiting example of such a rat ionophore lung lavage assay is as follows:
A rat ionophore lung lavage model (see Smith et al., J.P.E.T., 1995, 275, 1332-1338) was utilized to determine efficacy of leukotriene biosynthesis inhibitors in the target tissue for respiratory therapy. Male Sprague-Dawley rats (weighing 200-300 grams) were administered compound orally (3 ml/kg in 0.5% methylcellulose vehicle) 2 to 4 hours prior to lung lavage. $LTB_4$ and cysteinyl leukotrienes were stimulated within the lung via an intra-tracheal instillation of 10 ml PBS containing 20 µg/mL calcium ionophore. After a 3-min period the fluid was withdrawn from the lung and was centrifuged at 1,200 rpm for 10 minutes. $LTB_4$ and cysteinyl leukotriene concentrations in the supernatant were determined by ELISA. Drug concentrations to achieve 50% inhibition of lung $LTB_4$ and cysteinyl leukotrienes could be calculated by nonlinear regression (Graphpad Prism) of % inhibition versus log drug concentration.

Example 17

Pharmacokinetic Analysis

A non-limiting example of such a pharmacokinetic analysis is as follows:

Catheterized rats (SD-JVC from Charles River) were fasted over night (n=2/group) and then dosed with compound either at 2 mg/kg IV or 10 mg/kg PO. For IV dosing, compounds were given in solution using 10% EtOH/40% PEG/50% H2O as vehicle and blood samples were drawn at 5, 15 and 30 mins, 1, 2, 4, 6, 8 hours. For PO dosing, compounds were given in solution using 25% Hydroxypropyl-beta-cyclodextrin in water as vehicle and blood samples were drawn at 30 mins, 1, 2, 4, 6, 8 hours PO. Samples were then analyzed by HPLC-MS/MS.

In Vivo Rat Pharmacokinetics (Dosed at 1 mpk IV; 10 mpk PO

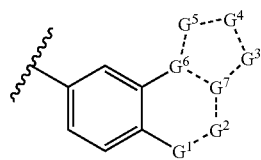

A1

(a) $G^3$ and $G^6$=N; $G^1$, $G^2$, $G^4$, $G^5$=CH and $G^7$=C; $T_{1/2}$=1.5 hr; $AUC_{PO}$ 2.4 hr*ug/mL
(b) $G^3$, $G^4$ and $G^6$=N; $G^1$, $G^2$ $G^5$=CH and $G^7$=C; $T_{1/2}$=1.3 hr; $AUC_{PO}$ 3.1 hr*ug/mL
(c) $G^3$, $G^4$, $G^5$ and $G^6$=N; $G^1$, $G^2$=CH and $G^7$=C; $T_{1/2}$=3 hr; $AUC_{PO}$ 0.6 hr*ug/mL.

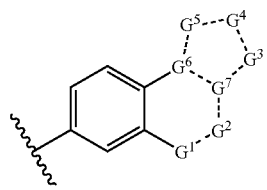

A2

$G^3$ and $G^6$=N; $G^1$, $G^2$, $G^4$, $G^5$=CH and $G^7$=C; $T_{1/2}$=2.2 hr; $AUC_{PO}$ 0.6 hr*ug/mL.

Example 18

Pharmaceutical Compositions

Example 18a

Parenteral Composition

To prepare a parenteral pharmaceutical composition suitable for administration by injection, 100 mg of a water-soluble salt of a compound described herein is dissolved in DMSO and then mixed with 10 mL of 0.9% sterile saline. The mixture is incorporated into a dosage unit form suitable for administration by injection.

Example 18b

Oral Composition

To prepare a pharmaceutical composition for oral delivery, 100 mg of a compound described herein is mixed with 750 mg of starch. The mixture is incorporated into an oral dosage unit for, such as a hard gelatin capsule, which is suitable for oral administration.

Example 18c

Sublingual (Hard Lozenge) Composition

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 18d

Inhalation Composition

To prepare a pharmaceutical composition for inhalation delivery, 20 mg of a compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

Example 18e

Rectal Gel Composition

To prepare a pharmaceutical composition for rectal delivery, 100 mg of a compound described herein is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 18f

Topical Gel Composition

To prepare a pharmaceutical topical gel composition, 100 mg of a compound described herein is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example 18g

Ophthalmic Solution Composition

To prepare a pharmaceutical ophthalmic solution composition, 100 mg of a compound described herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

The examples and embodiments described herein are for illustrative purposes only and various modifications or changes suggested to persons skilled in the art are to be included within the spirit and purview of this application and scope of the appended claims. All publications, patents, and patent applications cited herein are hereby incorporated by reference for all purposes.

What is claimed is:

1. A compound having a structure represented by Formula (IIIc):

Formula (IIIc)

wherein:
G$^1$ is CR$^1$;
G$^4$ is CR$^1$;
each R$^1$ is independently H, halide, —CN, —NO$_2$, —OH, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, —NHCH$_2$C(=O)OR$^3$, —C(=O)N(R$^3$)$_2$, —NHC(=O)R$^3$, or —C(OH)(R$^3$)$_2$, C$_1$-C$_6$alkyl, C$_1$-C$_6$fluoroalkyl, C$_3$-C$_8$cycloalkyl, or C$_1$-C$_6$fluoroalkoxy; or
R$^1$ is Q$^1$-Q$^2$ where Q$^1$ is phenyl or monocyclic heteroaryl; and Q$^2$ is H, halide, —CN, —NO$_2$, C$_1$-C$_6$alkyl, C$_1$-C$_6$alkoxy, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, or —C(=O)N(R$^3$)$_2$;
each R$^3$ is independently H, C$_1$-C$_6$alkyl, C$_3$-C$_8$cycloalkyl, phenyl, or benzyl;
L$^1$ is —(CHR$^4$)$_n$X$^1$(CHR$^4$)$_n$— wherein,
each n is independently 0, or 1;
X$^1$ is a O, S, S(=O), or S(=O)$_2$;
each R$^4$ is H;
R$^6$ and R$^7$ are independently H, C$_1$-C$_6$haloalkyl, C$_1$-C$_6$alkyl, or C$_3$-C$_8$cycloalkyl;
or R$^6$ and R$^7$ can together form an optionally substituted a 5-, or 6-membered non-aromatic monocyclic ring containing 0 or 1 oxygen atom, wherein the ring is optionally substituted with F, —CH$_3$ or —CF$_3$;
R$^8$ is H, —OH, —CONH$_2$, tetrazolyl, —CN, —CO$_2$H, —OR$^{12}$, —CON(R$^{12}$)$_2$, —CO$_2$—R$^{12}$, C(=O)R$^{12}$, C(OH)(R$^{12}$)$_2$, —CH=N—OR$^{12}$, —N(R$^{12}$)$_2$, NHC(=O)R$^{12}$, or —OC(=O)R$^{12}$; where each R$^{12}$ is independently H, or C$_1$-C$_6$alkyl;
R$^9$ is H;
R$^{13}$ is H, C$_1$-C$_6$alkyl, or halide;
R$^{14}$ is H, C$_1$-C$_6$alkyl, or halide;
or a pharmaceutically acceptable salt, or pharmaceutically acceptable N-oxide thereof.

2. The compound of claim 1, wherein:
L$^1$ is selected from among —(CHR$^4$)$_n$—, —(CHR$^4$)$_n$O—, —(CHR$^4$)$_n$S—, —O(CHR$^4$)$_n$—, and —S(CHR$^4$)$_n$—;
each R$^4$ is H;
n is 0, or 1.

3. The compound of claim 2, wherein:
R$^{13}$ is H or halide;
R$^{14}$ is H.

4. The compound of claim 3, wherein:
each R$^1$ is independently H, halide, —CN, —NO$_2$, —OH, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, —NHCH$_2$C(=O)OR$^3$, —C(=O)N(R$^3$)$_2$, —NHC(=O)R$^3$, or —C(OH)(R$^3$)$_2$, C$_1$-C$_6$alkyl, C$_1$-C$_6$fluoroalkyl, C$_3$-C$_8$cycloalkyl, or C$_1$-C$_6$fluoroalkoxy; or
R$^1$ is Q$^1$-Q$^2$ where Q$^1$ is phenyl, or monocyclic heteroaryl; and Q$^2$ is H, halide, —CN, —NO$_2$, C$_1$-C$_6$alkyl, C$_1$-C$_6$alkoxy, —OR$^3$, —SR$^3$, —S(=O)R$^3$, —S(=O)$_2$R$^3$, —C(=O)R$^3$, —C(=O)OR$^3$, —CH(R$^3$)$_2$, —N(R$^3$)$_2$, or —C(=O)N(R$^3$)$_2$.

5. The compound of claim 4, wherein:
R$^6$ and R$^7$ are independently H, C$_1$-C$_6$haloalkyl, C$_1$-C$_6$alkyl, or C$_3$-C$_8$cycloalkyl; or
R$^6$ and R$^7$ can together form an optionally substituted 5-, or 6-membered monocyclic ring containing 0, or 1 oxygen atom.

6. The compound of claim 5, wherein:
R$^6$ and R$^7$ are independently C$_1$-C$_6$haloalkyl, C$_1$-C$_6$alkyl, or C$_3$-C$_8$cycloalkyl; or
R$^6$ and R$^7$ can together form an optionally substituted cyclohexyl or tetrahydropyran.

7. The compound of claim 6, wherein:
R$^8$ is —OH, —CONH$_2$, tetrazolyl, —CN, —CO$_2$H, —OR$^{12}$, —CON(R$^{12}$)$_2$, —CO$_2$—R$^{12}$, C(=O)R$^{12}$, C(OH)(R$^{12}$)$_2$, —CH=N—OR$^{12}$, or —OC(=O)R$^{12}$; where each R$^{12}$ is independently H, or C$_1$-C$_6$alkyl.

8. A compound selected from among:
7-[3-(4-Methoxy-tetrahydro-pyran-4-yl)-benzyloxy-]-imidazo[1,2-a]quinoline; 7-[3-Fluoro-5-(4-methoxy-tetrahydro-pyran-4-yl)-phenoxymethyl]-imidazo[1,2-a]quinoline ; 4-[3-Fluoro-5-(imidazo[1,2-a]quinolin-7-ylmethoxy)-phenyl]-tetrahydro-pyran-4-carboxylic acid methyl ester; 4-[3-Fluoro-5-(imidazo[1,2-a]quinolin-7-ylmethoxy)-phenyl]-tetrahydro-pyran-4-carboxylic acid; 4-[3-Fluoro-5-(imidazo[1,2-a]quinolin-7-ylmethoxy)-phenyl ]-tetrahydr-pyran-4-carboxylic acid; 4-[3-Fluoro-5-(imidazo[1,2-a]quinolin-7-ylmethoxy)-phenyl]-tetrahydro-pyran-4-ol; 4-[3-(1-Bromo-imidazo[1,2-a]quinolin-7-ylmethoxy)-5-fluoro-phenyl]-tetrahydro-pyran-4-carboxylic acid methyl ester; 4-[3-Fluoro-5-(1-phenyl-imidazo[1,2-a]quinolin-7-ylmethoxy)-phenyl ]-tetrahydro-pyran-4-carboxylic acid methyl ester; 4-[3-(imidazo[1,2-a]quinolin-7-ylsulfanyl)-phenyl]tetrahydro-pyran-4-ol; 7-[3-(4-Methoxy-tetrahydro-pyran-4-yl)-phenylsulfanyl]-imidazo[1,2-a]quinoline; 4-[3-(imidazo [1,2-a]quinolin-7-ylsulfanyl)-phenyl]-tetrahydro-pyran-4-carboxylic acid amide; 4-[3-(2-Methyl-imidazo[1,2-a]quinolin-7-ylsulfanyl)-phenyl]tetrahydro-pyran-4-carbonitrile; 4-[3-(Imidazo[1,2-a]quinolin-7-ylsulfanyl)-phenyl]-tetrahydro-pyran-4-carbonitrile; 4-[3-(1-Methyl-imidazo[1,2-a]quinolin-7-ylsulfanyl)-phenyl]-tetrahydro-pyran-4-carbonitrile; 4-{3-[1-(1-Methyl-1H-pyrazol-4-yl)-imidazo [1,2-a]quinolin-7-ylsulfanyl)-phenyl-tetrahydro-pyran-4-carbonitrile;4-[3-Fluoro-5-(imidazo[1,2-a]quinolin-7-ylsulfanyl)-phenyl]tetrahydro-pyran-4-carbonitrile ; 4-[3-(1-Bromo-imidazo[1,2-a]quinolin-7-ylsulfanyl)-5-fluoro-phenyl]-tetrahydro-pyran-4-carbonitrile; 4-[3-Fluoro-5-(1-phenyl-imidazo[1,2-a]quinolin-7-ylsulfanyl)-phenyl]-tetrahydro-pyran-4-carbonitrile; 4-[3-Fluoro-5-(2-phenyl-imidazo [1,2-a]quinolin-7-ylsulfanyl)-phenyl]-tetrahydro-pyran-4-carbonitrile; 7-[3-(4-Cyano-tetrahydro-pyran-4-yl)-5-fluoro-phenylsulfanyl]-imidazo[1,2-a]quinoline-2-carboxylic acid ethyl ester; 7-[3-(4-Cyano-tetrahydro-pyran-4-yl)-5-fluoro-phenylsulfanyl]-imidazo [1,2-a]quinoline-2-carboxylic acid; 8-[3-Fluoro-5-(4-methoxy-tetrahydro-pyran-4-yl)-phenoxymethyl]-imidazo[1,2-a]quinoline; 4-[3-(5-Chloro-imidazo[1,2-a]quinolin-8-ylmethoxy)-5-fluoro-phenyl]-tetrahydro-pyran-4-carboxylic acid methyl ester; 4-[3-(5-Chloro-imidazo[1,2-a]dquinolin-8-ylmethoxy)-5-fluorophenyl]-tetrahydro-pyran-4-carboxylic acid amide; 4-[3-Fluoro-5-(5-methylsulfanyl-imidazo[1,2-a]quinolin-8-ylmethoxy)-phenyl]-tetrahydro-pyran-4-carboxylic acid; 4-[3-Fluoro-5-(5-methylsulfanyl-imidazo[1,2-a]quinolin-8-ylmethoxy)-phenyl]-tetrahydro-pyran-4-carboxylic acid amide; 4-[3-Fluoro-5-(5-phenyl-imidazo[1,2-a]quinolin-8-ylmethoxy)-phenyl]-tetrahydro-pyran-4-carboxylic acid methyl ester; 4-[3-(5-Cyclopentylsulfanyl-imidazo [1,2-a]quinolin-8-ylmethoxy)-5-fluoro-phenyl]-tetrahydro-pyran-4-carboxylic acid; 4-[3-(5-Cyclopentylsulfanyl-imidazo[1,2-a]quinolin-8-ylmethoxy)-5-fluoro-phenyl]-tetrahydro-pyran-4-carboxylic acid amide; 4-[3-(5-Bromo-imidazo [1,2-a]quinolin-8-ylmethoxy)-5-fluoro-phenyl]-tetrahydro-pyran-4-carboxylic acid methyl ester; 4-[3-(5-Bromo-imidazo[1,2-a]quinolin-8-ylmethoxy)-5-fluoro-phenyl ]-tetrahydro-pyran-4-carboxylic acid; 4-[3-(5-Bromo-imidazo[1,2-a]quinolin-8-ylmethoxy)-5-fluoro-pheny]-tetrahydro-pyran-4-carboxylic acid amide; 4-[3-Fluoro-5-(5-phenyl-imidazo[1,2-a]quinolin-8-ylmethoxy)-phenyl]-tetrahydro-pyran-4-carboxylic acid amide; 4-[3-Fluoro-5-(5-pyridin-3-yl-imidazo[1,2-a]quinolin-8-ylmethoxy)-phenyl-tetrahydro-pyran-4-carboxylic acid amide; 4-{3-Fluoro-5-[5-(3-methoxy-phenyl)-imidazo [1,2-a]quinolin-8-ylmethoxy]-phenyl}-tetrahydro-pyran-4-carboxylic acid amide; 4-{3-Fluoro-5[5-(1H-pyrazol-4-yl)-imidazo[1,2-a]quinolin-8-ylmethoxy]-phenyl}-tetrahydro-pyran-4-carboxylic acid amide; 4-{3-Fluoro-5[5-(1-methyl-1H-pyrazol-4-yl)-imidazo [1,2-a]quinolin-8-ylmethoxy]-phenyl)-tetrahydro-pyran-4-carboxylic acid amide; 4-[3-Fluoro-5-(5-pyridin-4-yl-imidazo[1,2-a]quinolin-8-ylmethoxy)-phenyl]-tetrahydro-pyran-4-carboxylic acid amide; 4-[3-Fluoro-5-(5-m-tolyl-imidazo [1,2-a]quinolin-8-ylmethoxy)-phenyl]-tetrahydro-pyran-4-carboxylic acid amide; 4-{3-[5-(4-Amino-phenyl)-imidazo[1,2-a]quinolin-8-ylmethoxy]-5-fluoro-phenyl}-tetrahydro-pyran-4-carboxylic acid amide; 4-{3-Fluoro-5-[5-(4-fluoro-phenyl)-imidazo[1,2-a]quinolin-8-ylmethoxy]-phenyl}-tetrahydro-pyran-4-carboxylic acid amide ; 4-{3-Fluoro-5-[5-(2-methoxy-phenyl)-imidazo[1,2-a]quinolin-8-ylmethoxy]-phenyl}-tetrahydro-pyran-4-carboxylic acid amide; 4-{3-Fluoro-5-[5-(4-methoxy-phenyl)-imidazo[1,2-a]quinolin-8-ylmethoxy]-phenyl}-tetrahydro-pyran-4-carboxylic acid amide; 4-[3-Fluoro-5-(5-pyrimidin-5-yl-imidazo[1,2-a]quinolin-8-ylmethoxy)-phenyl]-tetrahydro-pyran-4-carboxylic acid amide; 4-{3-Fluoro-5-[5-(4-methoxy-pyridin-3-yl)-imidazo[1,2-a]quinolin-8-ylmethoxy]-phenyl}-tetrahydro-pyran-4-carboxylic acid amide; 4-{3-Fluoro-5-[5-(6-methoxy-pyridin-3-yl)-imidazo[1,2-a]quinolin-8-ylmethoxy]-phenyl}-tetrahydro-pyran-4-carboxylic acid amide; 4-[3-(5-Phenyl-imidazo [1,2-a]quinolin-8-ylsulfanyl)-phenyl]-tetrahydro-pyran-4-carbonitrile; 4-[3-(5-Phenyl-imidazo[1 ,2-a]quinolin-8-ylsulfanyl)-phenyl]-tetrahydro-pyran-4-carboxylic acid amide; 5-Chloro-8-[3-(4-cyano-tetrahydro-pyran-4-yl)-phenylsulfanyl]-imidazo[1,2-a]quinoline-2-carboxylic acid ethyl ester; 5-Chloro-8-[3-(4-cyano-tetrahydro-pyran-4-yl)-phenylsulfanyl]-imidazo[1,2-a]quinoline-2-carboxylic acid; 5-Chloro-8-[3-(4-cyano-tetrahydro-pyran-4-yl)-phenylsulfanyl]-imidazo[1,2-a]quinoline-2-carboxylic acid amide; 4-[3-(2-Chloro-5-phenyl-imidazo[1,2-a]quinolin-8-ylsulfanyl)-phenyl]-tetrahydro-pyran-4-carbonitrile; 4-[3-(5-Phenyl-imidazo[1,2-a]quinolin-8-ylsulfanyl)-phenyl]-tetrahydro-pyran-4-ol; 4-[3-(5-Methyl-imidazo [1,2-a]quinolin-8-ylsulfanyl)-phenyl]-tetrahydro-pyran-4-carbonitrile; 4-[3-(2-Chloro-5-phenyl-imidazo[1,2-a]quinolin-8-ylsulfanyl)-phenyl]-tetrahydro-pyran-4-ol; 4-[3-(5-Isopropyl-imidazo[1,2-a]quinolin-8-ylsulfanyl)-phenyl]-tetrahydro-pyran-4-carbonitrile 4-[3-(5-Isopropyl-imidazo[1,2-a]quinolin-8-ylsulfanyl)-phenyl]-tetrahydro-pyran-4-ol; 8-[3-(4-Cyano-tetrahydro-pyran-4-yl)-phenylsulfanyl]-5-phenyl-imidazo[1,2-a]quinoline-2-carboxylic acid ethyl ester; 8-[3-(4-Cyano-tetrahydro-pyran-4-yl)-phenylsulfanyl]-5-phenyl-imidazo[1,2-a]quinoline-2-carboxylic acid; 4-[3-(5-Phenyl-imidazo[1,2-a]quinolin-8-ylsulfanyl)-phenyl]-tetrahydro-pyran-4-carboxylic acid methyl ester; 4-[3-(5-Phenyl-imidazo[1,2-a]quinolin-8-ylsulfanyl)-phenyl-tetrahydro-pyran-4-carboxylic acid; 4-[3-(2-Chloro-5-isopropyl-imidazo[—1,2-a]quinolin-8-ylsulfanyl)-phenyl]-tetrahydro-pyran-4-ol; 8-[3-(4-Hydroxy-tetrahydro-pyran-4-yl)-phenylsulfanyl]-5-isopropyl-imidazo[1,2-a]quinoline-2-carboxylic acid; 8-[3-(4-Hydroxy-tetrahydro-pyran-4-yl)-phenylsulfanyl]-5-phenyl-imidazo[1,2-a]quinoline-2-carboxylic acid; 4-[3-(5-Methyl-imidazo [1,2-a]quinolin-8-ylsulfanyl)-phenyl]tetrahydro-pyran-4-carboxylic acid amide; 4-[3-(5-Isopropyl-imidazo[1,2-a]quinolin-8-ylsulfanyl)-phenyl]tetrahydro-pyran-4-carboxylic acid amide; 5-Chloro-8-[3-(4-cyano-tetrahydro-pyran-4-yl)-phenylsulfanyl]-imidazo[1,2-a]quinoline-2-carbonitrile; 4-[3-(2-Chloro-5-isopropyl-imidazo[1,2-a]quinolin-8-ylsulfanyl)-phenyl]-tetrahydro-pyran-4-carbonitrile; 8-[3-(4-Hydroxy-tetrahydro-pyran-4-yl)-phenylsulfanyl]-5-isopropyl-imidazo[1,2-a]quinoline-2-carbonitrile; 8-[3-(4-Hydroxy-tetrahydro-pyran-4-yl)-phenylsulfanyl]-5-phenyl-imidazo[1,2-a]quinoline-2-carbonitrile; 4-[3-(2-Chloro-5-isopropyl-imidazo[l,2-a]quinolin-8-ylsulfanyl)-phenyl]-tetrahydro-pyran-4-carboxylic acid amide; 4-[3-(2-Hydroxymethyl-5-phenyl-imidazo[1,2-a]quinolin-8-ylsulfanyl)-phenyl]-tetrahydro-pyran-4-ol; 4-{3-[2-(1-Hydroxy-1-methyl-ethyl)-5-phenyl-imidazo[1,2-a]quinolin-8-ylsulfanyl]-phenyl}-tetrahydro-pyran-4-ol; 4-[3-(2-Hydroxymethyl-5-methyl-imidazo[1,2-a]quinolin-8-ylsulfanyl)-phenyl]-tetrahydro-pyran-4-ol; 4-{3-[2-(1-Hydroxy-1-methyl-ethyl)-5-methyl-imidazo[1,2-a]quinolin-8-ylsulfanyl]-phenyl}-tetrahydro-pyran-4-ol; 8-[3-(4-Hydroxy-tetrahydro-pyran-4-yl)-phenylsulfanyl]-5-methyl-imidazo[1,2-a]quinoline-2-carboxylic acid; 4-[3-(2-Fluoromethyl-5-phenyl-imidazo[1,2-a]quinolin-8-ylsulfanyl)-phenyl]-tetrahydro-pyran-4-ol; Succinie acid mono-{8-[3-(4-hydroxy-tetrahydro-pyran-4-yl)-phenylsulfanyl]-5-phenyl-imidazo[1,2-a]quinolin-2-ylmethyl}ester; 8-[3-(4-Hydroxy-tetrahydro-pyran-4-yl)-phenylsulfanyl]-5-phenyl-imidazo[1,2-a]quinoline-2-carboxylic acid ethyl ester; 1-{8-[3-(4-Hydroxy-tetrahydro-pyran-4-yl)-phenylsulfanyl]-5-phenyl-imidazo[1,2-a]quinolin-2-yl}-ethanone; 8-[3-(4-Hydroxy-tetrahydro-pyran-4-yl)-phenylsulfanyl]-5-phenyl-imidazo[1,2-a]quinoline-2-carbaldehyde; 4-[3-(5-Chloro-imidazo[1,2-a]quinolin-8-ylsulfanyl)-5-fluoro-pheny]tetrahydro-pyran-4-carbonitrile; and 3-[3-(5-Phenyl-imidazo[1,2-a]quinolin-8-ylsulfanyl)-phenyl]-pentan-3-ol; or a pharmaceutically acceptable salt thereof.

9. A pharmaceutical composition comprising a therapeutically effective amount of a compound of claim 1 or a pharmaceutically acceptable salt and a pharmaceutically acceptable excipient.

10. The compound of claim 1, wherein:

$L^1$ is selected from among —$(CHR^4)_nO$—, —$(CHR^4)_nS$—, —$O(CHR^4)_n$—, and —$S(CHR^4)_n$—;

each $R^4$ is H; n— is 0 or 1;

$R^6$ and $R^7$ are independently $C_1$-$C_6$haloalkyl, $C_1$-$C_6$alkyl, or $C_3$-$C_8$cycloalkyl;

or $R^6$ and $R^7$ can together form an optionally substituted tetrahydropyran;

$R^8$ is H, —OH, —$CONH_2$, —CN, —$CF_3$, —$CO_2H$, —$CON(R^{12})_2$, —$CO_2$-$R^{12}$, or —$OC(=O)R^{12}$;

where each $R^{12}$ is independently H, or $C_1$-$C_6$alkyl.

11. The compound of claim 10, wherein:

each $R^1$ is independently H, halide, —CN, —$NO_2$, —OH, —$OR^3$, —$SR^3$, —$S(=O)R^3$, —$S(=O)_2R^3$, —$C(=O)R^3$, —$C(=O)OR^3$, —$CH(R^3)_2$, —$N(R^3)_2$, —$NHCH_2C(=O)OR^3$, —$C(=O)N(R^3)_2$, —$NHC(=O)R^3$, or —$C(OH)(R^3)_2$, $C_1$-$C_6$alkyl, $C_1$-$C_6$fluoroalkyl, $C_3$-$C_8$cycloalkyl, or $C_1$-$C_6$fluoroalkoxy; or $R^1$ is $Q^1$-$Q^2$ where $Q^1$ is phenyl, or monocyclic heteroaryl; and $Q^2$ is H, halide, —CN, —$NO_2$, $C_1$-$C_6$alkyl, $C_1$-$C_6$alkoxy; —$OR^3$, —$SR^3$, —$S(=O)R^3$, —$S(=O)_2R^3$, —$C(=O)R^3$, —$C(=O)OR^3$, —$CH(R^3)_2$, —$N(R^3)_2$, or —$C(=O)N(R^3)_2$;

each $R^3$ is independently H or $C_1$-$C_6$alkyl;

$R^{13}$ is H or halide;

$R^{14}$ is H.

\* \* \* \* \*